(12) United States Patent
Trieselmann et al.

(10) Patent No.: US 11,254,688 B2
(45) Date of Patent: *Feb. 22, 2022

(54) BENZYL-, (PYRIDIN-3-YL)METHYL -OR (PYRIDIN-4-YL)-METHYL-SUBSTITUTED OXADIAZOLOPYRIDINE DERIVATIVES AS GHRELIN O-ACYL TRANSFERASE (GOAT) INHIBITORS

(71) Applicant: Boehringer Ingelheim International GmbH, Ingelheim am Rhein (DE)

(72) Inventors: Thomas Trieselmann, Mettenberg (DE); Cedrickx Godbout, Attenweiler (DE); Christoph Hoenke, Biberach an der Riss (DE); Viktor Vintonyak, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/966,483

(22) PCT Filed: Jan. 28, 2019

(86) PCT No.: PCT/EP2019/051989
§ 371 (c)(1),
(2) Date: Jul. 31, 2020

(87) PCT Pub. No.: WO2019/149657
PCT Pub. Date: Aug. 8, 2019

(65) Prior Publication Data
US 2021/0053985 A1  Feb. 25, 2021

(30) Foreign Application Priority Data
Feb. 2, 2018 (EP) .................. 18154824

(51) Int. Cl.
C07D 498/04 (2006.01)
C07D 519/00 (2006.01)

(52) U.S. Cl.
CPC ......... C07D 498/04 (2013.01); C07D 519/00 (2013.01)

(58) Field of Classification Search
CPC ................ C07D 498/04; C07D 519/00
USPC .................................... 514/302
See application file for complete search history.

(56) References Cited

U.S. PATENT DOCUMENTS

| | | | | |
|---|---|---|---|---|
| 9,994,591 | B2 * | 6/2018 | Godbout | .......... A61P 3/10 |
| 10,308,667 | B2 * | 6/2019 | Godbout | .......... C07D 498/04 |
| 2008/0275057 | A1 | 11/2008 | Kawabe | |
| 2011/0078154 | A1 | 3/2011 | Rickman et al. | |
| 2012/0009560 | A1 | 1/2012 | Coupe et al. | |
| 2015/0018547 | A1 | 1/2015 | Takakura et al. | |
| 2021/0038603 | A1 | 2/2021 | Trieselmann et al. | |
| 2021/0040077 | A1 | 2/2021 | Trieselmann et al. | |

FOREIGN PATENT DOCUMENTS

| | | |
|---|---|---|
| WO | 2008152403 | 6/2008 |
| WO | 2008101017 | 8/2008 |
| WO | 2008141843 A1 | 11/2008 |
| WO | 2010007255 | 1/2010 |
| WO | 2010007251 | 6/2010 |
| WO | 2010007253 | 6/2010 |
| WO | 2010070252 | 6/2010 |
| WO | 2011006497 | 1/2011 |
| WO | 2011160630 | 12/2011 |
| WO | 2011160633 | 12/2011 |
| WO | 2013092703 | 6/2013 |
| WO | 2004082383 | 8/2013 |
| WO | 2013125732 A1 | 8/2013 |
| WO | 2013192388 | 12/2013 |
| WO | 2014041195 | 3/2014 |
| WO | 2015073281 A1 | 5/2015 |
| WO | 2016044467 | 3/2016 |
| WO | 2016123275 | 8/2016 |
| WO | 2016168222 | 10/2016 |
| WO | 2016168225 | 10/2016 |
| WO | 2017070680 A1 | 4/2017 |
| WO | 2018024653 | 2/2018 |
| WO | 201844663 A1 | 3/2018 |
| WO | 2019149657 A1 | 8/2019 |
| WO | 2019149658 A1 | 8/2019 |
| WO | 2019149659 A1 | 8/2019 |

OTHER PUBLICATIONS

Vasil. Russian Chem Bulletin, Reactions of cyanoturazans with [beta]-dicarbonyl compiunds, 2001, vol. 50, p. 1280-1286.
International Search Authority and Written opinion, for PCT/EP2017/069274, dated Sep. 15, 2017.
Kuppens, "Elelvated Ration of acylated to unacylated ghrelin in children and yoiung adults with Prader-Willi syndrome", Endocrine, Humana Press, vol. 50, No. 3, 2015, p. 633-642.
Hirozane, SLAS Discovery, Identification and Characterization of a new series of Ghrelin O-Acyl Transferase Inhibitors, vol. 23, 2018.

(Continued)

*Primary Examiner* — Kahsay Habte
(74) *Attorney, Agent, or Firm* — David L. Kershner

(57) ABSTRACT

The present invention relates to compounds of general formula (I), wherein the groups $R^1$ and $R^2$ are defined as in claim 1, which have valuable pharmacological properties, in particular bind to ghrelin O-acyl transferase (GOAT) and modulate its activity. The compounds are suitable for treatment and prevention of diseases which can be influenced by this receptor, such as metabolic diseases, in particular obesity.

(I)

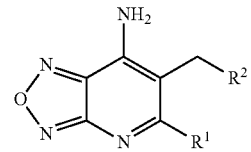

18 Claims, No Drawings

(56) References Cited

OTHER PUBLICATIONS

Vasil, Mendellev Communications, Effective Synthesis of Funtionalized furazano, 1994, vol. 2, p. 57-58.
Hirozane, Identification and Characterization of a new series of Ghrelin O-Acyl Transferase Inhibitors, SLAS Discoery, 2017.
Haffner, Intensive Lifestyle Intervention or Metofrmin on Inflammation and Coagulation in Participants with Impaired Glucose Tolerance, The Diabetes Prevention Research Group, vol. 54, 2007.
Cummings, A preprandial rise in plasma ghrelin, Diabetes, vol. 50, 2001.
Druce, Ghrelinincreases foodintake in obese as well as lean subjects, Int J. of Obesity, vol. 29, 2005.
Zhang, Effect of Des0acyl Ghrelinon Adiposity and Glucose Metabolism, Endocrinology, 2008.
Wierup, The ghrelin cell, Regulatory peptides, vol. 107, 2002.
Broglio, Non-AcelatedGhrelin Counteracts the metabolic but not the neuroendocrine response, J. of Endocrine & Metabolism, vol. 80, 2004.
Delparigi, High circulating Ghrelin, J. of Endocrinology & Metabolism, vol. 12, 2002.
Granata, Acylated and Unacylated Ghrelin promote Proliferation and and inhibit Apositis of pancreatic B-cells and Human Islets, Endocrinology, vol. 2, 2007.
Granata, Des-Acyl Ghrelin Fragment and analogues promote survival of pancreatic b-cells, ACS, vol. 55, 2012.
Andianov, Synthesis and Properties of 4-aminoo-3-cyanofurazan, Chem of heterocytic Compunds, vol. 30, 1994.
Pagoria, Synthesisand Characterization of mutlicyclic oxadiazoles, Cherm. of Heterocyclic Compunds, vol. 53, 2017, p. 760-778.
Bohle, Nucelophilic Addition of Hydroxylamine, J. Org Chem, 2000.
Vasil'ev, Effective Synthesis of Functionalized Furazano, Zelinsky Institute of Organix Chem., 1993.
Vasil'ev, Reaction of Cyanofurans, Russian Chem. Bulletin, vol. 50, 2001, p. 1280-1286.
Ichikawa, Central Research Labs, A new Synthesis of Adenine and 4-Aminoimdazole-5-carboxamide, 1965.
International Search Report for PCT/EP2021/063090 dated Jul. 1, 2021.
International Search Report for PCT/EP2021/063088 dated Jul. 1, 2021.

\* cited by examiner

BENZYL-, (PYRIDIN-3-YL)METHYL -OR (PYRIDIN-4-YL)-METHYL-SUBSTITUTED OXADIAZOLOPYRIDINE DERIVATIVES AS GHRELIN O-ACYL TRANSFERASE (GOAT) INHIBITORS

FIELD OF THE INVENTION

The present invention relates to novel oxadiazolopyridine derivatives, that are inhibitors of the ghrelin O-acyl transferase (GOAT), to processes for their preparation, to pharmaceutical compositions containing these compounds and to their medical use for the prophylaxis and/or treatment of diseases which can be influenced by the modulation of the function of the ghrelin O-acyl transferase (GOAT). Particularly, the pharmaceutical compositions of the invention are suitable for the prophylaxis and/or therapy of metabolic diseases, such as obesity, including, but not limited to obesity in patients suffering from Prader-Willi-Syndrome (PWS), insulin resistance and diabetes, particularly type 2 diabetes.

BACKGROUND OF THE INVENTION

Ghrelin O-Acyltransferase (GOAT) is a member of the membrane-bound O-acyl transferase (MBOAT) protein family, and the only enzyme in humans capable of promoting an acylation reaction on the peptide hormone ghrelin. By linking a medium-chain fatty acid to the Serine-3 position of the 28-amino acid peptide, GOAT converts unacylated ghrelin (UAG) to acylated ghrelin (AG) which is the natural ligand of the ghrelin receptor GHSR1a (growth hormone secretagogue receptor 1a). The ghrelin receptor is expressed in various areas of the brain involved in energy homeostasis. Activation of the receptor by AG results in stimulation of neuronal pathways leading to increased food intake, fat deposition and weight gain thus linking the ghrelin system to obesity. In humans, AG in plasma peaks immediately before mealtimes and drops in response to food intake (D. E. Cummings et al., Diabetes (2001) 50(8), 1714-1719). Infusion of AG has been shown to increase food intake in lean and obese subjects (M. R. Druce et al., Int. J. Obes. (2005), 29(9), 1130-1136). So far no receptor has been identified for UAG, but it has been shown to have functional antagonistic effects to AG at least with respect to its metabolic properties (W. Zhang et al., Endocrinology (2008) 149 (9), 4710-4716). Since an inhibitor of GOAT would substantially diminish the level of the GHSR1a ligand AG and concomitantly increase the functional antagonist UAG, it would be useful for the treatment of obesity as an adjunct to a reduced-calorie diet and increased physical activity for chronic weight management.

Insatiable hunger and severe obesity are characteristic features of the Prader-Willi-Syndrome (PWS), a genetically caused orphan disease with a complex pathology. AG levels in plasma of PWS subjects are elevated and AG/UAG ratios are increased suggesting a causal relationship (N. Wierup et al., Regulatory Peptides (2002) 107, 63-69; R. J. Kuppens et al., Endocrine (2015) 50(3), 633-642). Therefore GOAT inhibitors may be effective in reducing food craving behavior and body weight in PWS patients ameliorating one major burden affecting the patients and their families.

Furthermore the ghrelin system seems to play a major role in glucose homeostasis. Administration of AG to human subjects leads to suppression of glucose-induced insulin secretion and an increase in plasma glucose. Infusion of UAG is able to counteract the hyperglycemic effect of AG (F. Broglio et al., J. Clin. Endocrinol. Metab. (2004) 89, 3062-3065). The expression of GOAT, ghrelin and GHSR1a in human pancreatic islets suggests a paracrine role on insulin secretion (A. DelParigi et al., J. Clin. Endocrinol. Metab. (2002) 87(12), 5461-5464). In addition UAG promotes pancreatic β-cell and human islet cell survival in vitro (R. Granata et al., Endocrinology (2007) 148(2), 512-529) and prevents diabetes in streptozotocin treated rats (R. Granata et al., J. Med. Chem. (2012) 55(6), 2585-2596). Thus treatment with a GOAT inhibitor is expected to improve glucose homeostasis in patients with type 2 diabetes or obese with impaired glucose tolerance.

OBJECT OF THE PRESENT INVENTION

The object of the present invention is to provide new compounds, hereinafter described as compounds of formula I, in particular new oxadiazolopyridine derivatives, which are active with regard to the ghrelin O-acyl transferase (GOAT), notably they are ghrelin O-acyl transferase (GOAT) inhibitors.

A further object of the present invention is to provide new compounds, in particular oxadiazolopyridine derivatives, which have an inhibiting effect on ghrelin O-acyl transferase (GOAT) in vitro and/or in vivo and possess suitable pharmacological and pharmacokinetic properties to use them as medicaments.

A further object of the present invention is to provide effective ghrelin O-acyl transferase (GOAT) inhibitors, in particular for the treatment of metabolic disorders, for obesity, including, but not limited to obesity in patients suffering from Prader-Willi-Syndrome (PWS), insulin resistance and diabetes, in particular type 2 diabetes mellitus.

A further object of the present invention is to provide methods for treating a disease or condition mediated by the inhibition of ghrelin O-acyl transferase (GOAT) in a patient.

A further object of the present invention is to provide a pharmaceutical composition comprising at least one compound according to the invention.

A further object of the present invention is to provide a combination of at least one compound according to the invention with one or more additional therapeutic agents.

Further objects of the present invention become apparent to the one skilled in the art by the description hereinbefore and in the following and by the examples.

Ghrelin O-acyl transferase (GOAT) inhibitors are known in the art, see for example the compounds disclosed in WO 2013/125732 and WO 2015/073281. The oxadiazolopyridine derivatives of the present invention are structurally quite different and may provide several advantages, such as enhanced potency, high metabolic and/or chemical stability, high selectivity and tolerability, enhanced solubility, the ability to cross the blood-brain barrier and the possibility to form stable salts.

SUMMARY OF THE INVENTION

In a first aspect, the invention relates to a compound of formula

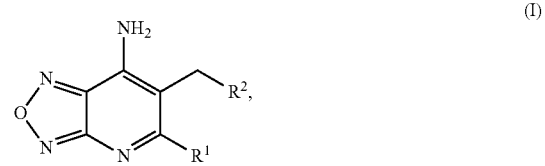

(I)

wherein
$R^1$ is selected from the group $R^1$-G1 consisting of Cl, Br, CN, $CH_3$, and $—N(CH_3)_2$, wherein the CH$_3$ group is optionally substituted with 1-3 F or with one OH;

R$^2$ is selected from the group R$^2$-G1 consisting of:
a) a phenyl, pyridin-3-yl or pyridin-4-yl group optionally substituted by 1-3 substituents R$^3$ independently of each other selected from the group R$^3$-G1 consisting of F, Cl, Br, I, CN, C$_{1-6}$-alkyl, C$_{3-7}$-cycloalkyl, OH, —O—(C$_{1-6}$-alkyl), —O—(C$_{1-3}$-alkyl)-(C$_{3-7}$-cycloalkyl), —O—(C$_{1-3}$-alkyl)-heterocyclyl, —O—(C$_{3-7}$-cycloalkyl), —O-heterocyclyl, —S—(C$_{1-3}$-alkyl), —SO—(C$_{1-3}$-alkyl), —SO$_2$—(C$_{1-3}$-alkyl), —C(=O)—NR$^{N1}$R$^{N2}$, —C(=O)OH, —C(=O)—O—(C$_{1-4}$-alkyl), and —N=S(=O)(C$_{1-3}$-alkyl)$_2$ and heteroaryl,
wherein R$^{N1}$ is selected from the group R$^{N1}$-G1 consisting of H, C$_{1-6}$-alkyl, —(C$_{1-3}$-alkyl)-(C$_{3-7}$-cycloalkyl), —(C$_{1-3}$-alkyl)-heterocyclyl, —(C$_{1-3}$-alkyl)-heteroaryl, C$_{3-7}$-cycloalkyl, heterocyclyl and heteroaryl;
and R$^{N2}$ is selected from the group R$^{N2}$-G1 consisting of H and C$_{1-4}$-alkyl, and
wherein each alkyl group is optionally substituted with 1-3 F or with one OH, CN, COOH or —C(=O)—NH$_2$;
wherein each cycloalkyl group is optionally substituted with one or two F and/or with one CN, COOH, —C(=O)—NH$_2$ or —CH$_3$, which is optionally substituted with 1-3 F or with one OH;
wherein each heterocyclyl group is selected from a mono- or spirocyclic 4-7-membered cycloalkyl group, in which 1, 2 or 3 CH$_2$-groups are independently of each other replaced by O, S, NH or C=O, and
wherein each heterocyclyl group is optionally substituted with 1 or 2 substituents independently of each other selected from F, CN, OH and C$_{1-3}$-alkyl,
wherein each heteroaryl group is selected from a 5-membered aromatic cycle containing 1, 2 or 3 heteroatoms independently selected from N, O and S or from a 6-membered aromatic cycle containing 1 or 2 N, and
wherein each heteroaryl group is optionally substituted with 1 or 2 substituents independently of each other selected from a group consisting of F, CN and C$_{1-3}$-alkyl, which is optionally substituted with one or more F;
b) a bicyclic heteroaryl selected from the group consisting of:

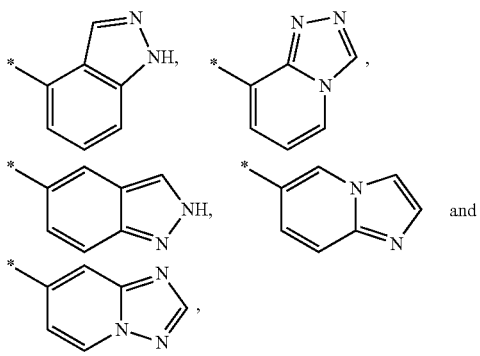

which are each optionally substituted by one substituent selected from the group consisting of Cl, C$_{1-3}$-alkyl, cyclopropyl, —O—(C$_{1-3}$-alkyl-), —C(=O)—O—(C$_{1-4}$-alkyl), and heteroaryl,
wherein each alkyl group is optionally substituted with 1-3 F;
wherein each heteroaryl group is selected from a 5-membered aromatic cycle containing 1 or 2 heteroatoms independently selected from N, O and S; and
wherein each heteroaryl group is optionally substituted with 1 or 2 CH$_3$ groups or with one CN group;
wherein each of the above-mentioned alkyl groups may be substituted with one or more F;
the isoforms, tautomers, stereoisomers, metabolites, prodrugs, solvates, hydrates, and the salts thereof, particularly the physiologically acceptable salts thereof with inorganic or organic acids or bases, or the combinations thereof.

The extension -Gn used within the definitions is meant to identify genus n of the respective substituent. For example, R-G1 defines genus 1 of the substituent R.

The expression "optionally substituted with 1 or more F atoms" means that none or one up to successively all H atoms bound to carbon atoms of the respective group or submoiety may be replaced by F atoms, preferably 1 to 5 H atoms or, more preferred, 1 to 3 H atoms may be replaced by F atoms.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by inhibiting ghrelin O-acyl transferase (GOAT) in a patient in need thereof characterized in that a compound of general formula I or a pharmaceutically acceptable salt thereof is administered to the patient.

According to another aspect of the invention, there is provided a method for treating a metabolic disease or disorder, such as obesity, including, but not limited to obesity in patients suffering from Prader-Willi-Syndrome, insulin resistance and diabetes, in particular type 2 diabetes mellitus, in a patient in need thereof characterized in that a therapeutically effective amount of a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the inhibition of ghrelin O-acyl transferase (GOAT) in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to the use of a compound of the general formula I or a pharmaceutically acceptable salt thereof in combination with one or more additional therapeutic agents for the treatment of diseases or conditions which are mediated by the inhibition of ghrelin O-acyl transferase (GOAT).

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $R^1$ and $R^2$ are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore.

$R^1$-G2:

In one embodiment, the group $R^1$ is selected from the group $R^1$-G2 consisting of Cl, Br, CN, $CH_3$, —$CH_2F$, —$CHF_2$, $CF_3$, —$CH_2OH$, and —$N(CH_3)_2$.

$R^1$-G3:

In another embodiment, the group $R^1$ is selected from the group $R^1$-G3 consisting of Cl, $CH_3$, —$CH_2F$, —$CHF_2$, and $CF_3$.

$R^1$-G4:

In another embodiment, the group $R^1$ is selected from the group $R^1$-G4 consisting of —$CH_3$ and Cl.

$R^1$-G5:

In another embodiment, the group $R^1$ is selected from the group $R^1$-G5 consisting of $CH_3$.

$R^1$-G6:

In another embodiment, the group $R^1$ is selected from the group $R^1$-G6 consisting of Cl.

$R^2$-G1:

The group $R^2$ is preferably selected from the group $R^2$-G1 as defined hereinbefore.

$R^2$-G1a:

In another embodiment, the group $R^2$ is independently of each other selected from the group $R^2$-G1a consisting of:

a) a phenyl, pyridin-3-yl or pyridin-4-yl group optionally substituted by 1-3 substituents $R^3$ independently of each other selected from the group $R^3$-G1 consisting of F, Cl, Br, I, CN, $C_{1-6}$-alkyl, $C_{3-7}$-cycloalkyl, OH, —O—($C_{1-6}$-alkyl), —O—($C_{1-3}$-alkyl)-($C_{3-7}$-cycloalkyl), —O—($C_{1-3}$-alkyl)-heterocyclyl, —O—($C_{3-7}$-cycloalkyl), —O— heterocyclyl, —S—($C_{1-3}$-alkyl), —SO—($C_{1-3}$-alkyl), —$SO_2$—($C_{1-3}$-alkyl), —C(=O)—$NR^{N1}R^{N2}$, —C(=O)OH, —C(=O)—O—($C_{1-4}$-alkyl), and —N=S(=O)($C_{1-3}$-alkyl)$_2$ and heteroaryl, wherein $R^{N1}$ is selected from the group $R^{N1}$-G1 consisting of H, $C_{1-6}$-alkyl, —($C_{1-3}$-alkyl)-($C_{3-7}$-cycloalkyl), —($C_{1-3}$-alkyl)-heterocyclyl, —($C_{1-3}$-alkyl)-heteroaryl, $C_{3-7}$-cycloalkyl, heterocyclyl and heteroaryl; and $R^{N2}$ is selected from the group $R^{N2}$-G1 consisting of H and $C_{1-4}$-alkyl, and wherein each alkyl group is optionally substituted with 1-3 F or with one OH, CN, COOH or —C(=O)—$NH_2$;

wherein each cycloalkyl group is optionally substituted with one or two F and/or with one CN, COOH, —C(=O)—$NH_2$ or —$CH_3$, which is optionally substituted with 1-3 F or with one OH;

wherein each heterocyclyl group is selected from a mono- or spirocyclic 4-7-membered cycloalkyl group, in which 1, 2 or 3 $CH_2$-groups are independently of each other replaced by O, S, NH or C=O, and wherein each heterocyclyl group is optionally substituted with 1 or 2 substituents independently of each other selected from F, CN, OH and $C_{1-3}$-alkyl, wherein each heteroaryl group is selected from a 5-membered aromatic cycle containing 1, 2 or 3 heteroatoms independently selected from N, O and S or from a 6-membered aromatic cycle containing 1 or 2 N, and wherein each heteroaryl group is optionally substituted with 1 or 2 substituents independently of each other selected from a group consisting of F, CN and $C_{1-3}$-alkyl, which is optionally substituted with one or more F;

b) a bicyclic heteroaryl selected from the group consisting of:

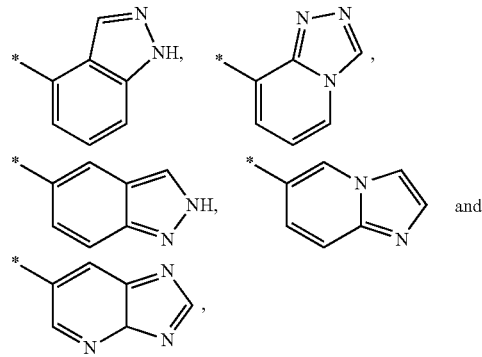

and which are each optionally substituted by one substituent selected from the group consisting of Cl, $C_{1-3}$-alkyl, cyclopropyl, —O—($C_{1-3}$-alkyl-), —C(=O)—O—($C_{1-4}$-alkyl), and heteroaryl, wherein each alkyl group is optionally substituted with 1-3 F;

wherein each heteroaryl group is selected from a 5-membered aromatic cycle containing 1 or 2 heteroatoms independently selected from N, O and S; and wherein each heteroaryl group is optionally substituted with 1 or 2 $CH_3$ groups or with one CN group.

$R^2$-G2:

In another embodiment, the group $R^2$ is independently of each other selected from the group $R^2$-G2 consisting of:

a1) a phenyl group optionally substituted by 1-3 substituents $R^3$ independently of each other selected from the group $R^3$-G2 consisting of F, Cl, Br, I, CN, $C_{1-6}$-alkyl, OH, —O—($C_{1-6}$-alkyl-), —O—($C_{1-3}$-alkyl)-($C_{3-7}$-cycloalkyl), —O-heterocyclyl, —S—($C_{1-3}$-alkyl), —SO—($C_{1-3}$-alkyl), —$SO_2$—($C_{1-3}$-alkyl), —C(=O)—$NR^{N1}R^{N2}$, —C(=O)OH, —C(=O)—O—($C_{1-4}$-alkyl), and —N=S(=O)($C_{1-3}$-alkyl)$_2$;

wherein $R^{N1}$ is selected from the group $R^{N1}$-G2 consisting of H, $C_{1-6}$-alkyl, —($C_{1-3}$-alkyl)-($C_{3-7}$-cycloalkyl), —($C_{1-3}$-alkyl)-heterocyclyl, —($C_{1-3}$-alkyl)-heteroaryl, $C_{3-7}$-cycloalkyl, heterocyclyl and heteroaryl;

and $R^{N2}$ is selected from the group $R^{N2}$-G2 consisting of H and $C_{1-4}$-alkyl, and wherein each alkyl group is optionally substituted with 1-3 F or with one OH or CN;

wherein each cycloalkyl group is optionally substituted with one or two F or with one —$CH_3$, which is optionally substituted with 1-3 F or with one OH;

wherein each heterocyclyl group is selected from a mono- or spirocyclic 4-7-membered cycloalkyl group, in which 1, 2 or 3 $CH_2$-groups are independently of each other replaced by O, S, NH or C=O, and wherein each heterocyclyl group is optionally substituted with 1 or 2 substituents independently of each other selected from F, OH and $C_{1-3}$-alkyl, wherein each heteroaryl group is selected from a 5-membered aromatic cycle containing 1, 2 or 3 heteroatoms independently selected from N, O and S or from a 6-membered aromatic cycle containing 1 or 2 N, and wherein each heteroaryl group is optionally substituted with 1 or 2 substituents independently of each other selected from a group consisting of F, CN and $C_{1-3}$-alkyl, which is optionally substituted with one or more F;

a2) a pyridin-3-yl or pyridin-4-yl group optionally substituted by 1-3 substituents $R^3$ independently of each other selected from the group $R^3$-G3 consisting of F, Cl, Br, I, CN, $C_{1-6}$-alkyl, $C_{3-7}$-cycloalkyl, OH, —O—($C_{1-6}$-alkyl), —O—($C_{1-3}$-alkyl)-($C_{3-7}$-cycloalkyl), —O—($C_{1-3}$-alkyl)-heterocyclyl, —O—($C_{3-7}$-cycloalkyl), —O-heterocyclyl and heteroaryl, wherein each alkyl group is optionally substituted with 1-3 F or with one OH, CN, COOH or —C(=O)—$NH_2$;

wherein each cycloalkyl group is optionally substituted with one or two F and/or with one CN, COOH, —C(=O)—$NH_2$ or —$CH_3$, which is optionally substituted with 1-3 F or with one OH;

wherein each heterocyclyl group is selected from a mono- or spirocyclic 4-7-membered cycloalkyl group, in which 1, 2 or 3 $CH_2$-groups are independently of each other replaced by O, S, NH or C=O, and wherein each heterocyclyl group is optionally substituted with 1 or 2 substituents independently of each other selected from CN and $C_{1-3}$-alkyl, wherein each heteroaryl group is selected from a 5-membered aromatic cycle containing 1 or 2 heteroatoms independently selected from N, O and S, and wherein each heteroaryl group is optionally substituted with 1 or 2 substituents independently of each other selected from a group consisting of CN and $C_{1-3}$-alkyl, which is optionally substituted with one or more F; or b) a bicyclic heteroaryl selected from the group consisting of:

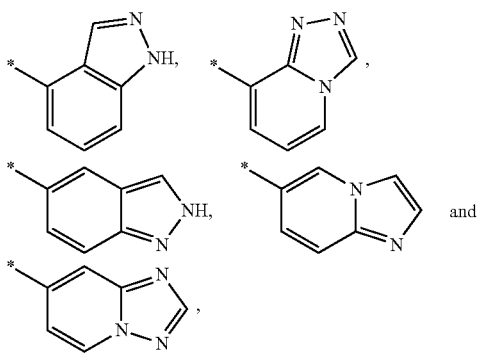

which are each optionally substituted by one substituent selected from the group consisting of Cl, $C_{1-3}$-alkyl, cyclopropyl, —O—($C_{1-3}$-alkyl-), —C(=O)—O—($C_{1-4}$-alkyl), and heteroaryl, wherein each alkyl group is optionally substituted with 1-3 F;

wherein each heteroaryl group is selected from a 5-membered aromatic cycle containing 1 or 2 heteroatoms independently selected from N, O and S; and wherein each heteroaryl group is optionally substituted with 1 or 2 $CH_3$ groups or with one CN group.

$R^2$-G2a:

In another embodiment, the group $R^2$ is independently of each other selected from the group $R^2$-G2a consisting of:

a1) a phenyl group optionally substituted by 1-3 substituents $R^3$ independently of each other selected from the group $R^3$-G2 consisting of F, Cl, Br, I, CN, $C_{1-6}$-alkyl, OH, —O—($C_{1-6}$-alkyl-), —O—($C_{1-3}$-alkyl)-($C_{3-7}$-cycloalkyl), —O-heterocyclyl, —S—($C_{1-3}$-alkyl), —SO—($C_{1-3}$-alkyl), —$SO_2$—($C_{1-3}$-alkyl), —C(=O)—$NR^{N1}R^{N2}$, —C(=O)OH, —C(=O)—O—($C_{1-4}$-alkyl), and —N=S(=O)($C_{1-3}$-alkyl)$_2$;

wherein $R^{N1}$ is selected from the group $R^{N1}$-G2 consisting of H, $C_{1-6}$-alkyl, —($C_{1-3}$-alkyl)-($C_{3-7}$-cycloalkyl), —($C_{1-3}$-alkyl)-heterocyclyl, —($C_{1-3}$-alkyl)-heteroaryl, $C_{3-7}$-cycloalkyl, heterocyclyl and heteroaryl;

and $R^{N2}$ is selected from the group $R^{N2}$-G2 consisting of H and $C_{1-4}$-alkyl, and wherein each alkyl group is optionally substituted with 1-3 F or with one OH or CN;

wherein each cycloalkyl group is optionally substituted with one or two F or with one —$CH_3$, which is optionally substituted with 1-3 F or with one OH;

wherein each heterocyclyl group is selected from a mono- or spirocyclic 4-7-membered cycloalkyl group, in which 1, 2 or 3 $CH_2$-groups are independently of each other replaced by O, S, NH or C=O, and wherein each heterocyclyl group is optionally substituted with 1 or 2 substituents independently of each other selected from F, OH and $C_{1-3}$-alkyl, wherein each heteroaryl group is selected from a 5-membered aromatic cycle containing 1, 2 or 3 heteroatoms independently selected from N, O and S or from a 6-membered aromatic cycle containing 1 or 2 N, and wherein each heteroaryl group is optionally substituted with 1 or 2 substituents independently of each other selected from a group consisting of F, CN and $C_{1-3}$-alkyl, which is optionally substituted with one or more F;

a2) a pyridin-3-yl or pyridin-4-yl group optionally substituted by 1-3 substituents $R^3$ independently of each other selected from the group $R^3$-G3 consisting of F, Cl, Br, I, CN, $C_{1-6}$-alkyl, $C_{3-7}$-cycloalkyl, OH, —O—($C_{1-6}$-alkyl), —O—($C_{1-3}$-alkyl)-($C_{3-7}$-cycloalkyl), —O—($C_{1-3}$-alkyl)-heterocyclyl, —O—($C_{3-7}$-cycloalkyl), —O-heterocyclyl and heteroaryl, wherein each alkyl group is optionally substituted with 1-3 F or with one OH, CN, COOH or —C(=O)—$NH_2$;

wherein each cycloalkyl group is optionally substituted with one or two F and/or with one CN, COOH, —C(=O)—$NH_2$ or —$CH_3$, which is optionally substituted with 1-3 F or with one OH;

wherein each heterocyclyl group is selected from a mono- or spirocyclic 4-7-membered cycloalkyl group, in which 1, 2 or 3 $CH_2$-groups are independently of each other replaced by O, S, NH or C=O, and wherein each heterocyclyl group is optionally substituted with 1 or 2 substituents independently of each other selected from CN and $C_{1-3}$-alkyl, wherein each heteroaryl group is selected from a 5-membered aromatic cycle containing 1 or 2 heteroatoms independently selected from N, O and S, and wherein each heteroaryl group is optionally substituted with 1 or 2 substituents independently of each other selected from a group consisting of CN and $C_{1-3}$-alkyl, which is optionally substituted with one or more F; or b) a bicyclic heteroaryl selected from the group consisting of:

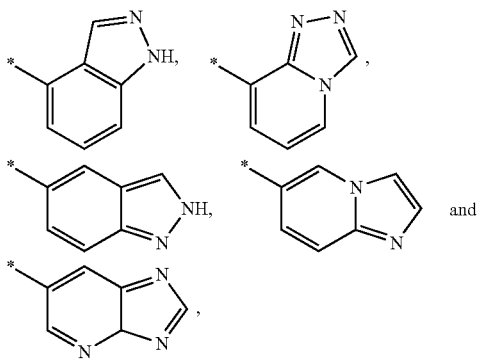

which are each optionally substituted by one substituent selected from the group consisting of Cl, $C_{1-3}$-alkyl, cyclopropyl, —O—($C_{1-3}$-alkyl-), —C(=O)—O—($C_{1-4}$-alkyl), and heteroaryl, wherein each alkyl group is optionally substituted with 1-3 F;

wherein each heteroaryl group is selected from a 5-membered aromatic cycle containing 1 or 2 heteroatoms independently selected from N, O and S; and wherein each heteroaryl group is optionally substituted with 1 or 2 $CH_3$ groups or with one CN group.

$R^2$-G3a:

In another embodiment, the group $R^2$ is independently of each other selected from the group $R^2$-G3a consisting of:

a phenyl group optionally substituted by 1-3 substituents $R^3$ independently of each other selected from the group $R^3$-G4 consisting of F, Cl, Br, I, CN, $CH_3$, OH, —O—($C_{1-4}$-alkyl), —O—($CH_2$)-cyclopropyl, —O-heterocyclyl, —S—$CH_3$, —SO—$CH_3$, —$SO_2$—$CH_3$, —C(=O)—$NR^{N1}R^{N2}$, —C(=O)OH, —C(=O)—O—$CH_3$, and —N=S(=O)($CH_3$)$_2$;

wherein $R^{N1}$ is selected from the group $R^{N1}$-G3a consisting of H, $C_{1-5}$-alkyl, —$CH_2$-cyclopropyl, —$CH_2$-heterocyclyl, —$CH_2$-heteroaryl, cyclopropyl, heterocyclyl and heteroaryl;

and $R^{N2}$ is selected from the group $R^{N2}$-G3a consisting of H and $CH_3$, and wherein each alkyl group within the substituents of $R^2$, within $R^{N1}$ and within $R^{N2}$ is optionally substituted with 1-3 F or with one OH or CN;

wherein each cyclopropyl group within the substituents of $R^2$ and within $R^{N1}$ is optionally substituted with one or two F or with one —$CH_3$, which is optionally substituted with 1-3 F or with one OH;

wherein each heterocyclyl group is selected from the group consisting of pyrrolidinyl, piperidinyl, oxetanyl, tetrahydrofuranyl, tetrahydropyranyl, and morpholinyl, wherein one $CH_2$-group is optionally replaced by C=O, and/or wherein each heterocyclyl group is optionally substituted with one $CH_3$ group, wherein each heteroaryl group is selected from the group consisting of pyrazolyl, triazolyl, pyridazinyl and pyrazinyl, wherein each heteroaryl group is optionally substituted with 1 or 2 substituents independently selected from $CF_3$ and $CH_3$.

The phenyl group of $R^2$ is preferably substituted by 1 or 2 of the above-mentioned $R^3$ groups.

Preferably, the phenyl group of $R^2$ is substituted in position 3 and/or 4.

$R^2$-G3b:

In another embodiment, the group $R^2$ is independently of each other selected from the group $R^2$-G3b consisting of:

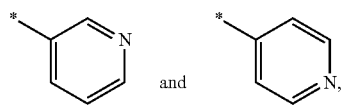 [SMILES: *c1cccnc1 ; *c1ccncc1]

which may be substituted with 1 or 2 substituents $R^3$ independently of each other selected from the group $R^3$-G5 consisting of: F, Cl, Br, I, CN, $C_{1-6}$-alkyl, $C_{3-6}$-cycloalkyl, —O—$CH_3$, —O—$CH_2$-cyclopropyl, —O—$CH_2$-heterocyclyl, —O-cyclobutyl, —O— heterocyclyl and heteroaryl, wherein each alkyl group is optionally substituted with 1-3 F or with one CN, COOH or —C(=O)—$NH_2$;

wherein each cycloalkyl group is optionally substituted with one or two F and/or with one CN, COOH or —C(=O)—$NH_2$;

wherein each heterocyclyl group is selected from the group consisting of oxetanyl, tetrahydrofuranyl, and tetrahydropyranyl, which may each be substituted with one CN or $CH_3$, wherein each heteroaryl group is selected from the group consisting of furanyl, pyrazolyl, imidazolyl, thienyl, oxazolyl, and isoxazolyl, wherein each heteroaryl group is optionally substituted with 1 or 2 substituents independently of each other selected from CN, $CF_3$ and $CH_3$.

$R^2$-G4a:

In another embodiment, the group $R^2$ is independently of each other selected from the group $R^2$-G4a consisting of:

a phenyl group optionally substituted by 1 or 2 substituents $R^3$ independently of each other selected from the group $R^3$-G6 consisting of F, Cl, Br, I, CN, $CH_3$, OH, —O—$CH_3$, —O—($CH_2$)-cyclopropyl, —O-heterocyclyl, and —C(=O)—$NR^{N1}R^{N2}$;

wherein $R^{N1}$ is selected from the group $R^{N1}$-G4a consisting of H and $C_{1-5}$-alkyl;

and $R^{N2}$ is selected from the group $R^{N2}$-G4a consisting of H and $CH_3$, and wherein each alkyl group within the substituents of $R^2$, within $R^{N1}$ and within $R^{N2}$ is optionally substituted with 1-3 F;

wherein each cyclopropyl group is optionally substituted with one or two F or with one —$CH_3$ or $CF_3$;

wherein each heterocyclyl group is selected from the group consisting of pyrrolidinyl and piperidinyl, wherein one $CH_2$-group is optionally replaced by C=O, and/or wherein each heterocyclyl group is optionally substituted with one $CH_3$ group.

Preferably, the phenyl group of $R^2$ is substituted in position 3 and/or 4.

$R^2$-G4b:

In another embodiment, the group $R^2$ is independently of each other selected from the group $R^2$-G4b consisting of:

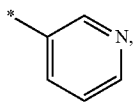

which may be substituted with 1 substituent R³ selected from the group R³-G7 consisting of: F, Cl, Br, I, CN, C₁₋₅-alkyl, C₃₋₅-cycloalkyl, —O—CH₃, —O—CH₂-cyclopropyl, —O—CH₂-heterocyclyl, —O-heterocyclyl and heteroaryl,

- wherein each alkyl group is optionally substituted with 1-3 F or with one CN, COOH or —C(=O)—NH₂;
- wherein each cycloalkyl group is optionally substituted with one or two F and/or with one CN, COOH or —C(=O)—NH₂;
- wherein each heterocyclyl group is selected from the group consisting of oxetanyl, tetrahydrofuranyl and tetrahydropyranyl, which may each be substituted with one CN or CH₃,
- wherein each heteroaryl group is selected from the group consisting of furanyl, pyrazolyl, imidazolyl, thienyl, oxazolyl, and isoxazolyl, wherein each heteroaryl group is optionally substituted with 1 or 2 substituents independently of each other selected from CN, CF₃ and CH₃.

R²-G5:

In another embodiment, the group R² is independently selected from the group R²-G5 consisting of:

a) an aryl group selected from the group consisting of:

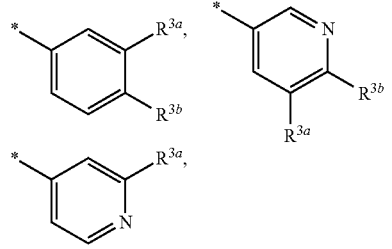

wherein

R^{3a} and R^{3b} are independently of each other selected from the group consisting of:

H, F, Cl, Br, I, —CN, —CH₃, —C(CH₃)₃, —CF₃, —CHF₂, —CH₂F, —CH₂—CN, —CH₂OH, —OH, —O—CH₃, —O—CF₃, —O—CHF₂, —O—CH₂F,

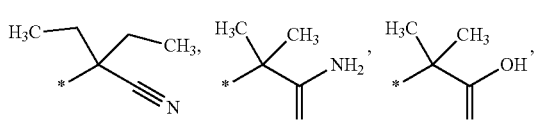

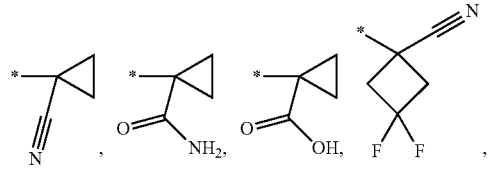

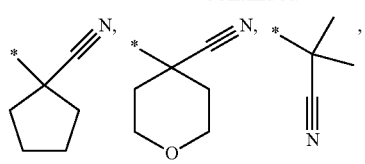

—O—CH₂—CHF₂, —O—CH₂—CF₃, —O—CH₂—CH₂—CF₃,

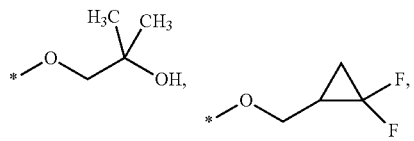

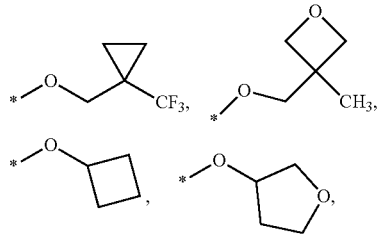

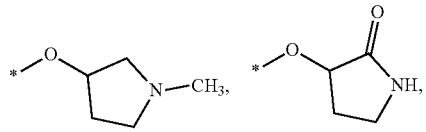

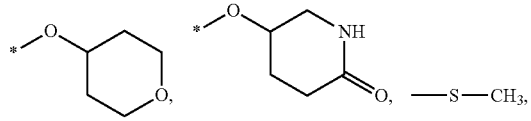

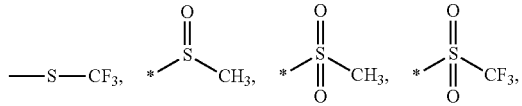, —S—CH₃,

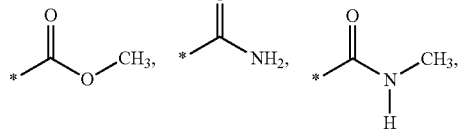

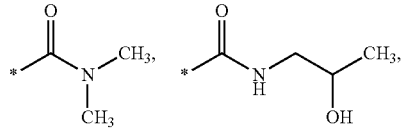

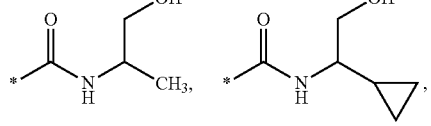

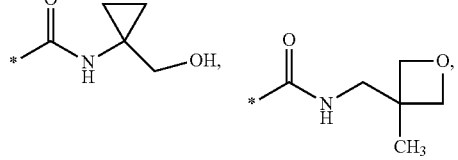

13
-continued
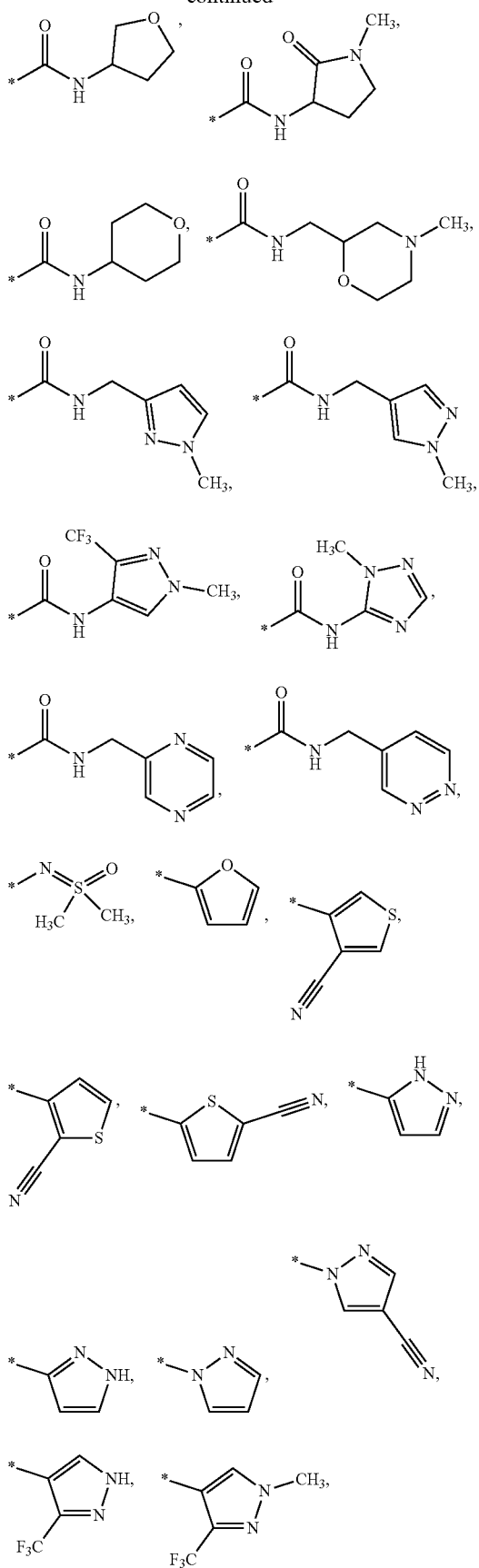
14
-continued
and
b) a bicyclic group selected from the group consisting of:
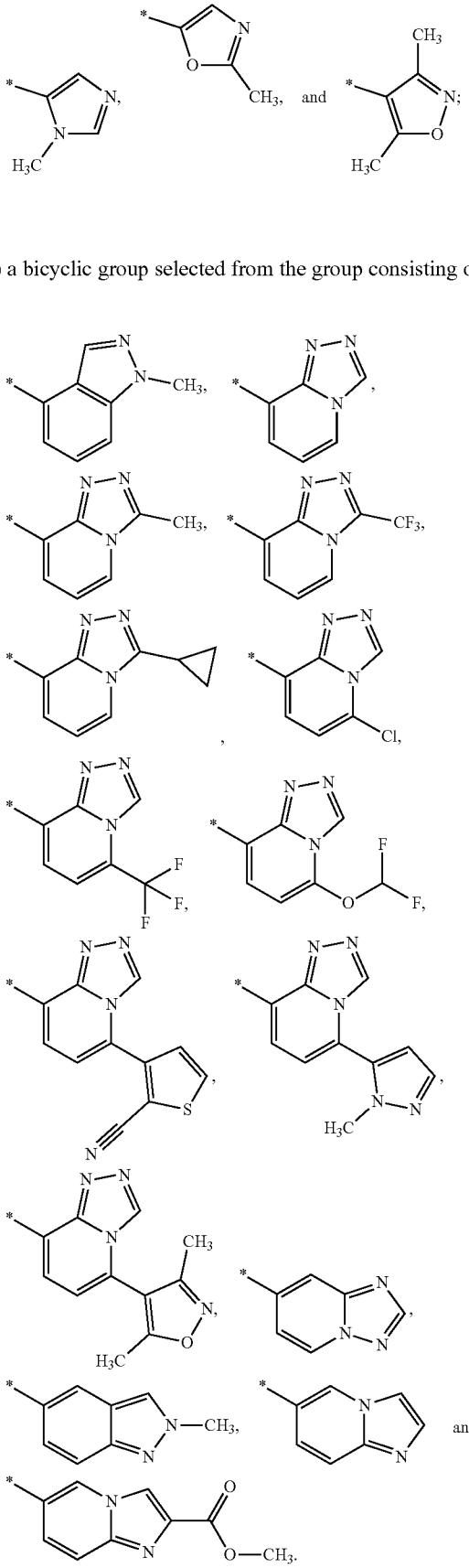

R²-G5a:
In another embodiment, the group R² is independently selected from the group R²-G5a consisting of:
a) an aryl group selected from the group consisting of:
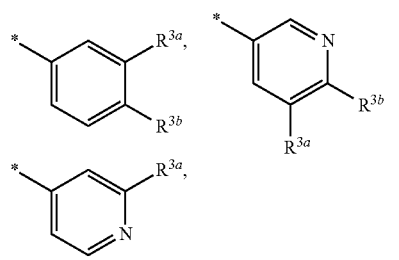
wherein
R³ᵃ and R³ᵇ are independently of each other selected from the group consisting of:
H, F, C, Br, I, —CN, —CH₃, —CF₃, —CHF₂, —CH₂F, —CH₂—CN, —CH₂OH, —OH, —O—CH₃, —O—CF₃, —O—CHF₂, —O—CH₂F,
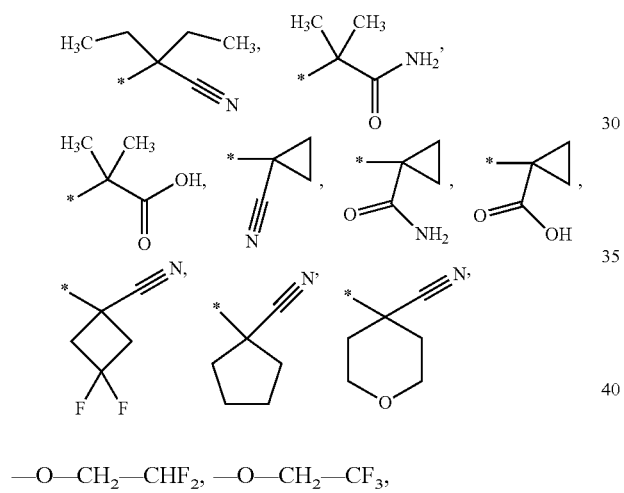
—O—CH₂—CHF₂, —O—CH₂—CF₃,
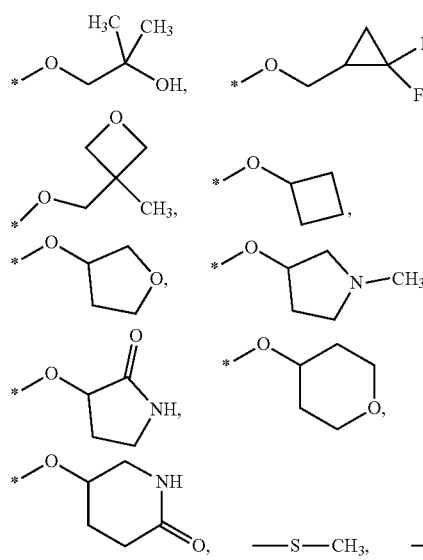
—S—CH₃, —S—CF₃,
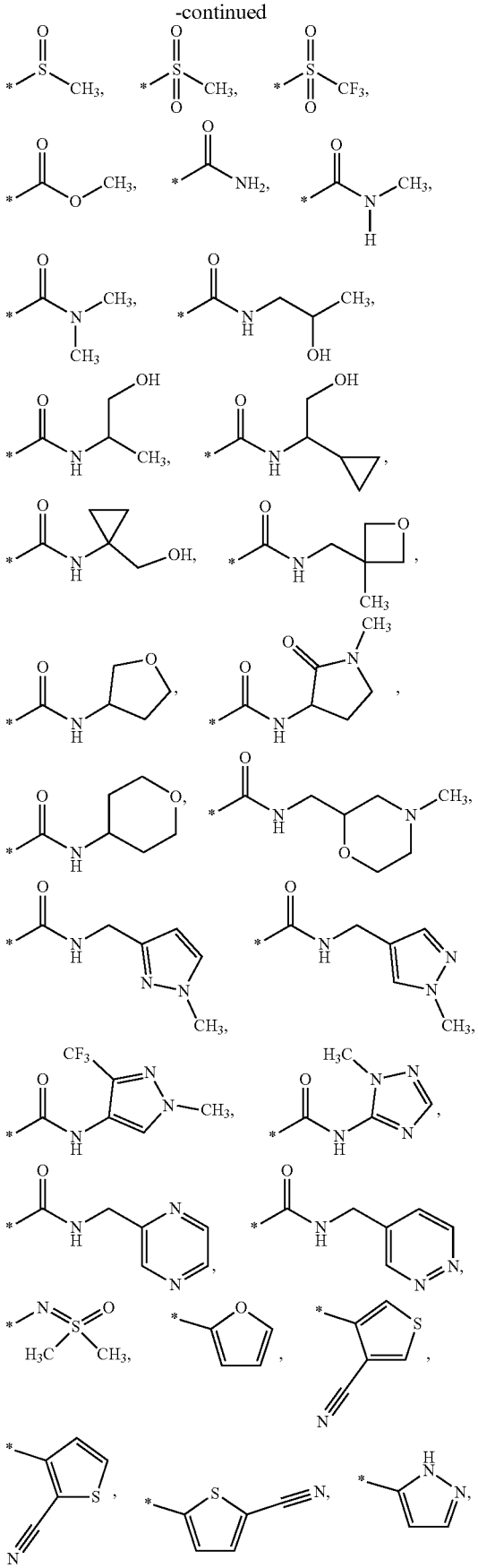

-continued

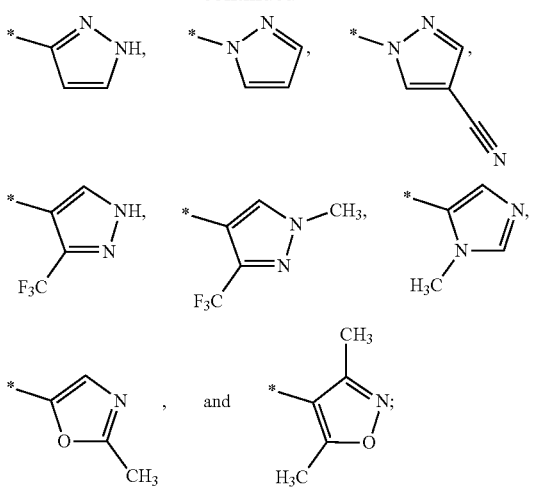

and b) a bicyclic group selected from the group consisting of:

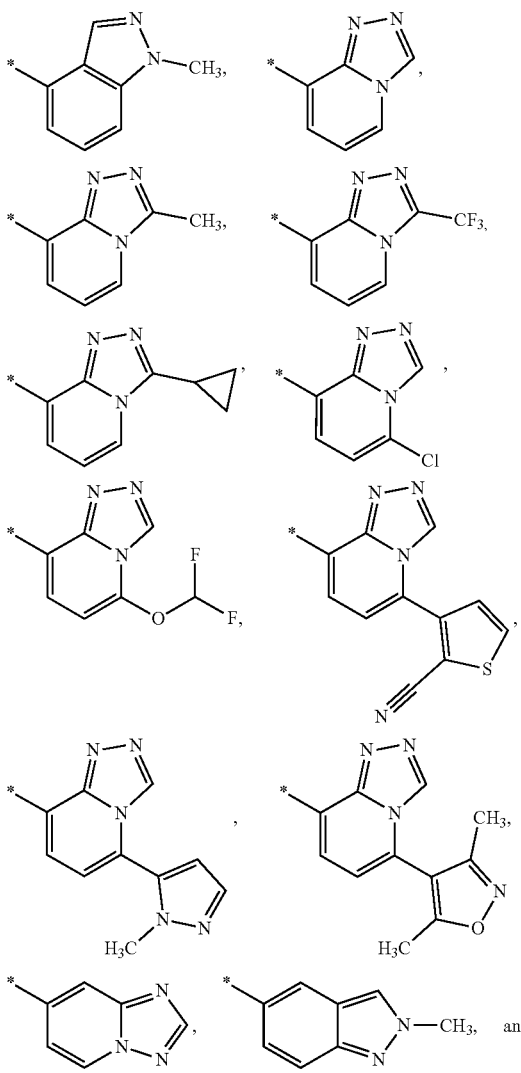

-continued

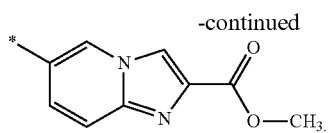

$R^2$-G6:

In another embodiment, the group $R^2$ is independently of each other selected from the group $R^2$-G6 consisting of:

a phenyl or pyridin-3-yl group optionally substituted by 1 or 2 substituents $R^3$ independently of each other selected from the group $R^3$-G8 consisting of F, C, Br, CN, —$CH_3$, —$CF_3$, —$CHF_2$, —$CH_2F$, —O—$CH_3$, —O—$CF_3$, —O—$CHF_2$, —O—$CH_2F$, and —CO—$NH_2$.

Preferably, the phenyl or pyridin-3-yl group of $R^2$ is substituted in position 3 and/or 4.

$R^2$-G6a:

In another embodiment, the group $R^2$ is independently of each other selected from the group $R^2$-G6a consisting of:

a phenyl group optionally substituted by 1 or 2 substituents $R^3$ independently of each other selected from the group $R^3$-G9 consisting of F, C, Br, I, CN, $CH_3$, —$CF_3$, —$CHF_2$, —$CH_2F$, —O—$CH_3$, —O—$CF_3$, —O—$CHF_2$, —O—$CH_2F$, and —CO—$NH_2$.

Preferably, the phenyl group of $R^2$ is substituted in position 3 and/or 4.

n

The index n is an integer selected from 1, 2 and 3.

Preferably, n is 2 or 3.

In another embodiment, n is 1 or 2.

More preferably, n is 2.

Most preferably, n is 1.

The following preferred embodiments of compounds of the formula I are described using generic formulae (I.1) to (I.14), wherein any tautomers, solvates, hydrates and salts thereof, in particular the pharmaceutically acceptable salts thereof, are encompassed. $R^3$ is as defined in this application for $R^3$, $R^{3a}$ or $R^{3b}$. $R^{3a}$ and $R^{3b}$ are each as defined in this application for $R^3$, $R^{3a}$ or $R^{3b}$.

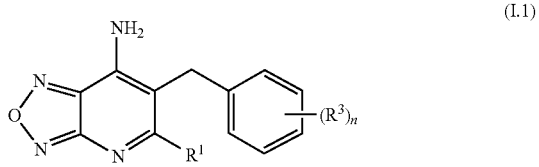

(I.1)

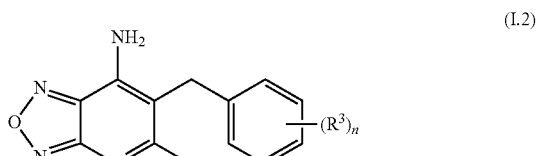

(I.2)

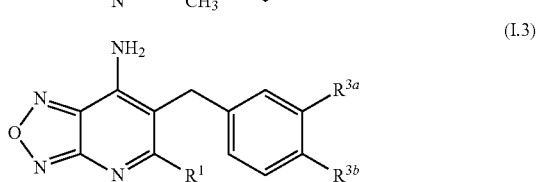

(I.3)

(I.4)
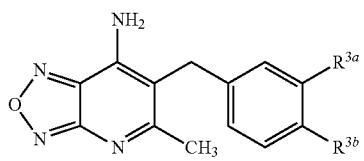

(I.5)
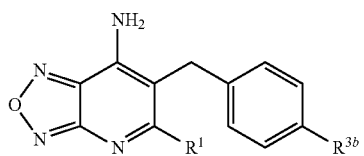

(I.6)
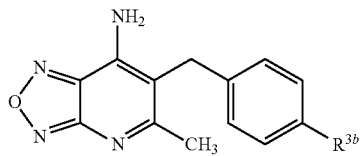

(I.7)
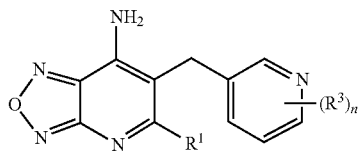

(I.8)
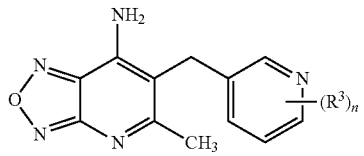

(I.9)
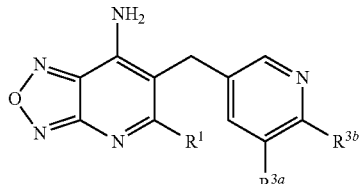

(I.10)
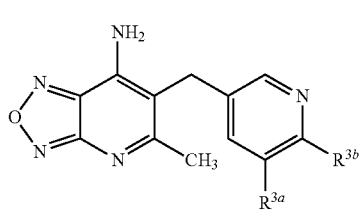

(I.11)
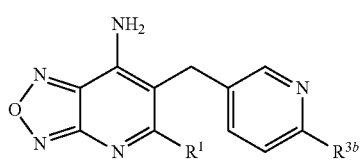

(I.12)
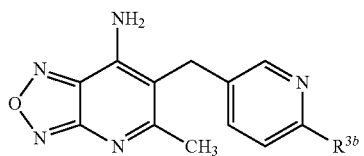

(I.13)

(I.14)

Examples of preferred subgeneric embodiments (E) according to the present invention are set forth in the following table 1, wherein each substituent group of each embodiment is defined according to the definitions set forth hereinbefore and wherein all other substituents of the formulae I, I.1, and, I.7 are defined according to the definitions set forth hereinbefore. For example, the entry -G1 in the column under R- and in the line of E1 means that in embodiment E1 substituent R is selected from the definition designated R-G1. The same applies analogously to the other variables incorporated in the general formulae.

TABLE 1

| E | formula | $R^1$- | $R^2$- | $R^3$- | number n of substituents $R^3$ |
|---|---|---|---|---|---|
| E1 | I | -G1 | -G1 | -G1 | 1, 2 or 3 |
| E1a | I | -G1 | -G1a | -G1 | 1, 2 or 3 |
| E2 | I | -G2 | -G1 | -G1 | 1, 2 or 3 |
| E2a | I | -G2 | -G1a | -G1 | 1, 2 or 3 |
| E3 | I | -G1 | -G2 | -G2 | 1, 2 or 3 |
| E3a | I | -G1 | -G2a | -G2 | 1, 2 or 3 |
| E4 | I | -G5 | -G2 | -G2 | 1, 2 or 3 |
| E4a | I | -G5 | -G2a | -G2 | 1, 2 or 3 |
| E5 | I | -G1 | -G3a + G3b | -G3a + G3b | 1, 2 or 3 resp. 1 or 2 |
| E6 | I | -G5 | -G3a + G3b | -G3a + G3b | 1, 2 or 3 resp. 1 or 2 |
| E7 | I | -G1 | -G3a | -G3a | 1, 2 or 3 |
| E8 | I | -G5 | -G3a | -G3a | 1, 2 or 3 |
| E9 | I | -G1 | -G3b | -G3b | 1 or 2 |
| E10 | I | -G5 | -G3b | -G3b | 1 or 2 |
| E11 | I | -G1 | -G4a + G4b | -G4a + G4b | 1 or 2 resp. 1 |
| E12 | I | -G5 | -G4a + G4b | -G4a + G4b | 1 or 2 resp. 1 |
| E13 | I | -G1 | -G4a | -G4a | 1 or 2 |
| E14 | I | -G5 | -G4a | -G4a | 1 or 2 |
| E15 | I | -G1 | -G4b | -G4b | 1 |
| E16 | I | -G5 | -G4b | -G4b | 1 |
| E17 | I | -G1 | -G5 | $R^{3a}$ and $R^{3b}$ are as defined in $R^2$-G5 | 1 or 2 resp. 1 |
| E17a | I | -G1 | -G5a | $R^{3a}$ and $R^{3b}$ are as defined in $R^2$-G5 | 1 or 2 resp. 1 |
| E18 | I | -G5 | -G5 | $R^{3a}$ and $R^{3b}$ are as defined in $R^2$-G5 | 1 or 2 resp. 1 |
| E18a | I | -G5 | -G5a | $R^{3a}$ and $R^{3b}$ are as defined in $R^2$-G5 | 1 or 2 resp. 1 |
| E19 | I | -G1 | -G6 | -G6 | 1 or 2 |
| E20 | I | -G5 | -G6 | -G6 | 1 or 2 |
| E21 | I | -G1 | -G6a | -G6a | 1 or 2 |
| E22 | I | -G5 | -G6a | -G6a | 1 or 2 |
| E23 | I | -G2 | -G2 | -G2 | 1, 2 or 3 |
| E23a | I | -G2 | -G2a | -G2 | 1, 2 or 3 |
| E24 | I | -G2 | -G3a + G3b | -G3a + G3b | 1, 2 or 3 resp. 1 or 2 |

TABLE 1-continued

| E | formula | R¹- | R²- | R³- | number n of substituents R³ |
|---|---|---|---|---|---|
| E25 | I | -G2 | -G3a | -G3a | 1, 2 or 3 |
| E26 | I | -G2 | -G3b | -G3b | 1 or 2 |
| E27 | I | -G2 | -G4a + G4b | -G4a + G4b | 1 or 2 resp. 1 |
| E28 | I | -G2 | -G4a | -G4a | 1 or 2 |
| E29 | I | -G2 | -G4b | -G4a | 1 |
| E30 | I | -G2 | -G5 | R³ᵃ and R³ᵇ are as defined in R²-G5 | 1 or 2 resp. 1 |
| E31 | I | -G2 | -G6 | -G6 | 1 or 2 |
| E32 | I.1 | -G1 | — | -G1 | 1, 2 or 3 |
| E33 | I.1 | -G2 | — | -G1 | 1, 2 or 3 |
| E34 | I.1 | -G3 | — | -G2 | 1 or 2 |
| E35 | I.1 | -G5 | — | -G2 | 1, 2 or 3 |
| E36 | I.1 | -G5 | — | -G2 | 1 or 2 |
| E37 | I.1 | -G5 | — | -G3a | 1, 2 or 3 |
| E38 | I.1 | -G5 | — | -G3a | 1 or 2 |
| E39 | I.1 | -G5 | — | -G4a | 1 or 2 |
| E40 | I.1 | -G5 | — | -G4a | 1 |
| E41 | I.1 | -G5 | — | G6a | 1 or 2 |
| E42 | I.1 | -G5 | — | -G6a | 1 |
| E43 | I.7 | -G1 | — | -G1 | 1, 2 or 3 |
| E44 | I.7 | -G2 | — | -G1 | 1, 2 or 3 |
| E45 | I.7 | -G3 | — | -G2 | 1 or 2 |
| E46 | I.7 | -G5 | — | -G2 | 1, 2 or 3 |
| E47 | I.7 | -G5 | — | -G2 | 1 or 2 |
| E48 | I.7 | -G5 | — | -G3b | 1 or 2 |
| E49 | I.7 | -G5 | — | -G3b | 1 |
| E50 | I.7 | -G5 | — | -G4b | 1 |

Another embodiment concerns compounds of formula

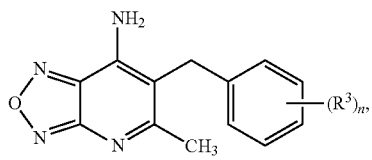

(I.2)

wherein
n is 1, 2 or 3; and
R³ is independently of each other selected from the group R³-G2 consisting of F, Cl, Br, I, CN, C$_{1-6}$-alkyl, OH, —O—(C$_{1-6}$-alkyl-), —O—(C$_{1-3}$-alkyl)-(C$_{3-7}$-cycloalkyl), —O— heterocyclyl, —S—(C$_{1-3}$-alkyl), —SO— (C$_{1-3}$-alkyl), —SO$_2$—(C$_{1-3}$-alkyl), —C(=O)— NR$^{N1}$R$^{N2}$, —C(=O)OH, —C(=O)—O—(C$_{1-4}$-alkyl), and —N=S(=O)(C$_{1-3}$-alkyl)$_2$;
wherein R$^{N1}$ is selected from the group R$^{N1}$-G2 consisting of: H, C$_{1-6}$-alkyl, —(C$_{1-3}$-alkyl)-(C$_{3-7}$-cycloalkyl), —(C$_{1-3}$-alkyl)-heterocyclyl, —(C$_{1-3}$-alkyl)-heteroaryl, C$_{3-7}$-cycloalkyl, heterocyclyl and heteroaryl;
and R$^{N2}$ is selected from the group R$^{N2}$-G2 consisting of: H and C$_{1-4}$-alkyl, and
wherein each alkyl group is optionally substituted with 1-3 F or with one OH or CN;
wherein each cycloalkyl group is optionally substituted with one or two F or with one —CH$_3$, which is optionally substituted with 1-3 F or with one OH;
wherein each heterocyclyl group is selected from a mono- or spirocyclic 4-7-membered cycloalkyl group, in which 1, 2 or 3 CH$_2$-groups are independently of each other replaced by O, S, NH or C=O, and
wherein each heterocyclyl group is optionally substituted with 1 or 2 substituents independently of each other selected from F, OH and C$_{1-3}$-alkyl, wherein each heteroaryl group is selected from a 5-membered aromatic cycle containing 1, 2 or 3 heteroatoms independently selected from N, O and S or from a 6-membered aromatic cycle containing 1 or 2 N, and wherein each heteroaryl group is optionally substituted with 1 or 2 substituents independently of each other selected from a group consisting of F, CN and C$_{1-3}$-alkyl, which is optionally substituted with one or more F;

or a salt thereof, particularly a pharmaceutically acceptable salt thereof.

Preferably, n is 1 or 2 and R³ is situated in position 3 and/or 4 of the phenyl ring.

More preferably, R³ is selected from the group R³-G4, R³-G6 or R³-G9.

Preferred compounds of the invention include:

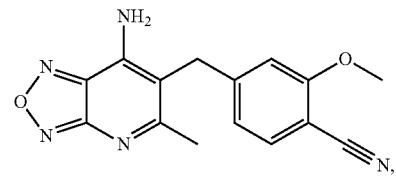

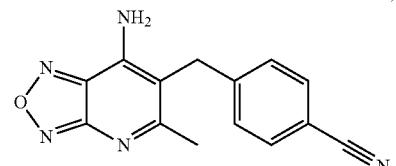

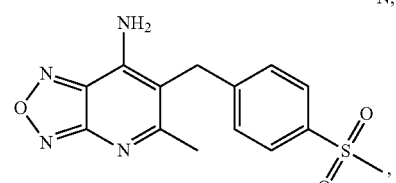

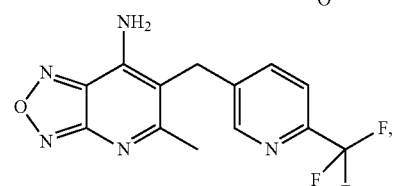

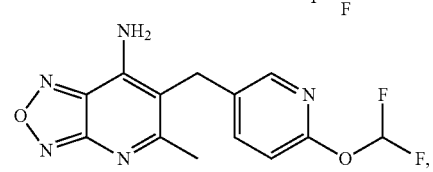

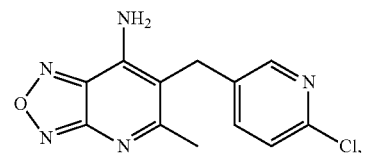

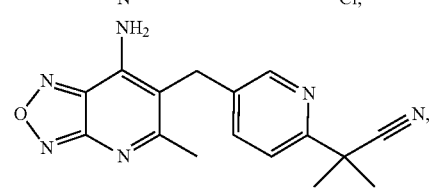

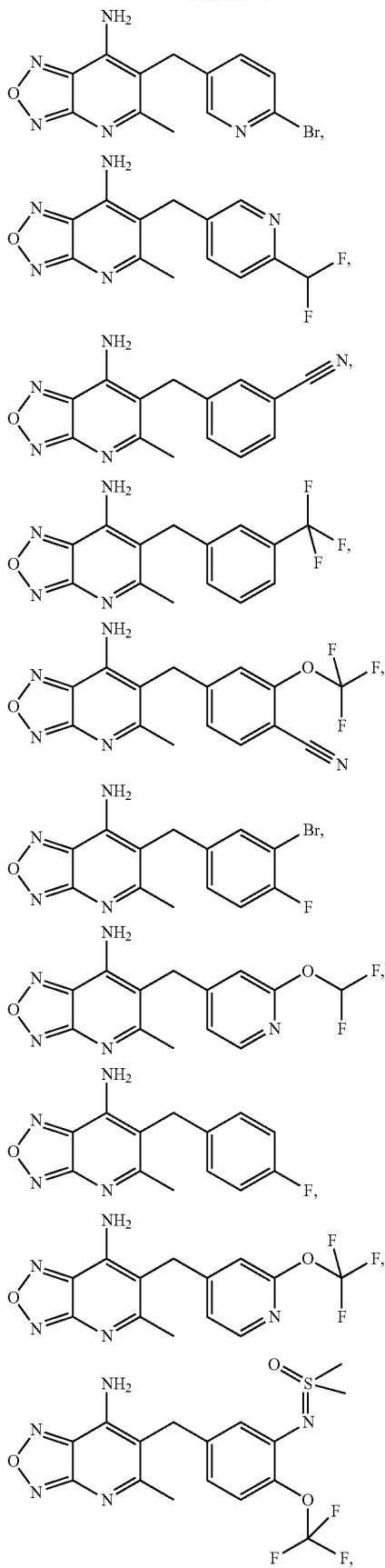

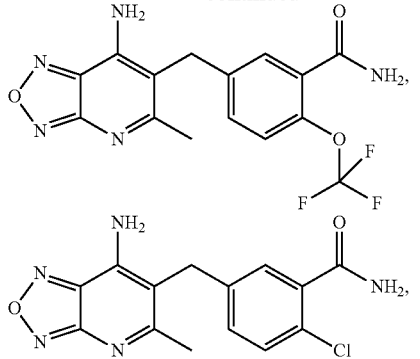

or a salt thereof, particularly a pharmaceutically acceptable salt thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis, for example.

Moreover, the invention provides processes for making a compound of Formula I.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as one skilled in the art will recognize, particular reagents or conditions could be modified as needed for individual compounds without undue experimentation. Starting materials and intermediates used in the methods below are either commercially available or easily prepared from commercially available materials by those skilled in the art.

A compound of Formula I may be made by the methods outlined in Schemes 1, 2, 3, 4 or 5:

Scheme 1

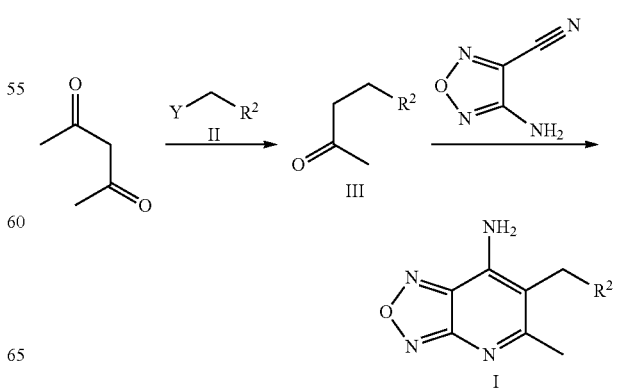

As illustrated in Scheme 1 reacting of the acetylacetone with an alkylating agent of Formula II (Y=Cl, Br, I, OMs, OTs) in the presence of a suitable base such as potassium, sodium or caesium carbonate, in a suitable solvent such as methanol or ethanol, provides a compound of Formula III.

Reacting of the compound of Formula III with the 4-amino-1,2,5-oxadiazole-3-carbonitrile (Chemistry of Heterocyclic Compounds (New York, N.Y., United States), 1994, vol. 30, #5 p. 608-611) in the presence of a suitable Lewis acid such as tin (IV) chloride, in a suitable solvent such as toluene or benzene, provides a compound of Formula I.

Scheme 2

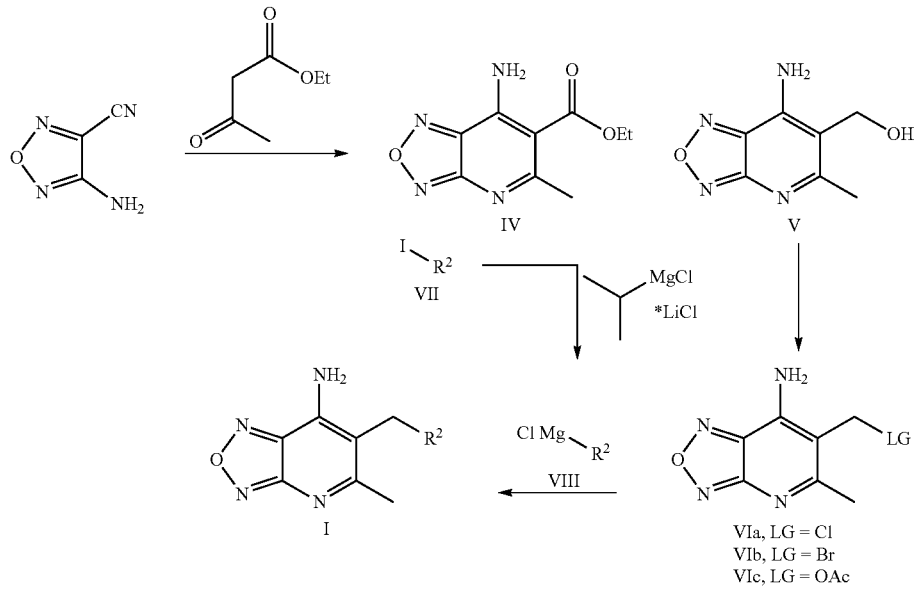

As illustrated in Scheme 2 reacting of the ethyl acetoacetate with the 4-amino-1,2,5-oxadiazole-3-carbonitrile (Chemistry of Heterocyclic Compounds (New York, N.Y., United States), 1994, vol. 30, #5 p. 608-611) in the presence of a suitable Lewis acid such as tin (IV) chloride, in a suitable solvent such as toluene or benzene, provides ester IV.

Reduction of the esther IV with the reducing agent such as sodium bis(2-methoxyethoxy)aluminumhydride (Red-Al®) or lithium aluminium hydride, in a suitable solvent such as toluene/tetrahydrofuran mixture, provides alcohol V. Alcohol V can be converted into the corresponding derivatives VI using suitable reagents and solvents, such as: thionylchloride in dimethylformamide (to prepare VIa); phosphorus tribromide in dichloromethane (to prepare VIb); glacial acetic acid (to prepare VIc). Iodide of formula VII can be converted into the corresponding magnesium reagent of formula VIII using suitable reagent such as isopropylmagnesium chloride lithium chloride complex, in a suitable solvent such as tetrahydrofuran. Reacting of the magnesium reagent of formula VIII with the compound of formula VI in the presence of copper(I)cyanide di(lithium chloride) complex, in a suitable solvent such as tetrahydrofuran, provides a compound of formula I.

Scheme 3

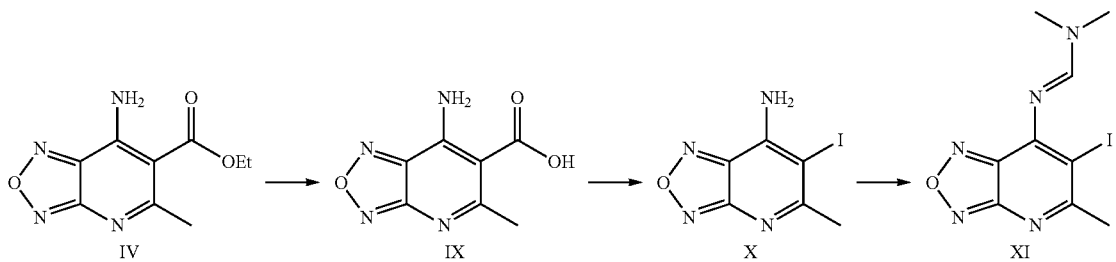

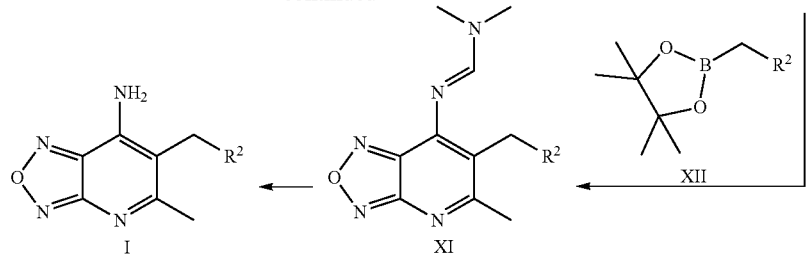

As illustrated in Scheme 3 saponification of the ester of formula IV, using a suitable reagent such as lithium, sodium or potassium hydroxide, in a suitable solvent such as tetrahydrofuran, methanol or ethanol, provides an acid of formula IX. Reacting of the acid of formula IX with N-iodosuccinimide, in the presence of a suitable base such as sodium hydrogen carbonate, in a suitable solvent such as N,N-dimethylformamide or acetonitrile, provides a compound of formula X. The protection and deprotection of functional groups is described in 'Protective Groups in Organic Synthesis', T. W. Greene and P. G. M. Wuts, Wiley-Interscience. For example, for the protection of an amine of Formula X, N,N-dimethylformamide dimethyl acetal may be used in a suitable solvent such as N,N-dimethylformamide to provide a compound of Formula XI. Coupling of the boron reagent XII in a (transition) metal catalyzed reaction using a suitable catalyst such as [1,1'-bis(di-tert-butylphosphino)ferrocene]dichloro-palladium(II), in a suitable solvent such tetrahydrofuran provides a compound of formula XIII. Deprotection of compound of formula XIII with concentrated aqueous hydrochloric acid, in a suitable solvent such as methanol or ethanol, provides a compound of formula I.

As illustrated in Scheme 4 reacting of the carboxylic acid XIV with 4-amino-1,2,5-oxadiazole-3-carbonitrile (Chemistry of Heterocyclic Compounds (New York, N.Y., United States), 1994, vol. 30, #5 p. 608-611) in the presence of a coupling reagent such as 1-propanephosphonic acid cyclic anhydride (PPA) provides an amide of formula XV. Reacting of the amide of formula XV with a base such as 1,8-diazabicyclo[5.4.0]undec-7-ene (DBU) in a suitable solvent such as dimethylsulfoxide provides a compound of formula XVI. Compound XVI can be converted into the corresponding derivatives XVII using suitable reagents, such as: neat phosphorus oxychloride (to prepare XVIIa); neat phosphorus oxybromide (to prepare XVIIb). Compound XVIIb can be converted into the corresponding derivatives XVIII using suitable reagents and solvents, such as: ethyl 2-bromo-2,2-difluoroacetate in the presence of bronze powder in dimethylsulfoxide (to prepare XVIIIa); potassium cyanide in N-methylpyrrolidine (to prepare XVIIIb); zinc cyanide in the presence of bis(diphenylphosphino) ferrocene in N,N-dimethylacetamide (to prepare XVIIIb); potassium cyanide in N-methylpyrrolidine (to prepare XVIIIc); sodium acetate with bis(diphenylphosphino) ferrocenedichloropalladium (II) in methanol under an atmosphere of carbone monoxide (to prepare XVIIId)

Scheme 4

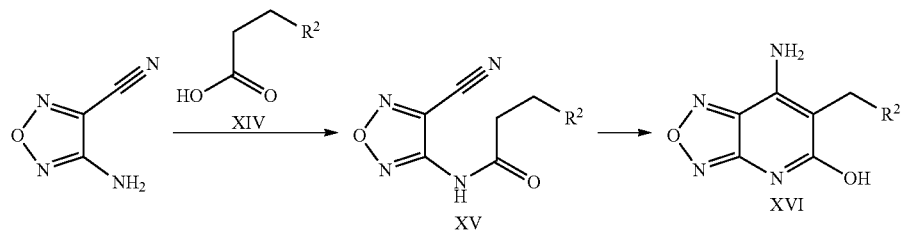

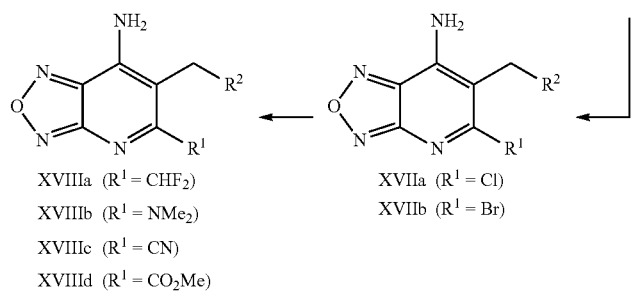

XVIIIa ($R^1$ = CHF$_2$)
XVIIIb ($R^1$ = NMe$_2$)
XVIIIc ($R^1$ = CN)
XVIIId ($R^1$ = CO$_2$Me)

XVIIa ($R^1$ = Cl)
XVIIb ($R^1$ = Br)

Scheme 5

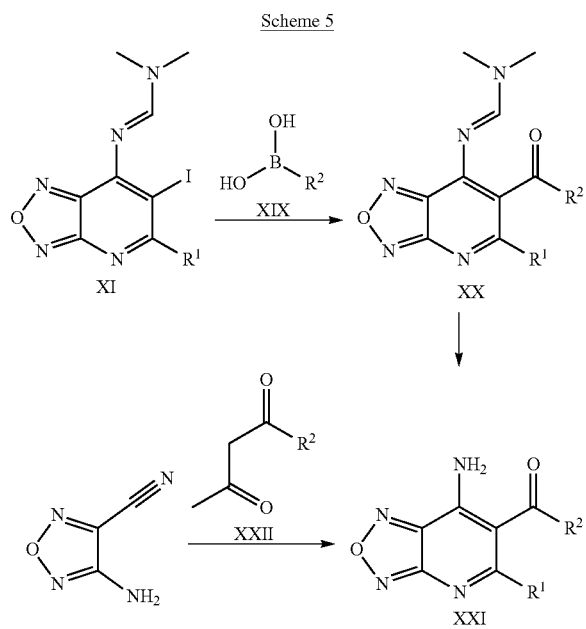

As illustrated in Scheme 5 reacting of the compound of formula XI with boronic acid reagent of formula XIX in the presence of a reagent mixture such as Molybdenum hexacarbonyl, PEPPSI-IPr™ catalyst and potassium carbonate in a solvent such as anisole provides a compound a formula XX. Deprotection of compound of formula XX with concentrated aqueous hydrochloric acid, in a suitable solvent such as methanol or ethanol, provides a compound of formula XXI.

Alternatively compound of formula XXI can be prepared by reacting a reagent of formula XXII with 4-amino-1,2,5-oxadiazole-3-carbonitrile (Chemistry of Heterocyclic Compounds (New York, N.Y., United States), 1994, vol. 30, #5 p. 608-611) in the presence of a suitable Lewis acid such as tin (IV) chloride, in a suitable solvent such as toluene or benzene.

Further modifications of compounds of formula I by methods known in the art and illustrated in the Examples below, may be used to prepare additional compounds of the invention.

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis for example in "Protecting Groups, 3$^{rd}$ Edition", Philip J. Kocienski, Theime, 2005 or "Greene's Protective Groups in Organic Synthesis, 4th Edition", Peter G. M. Wuts, Theadora W. Greene, John Wiley and Sons, 2007.

The compounds of general formula I may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the inhibition of the ghrelin O-acyl transferase (GOAT) with one or more compounds of the present invention.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

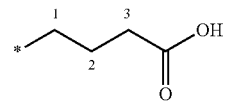

wherein the carboxy group is attached to the third carbon atom of the propyl group. The terms "1-methylpropyl-", "2,2-dimethylpropyl-" or "cyclopropylmethyl-" group represent the following groups:

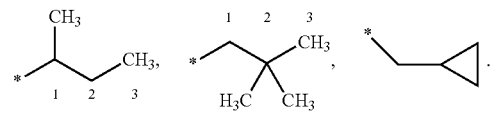

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the before mentioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—$ CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH₂)—, —(CH₂—CH₂)—, —(CH(CH₃))—, —(CH₂—CH₂—CH₂)—, —(C(CH₃)₂)—, —(CH(CH₂CH₃))—, —(CH(CH₃)—CH₂)—, —(CH₂—CH(CH₃))—, —(CH₂—CH₂—CH₂—CH₂)—, —(CH₂—CH₂—CH(CH₃))—, —(CH(CH₃)—CH₂—CH₂)—, —(CH₂—CH(CH₃)—CH₂)—, —(CH₂—C(CH₃)₂)—, —(C(CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)— and —C(CH₃)(CH₂CH₃)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH₂, —CH=CH—CH₃, —CH₂—CH=CH₂.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH₃, —CH₂—C≡CH.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclo-nonyl, cyclododecyl, bicyclo[3.2.1.]octyl, spiro[4.5]decyl, norpinyl, norbonyl, norcaryl, adamantyl, etc.

Many of the terms given above may be used repeatedly in the definition of a formula or group and in each case have one of the meanings given above, independently of one another.

Pharmacological Activity

Determination of hGOAT Activity in HEK293 Cells after Incubation with Test Compound Principle:

HEK293 cells stably transfected with two expression vectors, one coding for preproghrelin cDNA and a second for the expression of human GOATcDNA are used as a cellular model. After feeding the cells with octanoic acid for 5 hours, acyl-ghrelin is measured in cell culture medium by an ELISA procedure.

Materials:

Cellline: Hek293 hGOAT/PPGhrl Clone #1B8Sodium octanoate, Sigma, Cat.-No. C5038

BSA: Sigma, Cat.-No. A8806

BD Poly-D-Lysin 384-well Plates, black-clear polystyrene BD Bioscience Cat.-No. 356697348-well ELISA human acylated Ghrelin Kit purchased from Bertin Pharman (detailed composition of buffers e.g. wash-puffer, ELISA buffer not known)

All further reagents used were of highest analytical grade available.

Method:

Cells are plated with a density of 5000 cells/well in 384-well poly-D-lysin plates and incubated for 1 day at 37° C., 5% CO2 in DMEM medium, 10% FCS, 1×NEAA, Puromycin (0.5 µg/ml) and G418 (1 mg/ml). Then the medium is changed to a identical medium without FCS and containing Octanoate-BSA (final concentration 100 µM each) and compound in DMSO (final DMSO concentration 0,3%). After incubation for 5 hours acylghrelin in the medium is measured by ELISA.

The medium sample is diluted 1:25 in Elisa buffer, a 25 µl aliquot is transferred to a 384-well ELISA plate previously washed 4 times with 100 µL wash buffer, and 25 µl tracer-solution is added. After incubation overnight (~20 h) at 4° C. temperature the plate is washed 4 times with 100 µl wash-buffer per well. Finally 50 µl Ellman's reagent is added to each well and the plate is incubated in the dark for 20 minutes. The absorbance is measured at 405 nm in an Envision multilabel reader and the amount of acylated ghrelin is calculated according to a acylated ghrelin standard curve provided in the same plate.

Each assay plate contains wells with vehicle controls (1% DMSO) for the measurement of non-inhibited transfer reaction (=100% Ctl) and wells with 10 µM ([Dap3]-Ghrelin) as controls for fully inhibited GOAT enzyme The analysis of the data is performed by calculation of the percentage of acyl-ghrelin produced in the presence of test compound compared to the amount of acyl-ghrelin produced in the vehicle control samples. An inhibitor of the GOAT enzyme will give values between 100% CTL (no inhibition) and 0% CTL (complete inhibition).

IC50 values are calculated with Assay Explorer or other suited software based on curve fitting of results of 8 different compound concentrations.

Results:

| Compound | IC50 [nM] | Compound | IC50 [nM] | Compound | IC50 [nM] | Compound | IC50 [nM] |
|---|---|---|---|---|---|---|---|
| 1.1 | 0.225 | 4.22 | 4.810 | 11.1 | 0.068 | 18.1 | 0.921 |
| 1.2 | 0.387 | 4.23 | 7.760 | 12.1 | 0.079 | 19.1 | 4.530 |
| 1.3 | 0.294 | 4.24 | 0.838 | 12.2 | 0.043 | 19.2 | 8.420 |
| 1.4 | 0.127 | 4.25 | 0.081 | 12.3 | 0.509 | 19.3 | 0.555 |
| 2.1 | 0.092 | 4.26 | 0.098 | 12.4 | 1.520 | 19.4 | 0.534 |
| 2.2 | 0.066 | 4.27 | 1.650 | 12.5 | 3.660 | 19.5 | 2.221 |
| 2.3 | 0.060 | 4.28 | 1.500 | 12.6 | 0.402 | 19.6 | 2.055 |
| 2.4 | 0.133 | 4.29 | 1.270 | 12.7 | 1.170 | 19.7 | 7.965 |
| 2.5 | 0.402 | 4.30 | 1.394 | 12.8 | 0.531 | 20.1 | 4.630 |
| 2.6 | 1.400 | 4.31 | 0.487 | 12.9 | 1.490 | 20.2 | 3.240 |
| 2.7 | 0.353 | 4.32 | 0.064 | 12.10 | 0.437 | 21.1 | 0.099 |
| 2.8 | 0.416 | 4.33 | 0.114 | 12.11 | 1.312 | 21.10 | 2.570 |
| 2.9 | 2.014 | 4.34 | 1.400 | 12.12 | 1.250 | 21.11 | 1.920 |
| 2.10 | 0.132 | 4.35 | 0.111 | 12.13 | 2.790 | 21.12 | 0.978 |
| 2.11 | 1.070 | 4.36 | 5.800 | 13.1 | 1.538 | 21.13 | 0.718 |
| 2.12 | 0.490 | 4.37 | 0.534 | 13.2 | 0.033 | 21.2 | 0.176 |
| 2.13 | 0.660 | 4.38 | 0.268 | 14.1 | 6.295 | 21.3 | 1.580 |
| 2.14 | 0.096 | 4.39 | 9.388 | 14.2 | 0.665 | 21.4 | 0.786 |
| 2.15 | 0.887 | 4.40 | 2.210 | 14.3 | 2.930 | 21.5 | 0.198 |
| 2.16 | 3.033 | 4.41 | 0.428 | 14.4 | 2.250 | 21.6 | 0.150 |
| 3.1 | 5.833 | 4.42 | 0.377 | 14.5 | 2.370 | 21.7 | 0.278 |
| 4.0 | 0.494 | 4.43 | 0.052 | 14.6 | 4.270 | 21.8 | 1.090 |
| 4.1 | 0.246 | 4.44 | 0.573 | 14.7 | 1.830 | 21.9 | 17.000 |
| 4.2 | 2.260 | 4.45 | 0.233 | 14.8 | 3.640 | 22.1 | 0.432 |
| 4.3 | 1.580 | 4.46 | 0.052 | 14.9 | 3.060 | 22.2 | 2.490 |
| 4.4 | 4.065 | 4.47 | 1.800 | 14.10 | 4.700 | 23.1 | 0.485 |
| 4.5 | 1.593 | 4.48 | 3.005 | 14.11 | 4.160 | 23.2 | 0.232 |
| 4.6 | 3.100 | 4.49 | 35.700 | 14.12 | 3.020 | 23.3 | 0.298 |
| 4.7 | 0.124 | 4.50 | 0.751 | 14.13 | 4.990 | 23.4 | 0.139 |
| 4.8 | 1.410 | 4.51 | 0.673 | 14.14 | 5.550 | 23.5 | 0.737 |
| 4.9 | 4.010 | 4.52 | 1.590 | 14.15 | 5.120 | 23.6 | 0.078 |
| 4.10 | 5.360 | 4.53 | 0.147 | 14.16 | 3.730 | 23.7 | 0.178 |
| 4.11 | 3.420 | 4.54 | 0.495 | 14.17 | 4.500 | 24.1 | 0.475 |

| Compound | IC50 [nM] | Compound | IC50 [nM] | Compound | IC50 [nM] | Compound | IC50 [nM] |
|---|---|---|---|---|---|---|---|
| 4.12 | 0.571 | 4.55 | 6.270 | 14.18 | 7.770 | 24.2 | 5.730 |
| 4.13 | 0.890 | 4.56 | 0.519 | 15.1 | 0.183 | 24.3 | 6.120 |
| 4.14 | 0.665 | 4.57 | 0.121 | 15.2 | 0.096 | 24.4 | 2.420 |
| 4.15 | 0.330 | 4.58 | 0.752 | 15.3 | 1.584 | 24.5 | 0.289 |
| 4.16 | 0.642 | 4.59 | 2.510 | 15.4 | 0.933 | 25.1 | 3.500 |
| 4.17 | 0.371 | 4.60 | 6.740 | 15.5 | 0.475 | 25.2 | 4.840 |
| 4.18 | 1.646 | 4.61 | 0.542 | 15.6 | 1.260 | 25.3 | 7.360 |
| 4.19 | 0.174 | 8.1 | 1.086 | 16.1 | 0.260 | 25.4 | 1.350 |
| 4.20 | 5.510 | 9.1 | 9.470 | 17.1 | 0.726 | | |
| 4.21 | 3.410 | 10.1 | 0.594 | 17.2 | 0.171 | | |

In view of their ability to modulate the activity of ghrelin O-acyl transferase (GOAT), in particular an inhibitory activity, the compounds of general formula I according to the invention, including the corresponding salts thereof, are suitable for the treatment of all those diseases or conditions which may be affected or which are mediated by the inhibition of ghrelin O-acyl transferase (GOAT).

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the inhibition of ghrelin O-acyl transferase (GOAT) in a patient, preferably in a human.

In yet another aspect the present invention relates to a method for treating a disease or condition mediated by the inhibition of ghrelin O-acyl transferase (GOAT) in a mammal that includes the step of administering to a patient, preferably a human, in need of such treatment a therapeutically effective amount of a compound or a pharmaceutical composition of the present invention.

Diseases and conditions mediated by inhibitors of ghrelin O-acyl transferase (GOAT) embrace obesity, including, but not limited to obesity in patients suffering from Prader-Willi-Syndrome (PWS), body weight regain, diabetes, particularly type 2 diabetes mellitus, insulin resistance, hyperphagia in PWS, Binge eating disorder, nighttime eating syndrome and alcohol and/or narcotic dependence.

Preferably, the compounds of the invention are used for treating obesity, body weight regain, type 2 diabetes, insulin resistance, and hyperphagia and obesity in PWS.

More preferably, the compounds of the invention are used for treating obesity, body weight regain, type 2 diabetes and insulin resistance.

In particular, the compounds and pharmaceutical compositions according to the invention are suitable for the treatment of obesity, including, but not limited to obesity in patients suffering from Prader-Willi-Syndrome, body weight regain, diabetes, in particular type 2 diabetes mellitus, and insulin resistance.

The compounds according to the invention are most particularly suitable for treating obesity.

The present invention further provides a GOAT inhibitor of the invention for use in a method of medical treatment.

GOAT inhibitors are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes). It will be understood that the GOAT inhibitors may thus be administered to subjects affected by conditions characterised by inadequate control of appetite or otherwise over-feeding, such as binge-eating disorder and Prader-Willi syndrome.

Thus, the invention provides a GOAT inhibitor of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides a GOAT inhibitor of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides a GOAT inhibitor of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides a GOAT inhibitor of the invention for use in a method of lowering circulating LDL levels and/or increasing HDL/LDL ratio.

Effects of GOAT inhibitors on these conditions may be mediated in whole or in part via an effect on body weight, or may be independent thereof.

The invention further provides use of a GOAT inhibitor of the invention in the manufacture of a medicament for treating, inhibiting or reducing weight gain, promoting weight loss and/or reducing excess body weight.

The invention also provides use of a GOAT inhibitor of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The invention also provides use of a GOAT inhibitor of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The invention also provides use of a GOAT inhibitor of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of a GOAT inhibitor of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of a GOAT inhibitor of the invention to the subject.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke in a subject, comprising administering a therapeutically effective amount of a GOAT inhibitor of the invention to the subject.

The invention further provides a method of lowering circulating LDL levels and/or increasing HDL/LDL ratio in a subject, comprising administering a therapeutically effective amount of a GOAT inhibitor of the invention to the subject.

The invention further provides the use of a GOAT inhibitor as described above in a method of cosmetic (i.e. non-therapeutic) weight loss. It will be understood that references to therapeutic uses of GOAT inhibitors and methods comprising administration of GOAT inhibitors may equally be taken to encompass uses and administration of such compositions.

Further aspects and embodiments of the present invention will become apparent from the disclosure below.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

A compound of the invention may be administered as part of a combination therapy together with another active agent for the treatment of the disease or disorder in question, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus a compound of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), an SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, lixisenatide (Lyxumia™) and liraglutide (Victoza™)

Moreover, a compound of the invention may be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human prolslet Peptide (HIP), a melanocortin receptor 4 agonist, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), Orlistat™ Sibutramine™, phentermine, a melanin concentrating hormone receptor 1 antagonist, CCK, amylin, pramlintide and leptin, as well as analogues thereof.

A compound of the invention may further be used in combination with an anti-hypertension agent of a known type, including, but not limited to, an angiotensin-converting enzyme inhibitor, an angiotensin II receptor blocker, a diuretic, a beta-blocker and a calcium channel blocker.

A compound of the invention may still further be used in combination with an anti-dyslipidemia agent of known type, including, but not limited to, a statin, a fibrate, a niacin, a PSCK9 (Proprotein convertase subtilisin/kexin type 9) inhibitor, and a cholesterol absorption inhibitor.

A compound of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™, Pantoprazole™, Rabeprazole™, Zolpidem™, Alpidem™, Saripidem™ or Necopidem™.

In addition, with regard to anti-inflammatory treatment, a compound of the invention may be beneficial if administered in combination with an anti-inflammatory agent of known type, including, but not limited to:

steroids and corticosteroids, such as beclomethasone, methylprednisolone, betamethasone, prednisone, dexamethasone, and hydrocortisone;

non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1a or interferon beta-1 b);

and certain other compounds, such as 5-aminosalicylic acid and prodrugs and pharmaceutically acceptable salts thereof.

Metformin has also been demonstrated to have anti-inflammatory properties (see, e.g., Haffner et al., *Diabetes* 54: 1566-1572 (2005)) and as such may also be useful in combination with compounds of the invention.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the inhibition of ghrelin O-acyl transferase (GOAT), in particular diseases or conditions as described hereinbefore and hereinafter.

In yet another aspect the present invention relates a method for treating a disease or condition mediated by the inhibition of ghrelin O-acyl transferase (GOAT) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Examples

The following examples serve to further explain the invention without restricting it.

The hereinafter described compounds have been characterized through their characteristic mass after ionisation in a mass-spectrometer and/or their retention time on an analytical HPLC.

HPLC Methods:

Method 1: Column: Waters XBridge C18,
3 × 30 mm, 2.5 μm
Detection: Agilent 1200 with
DA- and MS-Detector
Eluent A: Water (0.1% NH$_3$);
Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 2: Column: Waters SunFire,
3 × 30 mm, 2.5 μm
Detection: Agilent 1200 with
DA- and MS-Detector
Eluent A: Water
(0.1% Trifluoroacetic acid);
Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 3: Column: Waters SunFire C18,
3 × 30 mm, 2.5 μm
Detection: Agilent 1200 with
DA- and MS-Detector
Eluent A: Water (0.1% Formic acid);
Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 4: Column: Waters XBridge C18,
3 × 30 mm, 2.5 μm
Detection: Agilent 1200 with
DA- and MS-Detector
Eluent A: Water (0.1% Formic acid);
Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 100 | 2.2 | 60 |
| | 1.25 | 100 | 3.0 | 60 |
| | 1.40 | 100 | 3.0 | 60 |

Method 5: Column: Waters XBridge C18,
3 × 30 mm, 2.5 μm
Detection: Agilent 1100 with DAD,
CTC Autosampler and
Waters MS-Detector
Eluent A: Water (0.1% NH$_4$OH);
Eluent B: Acetonitrile

| Gradient: | Time (min.) | % Eluent B | Flow [mL/min] | Temp [° C.] |
|---|---|---|---|---|
| | 0.00 | 2 | 2.0 | 60 |
| | 1.20 | 100 | 2.0 | 60 |
| | 1.40 | 100 | 2.0 | 60 |

Method 6: Column: Waters SunFire C18,
3 × 30 mm, 2.5 μm
Detection: Agilent 1100 with
DAD; Waters Autosampler
and MS-Detector
Eluent A: Water
(0.1% Trifluoroacetic acid);
Eluent B: Acetonitrile

| Gradient: | Time (min.) | % Eluent B | Flow [mL/min] | Temp [° C.] |
|---|---|---|---|---|
| | 0.00 | 2 | 2.0 | 60 |
| | 1.20 | 100 | 2.0 | 60 |
| | 1.40 | 100 | 2.0 | 60 |

Method 7: Column: Waters XBridge C18,
3 × 30 mm, 2.5 μm
Detection: Waters Acquity with DA- and
MS-Detector and CTC Autosampler
Eluent A: Water (0.1% NH$_4$OH);
Eluent B: Acetonitrile

| Gradient: | Time (min.) | % Eluent B | Flow [mL/min] | Temp [° C.] |
|---|---|---|---|---|
| | 0.00 | 2 | 2.0 | 60 |
| | 1.20 | 100 | 2.0 | 60 |
| | 1.40 | 100 | 2.0 | 60 |

Method 8: Column: Waters SunFire C18,
3 × 30 mm, 2.5 μm
Detection: Agilent 1100 with DAD,
Gilson Autosampler and MS-Detector
Eluent A: Water
(0.1% Trifluoroacetic acid);
Eluent B: Acetonitrile

| Gradient: | Time (min.) | % Eluent B | Flow [mL/min] | Temp [° C.] |
|---|---|---|---|---|
| | 0.00 | 1 | 2.0 | 60 |
| | 0.90 | 100 | 2.0 | 60 |
| | 1.10 | 100 | 2.0 | 60 |

Method 9: Column: Waters XBridge C18,
3 × 30 mm, 1.7 μm
Detection: Waters Acquity with 3100 MS
Eluent A: Water (0.1% NH₄OH);
Eluent B: Acetonitrile

| Gradient: | Time (min.) | % Eluent B | Flow [mL/min] | Temp [° C.] |
|---|---|---|---|---|
| | 0.00 | 5 | 1.5 | 60 |
| | 0.70 | 99.9 | 1.5 | 60 |
| | 0.80 | 99.9 | 1.5 | 60 |

Method 10: Column: Waters XBridge C18,
3 × 30 mm, 2.5 μm
Detection: Waters Acquity with 3100 MS
Eluent A: Water (0.1% NH₄OH);
Eluent B: Acetonitrile

| Gradient: | Time (min.) | % Eluent B | Flow [mL/min] | Temp [° C.] |
|---|---|---|---|---|
| | 0.00 | 5 | 1.5 | 60 |
| | 1.30 | 99.0 | 1.5 | 60 |
| | 1.50 | 99.0 | 1.5 | 60 |

Method 11: Column: X-terraTM MS C18,
4.6 × 30 mm, 2.5 μm
Detection: Waters PDA 996 Detektor,
Waters ZQ2000
Eluent A: Water (0.1% HCOOH);
Eluent B: Acetonitrile (0.1% HCOOH)

| Gradient: | Time (min.) | % Eluent B | Flow [mL/min] | Temp [° C.] |
|---|---|---|---|---|
| | 0.00 | 5 | 1.0 | RT |
| | 0.10 | 5 | 1.0 | RT |
| | 3.10 | 98.0 | 1.0 | RT |
| | 4.50 | 98.0 | 1.0 | RT |
| | 5.00 | 5 | 1.0 | RT |

Method 12: XBridge C18_
3 × 30 mm, 2.5 μm
Detection: Agilent 1200 with DA- and MS-Detector
Eluent A: Water (0.1% TFA);
Eluent B: Acetonitrile

| Gradient: | Time (min.) | % Eluent B | Flow [mL/min] | Temp [° C.] |
|---|---|---|---|---|
| | 0.00 | 3 | 2.2 | 60 |
| | 0.20 | 3 | 2.2 | 60 |
| | 1.20 | 0 | 2.2 | 60 |
| | 1.25 | 0 | 2.2 | 60 |
| | 1.40 | 0 | 2.2 | 60 |

Method 13: Sunfire C18_
3 × 30 mm, 2.5 μm
Detection: Waters Acquity,
QDa Detector
Eluent A: Water (0.1% TFA);
Eluent B: Acetonitrile (0.08% TFA)

| Gradient: | Time (min.) | % Eluent B | Flow [mL/min] | Temp [° C.] |
|---|---|---|---|---|
| | 0.00 | 5 | 1.5 | 40 |
| | 1.30 | 100 | 1.5 | 40 |
| | 1.50 | 100 | 1.5 | 40 |
| | 1.60 | 5 | 1.5 | 40 |

Method 14: XBridge C18_
3 × 30 mm, 2.5 μm
Detection: Waters Acquity,
QDa Detector
Eluent A: Water (0.1% NH3);
Eluent B: Acetonitrile

| Gradient: | Time (min.) | % Eluent B | Flow [mL/min] | Temp [° C.] |
|---|---|---|---|---|
| | 0.00 | 5 | 1.5 | 40 |
| | 1.30 | 100 | 1.5 | 40 |
| | 1.50 | 100 | 1.5 | 40 |
| | 1.60 | 5 | 1.5 | 40 |

Preparation of Intermediates:
Procedure 1
Intermediate 1.1a 3-(4-Bromo-phenyl)-N-methoxy-N-methyl-propanamide The reaction is carried out under an argon atmosphere. A mixture of 3-(4-bromo-phenyl)-propionic acid (500 mg; 2.18 mmol) and 1,1'-carbonyldiimidazole (389 mg; 2.40 mmol) in 10 mL dichloromethane is stirred at room temperature for 1 hour. Triethylamine (440 μL; 3.27 mmol) and N,O-dimethylhydroxylamine hydrochloride (234 mg; 2.40 mmol) are added. After stirring at room temperature for 18 hours the organic layer is washed with HCl (1 M aqueous solution), water and NaHCO₃ (saturated aqueous solution). The organic layer is dried and concentrated under reduced pressure. The residue is further used as crude product.
Yield: 560 mg (94% of theory)
HPLC (Method 2): Retention time=1.026 min.
Intermediate 1.1b 4-(4-Bromo-phenyl)-butan-2-one The reaction is carried out under an argon atmosphere. Intermediate 1.1a 3-(4-Bromo-phenyl)-N-methoxy-N- methyl-propanamide (560 mg; 2.06 mmol) is dissolved in tetrahydrofuran and cooled to 0° C. Methylmagnesium chloride (3 M solution in tetrahydrofuran; 1.03 mL; 3.09 mmol) is added dropwise. After stirring at room temperature for 18 hours $NH_4Cl$ (saturated aqueous solution) is added. The aqueous layer is extracted three times with dichloromethane. The combined organic layers are dried and concentrated under reduced pressure. The residue is further used as crude product.

Yield: 464 mg (99% of theory)
HPLC (Method 2): Retention time=1.057 min.
Intermediate 1.2a

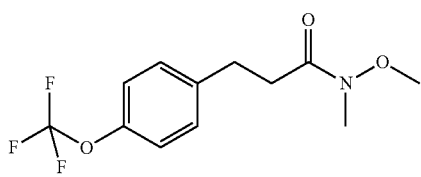 [SMILES: CON(C)C(=O)CCc1ccc(OC(F)(F)F)cc1]

N-Methoxy-N-methyl-3-(4-trifluoromethoxy-phenyl)-propanamide

Analogously to intermediate 1.1a the following compound is obtained by starting from 4-(trifluoromethoxy)hydrocinnamic acid and N,O-dimethylhydroxylamine.

HPLC (Method 2): Retention time=1.072 min.
Intermediate 1.2b

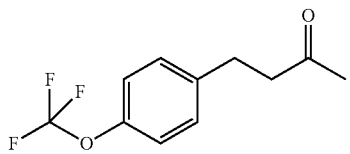 [SMILES: CC(=O)CCc1ccc(OC(F)(F)F)cc1]

4-(4-Trifluoromethoxy-phenyl)-butan-2-one

Analogously to intermediate 1.1b the following compound is obtained by starting from intermediate 1.2a N-methoxy-N-methyl-3-(4-trifluoromethoxy-phenyl)-propanamide and methylmagnesium chloride.

HPLC (Method 2): Retention time=1.101 min.
Intermediate 1.3a

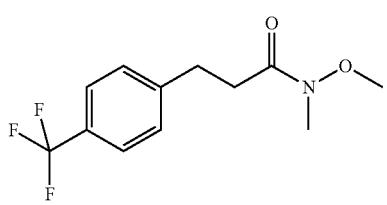 [SMILES: CON(C)C(=O)CCc1ccc(C(F)(F)F)cc1]

N-Methoxy-N-methyl-3-(4-trifluoromethyl-phenyl)-propanamide

Analogously to intermediate 1.1a the following compound is obtained by starting from 4-(trifluoromethyl)hydrocinnamic acid and N,O-dimethylhydroxylamine.

HPLC (Method 2): Retention time=1.054 min.
Intermediate 1.3b

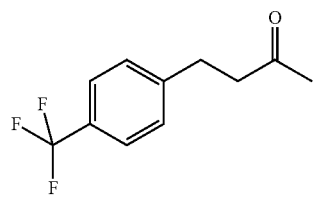

4-(4-Trifluoromethyl-phenyl)-butan-2-one

Analogously to intermediate 1.1b the following compound is obtained by starting from intermediate 1.3a N-methoxy-N-methyl-3-(4-trifluoromethyl-phenyl)-propanamide and methylmagnesium chloride.

HPLC (Method 2): Retention time=1.073 min.
Intermediate 1.4a

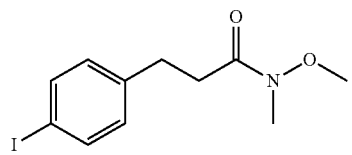

3-(4-Iodo-phenyl)-N-methoxy-N-methyl-propanamide

Analogously to intermediate 1.1a the following compound is obtained by starting from 3-(4-iodophenyl)propionic acid and N,O-dimethylhydroxylamine.

HPLC (Method 2): Retention time=1.055 min.
Intermediate 1.4b

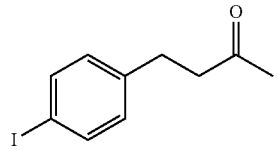

4-(4-Iodo-phenyl)-butan-2-one

Analogously to intermediate 1.1b the following compound is obtained by starting from intermediate 1.4a 3-(4-iodo-phenyl)-N-methoxy-N-methyl-propanamide and methylmagnesium chloride.

HPLC (Method 2): Retention time=1.098 min.
Procedure 2
Intermediate 2.1a

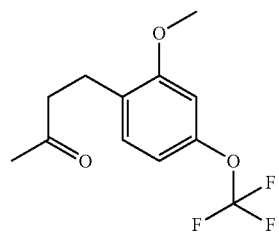 [SMILES: COc1cc(OC(F)(F)F)ccc1CCC(C)=O]

4-(2-Methoxy-4-trifluoromethoxy-phenyl)-butan-2-one

A mixture of 2-methoxy-4-(trifluoromethoxy)benzyl bromide (340 mg; 1.18 mmol), acetylacetone (120 µL; 1.18 mmol) and potassium carbonate (160 mg; 1.18 mmol) in 20 mL methanol is stirred at 80° C. for 18 hours. The solvent is evaporated and the residue is purified by reverse phase chromatography-HPLC (modifier: trifluoroacetic acid).

Yield: 240 mg (77% of theory)

HPLC (Method 3): Retention time=1.098 min.

Intermediate 2.2a

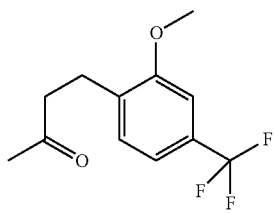 [SMILES: COc1cc(C(F)(F)F)ccc1CCC(C)=O]

4-(2-Methoxy-4-trifluoromethyl-phenyl)-butan-2-one

Analogously to intermediate 2.1a the following compound is obtained by starting from 1-bromomethyl-2-methoxy-4-trifluoromethyl-benzene and acetylacetone.

HPLC (Method 3): Retention time=1.100 min.

Intermediate 2.3a

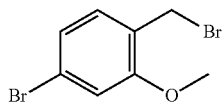

4-Bromo-1-bromomethyl-2-methoxy-benzene (4-Bromo-2-methoxy-phenyl)-methanol (500 mg; 2.30 mmol) in 10 mL dichloromethane is cooled in an ice bath. Phosphorus tribromide (130 µL; 1.39 mmol) is added dropwise. The mixture is allowed to warm up to room temperature and stirred for further 15 minutes. The mixture is poured on cooled NaHCO$_3$ (half saturated aqueous solution) and extracted with dichloromethane. The organic layer is separated, dried and evaporated.

Yield: 720 mg (100% of theory)

HPLC (Method 3): Retention time=1.133 min.

Intermediate 2.3b

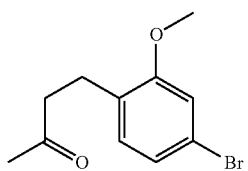

4-(4-Bromo-2-methoxy-phenyl)-butan-2-one

Analogously to intermediate 2.1a the following compound is obtained by starting from intermediate 2.3a [4-bromo-1-bromomethyl-2-methoxy-benzene] and acetylacetone. HPLC (Method 3): Retention time=1.073 min.

Intermediate 2.4a

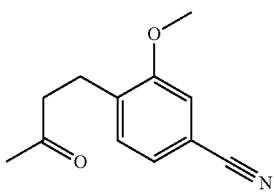

3-Methoxy-4-(3-oxo-butyl)-benzonitrile

Analogously to intermediate 2.1a the following compound is obtained by starting from 4-bromomethyl-3-methoxy-benzonitrile and acetylacetone.

Mass spectrometry (ESI$^+$): m/z=204 [M+H]$^+$

HPLC (Method 3): Retention time=0.931 min.

Intermediate 2.5a

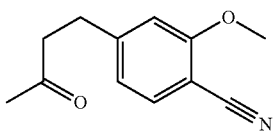

2-Methoxy-4-(3-oxo-butyl)-benzonitrile

Analogously to intermediate 2.1a the following compound is obtained by starting from 4-bromomethyl-2-methoxy-benzonitrile and acetylacetone.

Mass spectrometry (ESI$^+$): m/z=204 [M+H]$^+$

HPLC (Method 3): Retention time=0.904 min.

Intermediate 2.6a

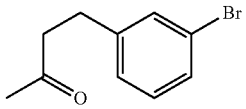

4-(3-Bromo-phenyl)-butan-2-one

Analogously to intermediate 2.1a the following compound is obtained by starting from 3-bromobenzyl bromide and acetylacetone. The mixture is purified by silica gel chromatography (eluent: petrol ether/ethyl acetate 0->15%)

Mass spectrometry (ESI$^+$): m/z=227 [M+H]$^+$

HPLC (Method 3): Retention time=1.038 min.

Intermediate 2.7a

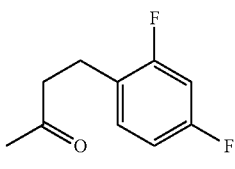

4-(2,4-Difluoro-phenyl)-butan-2-one

Analogously to intermediate 2.1a the following compound is obtained by starting from 2,4-difluorobenzyl bromide and acetylacetone. The mixture is purified by silica gel chromatography (eluent: petrol ether/ethyl acetate 0->15%)

Mass spectrometry (EI): m/z=184 [M]+
HPLC (Method 3): Retention time=0.933 min.
Intermediate 2.8a

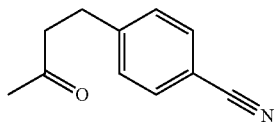

4-(3-Oxo-butyl)-benzonitrile

Analogously to intermediate 2.1a the following compound is obtained by starting from 4-(bromomethyl)benzonitrile and acetylacetone. The mixture is purified by silica gel chromatography (eluent: petrol ether/ethyl acetate 0->15%)

Mass spectrometry (ESI+): m/z=174 [M+H]+
HPLC (Method 3): Retention time=0.875 min.
Intermediate 2.9a

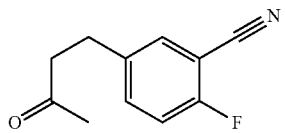

2-Fluoro-5-(3-oxo-butyl)-benzonitrile

Analogously to intermediate 2.1a the following compound is obtained by starting from 5-bromomethyl-2-fluorobenzonitrile and acetylacetone. The mixture is purified by silica gel chromatography (eluent: petrol ether/ethyl acetate 0->15%)

HPLC (Method 3): Retention time=0.946 min.
Intermediate 2.10a

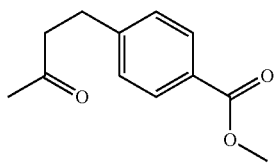

Methyl 4-(3-oxobutyl)benzoate

Analogously to intermediate 2.1a the following compound is obtained by starting from 4-bromomethyl-benzoic acid ethyl ester and acetylacetone. The mixture is purified by silica gel chromatography (eluent: petrol ether/ethyl acetate 0->15%)

Mass spectrometry (ESI+): m/z=207 [M+H]+
HPLC (Method 3): Retention time=0.916 min.
Intermediate 2.11a

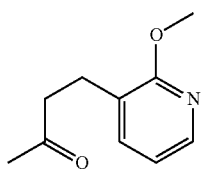

4-(2-Methoxy-pyridin-3-yl)-butan-2-one

Analogously to intermediate 2.1a the following compound is obtained by starting from 3-(chloromethyl)-2-methoxypyridine and acetylacetone. The mixture is purified by silica gel chromatography (eluent: petrol ether/ethyl acetate 0->15%).

Mass spectrometry (ESI+): m/z=180 [M+H]+
HPLC (Method 3): Retention time=0.838 min.
Intermediate 2.12a

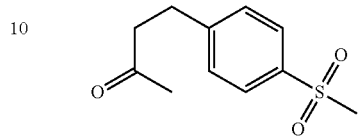

4-(4-Methanesulfonyl-phenyl)-butan-2-one

Analogously to intermediate 2.1a the following compound is obtained by starting from 1-bromomethyl-4-methanesulfonyl-benzene and acetylacetone.

Mass spectrometry (ESI+): m/z=227 [M+H]+
HPLC (Method 2): Retention time=0.771 min.
Intermediate 2.13a

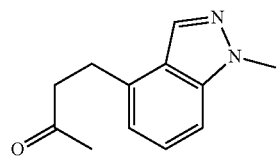

4-(1-Methyl-1H-indazol-4-yl)-butan-2-one

Analogously to intermediate 2.1a the following compound is obtained by starting from 4-(bromomethyl)-1-methyl-1H-indazole and acetylacetone.

Mass spectrometry (ESI+): m/z=203 [M+H]+
HPLC (Method 3): Retention time=0.857 min.
Intermediate 2.14a

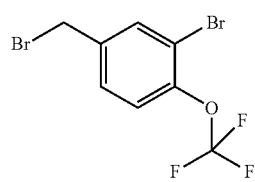 [SMILES: FC(F)(F)Oc1ccc(CBr)cc1Br]

2-Bromo-4-bromomethyl-1-trifluoromethoxy-benzene

3-Bromo-4-(trifluoromethoxy)benzyl alcohol (1.00 g; 3.69 mmol) in 10 mL dichloromethane is cooled in an ice bath. Phosphorus tribromide (208 μL; 2.21 mmol) is added dropwise and the mixture is allowed to warm up to room temperature. After stirring for 15 minutes the mixture is poured on cooled NaHCO3 (aqueous half saturated solution) and extracted with dichloromethane. The organic layer is separated, dried and concentrated under reduced pressure.

Yield: 916 mg (74% of theory)
HPLC (Method 3): Retention time=1.199 min.

Intermediate 2.14b

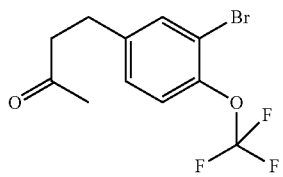 [SMILES: CC(=O)CCc1ccc(OC(F)(F)F)c(Br)c1]

4-(3-Bromo-4-trifluoromethoxy-phenyl)-butan-2-one

Analogously to intermediate 2.1a the following compound is obtained by starting from intermediate 2.14a [2-bromo-4-bromomethyl-1-trifluoromethoxy-benzene] and acetylacetone.
Mass spectrometry (EI): m/z=310 [M*]+
HPLC (Method 3): Retention time=1.131 min.
Intermediate 2.15a

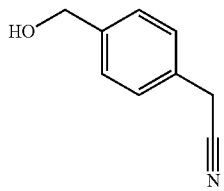 [SMILES: N#CCc1ccc(CO)cc1]

2-(4-Hydroxymethyl-phenyl)-acetonitrile

4-Cyanomethyl-benzoic acid (50 g; 310 mmol) is taken in 500 mL of tetrahydrofuran and CDI is added portion wise. The reaction is exothermique and reaches a temperature of 70° C. The reaction is maintained at a temperature of at least 60° C. for at least 1 hour. The mixture is then poured slowly into a solution of sodium borohydride in ice water. The internal temperature is maintained below 10° C. The reaction stirred over night at room temperature. The reaction is quenched using 37% aqueous HCl solution and stirred for 30 minutes. EtOAc and solid sodium chloride are added before the mixture is extracted. The organic layer is washed with an aqueous solution of sodium hydroxide and water, dried over magnesium sulfate, filtered and concentrated. The product is dissolved in dichloromethane to which activated carbon is added. The mixture is filtered and concentrated.
Yield: 36.2 g (79% of theory)
Mass spectrometry (EI): m/z=147 [M*]+
Intermediate 2.15b

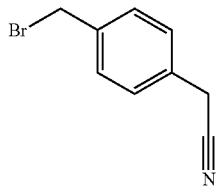 [SMILES: N#CCc1ccc(CBr)cc1]

2-(4-Bromomethyl-phenyl)-acetonitrile

Analogously to intermediate 2.14a the following compound is obtained by starting from intermediate 2.15a [2-(4-Hydroxymethyl-phenyl)-acetonitrile] and phosphorus tribromide using methyl tert-butyl ether as solvent instead of dichloromethane.
Yield: 18.2 g (71% of theory)
Mass spectrometry (ESI+): m/z=210/212 [M+H]+
Intermediate 2.15c

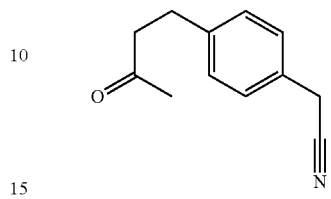

2-[4-(3-Oxo-butyl)-phenyl]-acetonitrile

Analogously to intermediate 2.1a the following compound is obtained by starting from intermediate 2.15b [2-(4-Bromomethyl-phenyl)-acetonitrile] and acetylacetone.
Yield: 60 mg (14% of theory)
Mass spectrometry (EI): m/z=188 [M*]+
HPLC (Method 3): Retention time=0.852 min.
Procedure 3
Intermediate 3a

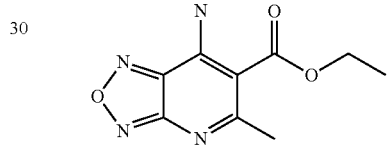

Ethyl-7-amino-5-methyl-[1,2,5]oxadiazolo[3,4-b]pyridin-6-carboxylate

4-Amino-1,2,5-oxadiazole-3-carbonitrile (1.00 g; 9.08 mmol) and ethyl acetoacetate (1.15 mL; 9.08 mmol) are solved in 10 mL toluene. Tin(IV)chloride (2.13 mL; 18.2 mmol) is added and the mixture is stirred at reflux for 30 minutes. The mixture is evaporated and the residue is taken up in NaHCO₃ (half saturated aqueous solution) and extracted twice with dichloromethane. The combined organic layers are dried and concentrated under reduced pressure.
Yield: 2.47 g (98% of theory)
Mass spectrometry (ESI+): m/z=223 [M+H]+
HPLC (Method 1): Retention time=0.853 min.
Intermediate 3b

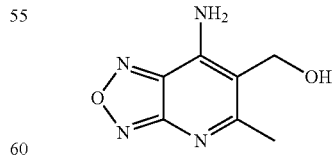

(7-Amino-5-methyl-[1,2,5]oxadiazolo[3,4-b]pyridin-6-yl)-methanol

The reaction is carried out under an argon atmosphere. A mixture of intermediate 3a [Ethyl-7-amino-5-methyl-[1,2,5]

oxadiazolo[3,4-b]pyridin-6-carboxylate] (1.00 g; 3.60 mmol) in 10 mL toluene and 5 mL tetrahydrofuran is cooled to −78° C. Sodium bis(2-methoxy ethoxy)aluminium hydride (65% in toluene; 1.13 mL; 3.78 mmol) is added. The mixture is allowed to warm up to room temperature. After stirring over night at room temperature additional sodium bis(2-methoxy ethoxy)aluminium hydride (65% in toluene; 1.13 mL; 3.78 mmol) is added. After stirring for further 1.5 hours the mixture is diluted with sodium-potassium-tartrate (saturated aqueous solution) and extracted twice with tetrahydrofuran/ethyl acetate. The combined organic layers are dried and concentrated under reduced pressure. The residue is purified by reverse phase chromatography-HPLC (modifier: trifluoroacetic acid).

Yield: 530 mg (81% of theory)

HPLC (Method 3): Retention time=0.239 min.

Intermediate 3c

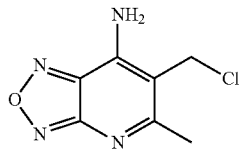

6-Chloromethyl-5-methyl-[1,2,5]oxadiazolo[3,4-b]pyridin-7-amine

Intermediate 3b (7-Amino-5-methyl-[1,2,5]oxadiazolo[3,4-b]pyridin-6-yl)-methanol (30.0 mg; 0.17 mmol) is taken up in 0.2 mL N,N-dimethylformamide. Thionylchloride (24.2 µL; 0.33 mmol) is slowly added dropwise and stirred for 20 minutes at room temperature. The mixture is evaporated and further used as crude product.

Yield: 33.0 mg (100% of theory)

HPLC (Method 2): Retention time=0.281 min.

Intermediate 3d

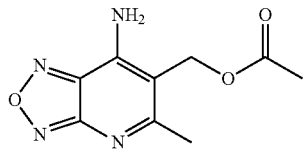 [SMILES: CC(=O)OCc1c(C)nc2nonc2c1N]

{7-Amino-5-methyl-[1,2,5]oxadiazolo[3,4-b]pyridin-6-yl}methyl Acetate

A suspension of Intermediate 3b (7-Amino-5-methyl-[1,2,5]oxadiazolo[3,4-b]pyridin-6-yl)-methanol (11 g; 61.06 mmol) in 70 mL concentrated acetic acid is stirred at 70° C. over night. The reaction is dissolved with 2-methoxy-2-methylpropane. The generated solid is filtered and washed with 2-methoxy-2-methylpropane. The solid is dried at 50° C. under vacuum.

Yield: 10.3 g (76% of theory)

Mass spectrometry (ESI+): m/z=223 [M+H]+

HPLC (Method 3): Retention time=0.677 min.

Intermediate 3e

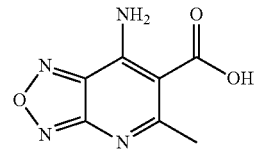

7-Amino-5-methyl-[1,2,5]oxadiazolo[3,4-b]pyridine-6-carboxylic Acid

Intermediate 3a Ethyl-7-amino-5-methyl-[1,2,5]oxadiazolo[3,4-b]pyridin-6-carboxylate (5.000 g; 22.502 mmol) is dissolved in 45 mL tetrahydrofuran and sodium hydroxide (1 M aqueous solution) (33.753 mL; 33.753 mmol) is added. The mixture is stirred over night at room temperature. Hydrochloric acid (4 M aqueous solution) (8.438 mL; 33.753 mmol) is added and tetrahydrofuran is evaporated. The precipitate is filtered, washed and dried.

Yield: 3.40 g (77% of theory)

Mass spectrometry (ESI+): m/z=195 [M+H]+

HPLC (Method 12): Retention time=0.203 min.

Intermediate 3f

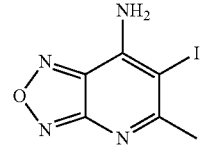

6-Iodo-5-methyl-[1,2,5]oxadiazolo[3,4-b]pyridin-7-amine

Intermediate 3e 7-Amino-5-methyl-[1,2,5]oxadiazolo[3,4-b]pyridine-6-carboxylic acid (3.400 g; 17.512 mmol) is dissolved in 40 mL N,N-dimethylformamide, sodium bicarbonate (1.765 g; 21.015 mmol) and N-iodosuccinimide (4.728 g; 21.015 mmol) are added. The mixture is stirred over night at room temperature, concentrated and diluted with water. After stirring for 10 minutes the precipitate is filtered, washed with water and dried.

Yield: 4.65 g (96% of theory)

Mass spectrometry (ESI+): m/z=277 [M+H]+

HPLC (Method 12): Retention time=0.673 min.

Intermediate 3g

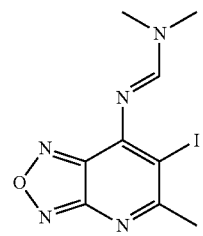 [SMILES: Cc1nc2nonc2c(/N=C/N(C)C)c1I]

(E)-N'-(6-Iodo-5-methyl-[1,2,5]oxadiazolo[3,4-b]pyridin-7-yl)-N,N-dimethylmethanimidamide Intermediate 3f 6-Iodo-5-methyl-[1,2,5]oxadiazolo[3,4-b]pyridin-7-amine (3.500 g; 12.680 mmol) is dissolved in 35 mL N,N-dimethylformamide and N,N-dimethylformamide dimethyl acetate (2.037 mL; 15.215 mmol) is added. The mixture is stirred for 1 h at room temperature. The mixture is diluted with diethyl ether and the precipitate is filtered.

Yield: 2.57 g (61% of theory)

Mass spectrometry (ESI$^+$): m/z=332 [M+H]$^+$

HPLC (Method 12): Retention time=0.946 min.

Procedure 4

Intermediate 4.1a

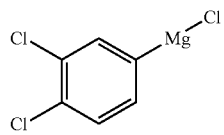

3,4-Dichlorophenylmagnesium Chloride 3,4-Dichloroiodobenzene (800 mg; 2.93 mmol) is taken up in 3 mL tetrahydrofuran and cooled to −45° C. Isopropylmagnesium chloride lithiumchloride complex (1.3 M solution; 2.25 mL; 2.93 mmol) is added dropwise. After stirring for 30 minutes at −45° C. the mixture is further used as crude product.

Yield: 600 mg (100% of theory)

Intermediate 4.2a

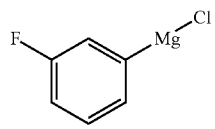

(3-Fluorophenyl)magnesium Chloride

Analogously to intermediate 4.1a the following compound is obtained by starting from 3-fluoroiodobenzene and isopropylmagnesium chloride lithiumchloride complex (1.3 M solution)

Intermediate 4.3a

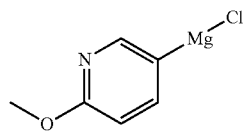

(6-Methoxypyridin-3-yl)magnesium Chloride

Analogously to intermediate 4.1a the following compound is obtained by starting from 5-iodo-2-methoxypyridine and isopropylmagnesium chloride lithiumchloride complex (1.3 M solution)

Intermediate 4.4a

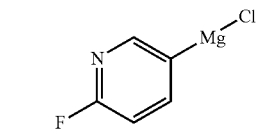

(6-Fluoropyridin-3-yl)magnesium Chloride

Analogously to intermediate 4.1a the following compound is obtained by starting from 2-fluoro-5-iodopyridine and isopropylmagnesium chloride lithiumchloride complex (1.3 M solution) at −40° C.

Intermediate 4.5a

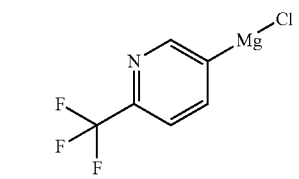

(6-Trifluoromethylpyridin-3-yl)magnesium Chloride

Analogously to intermediate 4.1a the following compound is obtained by starting from 5-bromo-2-trifluoromethylpyridine and isopropylmagnesium chloride lithiumchloride complex (1.3 M solution) at −45° C.

Intermediate 4.6a

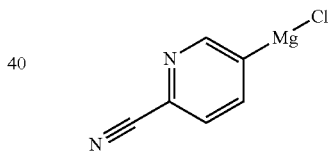

(6-Cyanopyridin-3-yl)magnesium Chloride

Analogously to intermediate 4.1a the following compound is obtained by starting from 2-cyano-5-iodopyridine and isopropylmagnesium chloride lithiumchloride complex (1.3 M solution) at −55° C.

Intermediate 4.7a

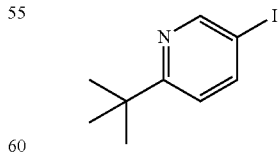

2-tert-Butyl-5-iodopyridine

5-Bromo-2-tert-butylpyridine (500 mg; 2.34 mmol) is dissolved in 5 mL of dioxane. Copper iodide (89 mg, 0.47 mmol) is added and the mixture is placed under argon atmosphere. Sodium iodide is added and the mixture is stirred for a few minutes under argon atmosphere. N,N'-dimethylethylenediamine (100 μL, 0.93 mmol) is added and the mixture is stirred at 130° C. over night. The mixture is allowed to cool to room temperature before being diluted with ethyl acetate and extracted with saturated aqueous solution of sodium bicarbonate twice. The organic layer is dried over magnesium sulfate, filtered and concentrated.

Yield: 610 mg (95% of theory)
Mass spectrometry (ESI$^+$): m/z=262 [M+H]$^+$
HPLC (Method 3): Retention time=1.176 min.
Intermediate 4.7b

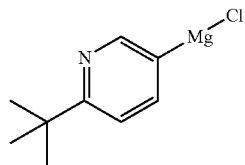

(6-tert-Butylpyridine-3-yl)magnesium Chloride

Analogously to intermediate 4.1a the following compounds is obtained by starting from intermediate 4.7a 2-tert-Butyl-5-iodopyridine and isopropylmagnesium chloride lithiumchloride complex (1.3 M solution) at −45° C.
Intermediate 4.8a

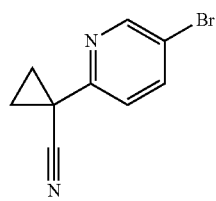 [SMILES: N#CC1(c2ccc(Br)cn2)CC1]

1-(5-bromo-pyridin-2-yl)-cyclopropane-1-carbonitrile (5-Bromo-pyridin-2-yl)-acetonitrile (2.0 g; 10.2 mmol) is dissolved in 20 mL of N,N-dimethylformamide. The mixture is cooled in an ice bath before sodium hydride (0.93 g; 21.3 mmol) is added. The reaction is stirred at room temperature for 30 minutes before 1,2-dibromoethane (2.1 g; 11.2 mmol) is added. The mixture is stirred for 2 hours at 0° C. The reaction is diluted with ethyl acetate and washed with water followed by a saturated aqueous solution of sodium chloride. The organic layer is dried over magnesium sulfate, filtered and concentrated.

Yield: 2.2 g (97% of theory)
Mass spectrometry (ESI$^+$): m/z=223/225 [M+H]$^+$
HPLC (Method 1): Retention time=0.934 min.
Intermediate 4.8b

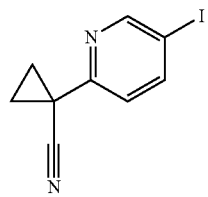 [SMILES: N#CC1(c2ccc(I)cn2)CC1]

1-(5-Iodo-pyridin-2-yl)-cyclopropane-1-carbonitrile

Analogously to intermediate 4.7a the following compound is obtained by starting from intermediate 4.8a 1-(5-bromo-pyridin-2-yl)-cyclopropane-1-carbonitrile.

Yield: 2.5 g (94% of theory)
Mass spectrometry (ESI$^+$): m/z=271 [M+H]$^+$
HPLC (Method 1): Retention time=0.974 min
Intermediate 4.8c

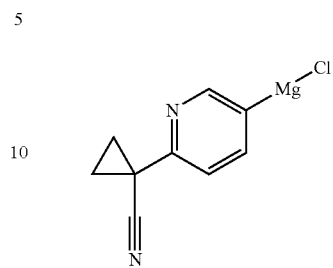

(6-(1-cyclopropanecarbonitrile)-pyridin-3-yl)magnesium Chloride

Analogously to intermediate 4.1a the following compounds is obtained by starting from 1-(5-Iodo-pyridin-2-yl)-cyclopropane-1-carbonitrile and isopropylmagnesium chloride lithiumchloride complex (1.3 M solution) at −45° C.
Intermediate 4.9a

3-Bromo-2-hydrazinylpyridine

Analogously to intermediate 4.12a the following compound is obtained by starting from 3-Bromo-2-chloro-pyridine Yield: 2.64 g (90.2% of theory)
Mass spectrometry (ESI$^+$): m/z=188/190 [M+H]$^+$
HPLC (Method 1): Retention time=0.639 min.
Intermediate 4.9b

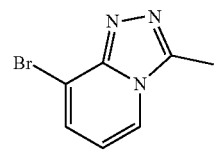

8-Bromo-3-methyl-[1,2,4]triazolo[4,3-a]pyridine

Intermediate 4.9a 3-Bromo-2-hydrazinylpyridine (350 mg; 1.9 mmol) is dissolved in 2 mL of acetic acid. The mixture is heated to reflux over night. The mixture is concentrated. The mixture is filtered before being purified by reverse phase chromatography-HPLC (modifier: trifluoroacetic acid). The product is dissolved in dichloromethane and washed with a saturated aqueous solution of sodium bicarbonate. The organic phase is dried by being run through a phase separator cartridge and concentrated.

Yield: 340 g (85% of theory)
Mass spectrometry (ESI$^+$): m/z=212/214 [M+H]$^+$
HPLC (Method 3): Retention time=0.591 min.

Intermediate 4.9c

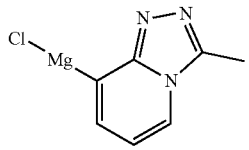

(3-methyl-[1,2,4]triazolo[4,3-a]pyridin-8-yl)magnesium Chloride

Analogously to intermediate 4.1a the following compound is obtained by starting from intermediate 4.9b 8-bromo-3-methyl-[1,2,4]triazolo[4,3-a]pyridine and isopropylmagnesium chloride lithiumchloride complex (1.3 M solution) at −45° C.

Intermediate 4.10a

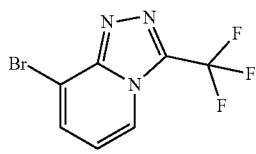 [SMILES: FC(F)(F)c1nnc2c(Br)cccn12]

8-Bromo-3-trifluoromethyl-[1,2,4]triazolo[4,3-a]pyridine

Analogously to intermediate 4.9b the following compound is obtained by starting from intermediate 4.9a 3-Bromo-2-hydrazinylpyridine and trifluoroacetic acid instead of acetic acid. The product is not purified by Prep LC-MS before being partitioned between dichloromethane and a saturated aqueous solution of sodium bicarbonate.

Yield: 420 mg (86% of theory)

Mass spectrometry (ESI$^+$): m/z=266/268 [M+H]$^+$

HPLC (Method 3): Retention time=0.782 min.

Intermediate 4.10b

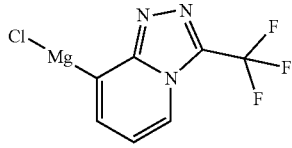

(3-Trifluoromethyl-[1,2,4]triazolo[4,3-a]pyridin-8-yl)magnesium Chloride

Analogously to intermediate 4.1a the following compound is obtained by starting from intermediate 4.10a 8-Bromo-3-trifluoromethyl-[1,2,4]triazolo[4,3-a]pyridine and isopropylmagnesium chloride lithiumchloride complex (1.3 M solution) at −45° C.

Intermediate 4.11a

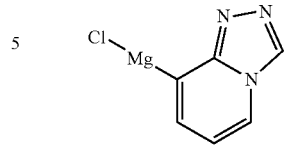

([1,2,4]triazolo[4,3-a]pyridin-8-yl)magnesium Chloride

Analogously to intermediate 4.1a the following compound is obtained by starting from 8-Bromo-[1,2,4]triazolo[4,3-a]pyridine and isopropylmagnesium chloride lithiumchloride complex (1.3 M solution) at −45° C.

Yield: 0.27 g (100% of theory)

Mass spectrometry (ESI$^+$): m/z=120 [M+H]$^+$ quenched with water

HPLC (Method 3): Retention time=0.212 min.

Intermediate 4.12a

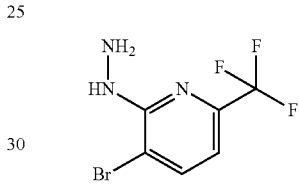

3-Bromo-2-hydrazinyl-6-(trifluoromethyl)pyridine

3-Bromo-2-chloro-6-trifluoromethyl-pyridine (0.975 g; 3.74 mmol) is dissolved in 5 mL of ethanol. Hydrazin monohydrate (0.765 mL; 14.98 mmol) is added and the mixture is stirred at 100° over night. The mixture is allowed to cool to room temperature. The precipitate is filtered and dried at 55° C.

Yield: 0.76 g (80% of theory)

Mass spectrometry (ESI$^+$): m/z=256/258 [M+H]$^+$

HPLC (Method 3): Retention time=0.694 min.

Intermediate 4.12b

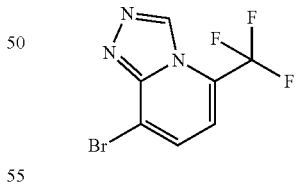

8-Bromo-5-trifluoromethyl-[1,2,4]triazolo[4,3-a]pyridine

Analogously to intermediate 4.9b the following compound is obtained by starting from intermediate 4.12a 3-Bromo-2-hydrazinyl-6-(trifluoromethyl)pyridine and formic acid instead of acetic acid.

Yield: 220 mg (54% of theory)

Mass spectrometry (ESI$^+$): m/z=266/268 [M+H]$^+$

HPLC (Method 3): Retention time=0.764 min

Intermediate 4.12c

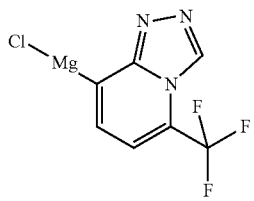

(5-Trifluoromethyl-[1,2,4]triazolo[4,3-a]pyridin-8-yl)magnesium Chloride

Analogously to intermediate 4.1a the following compounds is obtained by starting from intermediate 4.12b 8-Bromo-5-trifluoromethyl-[1,2,4]triazolo[4,3-a]pyridine and isopropylmagnesium chloride lithiumchloride complex (1.3 M solution) at −35° C.

Intermediate 4.13a

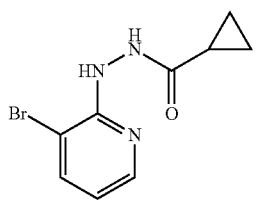 [SMILES: O=C(NNc1ncccc1Br)C1CC1]

N'-(3-bromopyridin-2-yl)cyclopropanecarbohydrazide

Intermediate 4.9a 3-Bromo-2-hydrazinylpyridine (0.50 g; 2.659 mmol), Cyclopropane-carbonyl chloride (0.241 mL; 2.659 mmol), N,N-Diisopropylethylamine (0.920 mL; 5.318 mmol) and 5 mL dichloromethane are stirred at 0° C. for 2.5 h. The mixture is concentrated under reduced pressure.

Yield: 0.75 g (110% of theory)
Mass spectrometry (ESI⁺): m/z=256/258 [M+H]⁺
HPLC (Method 3): Retention time=0.635 min.

Intermediate 4.13b

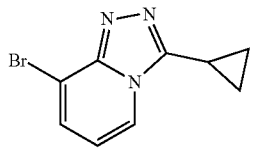 [SMILES: Brc1cccn2c(C3CC3)nnc12]

8-Bromo-3-cyclopropyl-[1,2,4]triazolo[4,3-a]pyridine

Analogously to intermediate 4.9b the following compound is obtained by starting from intermediate 4.13a N'-(3-bromopyridin-2-yl)cyclopropanecarbohydrazide and phosphorus oxychloride instead of acetic acid. The residue is purified by reverse phase chromatography (modifier: trifluoroacetic acid).

Yield: 0.74 g (106% of theory)
Mass spectrometry (ESI⁺): m/z=238/240 [M+H]⁺
HPLC (Method 3): Retention time=0.671 min.

Intermediate 4.13c

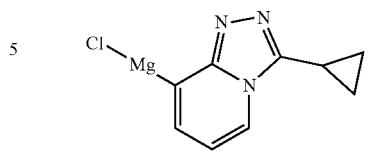

(3-Cyclopropyl-[1,2,4]triazolo[4,3-a]pyridin-8-yl)-magnesium Chloride

Analogously to intermediate 4.1a the following compound is obtained by starting from intermediate 4.13b 8-Bromo-3-cyclopropyl-[1,2,4]triazolo[4,3-a]pyridine and isopropylmagnesium chloride lithiumchloride complex (1.3 M solution) at −45° C.

Intermediate 4.14a

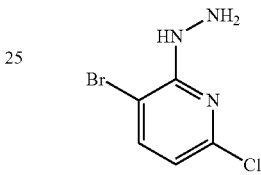

3-Bromo-6-chloro-2-hydrazinylpyridine

Analogously to intermediate 4.12a the following compound is obtained by starting from 3-Bromo-6-chloro-2-fluoro-pyridine Yield: 0.08 g (72% of theory)
Mass spectrometry (ESI⁺): m/z=222 [M+H]⁺
HPLC (Method 3): Retention time=0.526 min.

Intermediate 4.14b

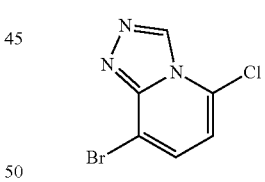

8-Bromo-5-chloro-[1,2,4]triazolo[4,3-a]pyridine

Intermediate 4.14a 3-Bromo-6-chloro-2-hydrazinylpyridine (2.637 g; 11.85 mmol) is dissolved in 30 mL dichloromethane. Trimethyl orthoformate (5.187 mL; 47.41 mmol) is added. The mixture is stirred for 1.25 h. Trifluoroacetic acid (0.914 mL; 11.85 mmol) is added. The mixture is stirred at room temperature over night and concentrated under reduced pressure. The residue is purified by silica gel chromatography (eluent: cyclohexane/ethyl acetate 0->35%).

Yield: 1.94 g (63% of theory)
Mass spectrometry (ESI⁺): m/z=232 [M+H]⁺
HPLC (Method 3): Retention time=0.659 min.

Intermediate 4.14c

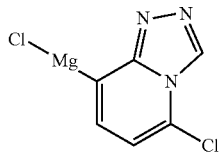

(5-Chloro[1,2,4]triazolo[4,3-a]pyridin-8-yl)-magnesium Chloride

Analogously to intermediate 4.1a the following compound is obtained by starting from intermediate 4.14b 8-Bromo-5-chloro-[1,2,4]triazolo[4,3-a]pyridine and isopropylmagnesium chloride lithiumchloride complex (1.3 M solution) at −45° C.

Intermediate 4.15a

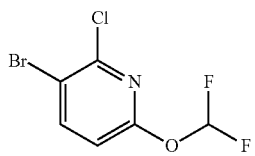 [SMILES: FC(F)Oc1ccc(Br)c(Cl)n1]

3-Bromo-2-chloro-6-difluoromethoxy-pyridine

5-Bromo-6-chloro-pyridin-2-ol (1.0 g; 4.8 mmol), sodium chloro-difluoro-acetate (1.5 g; 9.6 mmol) and potassium carbonate (0.8 g; 6.0 mmol) were dissolved in a mixture of water/DMF (2.0 mL: 20 mL). The mixture was stirred at 100° C. for 2 h, then extracted twice with ethyl acetate. The combined organic phase was dried by passing through a phase separator cartridge and concentrated.

Yield: 1.21 g (97% of theory)
Mass spectrometry (EI): m/z=257 [M*]+
HPLC (Method 3): Retention time=1.069 min.

Intermediate 4.15b

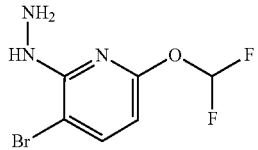 [SMILES: NNc1nc(OC(F)F)ccc1Br]

3-Bromo-6-(difluoromethoxy)-2-hydrazinylpyridine

Analogously to intermediate 4.12a the following compound is obtained by starting from intermediate 4.15a 3-Bromo-2-chloro-6-difluoromethoxy-pyridine.

Yield: 0.61 g (51% of theory)
Mass spectrometry (ESI+): m/z=254/256 [M+H]+
HPLC (Method 2): Retention time=0.692 min.

Intermediate 4.15c

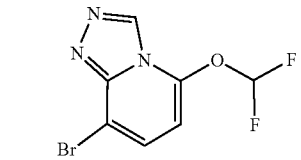 [SMILES: FC(F)Oc1ccc(Br)c2nncn12]

8-Bromo-5-difluoromethoxy-[1,2,4]triazolo[4,3-a]pyridine

Analogously to intermediate 4.14b the following compound is obtained by starting from intermediate 4.15b 3-Bromo-6-(difluoromethoxy)-2-hydrazinylpyridine. The mixture is concentrated and then purified by reverse phase chromatography-HPLC (modifier: trifluoroacetic acid). The residue is dissolved in methanol, exchanger resin is added and stirred for 15 min, filtered and concentrated.

Yield: 0.39 g (45% of theory)
Mass spectrometry (ESI+): m/z=264/266 [M+H]+
HPLC (Method 2): Retention time=0.734 min.

Intermediate 4.15d

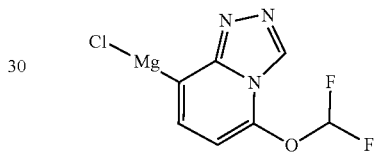

[5-(Difluoromethoxy)-[1,2,4]triazolo[4,3-a]pyridine-8-yl]-magnesium Chloride

Analogously to intermediate 4.1a the following compound is obtained by starting from intermediate 4.15c 8-Bromo-5-difluoromethoxy-[1,2,4]triazolo[4,3-a]pyridine and isopropylmagnesium chloride lithiumchloride complex (1.3 M solution) at −45° C.

Intermediate 4.16a

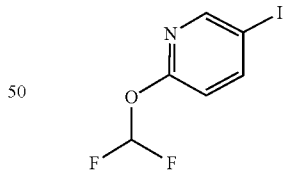

2-Difluoromethoxy-5-iodopyridine

5-Iodo-pyridin-2-ol (6.5 g; 29.4 mmol) is suspended in 100 mL of acetonitrile. Sodium hydride (3.47 g; 79 mmol) is added and the mixture is stirred for a few minutes. Difluoro-fluorosulfonyl-acetic acid (5.17 mL; 50.0 mmol) is added and the reaction is stirred at room temperature for 30 minutes. The reaction is quenched with water and concentrated. The reaction mixture is suspended in water and extracted three times with ethyl acetate. The organic layer is dried over a membrane filter and concentrated.

Yield: 7.96 g (99% of theory)

Mass spectrometry (ESI⁺): m/z=Not observed [M+H]⁺
HPLC (Method 3): Retention time=1.051 min.
Intermediate 4.16b

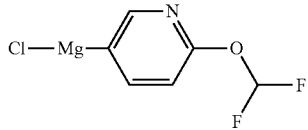

(2-Difluoromethoxy-pyridin-5-yl)magnesium Chloride

Analogously to intermediate 4.1a the following compound is obtained by starting from intermediate 4.16a 2-Difluoromethoxy-5-iodopyridine and isopropylmagnesium chloride lithiumchloride complex (1.3 M solution) at −60° C.

Intermediate 4.17a

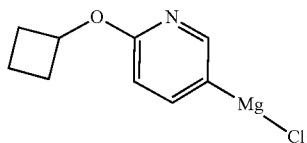

(2-Cyclobutoxy-pyridin-5-yl)magnesium Chloride

Analogously to intermediate 4.1a the following compound is obtained by starting from 5-Bromo-2-cyclobutoxy-pyridine and isopropylmagnesium chloride lithiumchloride complex (1.3 M solution) at −35° C.

Intermediate 4.18a

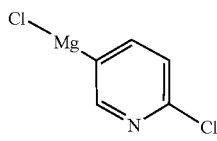

(2-Chloro-pyridin-5-yl)magnesium Chloride

Analogously to intermediate 4.1a the following compound is obtained by starting from 5-Bromo-2-chloro-pyridine and isopropylmagnesium chloride lithiumchloride complex (1.3 M solution) at −35° C.

Intermediate 4.19a

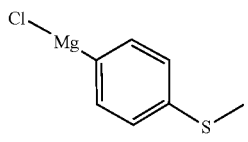

(4-Methylsulfanylphenyl)-magnesium Chloride

Analogously to intermediate 4.1a the following compound is obtained by starting from 4-Iodothioanisole and isopropylmagnesium chloride lithiumchloride complex (14%) at −50° C.

Intermediate 4.20a

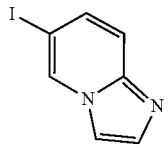

6-Iodo-imidazo[1,2-a]pyridine

2-Amino-5-iodopyridine (6.35 g; 28.858 mmol), Chloroacetaldehyde (50% in water) (4.215 mL; 33.186 mmol) and 70 mL Ethanol are refluxed over night. The mixture is concentrated and dissolved in water and dichloromethane. Saturated aqueous solution of sodium carbonate is added. The organic phase is separated and dried over magnesium sulfate and concentrated. The residue is crystallized from 2-Methoxy-2-methylpropane and petroleum ether (1/2).
Yield: 6.69 g (95% of theory)
Mass spectrometry (ESI⁺): m/z=245 [M+H]⁺

Intermediate 4.20b

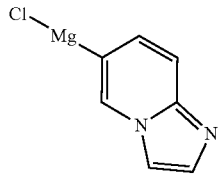

(Imidazo[1,2-a]pyridin-6-yl)-magnesium Chloride

Analogously to intermediate 4.1a the following compound is obtained by starting from intermediate 4.20a 6-Iodo-imidazo[1,2-a]pyridine and isopropylmagnesium chloride lithiumchloride complex (1.3 M solution) at −45° C.

Intermediate 4.21a

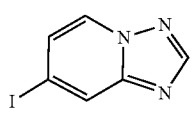

7-Iodo-[1,2,4]triazolo[1,5-a]pyridine

Analogously to intermediate 4.7a the following compound is obtained by starting from 7-Bromo[1,2,4]triazolo[1,5-a]pyridine.
Yield: 0.39 g (63% of theory)
Mass spectrometry (ESI⁺): m/z=246 [M+H]⁺
HPLC (Method 1): Retention time=0.700 min.

Intermediate 4.21b

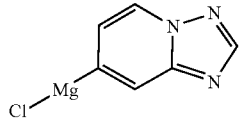

([1,2,4]Triazolo[1,5-a]pyridin-7-yl)-magnesium Chloride

Analogously to intermediate 4.1a the following compound is obtained by starting from intermediate 4.21a 7-Iodo-[1,2,4]triazolo[1,5-a]pyridine and isopropylmagnesium chloride lithiumchloride complex (1.3 M solution) at −60° C.

Intermediate 4.22a

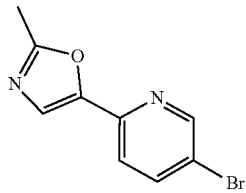

5-Bromo-2-(2-methyl-1,3-oxazol-5-yl)pyridine

The reaction is carried out under nitrogen atmosphere. To a solution of Iodo benzene diacetate (40.250 g; 0.125 mol) in 500 mL acetonitrile, trifluoromethanesulfonic acid (37.500 g; 0.250 mol) is added. The mixture is stirred for 1 hour. Then 1-(5-Bromopyridin-2-yl)ethan-1-one (25.000 g; 0.125 mol) is added. The mixture is stirred for 4 hours under reflux. The mixture is cooled to room temperature and poured into saturated aqueous sodium bicarbonate solution and extracted with dichloromethane. The organic layer is washed with brine, dried over magnesium sulfate, filtered and concentrated. The mixture is purified by reverse phase chromatography-HPLC.

Yield: 2.0 g (7% of theory)
Mass spectrometry (ESI⁺): m/z=239/241 [M+H]⁺

Intermediate 4.22b

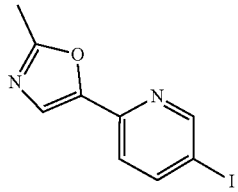

5-Iodo-2-(2-methyl-1,3-oxazol-5-yl)-pyridine

Analogously to intermediate 4.7a the following compound is obtained by starting from 5-Bromo-2-(2-methyl-oxazol-5-yl)-pyridine.

Yield: 0.53 g (88% of theory)
Mass spectrometry (ESI⁺): m/z=287 [M+H]⁺
HPLC (Method 1): Retention time=0.872 min.

Intermediate 4.22c

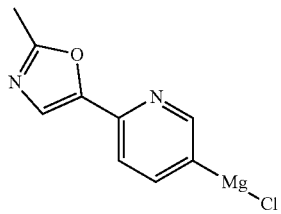

[2-(2-Methyl-1,3-oxazol-5-yl)pyridin-5-yl]-magnesium chloride

Analogously to intermediate 4.1a the following compound is obtained by starting from intermediate 4.22b 5-Iodo-2-(2-methyl-1,3-oxazol-5-yl)-pyridine and isopropylmagnesium chloride lithiumchloride complex (1.3 M solution) at −60° C.

Intermediate 4.23a

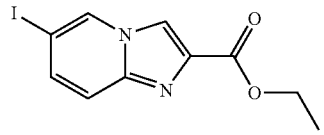

Ethyl-6-iodo-imidazo[1,2-a]pyridine-2-carboxylate

Analogously to intermediate 4.7a the following compound is obtained by starting from Ethyl-6-bromo-imidazo[1,2-a]pyridine-2-carboxylate.

Yield: 0.35 g (59% of theory)
Mass spectrometry (ESI⁺): m/z=317 [M+H]⁺
HPLC (Method 1): Retention time=0.835 min.

Intermediate 4.23b

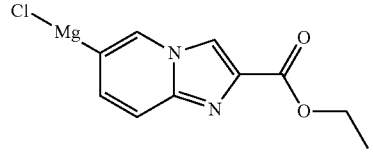

(2-Ethoxycarbonylimidazo[1,2-a]pyridin-6-yl)-magnesium Chloride

Analogously to intermediate 4.1a the following compound is obtained by starting from intermediate 4.23a Ethyl-6-iodo-imidazo[1,2-a]pyridine-2-carboxylate and isopropylmagnesium chloride lithiumchloride complex (1.3 M solution) at −60° C.

Intermediate 4.24a

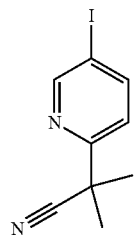

2-(5-Iodo-pyridin-2-yl)-2-methyl-propanenitrile

2-Bromo-5-iodo-pyridine (1.00 g; 3.522 mmol) and Isobutyronitrile (0.317 mL; 3.522 mmol) are dissolved in 10 mL of Toluol. Sodium bis(trimethylsilyl)amide 1 M solution in tetrahydrofuran (3.522 mL; 3.522 mmol) is added at 0° C. The mixture is stirred at room temperature over night and then 30 minutes at 100° C. The mixture is diluted with ethyl acetate and washed with a half saturated aqueous solution of sodium bicarbonate. The organic phase is dried and concentrated.

Yield: 0.90 g (94% of theory)

Mass spectrometry (ESI⁺): m/z=273 [M+H]⁺
HPLC (Method 3): Retention time=1.013 min.
Intermediate 4.24b

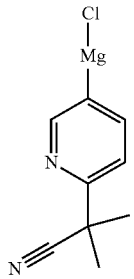

2-[5-(Chloromagnesio)pyridin-2-yl]-2-methylpropanenitrile

Analogously to intermediate 4.1a the following compound is obtained by starting from intermediate 4.24a 2-(5-Iodo-pyridin-2-yl)-2-methyl-propanenitrile and isopropylmagnesium chloride lithiumchloride complex (1.3 M solution) at −60° C.

Intermediate 4.25a

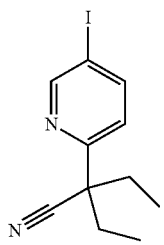

2-Ethyl-2-(5-iodo-pyridin-2-yl)-butanenitrile

Analogously to intermediate 4.24a the following compound is obtained by starting from 2-Bromo-5-iodo-pyridine and 2-Ethyl-butyronitrile in tetrahydrofuran instead of toluol.
Yield: 0.51 g (95% of theory)
Mass spectrometry (ESI⁺): m/z=301 [M+H]⁺
HPLC (Method 1): Retention time=1.121 min.
Intermediate 4.25b

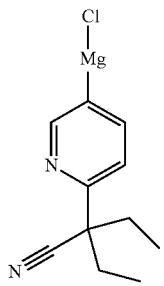

2-[5-(Chloromagnesio)pyridin-2-yl]-2-ethylbutanenitrile

Analogously to intermediate 4.1a the following compound is obtained by starting from intermediate 4.25a 2-Ethyl-2-(5-iodo-pyridin-2-yl)-butanenitrile and isopropylmagnesium chloride lithiumchloride complex (1.3 M solution) at −45° C.

Intermediate 4.26a

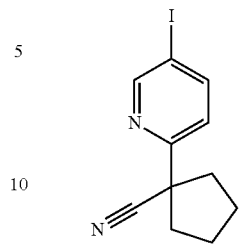

1-(5-Iodo-pyridin-2-yl)-cyclopentane-1-carbonitrile

Analogously to intermediate 4.24a the following compound is obtained by starting from 2-Bromo-5-iodo-pyridine and cyclopentanecarbonitrile.
Yield: 0.46 g (86% of theory)
Mass spectrometry (ESI⁺): m/z=299 [M+H]⁺
HPLC (Method 3): Retention time=1.086 min.
Intermediate 4.26b

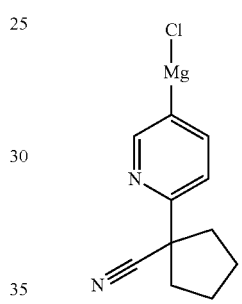

1-[5-(Chloromagnesio)pyridin-2-yl]cyclopentane-1-carbonitrile

Analogously to intermediate 4.1a the following compound is obtained by starting from intermediate 4.26a 1-(5-Iodo-pyridin-2-yl)-cyclopentane-1-carbonitrile and isopropylmagnesium chloride lithiumchloride complex (1.3 M solution) at −45° C.
Intermediate 4.27a

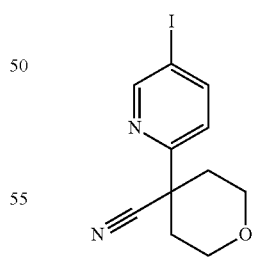

4-(5-Iodopyridin-2-yl)oxane-4-carbonitrile

Analogously to intermediate 4.24a the following compound is obtained by starting from 2-Bromo-5-iodo-pyridine and Tetrahydro-pyran-4-carbonitrile.
Yield: 0.40 g (73% of theory)
Mass spectrometry (ESI⁺): m/z=315 [M+H]⁺
HPLC (Method 3): Retention time=0.959 min.

Intermediate 4.27b

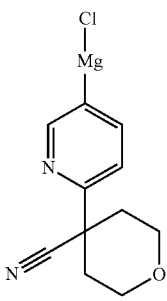

4-[5-(Chloromagnesio)pyridin-2-yl]oxane-4-carbonitrile

Analogously to intermediate 4.1a the following compound is obtained by starting from intermediate 4.27a 4-(5-Iodopyridin-2-yl)oxane-4-carbonitrile and isopropylmagnesium chloride lithiumchloride complex (1.3 M solution) at −45° C.

Intermediate 4.28a

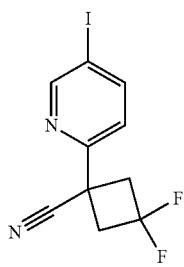

3,3-Difluoro-1-(5-iodo-pyridin-2-yl)-cyclobutane-1-carbonitrile

Analogously to intermediate 4.24a the following compound is obtained by starting from 2-Bromo-5-iodo-pyridine and 3,3-difluoro-cyclobutanecarbonitrile in tetrahydrofuran instead of toluol.

Yield: 0.58 g (93% of theory)
Mass spectrometry (ESI⁺): m/z=321 [M+H]⁺
HPLC (Method 1): Retention time=1.056 min.
Intermediate 4.28b

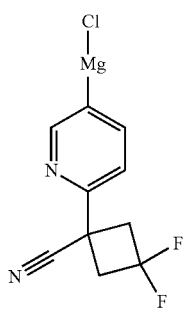

1-[5-(Chloromagnesio)pyridin-2-yl]-3,3-difluorocyclobutane-1-carbonitrile

Analogously to intermediate 4.1a the following compound is obtained by starting from intermediate 4.28a 3,3-Difluoro-1-(5-iodo-pyridin-2-yl)-cyclobutane-1-carbonitrile and isopropylmagnesium chloride lithiumchloride complex (1.3 M solution) at −45° C.

Intermediate 4.29a

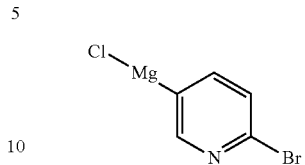

2-Bromo-5-(chloromagnesio)pyridine

Analogously to intermediate 4.1a the following compound is obtained by starting from 2-Bromo-5-iodopyridine and isopropylmagnesium chloride lithiumchloride complex (1.3 M solution) at −60° C.

Intermediate 4.30a

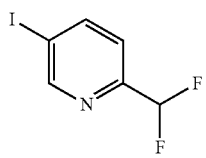

2-Difluoromethyl-5-iodo-pyridine

Analogously to intermediate 4.7a the following compound is obtained by starting from 5-Bromo-2-difluoromethyl-pyridine.

Yield: 0.61 g (99% of theory)
Mass spectrometry (ESI⁺): m/z=256 [M+H]⁺
HPLC (Method 3): Retention time=0.931 min.
Intermediate 4.30b

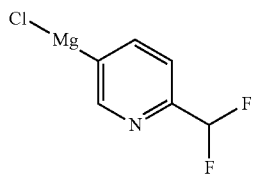

5-(Chloromagnesio)-2-(difluoromethyl)pyridine

Analogously to intermediate 4.1a the following compound is obtained by starting from intermediate 4.30a 2-Difluoromethyl-5-iodo-pyridine and isopropylmagnesium chloride lithiumchloride complex (1.3 M solution) at −60° C.

Intermediate 4.31a

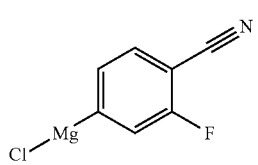

4-(Chloromagnesio)-2-fluorobenzonitrile

Analogously to intermediate 4.1a the following compound is obtained by starting from 2-Fluoro-4-iodobenzonitrile and isopropylmagnesium chloride lithiumchloride complex (1.3 M solution) at −65° C.
Intermediate 4.32a

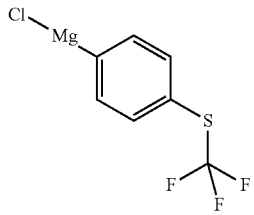

[4-(Trifluoromethylsulfanyl)phenyl]-magnesium Chloride

Analogously to intermediate 4.1a the following compound is obtained by starting from 4-[(Trifluoromethyl)thio]iodobenzene and isopropylmagnesium chloride lithiumchloride complex (1.3 M solution) at −50° C.
Intermediate 4.33a

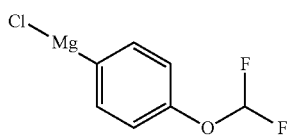

[4-(Difluoromethoxy)phenyl]-magnesium Chloride

Analogously to intermediate 4.1a the following compound is obtained by starting from 4-(Difluoromethoxy)iodobenzene and isopropylmagnesium chloride lithiumchloride complex (1.3 M solution) at −55° C.
Intermediate 4.34a

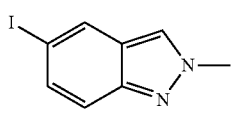

5-Iodo-2-methyl-2H-indazole

Analogously to intermediate 4.7a the following compound is obtained by starting from 5-Bromo-2-methyl-2H-indazole.
Yield: 0.53 g (87% of theory)
Mass spectrometry (ESI+): m/z=259 [M+H]+
HPLC (Method 3): Retention time=0.926 min.
Intermediate 4.34b

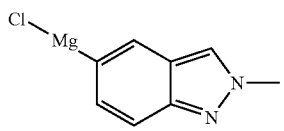

5-(Chloromagnesio)-2-methyl-2H-indazole

Analogously to intermediate 4.1a the following compound is obtained by starting from 5-Iodo-2-methyl-2H-indazole and isopropylmagnesium chloride lithiumchloride complex (1.3 M solution) at −60° C.
Intermediate 4.35a

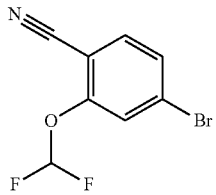 [SMILES: N#Cc1ccc(Br)cc1OC(F)F]

4-Bromo-2-difluoromethoxy-benzonitrile

Analogously to intermediate 4.15a the following compound is obtained by starting from 4-Bromo-2-hydroxybenzonitrile and sodium chloro-difluoro-acetate.
Yield: 1.00 g (100% of theory)
Mass spectrometry (EI): m/z=247 [M*]+
HPLC (Method 1): Retention time=1.025 min.
Intermediate 4.35b

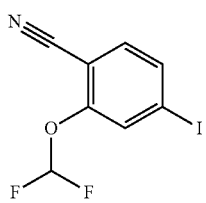 [SMILES: N#Cc1ccc(I)cc1OC(F)F]

2-Difluoromethoxy-4-iodo-benzonitrile

Analogously to intermediate 4.7a the following compound is obtained by starting from intermediate 4.35a 4-Bromo-2-difluoromethoxy-benzonitrile.
Yield: 1.04 g (87% of theory)
HPLC (Method 3): Retention time=1.001 min.
Intermediate 4.35c

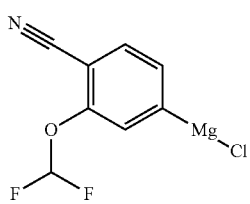

[4-Cyano-3-(difluoromethoxy)phenyl]-magnesium Chloride

Analogously to intermediate 4.1a the following compound is obtained by starting from intermediate 4.35b 2-Difluoromethoxy-4-iodo-benzonitrile and isopropylmagnesium chloride lithiumchloride complex (1.3 M solution) at −65° C.

Intermediate 4.36a

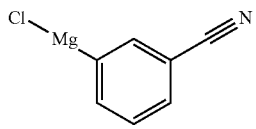

(3-Cyanophenyl)-magnesium Chloride

Analogously to intermediate 4.1a the following compound is obtained by starting from 3-Iodo-benzonitrile and isopropylmagnesium chloride lithiumchloride complex (1.3 M solution) at −70° C.

Intermediate 4.37a

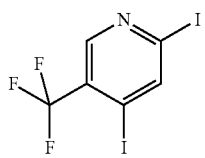 [SMILES: FC(F)(F)c1cnc(I)cc1I]

2,4-Diiodo-5-trifluoromethyl-pyridine 2,4-Dichloro-5-trifluoromethyl-pyridine (0.500 g; 2.315 mmol) is dissolved in 4 mL acetonitrile. Sodium iodide (0.867 g; 5.787 mmol) and acetyl chloride (0.197 mL; 2.778 mmol) are added. The mixture is stirred at 50° C. over night. The mixture is diluted with ethyl acetate. The phases are separated. The organic phase is washed with a saturated aqueous solution of sodium bicarbonate, a saturated aqueous solution of sodium thiosulfate and a saturated aqueous solution of sodium chloride. The organic phase is dried and concentrated under reduced pressure.

Yield: 900 mg (97% of theory)

Mass spectrometry (ESI$^+$): m/z=400 [M+H]$^+$

HPLC (Method 4): Retention time=1.048 min.

Intermediate 4.37b

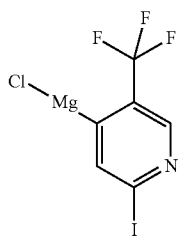

4-(Chloromagnesio)-2-iodo-5-(trifluoromethyl)pyridine

Analogously to intermediate 4.1a the following compound is obtained by starting from intermediate 4.37a 2,4-Diiodo-5-trifluoromethyl-pyridine and isopropylmagnesium chloride lithiumchloride complex (1.3 M solution) at −55° C.

Intermediate 4.38a

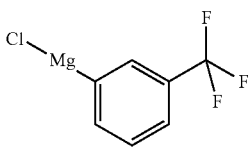

[3-(Trifluoromethyl)phenyl]-magnesium Chloride

Analogously to intermediate 4.1a the following compound is obtained by starting from 3-iodobenzotrifluoride and isopropylmagnesium chloride lithiumchloride complex (1.3 M solution) at −60° C.

Intermediate 4.39a

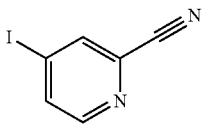

4-Iodo-pyridine-2-carbonitrile

Analogously to intermediate 4.7a the following compound is obtained by starting from 4-Bromopyridine-2-carbonitrile. Stirred at 110° C. for 20 h. Add ammonia 32% and then put the reaction to water and extract with dichloromethane, dried with sodium sulfate and concentrated.

Yield: 2.50 g (100% of theory)

Mass spectrometry (ESI$^+$): m/z=231 [M+H]$^+$

HPLC (Method 3): Retention time=0.834 min.

Intermediate 4.39b

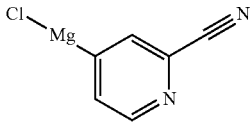

4-(Chloromagnesio)pyridine-2-carbonitrile

Analogously to intermediate 4.1a the following compound is obtained by starting from intermediate 4.39a 4-Iodo-pyridine-2-carbonitrile and isopropylmagnesium chloride lithiumchloride complex (1.3 M solution) at −70° C.

Intermediate 4.40a

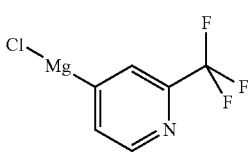

4-(Chloromagnesio)-2-(trifluoromethyl)pyridine

Analogously to intermediate 4.1a the following compound is obtained by starting from 4-Iodo-3-trifluoromethyl-pyridine and isopropylmagnesium chloride lithiumchloride complex (1.3 M solution) at −70° C.
Intermediate 4.41a

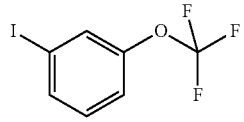 [SMILES: FC(F)(F)Oc1cccc(I)c1]

1-Iodo-3-trifluoromethoxy-benzene

Analogously to intermediate 4.7a the following compound is obtained by starting from 3-(Trifluoromethoxy) bromobenzene. Stirred at 110° C. for 20 h. Add ammonia 32% and then put the reaction to water and extract with dichloromethane, dried with sodium sulfate and concentrated.

Yield: 1.20 g (100% of theory)
Intermediate 4.41b

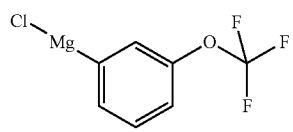

[3-(Trifluoromethoxy)phenyl]-magnesium Chloride

Analogously to intermediate 4.1a the following compound is obtained by starting from intermediate 4.41a 1-Iodo-3-trifluoromethoxy-benzene and isopropylmagnesium chloride lithiumchloride complex (1.3 M solution) at −65° C.
Intermediate 4.42a

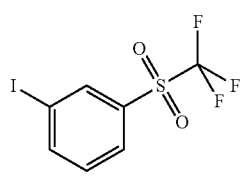 [SMILES: O=S(=O)(c1cccc(I)c1)C(F)(F)F]

1-Iodo-3-trifluoromethanesulfonyl-benzene 3-(Trifluoromethylsulfonyl)aniline (1.000 g; 4.441 mmol) suspended in hydrochloric acid (2 M aqueous solution) (8.881 mL; 17.763 mmol) and cooled to 0° C. Sodium nitrite is added (0.337 g; 4.885 mmol) in 7.5 mL water and reaction mixture is stirred for 20 minute at 0-5° C. Sodium iodide (1.331 g; 8.881 mmol) in 7.5 mL water is added dropwise and reaction mixture is stirred for 10 minutes at 0° C. A half saturated aqueous solution of ammonium chloride is added and the mixture is extracted twice with dichloromethane. The organic phase is dried with sodium sulfate and concentrated under reduced pressure. The residue is put on silica gel and purified by silica gel chromatography (eluent: cyclohexane/ethyl acetate 0%->20%).

Yield: 1.24 g (83% of theory)
Mass spectrometry (ESI$^+$): m/z=336 [M+H]$^+$
HPLC (Method 3): Retention time=1.135 min.

Intermediate 4.42b

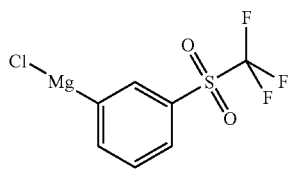

[3-(Trifluoromethylsulfonyl)phenyl]-magnesium Chloride

Analogously to intermediate 4.1a the following compound is obtained by starting from intermediate 4.42a 1-iodo-3-trifluoromethanesulfonyl-benzene and isopropylmagnesium chloride lithiumchloride complex (1.3 M solution) at −65° C.
Intermediate 4.43a

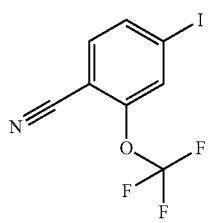 [SMILES: N#Cc1ccc(I)cc1OC(F)(F)F]

4-Iodo-2-trifluoromethoxy-benzonitrile

Analogously to intermediate 4.7a the following compound is obtained by starting from 4-bromo-2-trifluoromethoxy-benzonitrile and stirred at 110° C. over night. Aqueous ammonia (32%) is added, reaction mixture is poured into water and extracted with dichloromethane, dried with sodium sulfate and concentrated.

Yield: 203 mg (69% of theory)
Mass spectrometry (EI): m/z=313 [M]+
HPLC (Method 1): Retention time=1.055 min.

Intermediate 4.43b

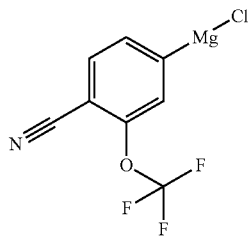

4-(Chloromagnesio)-2-(trifluoromethoxy)benzonitrile

Analogously to intermediate 4.1a the following compound is obtained by starting from intermediate 4.43a 4-iodo-2-trifluoromethoxy-benzonitrile and isopropylmagnesium chloride lithiumchloride complex (1.3 M solution) at −55° C.

Intermediate 4.44a

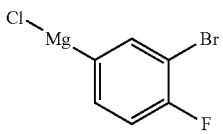

(3-Bromo-4-fluoro-phenyl)-magnesium Chloride

Analogously to intermediate 4.1a the following compound is obtained by starting from 2-bromo-1-fluoro-4-iodobenzene and isopropylmagnesium chloride lithiumchloride complex (1.3 M solution) at −60° C.

Intermediate 4.45a

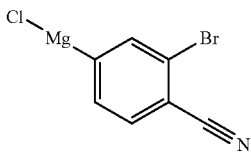

(3-Bromo-4-cyano-phenyl)-magnesium Chloride

Analogously to intermediate 4.1a the following compound is obtained by starting from 2-bromo-4-iodobenzonitrile and isopropylmagnesium chloride lithiumchloride complex (1.3 M solution) at −65° C.

Intermediate 4.46a

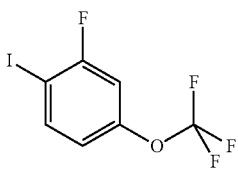 [SMILES: Fc1cc(OC(F)(F)F)ccc1I]

2-Fluoro-1-iodo-4-trifluoromethoxy-benzene

Analogously to intermediate 4.7a the following compound is obtained by starting from 1-bromo-2-fluoro-4-(trifluoromethoxy)benzene and stirred at 110° C. over night. Ammonia 32% solution in water and water are added, the mixture is extracted with dichloromethane, dried with magnesium sulfate and concentrated.

Yield: 1.30 g (52% of theory)
Mass spectrometry (EI): m/z=306 [M*]$^+$
HPLC (Method 2): Retention time=1.196 min.

Intermediate 4.46b

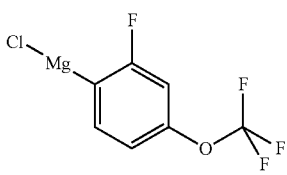

[2-Fluoro-4-(trifluoromethoxy)phenyl]-magnesium Chloride

Analogously to intermediate 4.1a the following compound is obtained by starting from intermediate 4.46a 2-fluoro-1-iodo-4-trifluoromethoxy-benzene and isopropylmagnesium chloride lithiumchloride complex (1.3 M solution) at −50° C.

Intermediate 4.47a

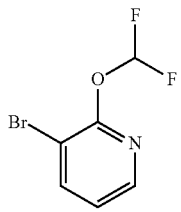 [SMILES: FC(F)Oc1ncccc1Br]

3-Bromo-2-difluoromethoxy-pyridine

Analogously to intermediate 4.16a the following compound is obtained by starting from 3-bromo-2-hydroxypyridine and difluoro-fluorosulfonyl-acetic acid.

Yield: 450 mg (32% of theory)
Mass spectrometry (ESI$^+$): m/z=224 [M+H]$^+$
HPLC (Method 2): Retention time=1.009 min.

Intermediate 4.47b

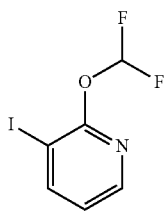 [SMILES: FC(F)Oc1ncccc1I]

2-Difluoromethoxy-3-iodo-pyridine

Analogously to intermediate 4.7a the following compound is obtained by starting from intermediate 4.47a 3-bromo-2-difluoromethoxy-pyridine. Extracted with ethyl acetate and a half saturated aqueous solution of sodium bicarbonate. The organic phases are dried with sodium sulfate and concentrated. The mixture is purified by reverse phase chromatography-HPLC (modifier: ammonium hydroxide).

Yield: 370 mg (71% of theory)
Mass spectrometry (ESI$^+$): m/z=272 [M+H]$^+$
HPLC (Method 2): Retention time=1.031 min.

Intermediate 4.47c

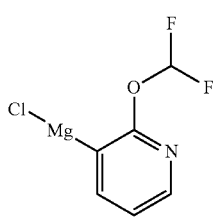

[2-(Difluoromethoxy)pyridine-3-yl]-magnesium Chloride

Analogously to intermediate 4.1a the following compound is obtained by starting from intermediate 4.47b 2-difluoromethoxy-3-iodo-pyridine and isopropylmagnesium chloride lithiumchloride complex (1.3 M solution) at −56° C.

Intermediate 4.48a

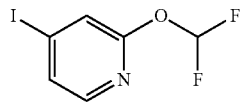 [SMILES: FC(F)Oc1cc(I)ccn1]

2-Difluoromethoxy-4-iodo-pyridine

Analogously to intermediate 4.7a the following compound is obtained by starting from 4-bromo-2-(difluoromethoxy)pyridine and stirred at 110° C. for 20 h. Aqueous ammonia (32%) is added, the reaction mixture is poured into water and extracted with dichloromethane, dried with sodium sulfate and concentrated.

Yield: 1.20 g (99% of theory)

HPLC (Method 3): Retention time=1.059 min.

Intermediate 4.48b

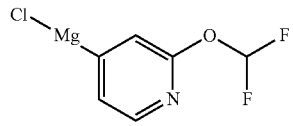

[2-(Difluoromethoxy)pyridine-4-yl]-magnesium Chloride

Analogously to intermediate 4.1a the following compound is obtained by starting from intermediate 4.48a 2-difluoromethoxy-4-iodo-pyridine and isopropylmagnesium chloride lithiumchloride complex (1.3 M solution) at −70° C.

Intermediate 4.49a

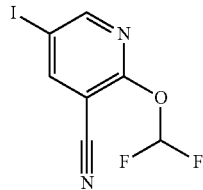 [SMILES: N#Cc1cc(I)cnc1OC(F)F]

2-(Difluoromethoxy)-5-iodopyridine-3-carbonitrile

Analogously to intermediate 4.16a the following compound is obtained by starting from 2-hydroxy-5-iodo-nicotinonitrile and difluoro-fluorosulfonyl-acetic acid. The mixture is purified by reverse phase chromatography-HPLC (modifier: ammonium hydroxide).

Yield: 271 mg (56% of theory)

Mass spectrometry (ESI⁻): m/z=295 [M−H]⁻

HPLC (Method 1): Retention time=0.954 min.

Intermediate 4.49b

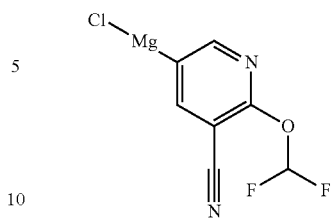

[5-Cyano-6-(difluoromethoxy)pyridine-3-yl]-magnesium Chloride

Analogously to intermediate 4.1a the following compound is obtained by starting from intermediate 4.49a 2-(difluoromethoxy)-5-iodopyridine-3-carbonitrile and isopropylmagnesium chloride lithiumchloride complex (1.3 M solution) at −65° C.

Intermediate 4.64a

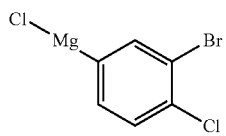

(3-Bromo-4-chloro-phenyl)magnesium Chloride

Analogously to intermediate 4.1a the following compound is obtained by starting from 2-bromo-1-chloro-4-iodobenzene and isopropylmagnesium chloride lithiumchloride complex (1.3 M solution) at −50° C.

Intermediate 4.65a

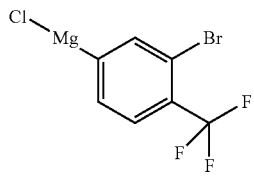

3-Bromo-4-(trifluoromethyl)phenyl]-magnesium Chloride

Analogously to intermediate 4.1a the following compound is obtained by starting from 2-bromo-4-iodo-1-(trifluoromethyl)benzene and isopropylmagnesium chloride lithiumchloride complex (1.3 M solution) at −50° C.

Preparation of Final Compounds:

Procedure 5

Compound 1.1

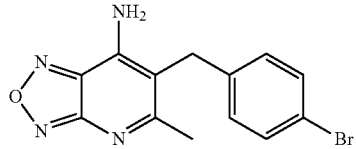 [SMILES: Cc1nc2nonc2c(N)c1Cc1ccc(Br)cc1]

6-[(4-Bromophenyl)methyl]-5-methyl-[1,2,5]oxadiazolo[3,4-b]pyridin-7-amine

This reaction is carried out under nitrogen atmosphere. To a mixture of 4-amino-1,2,5-oxadiazole-3-carbonitrile (225 mg; 2.04 mmol) and intermediate 1.1b 4-(4-bromo-phenyl)-butan-2-one (464 mg; 2.04 mmol) in 10 mL of toluene, tin(IV)chloride (478 µL; 4.09 mmol) is added dropwise. The mixture is stirred for 30 minutes at room temperature and for 2 hours at reflux. The solvent is evaporated and the residue is taken up in sodium hydroxide (1 M aqueous solution) and ethyl acetate and filtered off. The aqueous layer is extracted three times with ethyl acetate. The combined organic layers are dried over sodium sulfate, filtrated and concentrated under reduced pressure. The residue is purified by reverse phase chromatography-HPLC (modifier: NH₄OH).

Yield: 8.2 mg (1.3% of theory)

Mass spectrometry (ESI⁺): m/z=319/321 [M+H]⁺

HPLC (Method 1): Retention time=0.978 min.

Compound 1.2

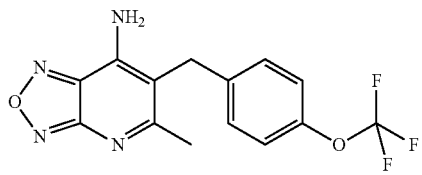 [SMILES: Cc1nc2nonc2c(N)c1Cc1ccc(OC(F)(F)F)cc1]

5-Methyl-6-{[4-(trifluoromethoxy)phenyl]methyl}-[1,2,5]oxadiazolo[3,4-b]pyridin-7-amine Analogously to compound 1.1 the following compound is obtained by starting from 4-amino-1,2,5-oxadiazole-3-carbonitrile and intermediate 1.2b 4-(4-trifluoromethoxy-phenyl)-butan-2-one.

Mass spectrometry (ESI⁺): m/z=325 [M+H]⁺

HPLC (Method 1): Retention time=1.019 min.

Compound 1.3

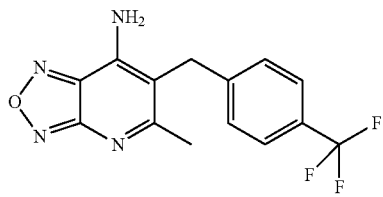 [SMILES: Cc1nc2nonc2c(N)c1Cc1ccc(C(F)(F)F)cc1]

5-Methyl-6-{[4-(trifluoromethyl)phenyl]methyl}-[1,2,5]oxadiazolo[3,4-b]pyridin-7-amine Analogously to compound 1.1 the following compound is obtained by starting from 4-amino-1,2,5-oxadiazole-3-carbonitrile and intermediate 1.3b 4-(4-trifluoromethyl-phenyl)-butan-2-one.

Mass spectrometry (ESI⁺): m/z=309 [M+H]⁺

HPLC (Method 1): Retention time=0.993 min.

Compound 1.4

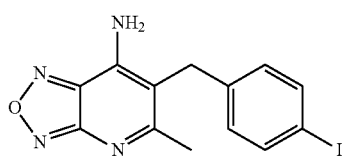 [SMILES: Cc1nc2nonc2c(N)c1Cc1ccc(I)cc1]

6-[(4-Iodophenyl)methyl]-5-methyl-[1,2,5]oxadiazolo[3,4-b]pyridin-7-amine

Analogously to compound 1.1 the following compound is obtained by starting from 4-amino-1,2,5-oxadiazole-3-carbonitrile and intermediate 1.4b 4-(4-iodo-phenyl)-butan-2-one. The mixture is purified by reverse phase chromatography-HPLC (modifier: trifluoroacetic acid).

Mass spectrometry (ESI⁺): m/z=367 [M+H]⁺

HPLC (Method 2): Retention time=0.891 min.

Compound 2.1

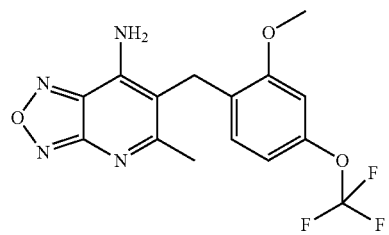 [SMILES: COc1cc(OC(F)(F)F)ccc1Cc1c(C)nc2nonc2c1N]

6-{[2-Methoxy-4-(trifluoromethoxy)phenyl]methyl}-5-methyl-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.1a 4-(2-methoxy-4-trifluoromethoxy-phenyl)-butan-2-one. The mixture is purified by reverse phase chromatography-HPLC (modifier: NH₄OH) and a second time by an achiral column (column: Viridis2EthylPhyridine 5 µm 30×100 mm; eluent: CO₂/methanol 5%->40%)

Mass spectrometry (ESI⁺): m/z=355 [M+H]⁺

HPLC (Method 3): Retention time=1.027 min.

Compound 2.2

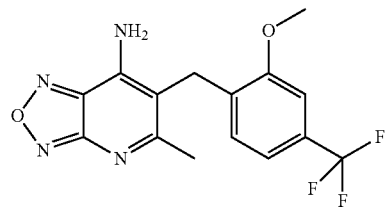 [SMILES: COc1cc(C(F)(F)F)ccc1Cc1c(C)nc2nonc2c1N]

6-{[2-Methoxy-4-(trifluoromethyl)phenyl]methyl}-5-methyl-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.2a 4-(2-methoxy-4-trifluoromethyl-phenyl)-butan-2-one. The mixture is purified by reverse phase chromatography-HPLC (modifier: trifluoroacetic acid) and a second time by an achiral column (column: Viridis2EthylPhyridine 5 µm 30×100 mm; eluent: CO₂/methanol 5%->40%)

Mass spectrometry (ESI⁺): m/z=339 [M+H]⁺

HPLC (Method 3): Retention time=1.048 min.

Compound 2.3

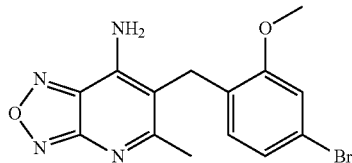 [SMILES: COc1cc(Br)ccc1Cc1c(C)nc2nonc2c1N]

6-[(4-Bromo-2-methoxyphenyl)methyl]-5-methyl-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.3b 4-(4-bromo-2-methoxy-phenyl)-butan-2-one. The mixture is purified by reverse phase chromatography-HPLC (modifier: trifluoroacetic acid) and a second time by an achiral column (column: Viridis2EthylPhyridine 5 μm 30×100 mm; eluent: CO₂/methanol 5%->40%)

Mass spectrometry (ESI⁺): m/z=349/351 [M+H]⁺
HPLC (Method 3): Retention time=1.001 min.

Compound 2.4

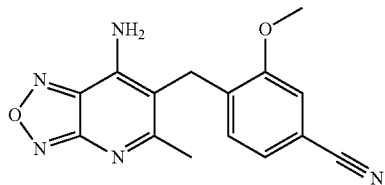 [SMILES: COc1cc(C#N)ccc1Cc1c(C)nc2nonc2c1N]

4-({7-Amino-5-methyl-[1,2,5]oxadiazolo[3,4-b]pyridin-6-yl}methyl)-3-methoxybenzonitrile Analogously to compound 1.1 the following compound is obtained by starting from 4-amino-1,2,5-oxadiazole-3-carbonitrile and intermediate 2.4a 3-methoxy-4-(3-oxo-butyl)-benzonitrile. The mixture is purified by reverse phase chromatography-HPLC (modifier: trifluoroacetic acid) and a second time by an achiral column (column: Viridis2EthylPhyridine 5 μm 30×100 mm; eluent: CO₂/methanol 5%->40%)

Mass spectrometry (ESI⁺): m/z=296 [M+H]⁺
HPLC (Method 3): Retention time=0.9 min.

Compound 2.5

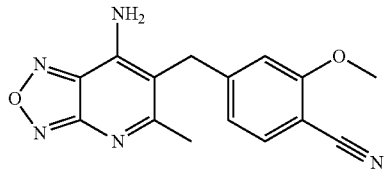 [SMILES: COc1cc(Cc2c(C)nc3nonc3c2N)ccc1C#N]

4-({7-Amino-5-methyl-[1,2,5]oxadiazolo[3,4-b]pyridin-6-yl}methyl)-2-methoxybenzonitrile Analogously to compound 1.1 the following compound is obtained by starting from 4-amino-1,2,5-oxadiazole-3-carbonitrile and intermediate 2.5a 2-methoxy-4-(3-oxo-butyl)-benzonitrile. The mixture is purified by reverse phase chromatography-HPLC (modifier: trifluoroacetic acid) and a second time by an achiral column (column: Viridis2EthylPhyridine 5 μm 30×100 mm; eluent: CO₂/methanol 5%->40%)

Mass spectrometry (ESI⁺): m/z=296 [M+H]⁺
HPLC (Method 3): Retention time=0.864 min.

Compound 2.6

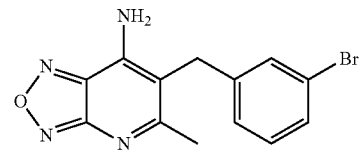 [SMILES: Cc1nc2nonc2c(N)c1Cc1cccc(Br)c1]

6-[(3-Bromophenyl)methyl]-5-methyl-[1,2,5]oxadiazolo[3,4-b]pyridin-7-amine

Analogously to compound 1.1 the following compound is obtained by starting from 4-amino-1,2,5-oxadiazole-3-carbonitrile and intermediate 2.6a 4-(3-bromo-phenyl)-butan-2-one. The mixture is purified by reverse phase chromatography-HPLC (modifier: trifluoroacetic acid).

Mass spectrometry (ESI⁺): m/z=319/321 [M+H]⁺
HPLC (Method 3): Retention time=0.978 min.

Compound 2.7

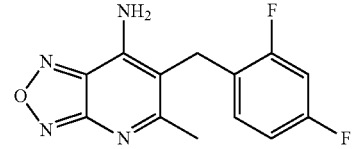 [SMILES: Cc1nc2nonc2c(N)c1Cc1ccc(F)cc1F]

6-[(2,4-Difluorophenyl)methyl]-5-methyl-[1,2,5]oxadiazolo[3,4-b]pyridin-7-amine

Analogously to compound 1.1 the following compound is obtained by starting from 4-amino-1,2,5-oxadiazole-3-carbonitrile and intermediate 2.7a 4-(2,4-difluoro-phenyl)-butan-2-one. The mixture is purified by reverse phase chromatography-HPLC (modifier: trifluoroacetic acid).

Mass spectrometry (ESI⁺): m/z=277 [M+H]⁺
HPLC (Method 2): Retention time=0.809 min.

Compound 2.8

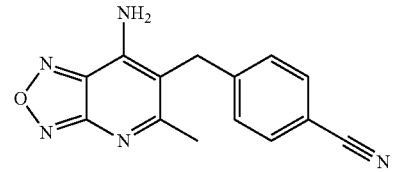 [SMILES: Cc1nc2nonc2c(N)c1Cc1ccc(C#N)cc1]

4-({7-Amino-5-methyl-[1,2,5]oxadiazolo[3,4-b]pyridin-6-yl}methyl)benzonitrile

Analogously to compound 1.1 the following compound is obtained by starting from 4-amino-1,2,5-oxadiazole-3-carbonitrile and intermediate 2.8a 4-(3-oxo-butyl)-benzonitrile. The mixture is purified by reverse phase chromatography-HPLC (modifier: trifluoroacetic acid).

Mass spectrometry (ESI⁺): m/z=266 [M+H]⁺
HPLC (Method 2): Retention time=0.721 min.
Compound 2.9

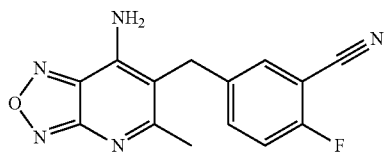 [SMILES: Cc1nc2nonc2c(N)c1Cc1ccc(F)c(C#N)c1]

5-({7-Amino-5-methyl-[1,2,5]oxadiazolo[3,4-b]pyridin-6-yl}methyl)-2-fluorobenzonitrile Analogously to compound 1.1 the following compound is obtained by starting from 4-amino-1,2,5-oxadiazole-3-carbonitrile and intermediate 2.9a 2-fluoro-5-(3-oxo-butyl)-benzonitrile. The mixture is purified by reverse phase chromatography-HPLC (modifier: trifluoroacetic acid).

Mass spectrometry (ESI⁺): m/z=284 [M+H]⁺
HPLC (Method 3): Retention time=0.864 min.
Compound 2.10

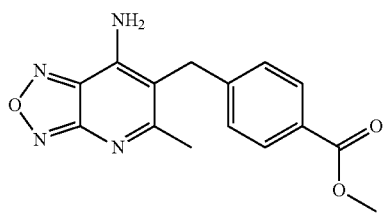 [SMILES: COC(=O)c1ccc(Cc2c(C)nc3nonc3c2N)cc1]

Methyl 4-({7-amino-5-methyl-[1,2,5]oxadiazolo[3,4-b]pyridin-6-yl}methyl)benzoate Analogously to compound 1.1 the following compound is obtained by starting from 4-amino-1,2,5-oxadiazole-3-carbonitrile and intermediate 2.10a methyl 4-(3-oxobutyl)benzoate. The mixture is purified by reverse phase chromatography-HPLC (modifier: trifluoroacetic acid).

Mass spectrometry (ESI⁺): m/z=299 [M+H]⁺
HPLC (Method 2): Retention time=0.772 min.
Compound 2.11

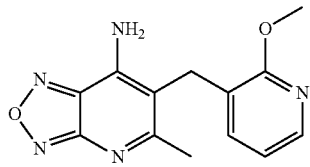 [SMILES: COc1ncccc1Cc1c(C)nc2nonc2c1N]

6-[(2-Methoxypyridin-3-yl)methyl]-5-methyl-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.11a 4-(2-methoxy-pyridin-3-yl)-butan-2-one. The mixture is purified by reverse phase chromatography-HPLC (modifier: trifluoroacetic acid).

Mass spectrometry (ESI⁺): m/z=272 [M+H]⁺
HPLC (Method 2): Retention time=0.677 min.
Compound 2.12

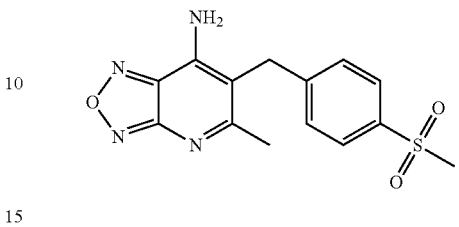

6-[(4-Methanesulfonylphenyl)methyl]-5-methyl-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.12a 4-(4-methanesulfonyl-phenyl)-butan-2-one. The mixture is purified by reverse phase chromatography-HPLC (modifier: trifluoroacetic acid).

Mass spectrometry (ESI⁺): m/z=319 [M+H]⁺
HPLC (Method 3): Retention time=0.719 min.
Compound 2.13

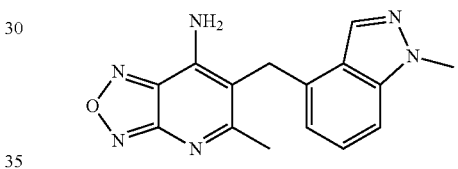

5-Methyl-6-[(1-methyl-1H-indazol-4-yl)methyl]-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.13a 4-(1-methyl-1H-indazol-4-yl)-butan-2-one. The mixture is purified by reverse phase chromatography-HPLC (modifier: trifluoroacetic acid).

Mass spectrometry (ESI⁺): m/z=295 [M+H]⁺
HPLC (Method 3): Retention time=0.822 min.
Compound 2.14

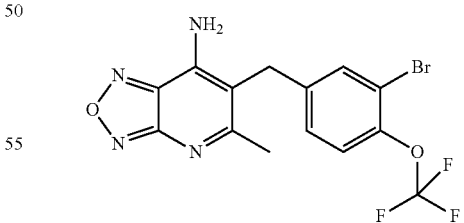

6-{[3-Bromo-4-(trifluoromethoxy)phenyl]methyl}-5-methyl-[1,2,5]oxadiazolo[3,4-b]pyridin-7-amine Analogously to compound 1.1 the following compound is obtained by starting from 4-amino-1,2,5-oxadiazole-3-carbonitrile and intermediate 2.14b 4-(3-bromo-4-trifluoromethoxy-phenyl)-butan-2-one.

Mass spectrometry (ESI⁺): m/z=403/405 [M+H]⁺
HPLC (Method 3): Retention time=1.081 min.
Compound 2.15

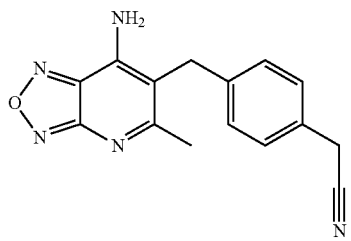 [SMILES: Cc1nc2nonc2c(N)c1Cc1ccc(CC#N)cc1]

2-[4-({7-Amino-5-methyl-[1,2,5]oxadiazolo[3,4-b]pyridin-6-yl}methyl)phenyl]acetonitrile Analogously to compound 1.1 the following compound is obtained by starting from 4-amino-1,2,5-oxadiazole-3-carbonitrile and intermediate 2.15c 2-[4-(3-oxo-butyl)-phenyl]-acetonitril.

Mass spectrometry (ESI⁺): m/z=280 [M+H]⁺
HPLC (Method 3): Retention time=0.803 min.
Compound 2.16

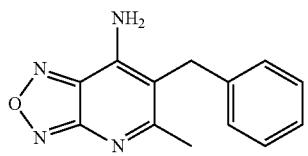 [SMILES: Cc1nc2nonc2c(N)c1Cc1ccccc1]

6-Benzyl-5-methyl-[1,2,5]oxadiazolo[3,4-b]pyridin-7-amine

Analogously to compound 1.1 the following compound is obtained by starting from 4-amino-1,2,5-oxadiazole-3-carbonitrile and 4-phenyl-2-butanone.

Mass spectrometry (ESI⁺): m/z=241 [M+H]⁺
HPLC (Method 1): Retention time=0.891 min
Procedure 6
Intermediate 3.1a

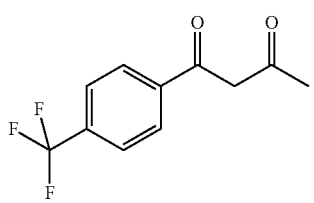 [SMILES: CC(=O)CC(=O)c1ccc(C(F)(F)F)cc1]

1-[4-(Trifluoromethyl)phenyl]butane-1,3-dione

1-[4-(Trifluoromethyl)phenyl]ethan-1-one (2 g; 10.63 mmol) is dissolved in 50 mL tetrahydrofurane and cooled to 0° C. Sodium hydride dispersion (60%; 1.275 g; 31.89 mmol) is added and reaction mixture is stirred for 30 minutes. At 0° C. ethyl acetate (waterfree 10.38 mL; 106.3 mmol) is added and the reaction mixture is stirred over night. The reaction is concentrated and then quenched with water, acidified with HCl (1 M aqueous solution) and extracted three times with ethyl acetate.

The organic layer is dried over sodium sulfate, filtrated and concentrated under reduced pressure. The residue is purified by silica gel chromatography (eluent: cyclohexane/ethyl acetate 0->30%).

Yield: 2.24 g (92% of theory)
Mass spectrometry (ESI-): m/z=229 [M-H]⁻
HPLC (Method 1): Retention time=0.679 min.
Compound 3.1

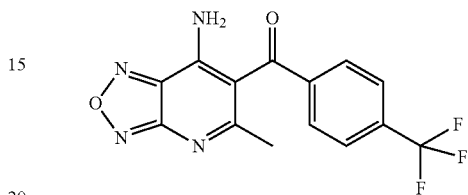

5-Methyl-6-[4-(trifluoromethyl)benzoyl]-[1,2,5]oxadiazolo[3,4-b]pyridin-7-amine

This reaction is carried out under nitrogen atmosphere. To a mixture of 4-amino-1,2,5-oxadiazole-3-carbonitrile (700 mg; 6.36 mmol) and intermediate 3.1a 1-[4-(trifluoromethyl)phenyl]butane-1,3-dione (2.295 g; 9.54 mmol) in 10 mL toluene, tin(IV)chloride (1.494 mL; 12.72 mmol) is added dropwise. The mixture is stirred for 30 minutes at room temperature and over night at reflux. The solvent is evaporated and the residue is purified by silica gel chromatography (eluent: cyclohexene/ethyl acetate 0->50%). The resulting product is dissolved in some dioxane and water is added. The generated solid was filtered, washed with water and dried.

Yield: 330 mg (16% of theory)
Mass spectrometry (ESI⁺): m/z=323 [M+H]⁺
HPLC (Method 1): Retention time=0.959 min.
Procedure 7
Compound 4.0

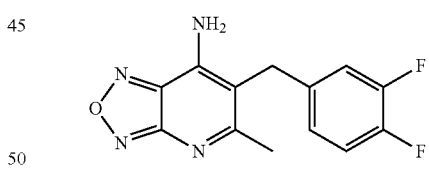

6-[(3,4-Difluorophenyl)methyl]-5-methyl-[1,2,5]oxadiazolo[3,4-b]pyridin-7-amine

The mixture is carried out under an argon atmosphere. Bromo-(3,4-difluorophenyl)-magnesium (3.63 mL; 1.81 mmol) in 1 mL tetrahydrofuran is cooled to -20° C. and intermediate 3c 6-chloromethyl-5-methyl-[1,2,5]oxadiazolo[3,4-b]pyridin-7-amine (100 mg; 0.45 mmol) in 2 mL tetrahydrofuran is added dropwise slowly. Due to incomplete conversion additional bromo-(3,4-difluorophenyl)magnesium (3 equivalents) in 1 mL tetrahydrofuran is added at -20° C. The mixture is purified by reverse phase chromatography-HPLC (modifier: first time trifluoroacetic acid and second time NH₄OH).

Yield: 14.0 mg (11% of theory)

Mass spectrometry (ESI⁺): m/z=277 [M+H]⁺
HPLC (Method 3): Retention time=0.923 min.
Compound 4.1

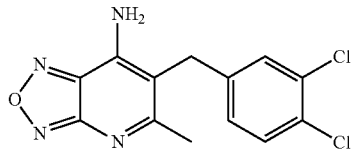 [SMILES: Cc1nc2nonc2c(N)c1Cc1ccc(Cl)c(Cl)c1]

6-[(3,4-Dichlorophenyl)methyl]-5-methyl-[1,2,5]
oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.1a 3,4-dichlorophenylmagnesium chloride. The mixture is purified by reverse phase chromatography-HPLC (modifier: trifluoroacetic acid).

Mass spectrometry (ESI⁺): m/z=309 [M+H]⁺
HPLC (Method 3): Retention time=1.010 min.
Compound 4.2

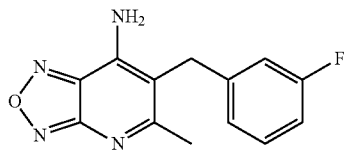 [SMILES: Cc1nc2nonc2c(N)c1Cc1cccc(F)c1]

6-[(3-Fluorophenyl)methyl]-5-methyl-[1,2,5]oxadi-
azolo[3,4-b]pyridin-7-amine

Analogously to compound 4.50 the following compound is obtained by starting from intermediate 3c 6-chloromethyl-5-methyl-[1,2,5]oxadiazolo[3,4-b]pyridin-7-amine and intermediate 4.2a (3-fluorophenyl)magnesium chloride.

Mass spectrometry (ESI⁺): m/z=259 [M+H]⁺
HPLC (Method 3): Retention time=0.900 min.
Compound 4.3

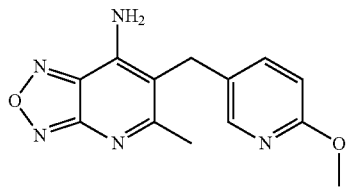 [SMILES: COc1ccc(Cc2c(C)nc3nonc3c2N)cn1]

6-[(6-Methoxypyridin-3-yl)methyl]-5-methyl-[1,2,5]
oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.3a (6-methoxypyridin-3-yl)magnesium chloride.

Mass spectrometry (ESI⁺): m/z=272 [M+H]⁺
HPLC (Method 3): Retention time=0.764 min.

Compound 4.4

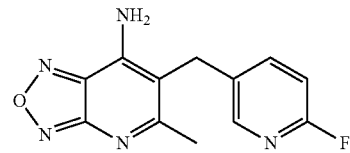 [SMILES: Cc1nc2nonc2c(N)c1Cc1ccc(F)nc1]

6-[(6-Fluoropyridin-3-yl)methyl]-5-methyl-[1,2,5]
oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.4a (6-fluoropyridin-3-yl)magnesium chloride. The mixture is cooled to −60° C. rather than 0° C. and is purified directly after being quenched. The mixture is purified by silica gel chromatography (eluent: cyclohexane/ethyl acetate 0%->50%).

Yield: 770 mg (67% of theory)
Mass spectrometry (ESI⁺): m/z=260 [M+H]⁺
HPLC (Method 1): Retention time=0.764 min.
Compound 4.5

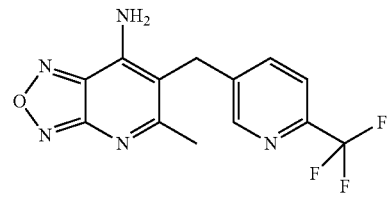 [SMILES: Cc1nc2nonc2c(N)c1Cc1ccc(C(F)(F)F)nc1]

5-Methyl-6-{[6-(trifluoromethyl)pyridin-3-yl]
methyl}-[1,2,5]oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.5a (6-trifluoromethylpyridin-3-yl)magnesium chloride. The mixture is cooled to −70° C. rather than 0° C. and is purified directly after being quenched. The mixture is purified by reverse phase chromatography-HPLC (modifier: ammonium hydroxide).

Yield: 18 mg (12% of theory)
Mass spectrometry (ESI⁺): m/z=310 [M+H]⁺
HPLC (Method 1): Retention time=0.862 min.
Compound 4.6

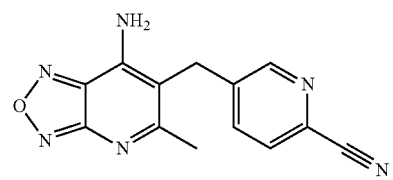 [SMILES: Cc1nc2nonc2c(N)c1Cc1ccc(C#N)nc1]

5-({7-Amino-5-methyl-[1,2,5]oxadiazolo[3,4-b]pyri-
din-6-yl}methyl)pyridine-2-carbonitrile Analogously to compound 4.50 the following compound is obtained by starting from intermediate 3c 6-chloromethyl- 5-methyl-[1,2,5]oxadiazolo[3,4-b]pyridin-7-amine and intermediate 4.6a (6-cyanopyridin-3-yl)magnesium chloride. The mixture is cooled to −65° C. rather than 0° C. and is purified directly after being quenched. The mixture is purified by reverse phase chromatography-HPLC (modifier: ammonium hydroxide).

Yield: 31 mg (23% of theory)
Mass spectrometry (ESI$^+$): m/z=267 [M+H]$^+$
HPLC (Method 1): Retention time=0.734 min.

Compound 4.7

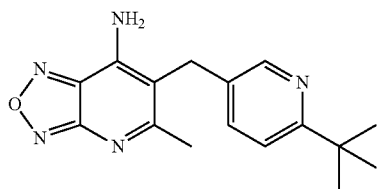 [SMILES: Cc1nc2nonc2c(N)c1Cc1ccc(C(C)(C)C)nc1]

6-[(6-tert-butylpyridine-3-yl)methyl]-5-methyl-[1,2,5]oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.7b (6-tert-butylpyridine-3-yl)magnesium chloride. The mixture is cooled to −65° C. rather than 0° C. and is purified directly after being quenched. The mixture is purified by reverse phase chromatography-HPLC (modifier: ammonium hydroxide).

Yield: 28 mg (19% of theory)
Mass spectrometry (ESI$^+$): m/z=298 [M+H]$^+$
HPLC (Method 1): Retention time=0.920 min.

Compound 4.8

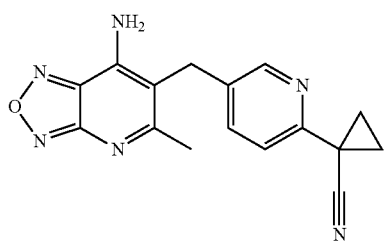 [SMILES: Cc1nc2nonc2c(N)c1Cc1ccc(C2(C#N)CC2)nc1]

1-[5-({7-Amino-5-methyl-[1,2,5]oxadiazolo[3,4-b]pyridin-6-yl}methyl)pyridin-2-yl]cyclopropane-1-carbonitrile Analogously to compound 4.50 the following compound is obtained by starting from intermediate 3c 6-chloromethyl-5-methyl-[1,2,5]oxadiazolo[3,4-b]pyridin-7-amine and intermediate 4.8c (6-(1-cyclopropanecarbonitrile)-pyridin-3-yl)magnesium chloride. The mixture is cooled to −65° C. rather than 0° C. and is purified directly after being quenched. The mixture is purified by silica gel chromatography (eluent: cyclohexane/ethyl acetate 0%->50%).

Yield: 260 mg (34% of theory)
Mass spectrometry (ESI$^+$): m/z=307 [M+H]$^+$
HPLC (Method 1): Retention time=0.828 min.

Compound 4.9

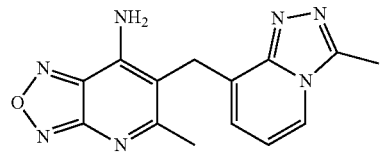 [SMILES: Cc1nc2nonc2c(N)c1Cc1cccn2c(C)nnc12]

5-Methyl-6-({3-methyl-[1,2,4]triazolo[4,3-a]pyridin-8-yl}methyl)-[1,2,5]oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.9c (3-cethyl-[1,2,4]triazolo[4,3-a]pyridine-8-yl)magnesium chloride. The mixture is cooled to −65° C. rather than 0° C. and is purified directly after being quenched. The mixture is purified by reverse phase chromatography-HPLC (modifier: ammonium hydroxide).

Yield: 30 mg (25% of theory)
Mass spectrometry (ESI$^+$): m/z=296 [M+H]$^+$
HPLC (Method 3): Retention time=0.677 min.

Compound 4.10

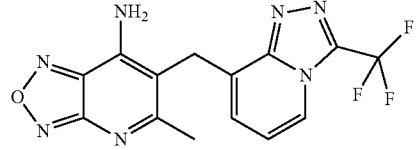 [SMILES: Cc1nc2nonc2c(N)c1Cc1cccn2c(C(F)(F)F)nnc12]

5-Methyl-6-({3-methyl-[1,2,4]triazolo[4,3-a]pyridin-8-yl}methyl)-[1,2,5]oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.10b (3-trifluoromethyl-[1,2,4]triazolo[4,3-a]pyridine-8-yl)magnesium chloride. The mixture is cooled to −65° C. rather than 0° C. and is purified directly after being quenched. The mixture is purified by reverse phase chromatography-HPLC (modifier: ammonium hydroxide). The product is then taken in MeCOH and filtered over a short pad of silica gel to remove ammonium salts.

Yield: 45 mg (32% of theory)
Mass spectrometry (ESI$^+$): m/z=350 [M+H]$^+$
HPLC (Method 1): Retention time=0.821 min.

Compound 4.11

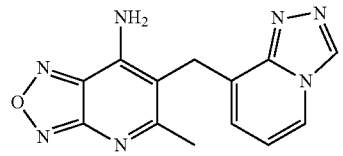 [SMILES: Cc1nc2nonc2c(N)c1Cc1cccn2cnnc12]

5-Methyl-6-({[1,2,4]triazolo[4,3-a]pyridin-8-yl}methyl)-[1,2,5]oxadiazolo[3,4-b]pyridin-7-amine Analogously to compound 4.50 the following compound is obtained by starting from intermediate 3c 6-chloromethyl- 5-methyl-[1,2,5]oxadiazolo[3,4-b]pyridin-7-amine and intermediate 4.11a ([1,2,4]triazolo[4,3-a]pyridine-8-yl)magnesium chloride. The mixture is cooled to −65° C. rather than 0° C. and is purified directly after being quenched. The mixture is purified by reverse phase chromatography-HPLC (modifier: ammonium hydroxide).

Yield: 15 mg (13% of theory)

Mass spectrometry (ESI⁺): m/z=282 [M+H]⁺

HPLC (Method 1): Retention time=0.639 min.

Compound 4.12

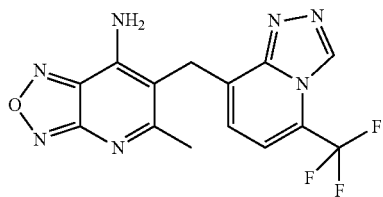 [SMILES: Cc1nc2nonc2c(N)c1Cc1ccc(C(F)(F)F)n2cnnc12]

5-Methyl-6-{[5-(trifluoromethyl)-[1,2,4]triazolo[4,3-a]pyridin-8-yl]methyl}-[1,2,5]oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.12c (5-trifluoromethyl-[1,2,4]triazolo[4,3-a]pyridine-8-yl)magnesium chloride. The mixture is cooled to −65° C. rather than 0° C. and is purified directly after being quenched. The mixture is purified by reverse phase chromatography-HPLC (modifier: trifluoroacetic acid).

Yield: 60 mg (36% of theory)

Mass spectrometry (ESI⁺): m/z=350 [M+H]⁺

HPLC (Method 1): Retention time=0.799 min.

Compound 4.13

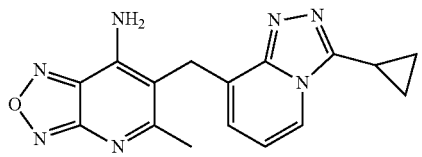 [SMILES: Cc1nc2nonc2c(N)c1Cc1cccn2c(C3CC3)nnc12]

6-({3-Cyclopropyl-[1,2,4]triazolo[4,3-a]pyridin-8-yl}methyl)-5-methyl-[1,2,5]oxadiazolo[3,4-b]pyridin-7-amine Analogously to compound 4.50 the following compound is obtained by starting from intermediate 3c 6-chloromethyl-5-methyl-[1,2,5]oxadiazolo[3,4-b]pyridin-7-amine and intermediate 4.13c (3-cyclopropyl-[1,2,4]triazolo[4,3-a]pyridine-8-yl)-magnesium chloride. The mixture is cooled to −65° C. rather than 0° C. and is purified directly after being quenched. The mixture is purified by reverse phase chromatography-HPLC (modifier: ammonium hydroxide).

Yield: 10 mg (6% of theory)

Mass spectrometry (ESI⁺): m/z=322 [M+H]⁺

HPLC (Method 1): Retention time=0.759 min.

Compound 4.14

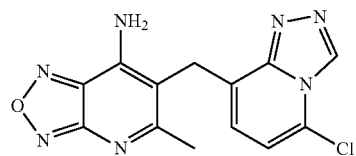 [SMILES: Cc1nc2nonc2c(N)c1Cc1ccc(Cl)n2cnnc12]

6-({5-Chloro-[1,2,4]triazolo[4,3-a]pyridin-8-yl}methyl)-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.14c (5-Chloro[1,2,4]triazolo[4,3-a]pyridine-8-yl)-magnesium chloride. The mixture is cooled to −65° C. rather than 0° C. and is extracted with ethyl acetate after being quenched with saturated aqueous solution of sodium bicarbonate. The organic phase is dried by being run through a phase separator cartridge and concentrated. The mixture is purified by reverse phase chromatography-HPLC (modifier: trifluoroacetic acid).

Yield: 16 mg (9% of theory)

Mass spectrometry (ESI⁺): m/z=316 [M+H]⁺

HPLC (Method 1): Retention time=0.717 min.

Compound 4.15

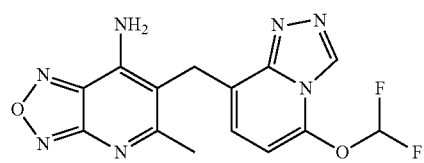 [SMILES: Cc1nc2nonc2c(N)c1Cc1ccc(OC(F)F)n2cnnc12]

6-{[5-(Difluoromethoxy)-[1,2,4]triazolo[4,3-a]pyridin-8-yl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.15d [5-(Difluoromethoxy)-[1,2,4]triazolo[4,3-a]pyridine-8-yl]-magnesium chloride. The mixture is cooled to −65° C. rather than 0° C. and is extracted with ethyl acetate after being quenched with saturated aqueous solution of sodium bicarbonate. The organic phase is dried by being run through a phase separator cartridge and concentrated. The mixture is purified by silica gel chromatography (eluent: cyclohexane/ethyl acetate 0%->30%; flushed with eluent: dichloromethane/methanol 1/1). The mixture is purified by reverse phase chromatography-HPLC (modifier: ammonium hydroxide).

Yield: 10 mg (5% of theory)

Mass spectrometry (ESI⁺): m/z=348 [M+H]⁺

HPLC (Method 1): Retention time=0.743 min.

Compound 4.16

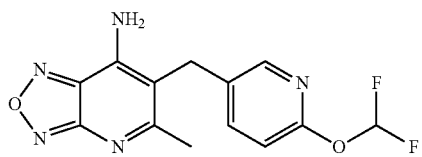 [SMILES: Cc1nc2nonc2c(N)c1Cc1ccc(OC(F)F)nc1]

6-{[6-(Difluoromethoxy)pyridin-3-yl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.16b (2-Difluoromethoxy-pyridin-5-yl)magnesium chloride. The mixture is cooled to –25° C. rather than 0° C. and is purified directly after being quenched. The product is then partitioned between ethyl acetate and a saturated aqueous solution of sodium bicarbonate. Solids present in the mixture are filtered and the organic phase is dried over magnesium sulfate and concentrated. The mixture is purified by reverse phase chromatography-HPLC (modifier: ammonium hydroxide). The product is further purified by silica gel chromatography (eluent: cyclohexane/ethyl acetate 0%->45%).

Yield: 2.19 g (41% of theory)

Mass spectrometry (ESI$^+$): m/z=308 [M+H]$^+$

HPLC (Method 1): Retention time=0.882 min.

Compound 4.17

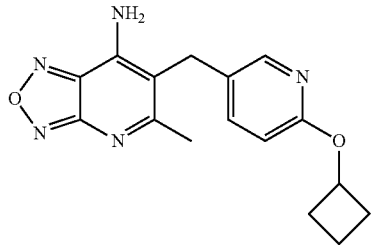 [SMILES: Cc1nc2nonc2c(N)c1Cc1ccc(OC2CCC2)nc1]

6-[(6-Cyclobutoxypyridin-3-yl)methyl]-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.17a (2-Cyclobutoxy-pyridine-5-yl)magnesium chloride. The mixture is cooled to –60° C. rather than 0° C. and is purified directly after being quenched. The mixture is purified by reverse phase chromatography-HPLC (modifier: ammonium hydroxide).

Yield: 18 mg (12% of theory)

Mass spectrometry (ESI$^+$): m/z=312 [M+H]$^+$

HPLC (Method 1): Retention time=0.874 min.

Compound 4.18

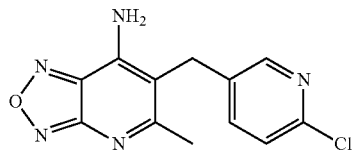 [SMILES: Cc1nc2nonc2c(N)c1Cc1ccc(Cl)nc1]

6-[(6-Chloropyridin-3-yl)methyl]-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.18a (2-Chloro-pyridin-5-yl)magnesium chloride. The mixture is cooled to –65° C. rather than 0° C. and is purified directly after being quenched. The mixture is purified by silica gel chromatography (eluent: cyclohexane/ethyl acetate 0%->50%).

Yield: 1.15 g (83% of theory)

Mass spectrometry (ESI$^+$): m/z=276 [M+H]$^+$

HPLC (Method 1): Retention time=0.800 min.

Compound 4.19

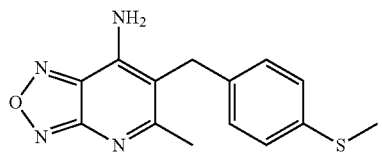 [SMILES: CSc1ccc(Cc2c(C)nc3nonc3c2N)cc1]

5-Methyl-6-{[4-(methylsulfanyl)phenyl]methyl}-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.19a (4-Methylsulfanylphenyl)-magnesium chloride. The mixture is cooled to –55° C. rather than 0° C. The Product is quenched with methanol instead of a saturated aqueous solution of sodium bicarbonate. The reaction mixture is concentrated under reduced pressure and then partitioned between dichloromethane and a half saturated aqueous solution of ammonium chloride. The organic phase is dried over magnesium sulfate and concentrated. The mixture is purified by reverse phase chromatography-HPLC (modifier: trifluoroacetic acid).

Yield: 70 mg (22% of theory)

Mass spectrometry (ESI$^+$): m/z=287 [M+H]$^+$

HPLC (Method 3): Retention time=0.946 min.

Compound 4.20

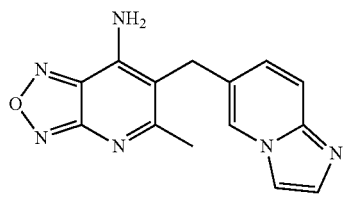 [SMILES: Cc1nc2nonc2c(N)c1Cc1ccc2nccn2c1]

6-Imidazo[1,2-a]pyridin-6-ylmethyl-5-methyl-[1,2,5]oxadiazolo[3,4-b]pyridin-7-ylamine Analogously to compound 4.50 the following compound is obtained by starting from intermediate 3c 6-Chloromethyl-5-methyl-[1,2,5]oxadiazolo[3,4-b]pyridin-7-amine and intermediate 4.20b (Imidazo[1,2-a]pyridin-6-yl)-magnesium chloride. The mixture is cooled to −65° C. rather than 0° C. and is extracted with ethyl acetate after being quenched with a half saturated aqueous solution of sodium bicarbonate. The organic phase is concentrated. The mixture is purified by reverse phase chromatography-HPLC (modifier: ammonium hydroxide).

Yield: 34 mg (24% of theory)
Mass spectrometry (ESI⁺): m/z=281 [M+H]⁺
HPLC (Method 1): Retention time=0.731 min.
Compound 4.21

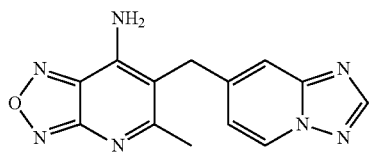 [SMILES: Cc1nc2nonc2c(N)c1Cc1ccn2ncnc2c1]

5-Methyl-6-({[1,2,4]triazolo[1,5-a]pyridin-7-yl}methyl)-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.21b ([1,2,4]Triazolo[1,5-a]pyridin-7-yl)-magnesium chloride. The mixture is cooled to −65° C. rather than 0° C. and is extracted with ethyl acetate after being quenched with a half saturated aqueous solution of sodium bicarbonate. The organic phase is concentrated. The mixture is purified by reverse phase chromatography-HPLC (modifier: ammonium hydroxide).

Yield: 29 mg (20% of theory)
Mass spectrometry (ESI⁺): m/z=282 [M+H]⁺
HPLC (Method 1): Retention time=0.652 min.
Compound 4.22

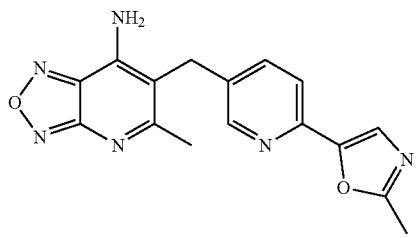 [SMILES: Cc1ncc(-c2ccc(Cc3c(C)nc4nonc4c3N)cn2)o1]

5-Methyl-6-{[6-(2-methyl-1,3-oxazol-5-yl)pyridin-3-yl]methyl}-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.22c [2-(2-Methyl-1,3-oxazol-5-yl)pyridin-5-yl]-magnesium chloride. The mixture is cooled to −65° C. rather than 0° C. and is purified directly after being quenched. The mixture is purified by reverse phase chromatography-HPLC (modifier: ammonium hydroxide)

Yield: 41 mg (25% of theory)
Mass spectrometry (ESI⁺): m/z=323 [M+H]⁺
HPLC (Method 1): Retention time=0.758 min.
Compound 4.23

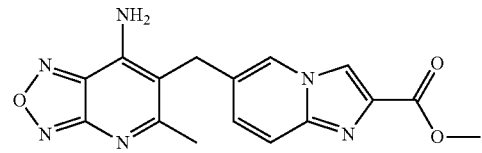 [SMILES: COC(=O)c1cn2cc(Cc3c(C)nc4nonc4c3N)ccc2n1]

Methyl 6-({7-amino-5-methyl-[1,2,5]oxadiazolo[3,4-b]pyridin-6-yl}methyl)imidazo[1,2-a]pyridine-2-carboxylate Analogously to compound 4.50 the following compound is obtained by starting from intermediate 3c 6-Chloromethyl-5-methyl-[1,2,5]oxadiazolo[3,4-b]pyridin-7-amine and intermediate 4.23b (2-Ethoxycarbonylimidazo[1,2-a]pyridin-6-yl)-magnesium chloride. The mixture is cooled to −65° C. rather than 0° C. and is purified directly after being quenched. The mixture is purified by reverse phase chromatography-HPLC (modifier: ammonium hydroxide)

Yield: 25 mg (14% of theory)
Mass spectrometry (ESI⁺): m/z=339 [M+H]⁺
HPLC (Method 1): Retention time=0.718 min.
Compound 4.24

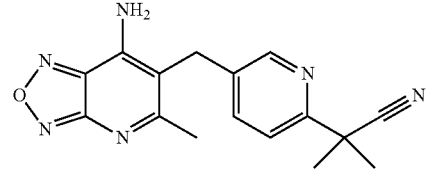 [SMILES: Cc1nc2nonc2c(N)c1Cc1ccc(C(C)(C)C#N)nc1]

2-[5-({7-Amino-5-methyl-[1,2,5]oxadiazolo[3,4-b]pyridin-6-yl}methyl)pyridin-2-yl]-2-methylpropanenitrile Analogously to compound 4.50 the following compound is obtained by starting from intermediate 3c 6-Chloromethyl-5-methyl-[1,2,5]oxadiazolo[3,4-b]pyridin-7-amine and intermediate 4.24b 2-[5-(Chloromagnesio)pyridin-2-yl]-2-methylpropanenitrile. The mixture is cooled to −65° C. rather than 0° C. and is extracted with ethyl acetate after being quenched with half saturated aqueous solution of sodium bicarbonate. The organic phase is concentrated. The mixture is purified by reverse phase chromatography-HPLC (modifier: ammonium hydroxide).

Yield: 55 mg (18% of theory)
Mass spectrometry (ESI⁺): m/z=309 [M+H]⁺
HPLC (Method 1): Retention time=0.816 min.
Compound 4.25

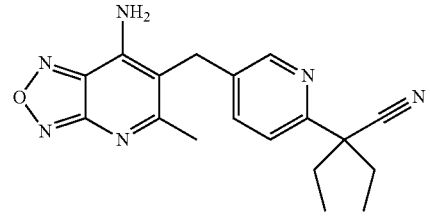 [SMILES: CCC(C#N)(CC)c1ccc(Cc2c(C)nc3nonc3c2N)cn1]

2-[5-({7-Amino-5-methyl-[1,2,5]oxadiazolo[3,4-b]pyridin-6-yl}methyl)pyridin-2-yl]-2-ethylbutanenitrile Analogously to compound 4.50 the following compound is obtained by starting from intermediate 3c 6-Chloromethyl-5-methyl-[1,2,5]oxadiazolo[3,4-b]pyridin-7-amine and intermediate 4.25b 2-[5-(Chloromagnesio)pyridin-2-yl]-2-ethylbutanenitrile. The mixture is cooled to −65° C. rather than 0° C. and is extracted with ethyl acetate after being quenched with saturated aqueous solution of sodium bicarbonate. The organic phase is concentrated. The mixture is purified by reverse phase chromatography-HPLC (modifier: ammonium hydroxide).

Yield: 81 mg (43% of theory)
Mass spectrometry (ESI+): m/z=337 [M+H]+
HPLC (Method 1): Retention time=0.894 min.
Compound 4.26

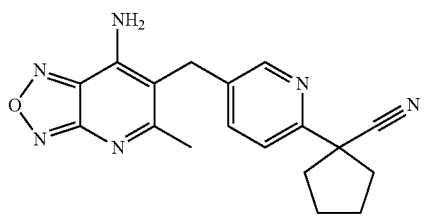 [SMILES: Cc1nc2nonc2c(N)c1Cc1ccc(C2(C#N)CCCC2)nc1]

1-[5-({7-Amino-5-methyl-[1,2,5]oxadiazolo[3,4-b]pyridin-6-yl}methyl)pyridin-2-yl]cyclopentane-1-carbonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.26b 1-[5-(Chloromagnesio)pyridin-2-yl]cyclopentane-1-carbonitrile. The mixture is cooled to −65° C. rather than 0° C. and is extracted with ethyl acetate after being quenched with half saturated aqueous solution of sodium bicarbonate. The organic phase is concentrated. The mixture is purified by reverse phase chromatography-HPLC (modifier: ammonium hydroxide).

Yield: 45 mg (24% of theory)
Mass spectrometry (ESI+): m/z=335 [M+H]+
HPLC (Method 3): Retention time=0.907 min.
Compound 4.27

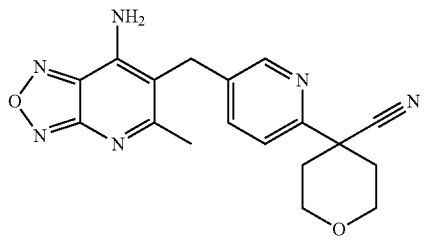 [SMILES: Cc1nc2nonc2c(N)c1Cc1ccc(C2(C#N)CCOCC2)nc1]

4-[5-({7-Amino-5-methyl-[1,2,5]oxadiazolo[3,4-b]pyridin-6-yl}methyl)pyridin-2-yl]oxane-4-carbonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.27b 4-[5-(Chloromagnesio)pyridin-2-yl]oxane-4-carbonitrile. The mixture is cooled to −65° C. rather than 0° C. and is extracted with ethyl acetate after being quenched with half saturated aqueous solution of sodium bicarbonate. The organic phase is concentrated. The mixture is purified by reverse phase chromatography-HPLC (modifier: ammonium hydroxide).

Yield: 54 mg (28% of theory)
Mass spectrometry (ESI+): m/z=351 [M+H]+
HPLC (Method 1): Retention time=0.777 min.
Compound 4.28

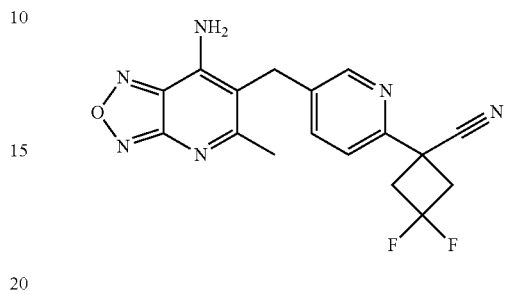

1-[5-({7-Amino-5-methyl-[1,2,5]oxadiazolo[3,4-b]Pyridin-6-yl}methyl)pyridin-2-yl]-3,3-difluorocyclobutane-1-carbonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.28b 1-[5-(Chloromagnesio)pyridin-2-yl]-3,3-difluorocyclobutane-1-carbonitrile. The mixture is cooled to −65° C. rather than 0° C. and is extracted with ethyl acetate after being quenched with half saturated aqueous solution of sodium bicarbonate. The organic phase is concentrated. The mixture is purified by reverse phase chromatography-HPLC (modifier: ammonium hydroxide).

Yield: 64 mg (32% of theory)
Mass spectrometry (ESI+): m/z=357 [M+H]+
HPLC (Method 1): Retention time=0.870 min.
Compound 4.29

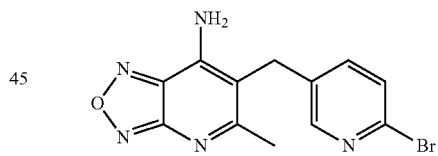

6-[(6-Bromopyridin-3-yl)methyl]-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.29a 2-Bromo-5-(chloromagnesio)pyridine. The mixture is cooled to −65° C. rather than 0° C. and is extracted with ethyl acetate after being quenched with half saturated aqueous solution of sodium bicarbonate. The organic phase is concentrated. The mixture is purified by silica gel chromatography (eluent: cyclohexane/ethyl acetate 0%->50%).

Yield: 0.51 g (32% of theory)
Mass spectrometry (ESI+): m/z=320 [M+H]+
HPLC (Method 3): Retention time=0.81 min.

Compound 4.30

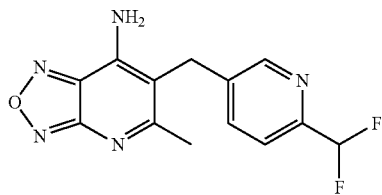 [SMILES: Cc1nc2nonc2c(N)c1Cc1ccc(C(F)F)nc1]

6-{[6-(Difluoromethyl)pyridin-3-yl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.30b 5-(Chloromagnesio)-2-(difluoromethyl)pyridine. The mixture is cooled to −25° C. rather than 0° C. and is extracted with ethyl acetate after being quenched with half saturated aqueous solution of sodium bicarbonate. The organic phase is concentrated. The mixture is purified by reverse phase chromatography-HPLC (modifier: ammonium hydroxide).

Yield: 0.12 g (84% of theory)
Mass spectrometry (ESI+): m/z=292 [M+H]+
HPLC (Method 1): Retention time=0.685 min.

Compound 4.31

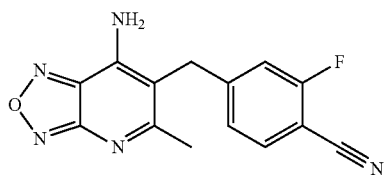 [SMILES: Cc1nc2nonc2c(N)c1Cc1ccc(C#N)c(F)c1]

4-({7-Amino-5-methyl-[1,2,5]oxadiazolo[3,4-b]pyridin-6-yl}methyl)-2-fluorobenzonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.31a 4-(Chloromagnesio)-2-fluorobenzonitrile. The mixture is cooled to −65° C. rather than 0° C. and is purified directly after being quenched. The mixture is purified by reverse phase chromatography-HPLC (modifier: ammonium hydroxide).

Yield: 52 mg (33% of theory)
Mass spectrometry (ESI+): m/z=284 [M+H]+
HPLC (Method 1): Retention time=0.828 min.

Compound 4.32

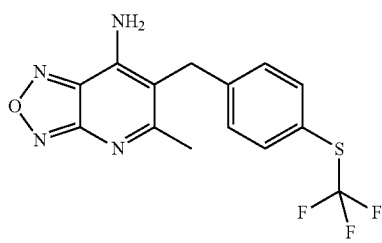 [SMILES: Cc1nc2nonc2c(N)c1Cc1ccc(SC(F)(F)F)cc1]

5-Methyl-6-({4-[(trifluoromethyl)sulfanyl]phenyl}methyl)-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.32a [4-(Trifluoromethylsulfanyl)phenyl]-magnesium chloride. The mixture is cooled to −65° C. rather than 0° C. The product is quenched with methanol instead of a saturated aqueous solution of sodium bicarbonate. The reaction mixture is concentrated under reduced pressure and then partitioned between dichloromethane and water. The organic phase is dried and concentrated. The mixture is purified by reverse phase chromatography-HPLC (modifier: ammonium hydroxide).

Yield: 72 mg (33% of theory)
Mass spectrometry (ESI+): m/z=341 [M+H]+
HPLC (Method 1): Retention time=1.023 min.

Compound 4.33

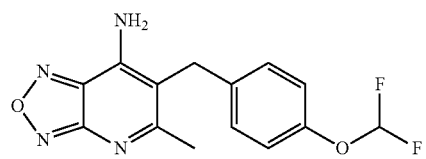 [SMILES: Cc1nc2nonc2c(N)c1Cc1ccc(OC(F)F)cc1]

6-{[4-(Difluoromethoxy)phenyl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.33a [4-(Difluoromethoxy)phenyl]-magnesium chloride. The mixture is cooled to −55° C. rather than 0° C. The Product is quenched with methanol instead of a saturated aqueous solution of sodium bicarbonate. The reaction mixture is concentrated under reduced pressure and then partitioned between dichloromethane and water. The organic phase is dried and concentrated. The mixture is purified by reverse phase chromatography-HPLC (modifier: ammonium hydroxide).

Yield: 41 mg (26% of theory)
Mass spectrometry (ESI+): m/z=307 [M+H]+
HPLC (Method 1): Retention time=0.900 min.

Compound 4.34

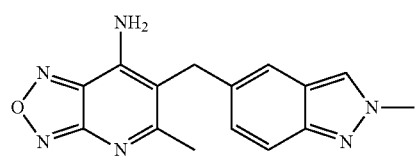 [SMILES: Cc1nc2nonc2c(N)c1Cc1ccc2nn(C)cc2c1]

5-Methyl-6-[(2-methyl-2H-indazol-5-yl)methyl]-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.34b 5-(Chloromagnesio)-2-methyl-2H-indazole. The mixture is cooled to −25° C. rather than 0° C. and is extracted with ethyl acetate after being quenched with half saturated aqueous solution of sodium bicarbonate. The organic phase is dried and concentrated. The mixture is purified by reverse phase chromatography-HPLC (modifier: trifluoroacetic acid).

Yield: 14 mg (9% of theory)
Mass spectrometry (ESI+): m/z=295 [M+H]+
HPLC (Method 3): Retention time=0.755 min.

Compound 4.35

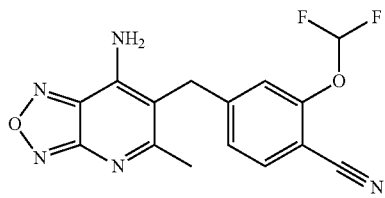 [SMILES: Cc1nc2nonc2c(N)c1Cc1ccc(C#N)c(OC(F)F)c1]

4-({7-Amino-5-methyl-[1,2,5]oxadiazolo[3,4-b]pyridin-6-yl}methyl)-2-(difluoromethoxy)benzonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.35c [4-Cyano-3-(difluoromethoxy)phenyl]-magnesium chloride. The mixture is cooled to −25° C. rather than 0° C. and is extracted with ethyl acetate after being quenched with half saturated aqueous solution of sodium bicarbonate. The organic phase is dried and concentrated. The mixture is purified by reverse phase chromatography-HPLC (modifier: ammonium hydroxide).

Yield: 67 mg (40% of theory)
Mass spectrometry (ESI$^+$): m/z=332 [M+H]$^+$
HPLC (Method 1): Retention time=0.872 min.

Compound 4.36

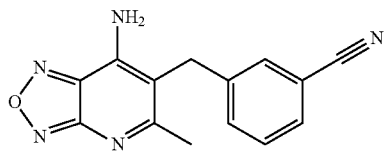 [SMILES: Cc1nc2nonc2c(N)c1Cc1cccc(C#N)c1]

3-(7-Amino-5-methyl-[1,2,5]oxadiazolo[3,4-b]pyridin-6-ylmethyl)-benzonitrile

Analogously to compound 4.50 the following compound is obtained by starting from intermediate 3c 6-Chloromethyl-5-methyl-[1,2,5]oxadiazolo[3,4-b]pyridin-7-amine and intermediate 4.36a (3-Cyanophenyl)-magnesium chloride. The mixture is cooled to −70° C. rather than 0° C., quenched with methanol and put on silica gel. The mixture is purified by silica gel chromatography (eluent: cyclohexane/ethyl acetate 0%->50%).

Yield: 850 mg (58% of theory)
Mass spectrometry (ESI$^+$): m/z=266 [M+H]$^+$
HPLC (Method 1): Retention time=0.822 min.

Compound 4.37

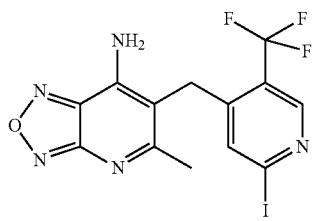 [SMILES: Cc1nc2nonc2c(N)c1Cc1cc(I)ncc1C(F)(F)F]

6-{[2-Iodo-5-(trifluoromethyl)pyridin-4-yl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.37b 4-(Chloromagnesio)-2-iodo-5-(trifluoromethyl)pyridine. The mixture is cooled to −78° C. rather than 0° C. and quenched with methanol instead of a saturated aqueous solution of sodium bicarbonate. The mixture is purified by reverse phase chromatography-HPLC (modifier: ammonium hydroxide).

Yield: 100 mg (21% of theory)
Mass spectrometry (ESI$^+$): m/z=436 [M+H]$^+$
HPLC (Method 1): Retention time=0.943 min.

Compound 4.38

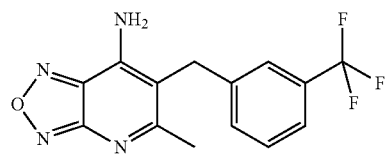 [SMILES: Cc1nc2nonc2c(N)c1Cc1cccc(C(F)(F)F)c1]

5-Methyl-6-{[3-(trifluoromethyl)phenyl]methyl}-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.38a [3-(Trifluoromethyl)phenyl]-magnesium chloride. The mixture is cooled to −65° C. rather than 0° C., quenched with methanol and put on silica gel. The mixture is purified by silica gel chromatography (eluent: cyclohexane/ethyl acetate 0%->70%). The residue is crystallized with diethyl ether and filtered.

Yield: 125 mg (24% of theory)
Mass spectrometry (ESI$^+$): m/z=309 [M+H]$^+$
HPLC (Method 3): Retention time=1.006 min.

Compound 4.39

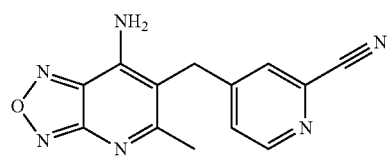 [SMILES: Cc1nc2nonc2c(N)c1Cc1ccnc(C#N)c1]

4-({7-Amino-5-methyl-[1,2,5]oxadiazolo[3,4-b]pyridin-6-yl}methyl)pyridine-2-carbonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.39b 4-(Chloromagnesio)pyridine-2-carbonitrile. The mixture is cooled to −70° C. rather than 0° C., quenched with methanol and put on silica gel. The mixture is purified by silica gel chromatography (eluent: cyclohexane/ethyl acetate 0%->100%). The residue is crystallized with ethyl acetate and filtered.

Yield: 125 mg (28% of theory)
Mass spectrometry (ESI$^+$): m/z=267 [M+H]$^+$
HPLC (Method 3): Retention time=0.730 min.

Compound 4.40

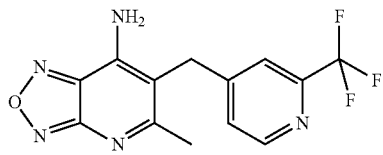 [SMILES: Cc1nc2nonc2c(N)c1Cc1ccnc(C(F)(F)F)c1]

5-Methyl-6-{[2-(trifluoromethyl)pyridin-4-yl]methyl}-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.40a 4-(Chloromagnesio)-2-(trifluoromethyl)pyridine. The mixture is cooled to −70° C. rather than 0° C., quenched with methanol and put on silica gel. The mixture is purified by silica gel chromatography (eluent: cyclohexane/ethyl acetate 0%->80%). The residue is crystallized with diethyl ether and filtered.

Yield: 42 mg (49% of theory)
Mass spectrometry (ESI⁺): m/z=310 [M+H]⁺
HPLC (Method 4): Retention time=0.866 min.

Compound 4.41

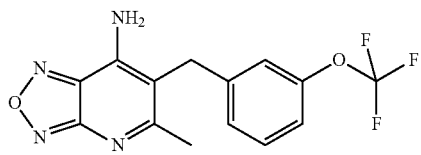 [SMILES: Cc1nc2nonc2c(N)c1Cc1cccc(OC(F)(F)F)c1]

5-Methyl-6-{[3-(trifluoromethoxy)phenyl]methyl}-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.41b [3-(Trifluoromethoxy)phenyl]-magnesium chloride. The mixture is cooled to −65° C. rather than 0° C., quenched with methanol and put on silica gel. The mixture is purified by silica gel chromatography (eluent: cyclohexane/ethyl acetate 0%->80%). The residue is crystallized with diethyl ether and filtered.

Yield: 34 mg (19% of theory)
Mass spectrometry (ESI⁺): m/z=325 [M+H]⁺
HPLC (Method 3): Retention time=1.026 min.

Compound 4.42

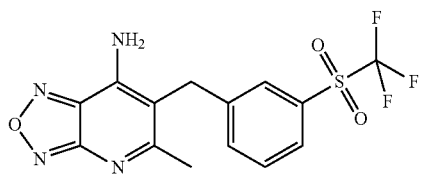 [SMILES: Cc1nc2nonc2c(N)c1Cc1cccc(S(=O)(=O)C(F)(F)F)c1]

5-Methyl-6-[(3-trifluoromethanesulfonylphenyl)methyl]-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.42b [3-(Trifluoromethylsulfonyl)phenyl]-magnesium chloride. The mixture is cooled to −65° C. rather than 0° C., quenched with methanol and put on silica gel. The mixture is purified by silica gel chromatography (eluent: cyclohexane/ethyl acetate 0%->40%). The residue is crystallized with diethyl ether and filtered.

Yield: 74 mg (36% of theory)
Mass spectrometry (ESI⁺): m/z=373 [M+H]⁺
HPLC (Method 3): Retention time=0.990 min.

Compound 4.43

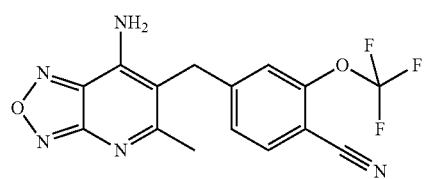 [SMILES: Cc1nc2nonc2c(N)c1Cc1ccc(C#N)c(OC(F)(F)F)c1]

4-({7-Amino-5-methyl-[1,2,5]oxadiazolo[3,4-b]pyridin-6-yl}methyl)-2-(trifluoromethoxy)benzonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.43b 4-(Chloromagnesio)-2-(trifluoromethoxy)benzonitrile. The mixture is cooled to −80° C. rather than 0° C. and quenched with methanol instead of a saturated aqueous solution of sodium bicarbonate and concentrated. The mixture is purified by reverse phase chromatography-HPLC (modifier: ammonium hydroxide).

Yield: 25 mg (23% of theory)
Mass spectrometry (ESI⁺): m/z=350 [M+H]⁺
HPLC (Method 1): Retention time=0.936 min.

Compound 4.44

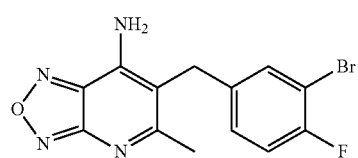 [SMILES: Cc1nc2nonc2c(N)c1Cc1ccc(F)c(Br)c1]

6-(3-Bromo-4-fluoro-benzyl)-5-methyl-[1,2,5]oxadiazolo[3,4-b]pyridin-7-ylamine

Analogously to compound 4.50 the following compound is obtained by starting from intermediate 3c 6-Chloromethyl-5-methyl-[1,2,5]oxadiazolo[3,4-b]pyridin-7-amine and intermediate 4.44a (3-Bromo-4-fluoro-phenyl)-magnesium chloride. The mixture is cooled to −65° C. rather than 0° C., quenched with methanol and put on silica gel. The mixture is purified by silica gel chromatography (eluent: cyclohexane/ethyl acetate 0%->40%).

Yield: 82 mg (44% of theory)
Mass spectrometry (ESI⁺): m/z=337 [M+H]⁺
HPLC (Method 3): Retention time=0.953 min.

Compound 4.45

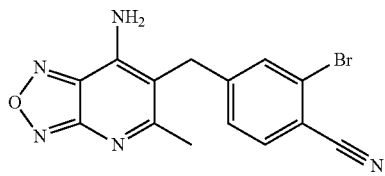 [SMILES: Cc1nc2nonc2c(N)c1Cc1ccc(C#N)c(Br)c1]

4-(7-Amino-5-methyl-[1,2,5]oxadiazolo[3,4-b]pyridin-6-ylmethyl)-2-bromo-benzonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.45a (3-Bromo-4-cyano-phenyl)-magnesium chloride. The mixture is cooled to −65° C. rather than 0° C., quenched with methanol and put on silica gel. The mixture is purified by silica gel chromatography (eluent: cyclohexane/ethyl acetate 0%->40%).
Yield: 37 mg (38% of theory)
Mass spectrometry (ESI$^+$): m/z=344 [M+H]$^+$
HPLC (Method 1): Retention time=0.873 min.

Compound 4.46

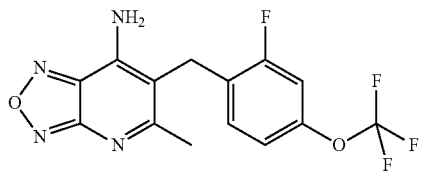 [SMILES: Cc1nc2nonc2c(N)c1Cc1ccc(OC(F)(F)F)cc1F]

6-(2-Fluoro-4-trifluoromethoxy-benzyl)-5-methyl-[1,2,5]oxadiazolo[3,4-b]pyridin-7-ylamine Analogously to compound 4.50 the following compound is obtained by starting from intermediate 3c 6-Chloromethyl-5-methyl-[1,2,5]oxadiazolo[3,4-b]pyridin-7-amine and intermediate 4.46b [2-Fluoro-4-(trifluoromethoxy)phenyl]-magnesium chloride. The mixture is cooled to −65° C. rather than 0° C., quenched with methanol and concentrated. The mixture is extracted with dichloromethane and half saturated aqueous solution of sodium bicarbonate. The organic phase is dried with magnesium sulfate and concentrated under reduce pressure. The mixture is purified by reverse phase chromatography-HPLC (modifier: ammonium hydroxide).
Yield: 115 mg (33% of theory)
Mass spectrometry (ESI$^+$): m/z=343 [M+H]$^+$
HPLC (Method 1): Retention time=1.028 min.

Compound 4.47

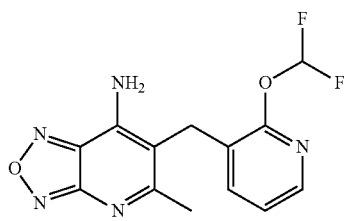 [SMILES: Cc1nc2nonc2c(N)c1Cc1cccnc1OC(F)F]

6-{[2-(Difluoromethoxy)pyridin-3-yl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.47c [2-(Difluoromethoxy)pyridine-3-yl]-magnesium chloride. The mixture is cooled to −55° C. rather than 0° C., quenched with methanol and concentrated. The mixture is extracted with dichloromethane and a half saturated aqueous solution of ammonium chloride and once with saturated aqueous solution of sodium chloride. The organic phase is dried with magnesium sulfate and concentrated under reduce pressure. The mixture is purified by reverse phase chromatography-HPLC (modifier: ammonium hydroxide).
Yield: 6 mg (2% of theory)
Mass spectrometry (ESI$^+$): m/z=308 [M+H]$^+$
HPLC (Method 1): Retention time=0.899 min.

Compound 4.48

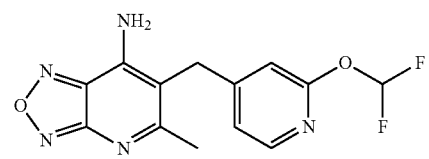 [SMILES: Cc1nc2nonc2c(N)c1Cc1ccnc(OC(F)F)c1]

6-(2-Difluoromethoxy-pyridin-4-ylmethyl)-5-methyl-[1,2,5]oxadiazolo[3,4-b]pyridin-7-ylamine Analogously to compound 4.50 the following compound is obtained by starting from intermediate 3c 6-Chloromethyl-5-methyl-[1,2,5]oxadiazolo[3,4-b]pyridin-7-amine and intermediate 4.48b 2-Difluoromethoxy-4-iodo-pyridine. The mixture is cooled to −70° C. rather than 0° C., quenched with methanol and put on silica gel. The mixture is purified by silica gel chromatography (eluent: cyclohexane/ethyl acetate 0%->80%).
Yield: 14 mg (16% of theory)
Mass spectrometry (ESI$^+$): m/z=308 [M+H]$^+$
HPLC (Method 3): Retention time=0.883 min.

Compound 4.49

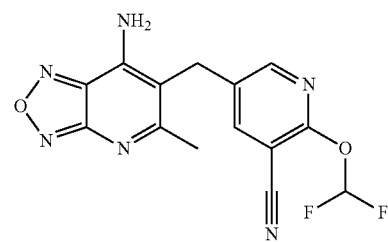 [SMILES: Cc1nc2nonc2c(N)c1Cc1cnc(OC(F)F)c(C#N)c1]

5-({7-Amino-5-methyl-[1,2,5]oxadiazolo[3,4-b]pyridin-6-yl}methyl)-2-(difluoromethoxy)pyridine-3-carbonitrile Analogously to compound 4.50 the following compound is obtained by starting from intermediate 3c 6-Chloromethyl-5-methyl-[1,2,5]oxadiazolo[3,4-b]pyridin-7-amine and intermediate 4.49b [5-Cyano-6-(difluoromethoxy)pyridine-3-yl]-magnesium chloride. The mixture is cooled to −65° C. rather than 0° C. and quenched with methanol instead of a saturated aqueous solution of sodium bicarbonate and concentrated. The residue is dissolved and the mixture is purified by reverse phase chromatography-HPLC (modifier: ammonium hydroxide).
Yield: 36 mg (43% of theory)
Mass spectrometry (ESI$^+$): m/z=333 [M+H]$^+$
HPLC (Method 1): Retention time=0.862 min.

Compound 4.50

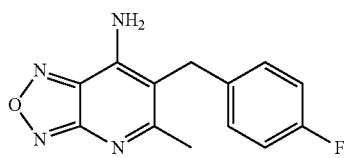 [SMILES: Cc1nc2nonc2c(N)c1Cc1ccc(F)cc1]

6-[(4-Fluorophenyl)methyl]-5-methyl-[1,2,5]oxadi-
azolo[3,4-b]pyridin-7-amine

4-Fluorophenylmagnesium bromide (300 μL; 0.60 mmol) in 0.5 mL tetrahydrofuran is cooled to −12° C. Copper(I) cyanide di(lithium chloride) complex (120 mg; 0.12 mmol) in 0.5 mL tetrahydrofuran is added and stirred for a moment. Thereafter intermediate 3c 6-Chloromethyl-5-methyl-[1,2,5]oxadiazolo[3,4-b]pyridin-7-amine (95.3 mg; 0.48 mmol) in 1 mL N-methylpyrrolidinone is added dropwise. After stirring for 1 hour at −10° C. the mixture is allowed to warm up to room temperature. The mixture is diluted with water and methanol and purified by reverse phase chromatography-HPLC (modifier: trifluoroacetic acid).

Yield: 33.0 mg (21% of theory)
Mass spectrometry (ESI+): m/z=259 [M+H]+
HPLC (Method 3): Retention time=0.881 min.

Compound 4.51

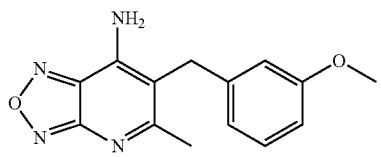 [SMILES: COc1cccc(Cc2c(C)nc3nonc3c2N)c1]

6-[(3-Methoxyphenyl)methyl]-5-methyl-[1,2,5]oxa-
diazolo[3,4-b]pyridin-7-amine

Analogously to compound 4.50 the following compound is obtained by starting from intermediate 3c 6-Chloromethyl-5-methyl-[1,2,5]oxadiazolo[3,4-b]pyridin-7-amine and 3-Methoxyphenylmagnesium bromide.

Mass spectrometry (ESI+): m/z=271 [M+H]+
HPLC (Method 3): Retention time=0.982 min.

Compound 4.52

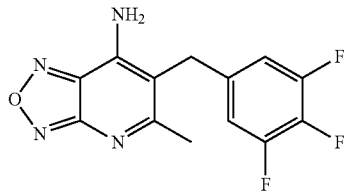 [SMILES: Cc1nc2nonc2c(N)c1Cc1cc(F)c(F)c(F)c1]

5-Methyl-6-[(3,4,5-trifluorophenyl)methyl]-[1,2,5]
oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and 3,4,5-Trifluorophenylmagnesium bromide.

Mass spectrometry (ESI+): m/z=295 [M+H]+
HPLC (Method 3): Retention time=0.949 min.

Compound 4.53

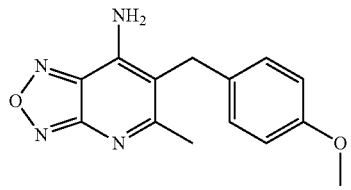 [SMILES: COc1ccc(Cc2c(C)nc3nonc3c2N)cc1]

6-[(4-Methoxyphenyl)methyl]-5-methyl-[1,2,5]oxa-
diazolo[3,4-b]pyridin-7-amine

Analogously to compound 4.50 the following compound is obtained by starting from intermediate 3c 6-Chloromethyl-5-methyl-[1,2,5]oxadiazolo[3,4-b]pyridin-7-amine and 4-Methoxyphenylmagnesium bromide.

Mass spectrometry (ESI+): m/z=271 [M+H]+
HPLC (Method 3): Retention time=0.857 min.

Compound 4.54

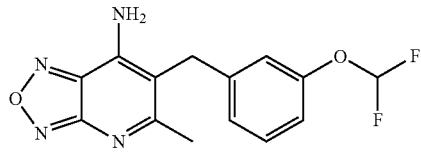 [SMILES: Cc1nc2nonc2c(N)c1Cc1cccc(OC(F)F)c1]

6-{[3-(Difluoromethoxy)phenyl]methyl}-5-methyl-
[1,2,5]oxadiazolo[3,4-b]pyridin-7-amine 1-(Difluoromethoxy)-3-iodobenzene (350 mg; 1.30 mmol) is taken up in 10 mL tetrahydrofuran and cooled to −70° C. Isopropylmagnesium chloride lithiumchloride complex (1.3 M solution in tetrahydrofuran; 0.997 mL; 1.30 mmol) is added dropwise. After stirring for 30 minutes at −70° C. the mixture is further used as crude product.

Yield: 263 mg (100% of theory)
Intermediate 3c 6-Chloromethyl-5-methyl-[1,2,5]oxadiazolo[3,4-b]pyridin-7-amine (55 mg; 0.28 mmol) in 90 mL tetrahydrofuran is cooled to −70° C. Chloro[3-(difluoromethoxy)phenyl]magnesium (260 mg; 1.28 mmol) is cooled to −70° C., Copper(I)cyanide di(lithium chloride) complex (1.0 M in tetrahydrofuran; 0.111 mL; 0.11 mmol) is added and stirred for 5 minutes. Thereafter the mixture is quenched with methanol and purified by silica gel chromatography (eluent: cyclohexene/ethyl acetate 0->50%).

Yield: 57.0 mg (67% of theory)
Mass spectrometry (ESI+): m/z=307 [M+H]+
HPLC (Method 1): Retention time=0.930 min.

Compound 4.55

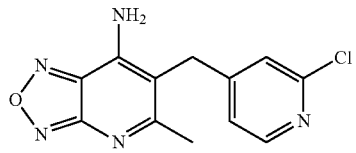 [SMILES: Cc1nc2nonc2c(N)c1Cc1ccnc(Cl)c1]

6-[(2-Chloropyridin-4-yl)methyl]-5-methyl-[1,2,5]
oxadiazolo[3,4-b]pyridin-7-amine Analogously to compound 4.54 the following compound is obtained by starting from intermediate 3c 6-Chloromethyl-5-methyl-[1,2,5]oxadiazolo[3,4-b]pyridin-7-amine and 2-Chloro-4-iodopyridine.

Yield: 44.0 mg (58% of theory)
Mass spectrometry (ESI⁺): m/z=276 [M+H]⁺
HPLC (Method 1): Retention time=0.784 min.
Compound 4.56

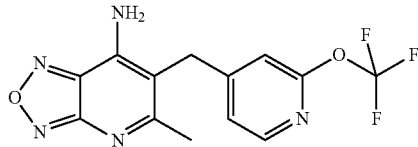 [SMILES: Cc1nc2nonc2c(N)c1Cc1ccnc(OC(F)(F)F)c1]

5-Methyl-6-{[2-(trifluoromethoxy)pyridin-4-yl]methyl}-[1,2,5]oxadiazolo[3,4-b]pyridin-7-amine Analogously to compound 4.54 the following compound is obtained by starting from intermediate 3c 6-Chloromethyl-5-methyl-[1,2,5]oxadiazolo[3,4-b]pyridin-7-amine and 4-Iodo-2-(trifluoromethoxy)pyridine.
Yield: 60.0 mg (67% of theory)
Mass spectrometry (ESI⁺): m/z=326 [M+H]⁺
HPLC (Method 1): Retention time=0.894 min.
Compound 4.57

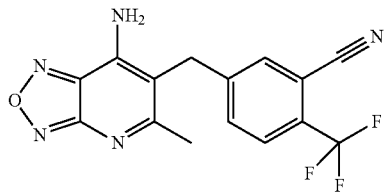 [SMILES: Cc1nc2nonc2c(N)c1Cc1ccc(C(F)(F)F)c(C#N)c1]

5-({7-Amino-5-methyl-[1,2,5]oxadiazolo[3,4-b]pyridin-6-yl}methyl)-2-(trifluoromethyl)benzonitrile 5-Iodo-2-(trifluoromethyl)benzonitrile (300 mg; 1.01 mmol) is taken up in 4 mL tetrahydrofuran and cooled to −65° C. Isopropylmagnesium chloride lithiumchloride complex (1.3 M solution in tetrahydrofuran; 0.855 mL; 1.11 mmol) is added dropwise and stirred for 5 minutes at −65° C.
A solution of intermediate 3c 6-Chloromethyl-5-methyl-[1,2,5]oxadiazolo[3,4-b]pyridin-7-amine (100 mg; 0.50 mmol) and Copper(I)cyanide di(lithium chloride) complex (1.0 M in tetrahydrofuran; 0.201 mL; 0.20 mmol) in 4 mL tetrahydrofuran is added at −65° C. The reaction is quenched with methanol and purified by reverse phase chromatography-HPLC (modifier: ammonium hydroxide).
Yield: 39 mg (23% of theory)
Mass spectrometry (ESI⁺): m/z=334 [M+H]⁺
HPLC (Method 1): Retention time=0.927 min.
Compound 4.58

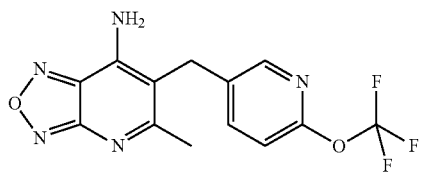 [SMILES: Cc1nc2nonc2c(N)c1Cc1ccc(OC(F)(F)F)nc1]

5-Methyl-6-{[6-(trifluoromethoxy)pyridin-3-yl]methyl}-[1,2,5]oxadiazolo[3,4-b]pyridin-7-amine Analogously to compound 4.57 the following compound is obtained by starting from intermediate 3c 6-Chloromethyl-5-methyl-[1,2,5]oxadiazolo[3,4-b]pyridin-7-amine and 5-Iodo-2-(trifluoromethoxy)pyridine.
Yield: 11.0 mg (22% of theory)
Mass spectrometry (ESI⁺): m/z=326 [M+H]⁺
HPLC (Method 1): Retention time=0.907 min.
Compound 4.59

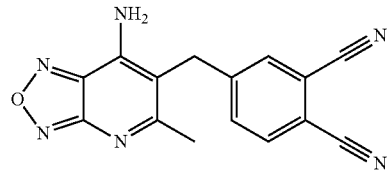 [SMILES: Cc1nc2nonc2c(N)c1Cc1ccc(C#N)c(C#N)c1]

4-({7-Amino-5-methyl-[1,2,5]oxadiazolo[3,4-b]pyridin-6-yl}methyl)benzene-1,2-dicarbonitrile Analogously to compound 4.57 the following compound is obtained by starting from intermediate 3c 6-Chloromethyl-5-methyl-[1,2,5]oxadiazolo[3,4-b]pyridin-7-amine and 4-Iodobenzene-1,2-dicarbonitrile.
Yield: 35.0 mg (24% of theory)
Mass spectrometry (ESI⁺): m/z=291 [M+H]⁺
HPLC (Method 1): Retention time=0.795 min
Compound 4.60

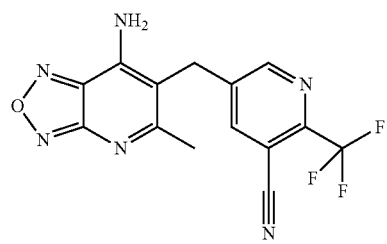 [SMILES: Cc1nc2nonc2c(N)c1Cc1cnc(C(F)(F)F)c(C#N)c1]

5-({7-Amino-5-methyl-[1,2,5]oxadiazolo[3,4-b]pyridin-6-yl}methyl)-2-(trifluoromethyl)pyridine-3-carbonitrile Analogously to compound 4.57 the following compound is obtained by starting from intermediate 3c 6-Chloromethyl-5-methyl-[1,2,5]oxadiazolo[3,4-b]pyridin-7-amine and 5-iodo-2-(trifluoromethyl)pyridine-3-carbonitrile.
Yield: 34.0 mg (31% of theory)
Mass spectrometry (ESI⁺): m/z=335 [M+H]⁺
HPLC (Method 1): Retention time=0.876 min.
Compound 4.61

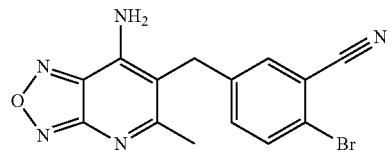 [SMILES: Cc1nc2nonc2c(N)c1Cc1ccc(Br)c(C#N)c1]

5-({7-Amino-5-methyl-[1,2,5]oxadiazolo[3,4-b]pyridin-6-yl}methyl)-2-bromobenzonitrile Analogously to compound 4.57 the following compound is obtained by starting from intermediate 3c 6-Chloromethyl-5-methyl-[1,2,5]oxadiazolo[3,4-b]pyridin-7-amine and 2-Bromo-5-iodobenzonitrile.
Yield: 31.0 mg (7% of theory)

Procedure 8

Intermediate 8.1a

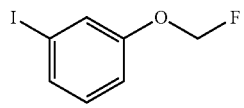

1-(Fluoromethoxy)-3-iodobenzene

3-Iodophenol (2.200 g; 10.000 mmol) is dissolved in 5 mL N,N-Dimethylformamide. Potassium carbonate (1.659 g; 12.000 mmol) is added. The mixture is stirred for 10 minutes. Bromo(fluoro)methane (5.500 mL; 11.000 mmol) is added. The mixture is stirred 10 minutes at 80° C. and over night at room temperature. Then it is stirred two hours at 80° C. The mixture is filtered. The solvent is evaporated under reduced pressure. The residue is dissolved in ethyl acetate and washed once with water, twice with sodium hydroxide (1 M aqueous solution) and once with brine. The organic phase is dried over sodium sulfate, filtered and concentrated.

Yield: 1.250 g (50% of theory)

Mass spectrometry (EI): m/z=252 [M*]+

HPLC (Method 3): Retention time=0.465 min.

Compound 8.1

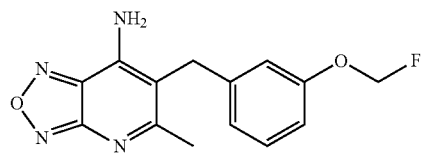 [SMILES: Cc1nc2nonc2c(N)c1Cc1cccc(OCF)c1]

6-{[3-(Fluoromethoxy)phenyl]methyl}-5-methyl-[1,2,5]oxadiazolo[3,4-b]pyridin-7-amine Intermediate 8.1a 1-(Fluoromethoxy)-3-iodobenzene (1.20 g; 4.76 mmol) is taken up in 8 mL tetrahydrofuran and cooled to −60° C. Isopropylmagnesium chloride lithiumchloride complex (1.3 M solution in tetrahydrofuran; 4.14 mL; 5.38 mmol) is added dropwise and stirred for 5 minutes at −65° C.

A solution of intermediate 3d {7-Amino-5-methyl-[1,2,5]oxadiazolo[3,4-b]pyridin-6-yl}methyl acetate (300 mg; 1.35 mmol) and Copper(I)cyanide di(lithium chloride) complex (1.0 M in tetrahydrofuran; 0.540 mL; 0.54 mmol) is cooled at −65° C. To this solution is added the Grignard-solution and the reaction is stirred for 10 minutes.

The reaction is quenched with NaHCO₃ (saturated aqueous solution), ethyl acetate is added and the generate solid was filtered and washed with ethyl acetate. The filtrate is washed with NaHCO₃ (saturated aqueous solution), water and brine. The solvent is evaporated and the residue is purified by reverse phase chromatography (modifier: ammonium hydroxide).

Yield: 51 mg (13% of theory)

Mass spectrometry (ESI⁺): m/z=289 [M+H]⁺

HPLC (Method 1): Retention time=0.892 min.

Mass spectrometry (ESI⁺): m/z=344 [M+H]⁺

HPLC (Method 1): Retention time=0.908 min.

Procedure 9

Intermediate 9a

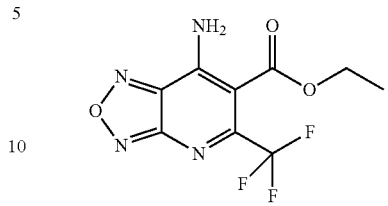

Ethyl 7-amino-5-(trifluoromethyl)-[1,2,5]oxadiazolo[3,4-b]pyridine-6-carboxylate To a mixture of 4-amino-1,2,5-oxadiazole-3-carbonitrile (2.5 g; 22.71 mmol) and ethyl 4,4,4-trifluoro-3-oxobutanoate (4.18 g; 22.71 mmol) in 25 mL toluene, tin(IV)chloride (3.99 mL; 34.07 mmol) is added dropwise. The mixture is stirred for 30 minutes at reflux. The reaction is quenched with NaHCO₃ (half saturated aqueous solution) and extracted two times with dichloromethane. The organic layer is dried and concentrated under reduced pressure. The residue is further used as crude product.

Yield: 5.78 mg (92% of theory)

Mass spectrometry (ESI⁺): m/z=277 [M+H]⁺

HPLC (Method 1): Retention time=0.688 min.

Intermediate 9b

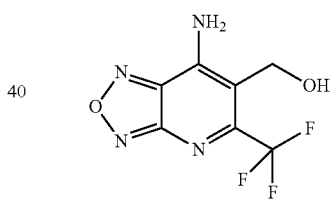

[7-Amino-5-(trifluoromethyl)-[1,2,5]oxadiazolo[3,4-b]pyridin-6-yl]methanol

Intermediate 9a [Ethyl 7-amino-5-(trifluoromethyl)-[1,2,5]oxadiazolo[3,4-b]pyridine-6-carboxylate] (500 mg; 1.81 mmol) is dissolved in 5 mL tetrahydrofuran and cooled to 8° C. lithium aluminium hydride (10% solution in tetrahydrofuran)(5 mL; 62.34 mmol) is added dropwise between 8-10° C. It is stirred for 5 minutes and then the reaction is quenched with 40 mL Na₂SO₄ (saturated aqueous solution) and vigorously stirred. The generate solid was filtered over Celite. The filtrate is washed three times with Na₂SO₄ (saturated aqueous solution), dried and concentrated under reduced pressure. The residue is further used as crude product.

Mass spectrometry (ESI−): m/z=233 [M−H]⁻

HPLC (Method 1): Retention time=0.672 min.

Intermediate 9c

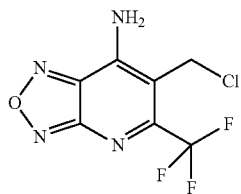 [SMILES: Nc1c(CCl)c(C(F)(F)F)nc2nonc12]

6-(Chloromethyl)-5-(trifluoromethyl)-[1,2,5]oxadiazolo[3,4-b]pyridin-7-amine

Intermediate 9b [7-Amino-5-(trifluoromethyl)-[1,2,5]oxadiazolo[3,4-b]pyridin-6-yl]methanol (125 mg; 0.53 mmol) is suspended in 4 ml tetrahydrofuran. Oxalylchloride (60 μl; 0.69 mmol) is added and stirred over night at room temperature. The residue is further used as crude product.
Yield: 135 mg (100% of theory)
Mass spectrometry (ESI$^+$): m/z=249 [M+H]$^+$ methylester
HPLC (Method 1): Retention time=0.830 min.

Intermediate 9d 4-(Trifluoromethyl)phenylmagnesium Chloride

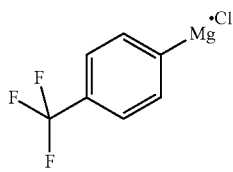

1-Iodo-4-(trifluoromethyl)benzene (500 mg; 1.84 mmol) is taken up in 10 mL tetrahydrofuran and cooled to −60° C. Isopropylmagnesium chloride lithiumchloride complex (1.3 M solution in tetrahydrofuran; 2.12 mL; 2.76 mmol) is added dropwise. After stirring for 15 minutes at −60° C. the mixture is further used as crude product.
Yield: 377 mg (100% of theory)

Compound 9.1

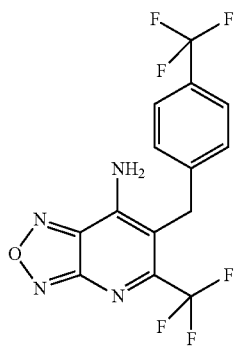 [SMILES: Nc1c(Cc2ccc(C(F)(F)F)cc2)c(C(F)(F)F)nc2nonc12]

5-(Trifluoromethyl)-6-{[4-(trifluoromethyl)phenyl]methyl}-[1,2,5]oxadiazolo[3,4-b]pyridin-7-amine Intermediate 9c 6-(Chloromethyl)-5-(trifluoromethyl)-[1,2,5]oxadiazolo[3,4-b]pyridin-7-amine (135 mg; 0.53 mmol) in 4 mL tetrahydrofuran is cooled to −65° C. In a separate flask, Intermediate 9d 4-(Trifluoromethyl)phenylmagnesium chloride (377 mg; 1.84 mmol) in THF is cooled to −65° C., Copper(I)cyanide di(lithium chloride) complex (1.0 M in tetrahydrofuran; 0.214 mL; 0.21 mmol) is added and stirred for 5 minutes. This solution is then transferred to the previously prepared chloride (intermediate 9C) at −65° C. and stirred for 5 minutes. The mixture is allowed to warm up to room temperature, diluted with ethyl acetate and washed with NaHCO$_3$ (saturated aqueous solution). The organic layer is dried and concentrated under reduced pressure. The crude product is purified by reverse phase chromatography-HPLC (modifier: ammonium hydroxide).
Yield: 61 mg (32% of theory)
Mass spectrometry (ESI$^+$): m/z=363 [M+H]$^+$
HPLC (Method 1): Retention time=1.074 min.

Procedure 10

Compound 10.1

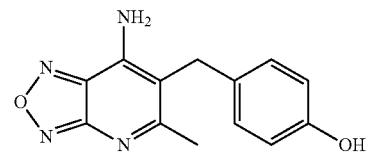 [SMILES: Cc1nc2nonc2c(N)c1Cc1ccc(O)cc1]

4-(7-Amino-5-methyl-[1,2,5]oxadiazolo[3,4-b]pyridin-6-ylmethyl)-phenol

To the intermediate 3c 6-Chloromethyl-5-methyl-[1,2,5]oxadiazolo[3,4-b]pyridin-7-amine (457 mg, 2.30 mmol) in THF at −40° C. is slowly added (4-(Trimethylsilyloxy)phenyl)zinc bromide (0.5 mol/L solution; 11.5 mL, 5.75 mmol), stirred at −25° C. for 20 min. The product is quenched with methanol and concentrated. The residue is diluted with ethyl acetate and water. The organic phase is extracted once with a saturated aqueous solution of sodium chloride and dried with sodium sulfate, filtered and concentrated. The residue is dissolved in minimum methanol and purified by reverse phase chromatography-HPLC (modifier: ammonium hydroxide).
Yield: 210 mg (35% of theory)
Mass spectrometry (ESI$^+$): m/z=257 [M+H]$^+$
HPLC (Method 1): Retention time=0.702 min.

Procedure 11

Intermediate 11a

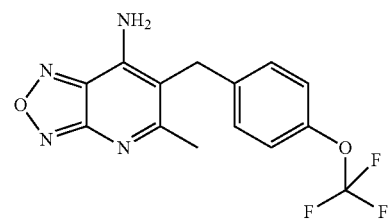 [SMILES: Cc1nc2nonc2c(N)c1Cc1ccc(OC(F)(F)F)cc1]

5-Methyl-6-{[4-(trifluoromethoxy)phenyl]methyl}-[1,2,5]oxadiazolo[3,4-b]pyridin-7-amine Intermediate 3c 6-Chloromethyl-5-methyl-[1,2,5]oxadiazolo[3,4-b]pyridin-7-amine (3.8 g; 19.13 mmol) is dissolved in 80 mL tetrahydrofuran and cooled to −40° C. Bromo[4-(trifluoromethoxy)phenyl]zinc (0.5 M in tetrahydrofuran; 95.6 mL; 47.83 mmol) is added at temperature between −40° to −20° C. The mixture is allowed to warm up to room temperature and stirred for 2 hours.

The mixture is concentrated and purified by silica gel chromatography (eluent: cyclohexane/ethyl acetate 0->40%)

Yield: 1.35 g (22% of theory)
Mass spectrometry (ESI⁺): m/z=325 [M+H]⁺
HPLC (Method 3): Retention time=1.015 min
Intermediate 11b

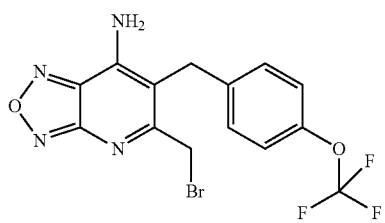 [SMILES: Nc1c(Cc2ccc(OC(F)(F)F)cc2)c(CBr)nc2nonc12]

5-(Bromomethyl)-6-{[4-(trifluoromethoxy)phenyl]methyl}-[1,2,5]oxadiazolo[3,4-b]pyridin-7-amine Intermediate 11a 5-Methyl-6-{[4-(trifluoromethoxy)phenyl]methyl}-[1,2,5]oxadiazolo[3,4-b]pyridin-7-amine (1.2 g; 3.70 mmol) is dissolved in 10 mL DMF and N-bromosuccinimide (658 mg; 3.70 mmol) is added. Stirred at room temperature for 18 hours. The solvent is evaporated and the residue is purified by reverse phase chromatography-HPLC (modifier: trifluoroacetic acid). The acetonitrile is removed and NaHCO₃ is given to the aqueous layer to adjust to an alkaline pH. The aqueous layer was extracted 3 times with ethyl acetate, dried and concentrated under reduced pressure.

Yield: 870 mg (58% of theory)
Mass spectrometry (ESI⁺): m/z=403 [M+H]⁺
HPLC (Method 3): Retention time=1.086 min Compound 11.1

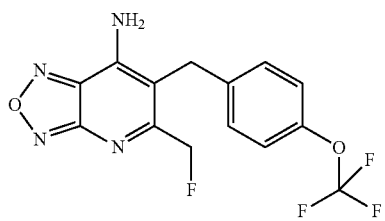 [SMILES: Nc1c(Cc2ccc(OC(F)(F)F)cc2)c(CF)nc2nonc12]

5-(Fluoromethyl)-6-{[4-(trifluoromethoxy)phenyl]methyl}-[1,2,5]oxadiazolo[3,4-b]pyridin-7-amine The reaction is carried out under an argon atmosphere. Intermediate 11b 5-(Bromomethyl)-6-{[4-(trifluoromethoxy)phenyl]methyl}-[1,2,5]oxadiazolo[3,4-b]pyridin-7-amine (200 mg; 0.50 mmol), cesium fluoride (113 mg; 0.74 mmol) and 12-CROWN-4 (120 μl; 0.74 mmol) is suspended in 4 mL acetonitrile. The reaction is stirred for 45 minutes at 100° C. in the microwave. The mixture is poured into ice water and extracted 3 times with ethyl acetate, dried and concentrated under reduced pressure. The residue is purified by reverse phase chromatography (modifier: ammonium hydroxide).

Yield: 8 mg (5% of theory)
Mass spectrometry (ESI⁺): m/z=343 [M+H]⁺
HPLC (Method 3): Retention time=1.050 min Procedure 12

Compound 12.1

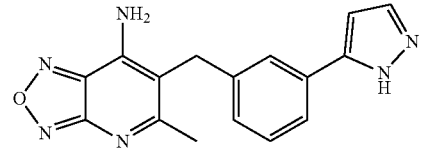 [SMILES: Cc1nc2nonc2c(N)c1Cc1cccc(-c2ccn[nH]2)c1]

5-Methyl-6-{[3-(1H-pyrazol-5-yl)phenyl]methyl}-[1,2,5]oxadiazolo[3,4-b]pyridin-7-amine To a mixture of compound 2.6 6-[(3-Bromophenyl)methyl]-5-methyl-[1,2,5]oxadiazolo[3,4-b]pyridin-7-amine (50.0 mg; 0.16 mmol) and 1H-Pyrazol-3-yl boronic acid (26.3 mg; 0.24 mmol) in 1.5 mL dioxane sodium carbonate (2M aqueous solution; 1.00 mL) is added. Thereafter 1,1′-bis(diphenylphosphino)ferrocene-dichloropalladium(II) (7.50 mg; 0.07 mmol) is added and the mixture is stirred at 150° C. for 30 minutes in a microwave. The mixture is diluted with water and extracted three times with dichloromethane. The combined organic layers are dried and concentrated under reduced pressure. The residue is purified by reverse phase chromatography-HPLC (modifier: trifluoroacetic acid).

Yield: 43.0 mg (90% of theory)
Mass spectrometry (ESI⁺): m/z=307 [M+H]⁺
HPLC (Method 3): Retention time=0.810 min.

Compound 12.2

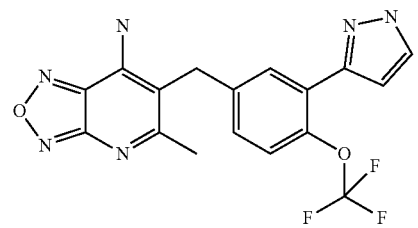 [SMILES: Cc1nc2nonc2c(N)c1Cc1ccc(OC(F)(F)F)c(-c2cc[nH]n2)c1]

5-Methyl-6-[3-(1H-pyrazol-3-yl)-4-trifluoromethoxy-benzyl]-[1,2,5]oxadiazolo[3,4-b]pyridin-7-ylamine Analogously to compound 12.1 the following compound is obtained by starting from compound 2.14 6-{[3-Bromo-4-(trifluoromethoxy)phenyl]methyl}-5-methyl-[1,2,5]oxadiazolo[3,4-b]pyridin-7-amine and 1H-Pyrazol-3-yl boronic acid.

Mass spectrometry (ESI⁺): m/z=391 [M+H]⁺
Yield: 13.0 mg (38% of theory)
HPLC (Method 3): Retention time=0.943 min.

Compound 12.3

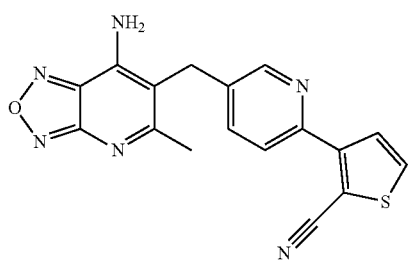 [SMILES: Cc1nc2nonc2c(N)c1Cc1ccc(-c2ccsc2C#N)nc1]

3-[5-(7-Amino-5-methyl-[1,2,5]oxadiazolo[3,4-b]pyridin-6-ylmethyl)-pyridin-2-yl]-thiophene-2-carbonitrile Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and 2-Cyanothiophene-3-boronic acid pinacol ester. Use of potassium carbonate instead of sodium carbonate. The mixture is purified by reverse phase chromatography-HPLC (modifier: ammonium hydroxide).

Yield: 31 mg (49% of theory)

Mass spectrometry (ESI$^+$): m/z=349 [M+H]$^+$

HPLC (Method 1): Retention time=0.885 min.

Compound 12.4

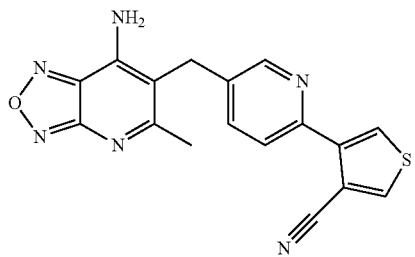 [SMILES: Cc1nc2nonc2c(N)c1Cc1ccc(-c2cscc2C#N)nc1]

4-[5-(7-Amino-5-methyl-[1,2,5]oxadiazolo[3,4-b]pyridin-6-ylmethyl)-pyridin-2-yl]-thiophene-3-carbonitrile Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and 4-Cyanothiophene-3-boronic acid pinacol ester. Use of potassium carbonate instead of sodium carbonate. The mixture is purified by reverse phase chromatography-HPLC (modifier: ammonium hydroxide).

Yield: 3 mg (4.7% of theory)

Mass spectrometry (ESI$^+$): m/z=349 [M+H]$^+$

HPLC (Method 1): Retention time=0.85 min.

Compound 12.5

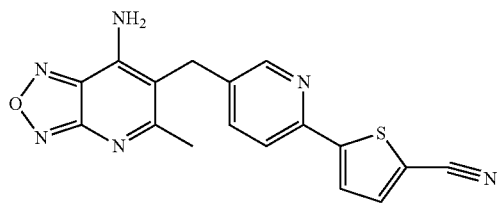 [SMILES: Cc1nc2nonc2c(N)c1Cc1ccc(-c2ccc(C#N)s2)nc1]

5-[5-(7-Amino-5-methyl-[1,2,5]oxadiazolo[3,4-b]pyridin-6-ylmethyl)-pyridin-2-yl]-thiophene-2-carbonitrile Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and 5-Cyanothiophene-2-boronic acid. Use of potassium carbonate instead of sodium carbonate. The mixture is purified by reverse phase chromatography-HPLC (modifier: ammonium hydroxide).

Yield: 9 mg (15% of theory)

Mass spectrometry (ESI$^+$): m/z=349 [M+H]$^+$

HPLC (Method 1): Retention time=0.910 min.

Compound 12.6

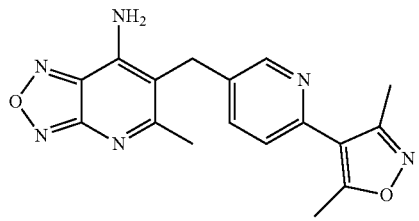 [SMILES: Cc1nc2nonc2c(N)c1Cc1ccc(-c2c(C)noc2C)nc1]

6-{[6-(3,5-Dimethyl-1,2-oxazol-4-yl)pyridin-3-yl]methyl}-5-methyl-[1,2,5]oxadiazolo[3,4-b]pyridin-7-amine Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and (3,5-Dimethyl-1,2-oxazol-4-yl)boronic acid. Use of potassium carbonate instead of sodium carbonate. The mixture is purified by reverse phase chromatography-HPLC (modifier: ammonium hydroxide).

Yield: 23 mg (37% of theory)

Mass spectrometry (ESI$^+$): m/z=337 [M+H]$^+$

HPLC (Method 1): Retention time=0.816 min.

Compound 12.7

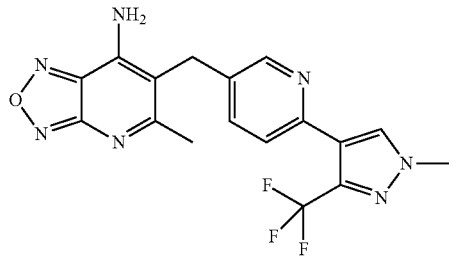 [SMILES: Cc1nc2nonc2c(N)c1Cc1ccc(-c2cn(C)nc2C(F)(F)F)nc1]

5-Methyl-6-({6-[1-methyl-3-(trifluoromethyl)-1H-pyrazol-4-yl]pyridin-3-yl}methyl)-[1,2,5]oxadiazolo[3,4-b]pyridin-7-amine Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and 1-Methyl-3-trifluoromethylpyrazole-4-boronic acid. Use of potassium carbonate instead of sodium carbonate. The mixture is purified by reverse phase chromatography-HPLC (modifier: ammonium hydroxide).

Yield: 23 mg (32% of theory)

Mass spectrometry (ESI+): m/z=390 [M+H]+

HPLC (Method 1): Retention time=0.869 min.

Compound 12.8

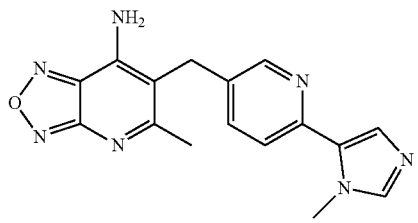 [SMILES: Cc1nc2nonc2c(N)c1Cc1ccc(-c2cncn2C)nc1]

5-Methyl-6-{[6-(1-methyl-1H-imidazol-5-yl)pyridin-3-yl]methyl}-[1,2,5]oxadiazolo[3,4-b]pyridin-7-amine Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and (1-Methyl-1H-imidazol-5-yl)boronic acid pinacol ester. Use of potassium carbonate instead of sodium carbonate. The mixture is purified by reverse phase chromatography-HPLC (modifier: ammonium hydroxide).

Yield: 11 mg (19% of theory)

Mass spectrometry (ESI+): m/z=322 [M+H]+

HPLC (Method 1): Retention time=0.724 min.

Compound 12.9

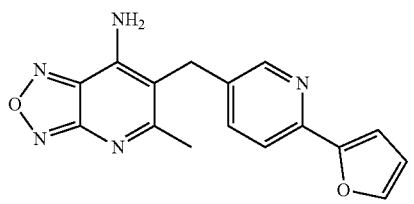 [SMILES: Cc1nc2nonc2c(N)c1Cc1ccc(-c2ccco2)nc1]

6-{[6-(Furan-2-yl)pyridin-3-yl]methyl}-5-methyl-[1,2,5]oxadiazolo[3,4-b]pyridin-7-amine Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and 2-Furanboronic acid. Use of potassium carbonate instead of sodium carbonate. The mixture is purified by reverse phase chromatography-HPLC (modifier: ammonium hydroxide).

Yield: 15 mg (27% of theory)

Mass spectrometry (ESI+): m/z=308 [M+H]+

HPLC (Method 1): Retention time=0.852 min.

Compound 12.10

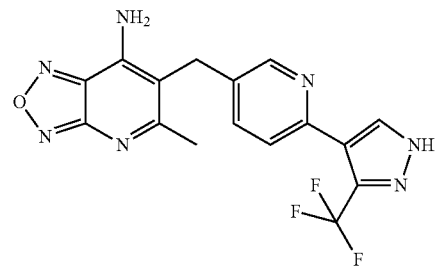 [SMILES: Cc1nc2nonc2c(N)c1Cc1ccc(-c2c[nH]nc2C(F)(F)F)nc1]

5-Methyl-6-({6-[3-(trifluoromethyl)-1H-pyrazol-4-yl]pyridin-3-yl}methyl)-[1,2,5]oxadiazolo[3,4-b]pyridin-7-amine Analogously to compound 12.1 the following compound is obtained by starting from compound 4.18 6-[(6-Chloropyridin-3-yl)methyl]-5-methyl-[1,2,5]oxadiazolo[3,4-b]pyridin-7-amine and 4-(4,4,5,5-Tetramethyl-1,3,2-dioxaborolan-2-yl)-3-(trifluoromethyl)-1H-pyrazole. Use of potassium carbonate instead of sodium carbonate. The mixture is purified by reverse phase chromatography-HPLC (modifier: ammonium hydroxide).

Yield: 3 mg (4% of theory)

Mass spectrometry (ESI+): m/z=376 [M+H]+

HPLC (Method 1): Retention time=0.794 min.

Compound 12.11

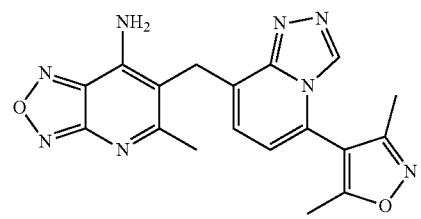 [SMILES: Cc1nc2nonc2c(N)c1Cc1ccc(-c2c(C)noc2C)n2cnnc12]

6-{[5-(3,5-Dimethyl-1,2-oxazol-4-yl)-[1,2,4]triazolo[4,3-a]pyridin-8-yl]methyl}-5-methyl-[1,2,5]oxadiazolo[3,4-b]pyridin-7-amine Analogously to compound 12.1 the following compound is obtained by starting from compound 4.14 6-({5-Chloro-[1,2,4]triazolo[4,3-a]pyridin-8-yl}methyl)-5-methyl-[1,2,5]oxadiazolo[3,4-b]pyridin-7-amine and 3,5-Dimethyl-4-(4,4,5,5-tetramethyl-[1,3,2]dioxaborolan-2-yl)isoxazole. Use of tetrakis(triphenylphosphine)palladium(0) instead of 1,1'-bis(diphenylphosphino)ferrocenedichloropalladium(II). The mixture is purified by silica gel chromatography (eluent: ethyl acetate/ethanol 0%->15%).

Yield: 7.00 mg (13% of theory)

Mass spectrometry (ESI+): m/z=377 [M+H]+

HPLC (Method 1): Retention time=0.790 min.

Compound 12.12

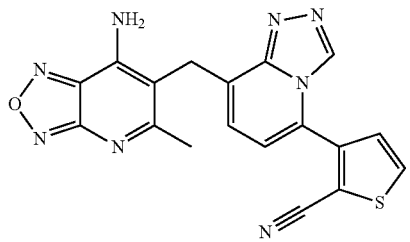 [SMILES: Cc1nc2nonc2c(N)c1Cc1ccc(-c2ccsc2C#N)n2cnnc12]

3-[8-({7-Amino-5-methyl-[1,2,5]oxadiazolo[3,4-b]pyridin-6-yl}methyl)-[1,2,4]triazolo[4,3-a]pyridin-5-yl]thiophene-2-carbonitrile Analogously to compound 12.1 the following compound is obtained by starting from compound 4.14 6-({5-Chloro-[1,2,4]triazolo[4,3-a]pyridin-8-yl}methyl)-5-methyl-[1,2,5]oxadiazolo[3,4-b]pyridin-7-amine and 3-(4,4,5,5-Tetramethyl-[1,3,2]dioxa-borolan-2-yl)-thiophene-2-carbonitrile. Use of tetrakis(triphenylphosphine)palladium(0) instead of 1,1'-bis(diphenylphosphino)ferrocenedichloropalladium(II). The mixture is purified by reverse phase chromatography-HPLC (modifier: ammonium hydroxide).

Yield: 4.00 mg (5% of theory)

Mass spectrometry (ESI+): m/z=389 [M+H]+

HPLC (Method 1): Retention time=0.810 min.

Compound 12.13

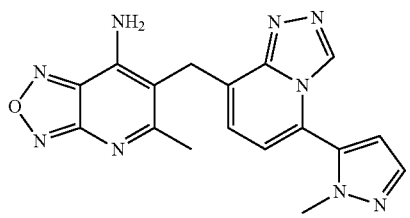 [SMILES: Cc1nc2nonc2c(N)c1Cc1ccc(-c2ccnn2C)n2cnnc12]

5-Methyl-6-[5-(2-methyl-2H-pyrazol-3-yl)-[1,2,4]triazolo[4,3-a]pyridin-8-ylmethyl]-[1,2,5]oxadiazolo[3,4-b]pyridin-7-ylamine Analogously to compound 12.1 the following compound is obtained by starting from compound 4.14 6-({5-Chloro-[1,2,4]triazolo[4,3-a]pyridin-8-yl}methyl)-5-methyl-[1,2,5]oxadiazolo[3,4-b]pyridin-7-amine and 1-Methyl-5-(4,4,5,5-tetramethyl-[1,3,2]dioxaborolan-2-yl)-1H-pyrazole. Use of tetrakis(triphenylphosphine)palladium(0) instead of 1,1'-bis(diphenylphosphino)ferrocenedichloropalladium(II). The mixture is filtered over silica gel and concentrated. The mixture is purified by reverse phase chromatography-HPLC (modifier: trifluoroacetic acid).

Yield: 36.00 mg (52% of theory)

Mass spectrometry (ESI+): m/z=362 [M+H]+

HPLC (Method 12): Retention time=0.592 min.

Procedure 13

Compound 13.1

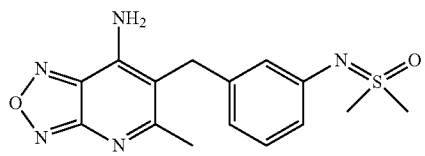 [SMILES: Cc1nc2nonc2c(N)c1Cc1cccc(N=S(C)(C)=O)c1]

{[3-({7-Amino-5-methyl-[1,2,5]oxadiazolo[3,4-b]pyridin-6-yl}methyl)phenyl]imino}dimethyl-$\lambda^6$-sulfanone The reaction is carried out under an argon atmosphere. To a mixture of compound 2.6 6-[(3-Bromophenyl)methyl]-5-methyl-[1,2,5]oxadiazolo[3,4-b]pyridin-7-amine (50.0 mg; 0.16 mmol), (methylsulfonimidoyl)methane (18.2 mg; 0.20 mmol), 2-(di-tert-butylphosphino)biphenyl (9.35 mg; 0.03 mmol) and sodium tert-butoxide (22.6 mg; 0.23 mmol) in 2 mL N,N-dimethylformamide is flushed with argon. Tris(dibenzylideneacetone)dipalladium(0) (11.5 mg; 0.01 mmol) is added and the mixture is stirred at 80° C. for 2 hours. Thereafter the mixture is filtered and the filtrate is purified by reverse phase chromatography-HPLC (modifier: trifluoroacetic acid).

Yield: 14.7 mg (28% of theory)

Mass spectrometry (ESI+): m/z=332 [M+H]+

HPLC (Method 3): Retention time=0.700 min.

Compound 13.2

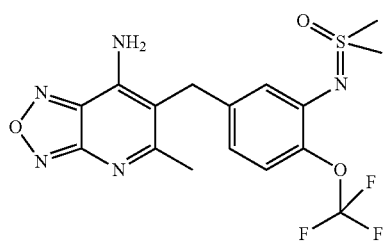 [SMILES: Cc1nc2nonc2c(N)c1Cc1ccc(OC(F)(F)F)c(N=S(C)(C)=O)c1]

{[5-({7-Amino-5-methyl-[1,2,5]oxadiazolo[3,4-b]pyridin-6-yl}methyl)-2-(trifluoromethoxy)phenyl]imino}dimethyl-$\lambda^6$-sulfanone Analogously to compound 13.1 the following compound is obtained by starting from compound 2.14 6-{[3-Bromo-4-(trifluoromethoxy)phenyl]methyl}-5-methyl-[1,2,5]oxadiazolo[3,4-b]pyridin-7-amine and (methylsulfonimidoyl)methane. The mixture is purified by reverse phase chromatography-HPLC (modifier: NH4OH).

Yield: 4 mg (13% of theory)

Mass spectrometry (ESI+): m/z=416 [M+H]+

HPLC (Method 1): Retention time=0.972 min.

Procedure 14
Intermediate 14a

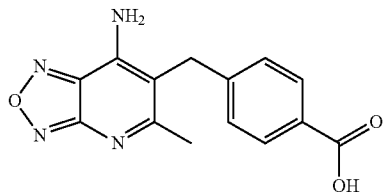 [SMILES: Cc1nc2nonc2c(N)c1Cc1ccc(C(=O)O)cc1]

4-({7-Amino-5-methyl-[1,2,5]oxadiazolo[3,4-b]pyri-din-6-yl}methyl)benzoic Acid

Analogously to intermediate 3a the following compound is obtained by starting from compound 2.10 Methyl 4-({7-amino-5-methyl-[1,2,5]oxadiazolo[3,4-b]pyridin-6-yl}methyl)benzoate and lithium hydroxide (2 M aqueous solution). The mixture is purified by extraction between citric acid and ethyl acetate. The organic layer is evaporated and the residue is stirred in methanol/ethyl acetate, filtered off and dried.

Mass spectrometry (ESI$^+$): m/z=285 [M+H]$^+$
HPLC (Method 3): Retention time=0.730 min.
Compound 14.1

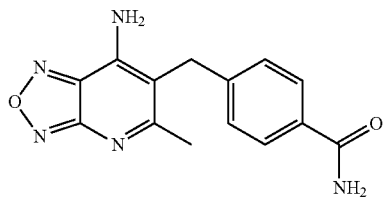 [SMILES: Cc1nc2nonc2c(N)c1Cc1ccc(C(N)=O)cc1]

4-({7-Amino-5-methyl-[1,2,5]oxadiazolo[3,4-b]pyri-din-6-yl}methyl)benzamide

To a solution of intermediate 14a 4-({7-Amino-5-methyl-[1,2,5]oxadiazolo[3,4-b]pyridin-6-yl}methyl)benzoic acid (50 mg; 0.18 mmol), N,N-diisopropylethylamine (71 μL; 0.39 mmol) and O-(7-Azabenzotriazol-1-yl)-N,N,N',N'-tetramethyluronium hexafluoro-phosphate (73.5 mg; 0.19 mmol) in 0.5 mL N,N-dimethylformamide is added after 5 minutes ammonia (0.5 M solution in dioxane 0.70 mL; 0.35 mmol). The reaction is stirred for three hours at room temperature and purified by reverse phase chromatography (modifier: ammonium hydroxide)

Yield: 20.4 mg (41% of theory)
Mass spectrometry (ESI$^+$): m/z=284 [M+H]$^+$
HPLC (Method 5): Retention time=0.46 min.
Compound 14.2

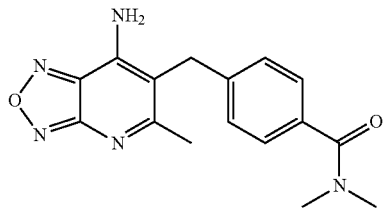 [SMILES: Cc1nc2nonc2c(N)c1Cc1ccc(C(=O)N(C)C)cc1]

4-({7-Amino-5-methyl-[1,2,5]oxadiazolo[3,4-b]pyri-din-6-yl}methyl)-N,N-dimethylbenzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and dimethylamine (2 M solution in tetrahydrofuran).

Yield: 18.6 mg (34% of theory)
Mass spectrometry (ESI$^+$): m/z=312 [M+H]$^+$
HPLC (Method 5): Retention time=0.55 min.
Compound 14.3

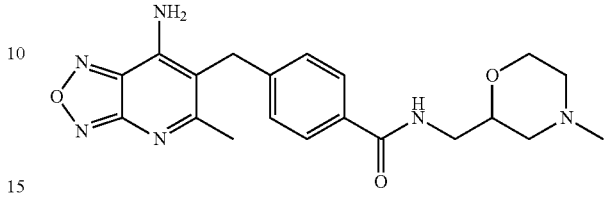

4-({7-Amino-5-methyl-[1,2,5]oxadiazolo[3,4-b]pyri-din-6-yl}methyl)-N-[(4-methylmorpholin-2-yl)methyl]benzamide Analogously to compound 14.1 the following compound is obtained by starting from intermediate 14a 4-({7-Amino-5-methyl-[1,2,5]oxadiazolo[3,4-b]pyridin-6-yl}methyl)benzoic acid and C-(4-Methyl-morpholin-2-yl)-methylamine. Use of triethylamine instead of N,N-diisopropylethylamine.
Mass spectrometry (ESI$^+$): m/z=397 [M+H]$^+$
HPLC (Method 1): Retention time=0.76 min.
Compound 14.4

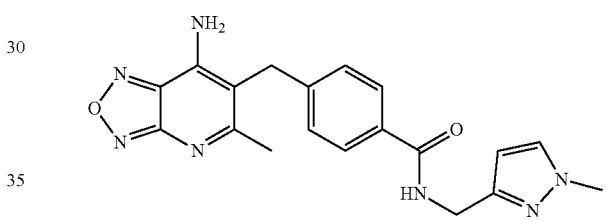

4-({7-Amino-5-methyl-[1,2,5]oxadiazolo[3,4-b]pyri-din-6-yl}methyl)-N-[(1-methyl-1H-pyrazol-3-yl)methyl]benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and C-(1-Methyl-1H-pyrazol-3-yl)-methylamine. Use of triethylamine instead of N,N-diisopropylethylamine.
Mass spectrometry (ESI$^+$): m/z=378 [M+H]$^+$
HPLC (Method 6): Retention time=0.438 min.
Compound 14.5

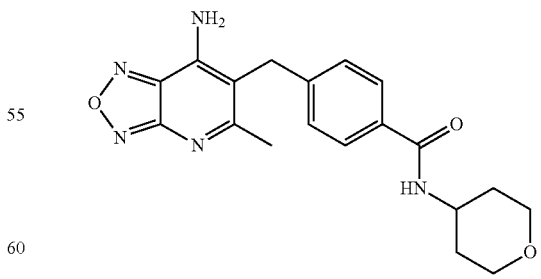

4-({7-Amino-5-methyl-[1,2,5]oxadiazolo[3,4-b]pyri-din-6-yl}methyl)-N-(oxan-4-yl)benzamide Analogously to compound 14.1 the following compound is obtained by starting from intermediate 14a 4-({7-Amino- 5-methyl-[1,2,5]oxadiazolo[3,4-b]pyridin-6-yl}methyl)-benzoic acid and 4-Aminotetrahydropyran. Use of triethylamine instead of N,N-diisopropylethylamine.

Mass spectrometry (ESI⁺): m/z=368 [M+H]⁺

HPLC (Method 6): Retention time=0.445 min.

Compound 14.6

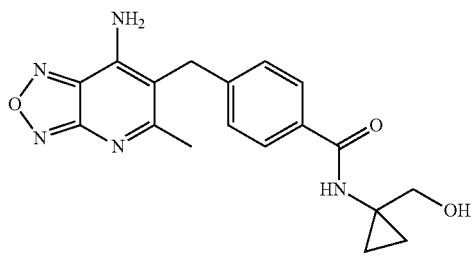 [SMILES: Cc1nc2nonc2c(N)c1Cc1ccc(C(=O)NC2(CO)CC2)cc1]

4-({7-Amino-5-methyl-[1,2,5]oxadiazolo[3,4-b]pyridin-6-yl}methyl)-N-[1-(hydroxymethyl)cyclopropyl] benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 1-Amino-cyclopropanemethanol. Use of triethylamine instead of N,N-diisopropylethylamine.

Mass spectrometry (ESI⁺): m/z=354 [M+H]⁺

HPLC (Method 6): Retention time=0.399 min.

Compound 14.7

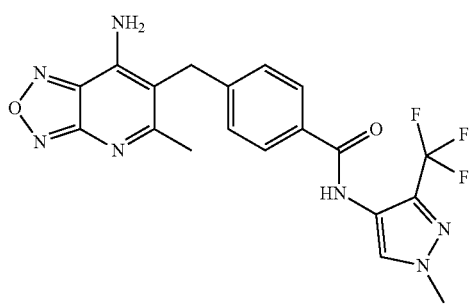 [SMILES: Cc1nc2nonc2c(N)c1Cc1ccc(C(=O)Nc2cn(C)nc2C(F)(F)F)cc1]

4-({7-Amino-5-methyl-[1,2,5]oxadiazolo[3,4-b]pyridin-6-yl}methyl)-N-[1-methyl-3-(trifluoromethyl)-1H-pyrazol-4-yl]benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 1-Methyl-3-trifluoromethyl-1H-pyrazol-4-ylamine. Use of triethylamine instead of N,N-diisopropylethylamine.

Mass spectrometry (ESI⁺): m/z=432 [M+H]⁺

HPLC (Method 6): Retention time=0.590 min.

Compound 14.8

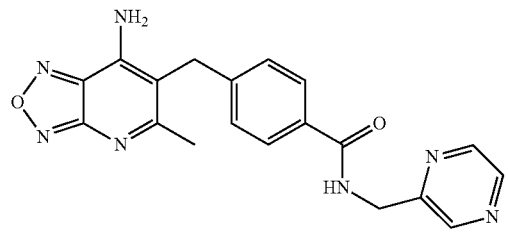 [SMILES: Cc1nc2nonc2c(N)c1Cc1ccc(C(=O)NCc2cnccn2)cc1]

4-({7-Amino-5-methyl-[1,2,5]oxadiazolo[3,4-b]pyridin-6-yl}methyl)-N-[(pyrazin-2-yl)methyl]benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 2-aminomethylpyrazine. Use of triethylamine instead of N,N-diisopropylethylamine.

Mass spectrometry (ESI⁺): m/z=376 [M+H]⁺

HPLC (Method 6): Retention time=0.412 min.

Compound 14.9

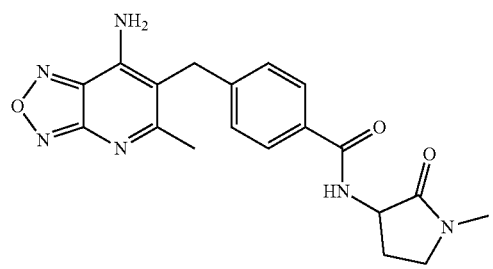 [SMILES: Cc1nc2nonc2c(N)c1Cc1ccc(C(=O)NC2CCN(C)C2=O)cc1]

4-({7-Amino-5-methyl-[1,2,5]oxadiazolo[3,4-b]pyridin-6-yl}methyl)-N-(1-methyl-2-oxopyrrolidin-3-yl) benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 3-Amino-1-methylpyrrolidin-2-one. Use of triethylamine instead of N,N-diisopropylethylamine.

Mass spectrometry (ESI⁺): m/z=381 [M+H]⁺

HPLC (Method 6): Retention time=0.337 min.

Compound 14.10

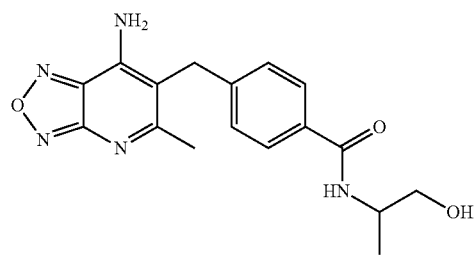 [SMILES: Cc1nc2nonc2c(N)c1Cc1ccc(C(=O)NC(C)CO)cc1]

4-({7-amino-5-methyl-[1,2,5]oxadiazolo[3,4-b]pyridin-6-yl}methyl)-N-(1-hydroxypropan-2-yl)benzamide Analogously to compound 14.1 the following compound is obtained by starting from intermediate 14a 4-({7-Amino- 5-methyl-[1,2,5]oxadiazolo[3,4-b]pyridin-6-yl}methyl)-benzoic acid and 2-Amino-1-propanol. Use of triethylamine instead of N,N-diisopropylethylamine.

Mass spectrometry (ESI⁺): m/z=342 [M+H]⁺

HPLC (Method 6): Retention time=0.339 min.

Compound 14.11

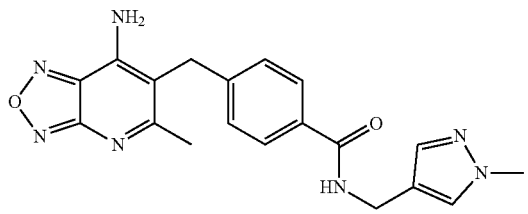 [SMILES: Cc1nc2nonc2c(N)c1Cc1ccc(C(=O)NCc2cnn(C)c2)cc1]

4-({7-Amino-5-methyl-[1,2,5]oxadiazolo[3,4-b]pyridin-6-yl}methyl)-N-[(1-methyl-1H-pyrazol-4-yl)methyl]benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 1-(1-Methyl-1H-pyrazol-4-yl)methanamine. Use of triethylamine instead of N,N-diisopropylethylamine.

Mass spectrometry (ESI⁺): m/z=378 [M+H]⁺

HPLC (Method 6): Retention time=0.376 min.

Compound 14.12

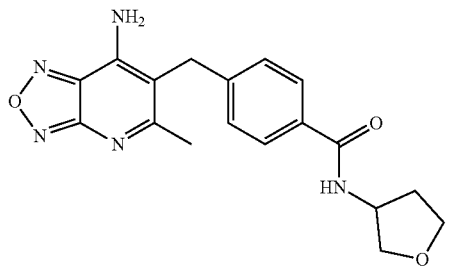 [SMILES: Cc1nc2nonc2c(N)c1Cc1ccc(C(=O)NC2CCOC2)cc1]

4-({7-Amino-5-methyl-[1,2,5]oxadiazolo[3,4-b]pyridin-6-yl}methyl)-N-(oxolan-3-yl)benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and Tetrahydro-furan-3-ylamine. Use of triethylamine instead of N,N-diisopropylethylamine.

Mass spectrometry (ESI⁺): m/z=354 [M+H]⁺

HPLC (Method 6): Retention time=0.420 min.

Compound 14.13

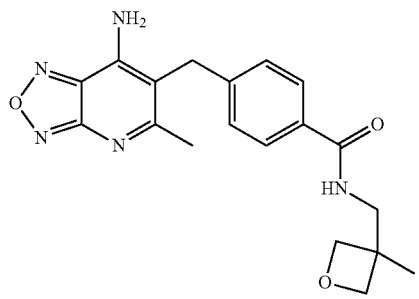 [SMILES: Cc1nc2nonc2c(N)c1Cc1ccc(C(=O)NCC2(C)COC2)cc1]

4-({7-Amino-5-methyl-[1,2,5]oxadiazolo[3,4-b]pyridin-6-yl}methyl)-N-[(3-methyloxetan-3-yl)methyl]benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and C-(3-Methyl-oxetan-3-yl)-methylamine. Use of triethylamine instead of N,N-diisopropylethylamine.

Mass spectrometry (ESI⁺): m/z=368 [M+H]⁺

HPLC (Method 6): Retention time=0.446 min.

Compound 14.14

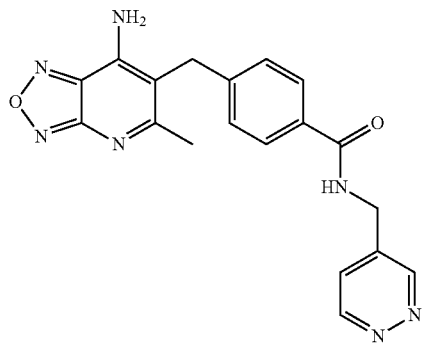 [SMILES: Cc1nc2nonc2c(N)c1Cc1ccc(C(=O)NCc2ccnnc2)cc1]

4-({7-Amino-5-methyl-[1,2,5]oxadiazolo[3,4-b]pyridin-6-yl}methyl)-N-[(pyridazin-4-yl)methyl]benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 4-Pyridazinemethanamine. Use of triethylamine instead of N,N-diisopropylethylamine.

Mass spectrometry (ESI⁺): m/z=376 [M+H]⁺

HPLC (Method 6): Retention time=0.362 min.

Compound 14.15

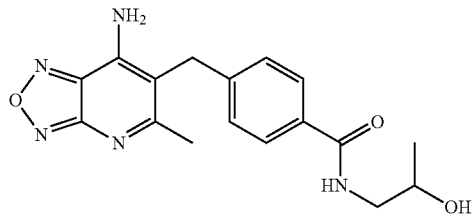 [SMILES: Cc1nc2nonc2c(N)c1Cc1ccc(C(=O)NCC(C)O)cc1]

4-({7-Amino-5-methyl-[1,2,5]oxadiazolo[3,4-b]pyridin-6-yl}methyl)-N-(2-hydroxypropyl)benzamide Analogously to compound 14.1 the following compound is obtained by starting from intermediate 14a 4-({7-Amino- 5-methyl-[1,2,5]oxadiazolo[3,4-b]pyridin-6-yl}methyl)-benzoic acid and 1-Amino-2-propanol. Use of triethylamine instead of N,N-diisopropylethylamine.

Mass spectrometry (ESI⁺): m/z=342 [M+H]⁺

HPLC (Method 6): Retention time=0.386 min.

Compound 14.16

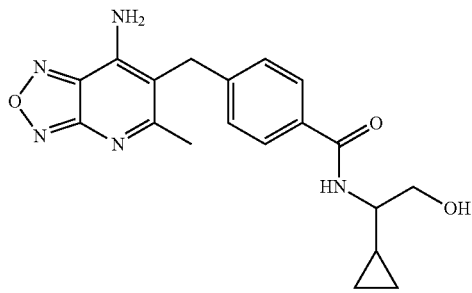 [SMILES: Cc1nc2nonc2c(N)c1Cc1ccc(C(=O)NC(CO)C2CC2)cc1]

4-({7-Amino-5-methyl-[1,2,5]oxadiazolo[3,4-b]pyridin-6-yl}methyl)-N-(1-cyclopropyl-2-hydroxyethyl)benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 2-Amino-2-cyclopropylethan-1-ol. Use of triethylamine instead of N,N-diisopropylethylamine.

Mass spectrometry (ESI⁺): m/z=368 [M+H]⁺

HPLC (Method 6): Retention time=0.455 min.

Compound 14.17

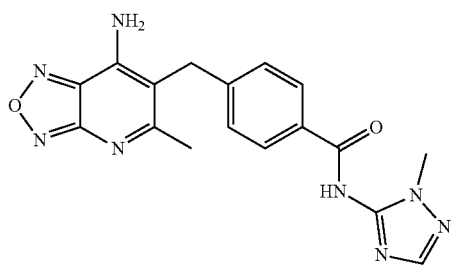 [SMILES: Cc1nc2nonc2c(N)c1Cc1ccc(C(=O)Nc2ncnn2C)cc1]

4-({7-Amino-5-methyl-[1,2,5]oxadiazolo[3,4-b]pyridin-6-yl}methyl)-N-(1-methyl-1H-1,2,4-triazol-5-yl)benzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and 1-Methyl-1H-1,2,4-triazole-5-amine. Use of triethylamine instead of N,N-diisopropylethylamine.

Mass spectrometry (ESI⁺): m/z=365 [M+H]⁺

HPLC (Method 7): Retention time=0.585 min.

Compound 14.18

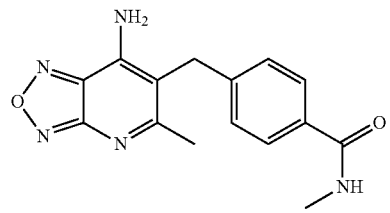 [SMILES: CNC(=O)c1ccc(Cc2c(C)nc3nonc3c2N)cc1]

4-({7-Amino-5-methyl-[1,2,5]oxadiazolo[3,4-b]pyridin-6-yl}methyl)-N-methylbenzamide Analogously to compound 14.1 the following compound is obtained by starting from intermediate 14a 4-({7-Amino-5-methyl-[1,2,5]oxadiazolo[3,4-b]pyridin-6-yl}methyl)-benzoic acid and Methylamine (2 M solution in tetrahydrofuran).

Mass spectrometry (ESI⁺): m/z=298 [M+H]⁺

HPLC (Method 5): Retention time=0.51 min.

Procedure 15

Intermediate 15a

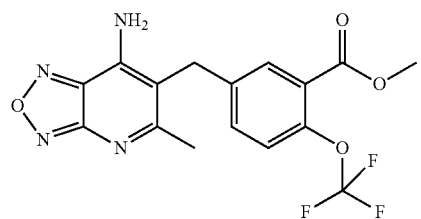 [SMILES: COC(=O)c1cc(Cc2c(C)nc3nonc3c2N)ccc1OC(F)(F)F]

Methyl 5-({7-amino-5-methyl-[1,2,5]oxadiazolo[3,4-b]pyridin-6-yl}methyl)-2-(trifluoromethoxy)benzoate Compound 2.14 6-{[3-Bromo-4-(trifluoromethoxy)phenyl]methyl}-5-methyl-[1,2,5]oxadiazolo[3,4-b]pyridin-7-amine (0.17 g; 0.422 mmol) is dissolved in 5 mL of methanol. Triethylamine (0.175 mL; 1.265 mmol), Palladium(II) acetate (14.2 mg; 0.063 mmol) and 1,1'-Bis-(diphenylphospino)-ferrocene (35.065 mg; 0.063 mmol) are added. The mixture is stirred over night at 80° C. under 5 bar Carbonic oxide atmosphere. The mixture is filtered and concentrated under reduced pressure. The residue is purified by reverse phase chromatography-HPLC (modifier: trifluoroacetic acid).

Yield: 0.10 g (62% of theory)

Mass spectrometry (ESI⁺): m/z=383 [M+H]⁺

HPLC (Method 3): Retention time=0.996 min.

Intermediate 15b

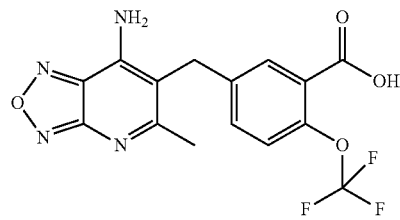 [SMILES: Cc1nc2nonc2c(N)c1Cc1ccc(OC(F)(F)F)c(C(=O)O)c1]

5-({7-Amino-5-methyl-[1,2,5]oxadiazolo[3,4-b]pyridin-6-yl}methyl)-2-(trifluoromethoxy)benzoic acid Analogously to intermediate 3a the following compound is obtained by starting from intermediate 15a Methyl 5-({7- amino-5-methyl-[1,2,5]oxadiazolo[3,4-b]pyridin-6-yl}methyl)-2-(trifluoromethoxy)benzoate and lithium hydroxide (2 M aqueous solution). The mixture is stirred over night instead of 2 h. The residue is acidified with conc. HCl.

Yield: 55 mg (57% of theory)
Mass spectrometry (ESI$^+$): m/z=369 [M+H]$^+$
HPLC (Method 3): Retention time=0.896 min.
Compound 15.1

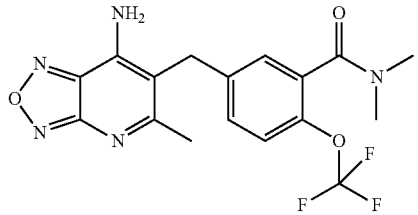 [SMILES: Cc1nc2nonc2c(N)c1Cc1ccc(OC(F)(F)F)c(C(=O)N(C)C)c1]

5-({7-Amino-5-methyl-[1,2,5]oxadiazolo[3,4-b]pyridin-6-yl}methyl)-N,N-dimethyl-2-(trifluoromethoxy)benzamide Analogously to compound 14.1 the following compound is obtained by starting from intermediate 15b 5-({7-Amino-5-methyl-[1,2,5]oxadiazolo[3,4-b]pyridin-6-yl}methyl)-2-(trifluoromethoxy)benzoic acid and Dimethylamine (2 M solution in tetrahydrofuran).

Yield: 5 mg (21% of theory)
Mass spectrometry (ESI$^+$): m/z=396 [M+H]$^+$
HPLC (Method 1): Retention time=0.795 min.
Compound 15.2

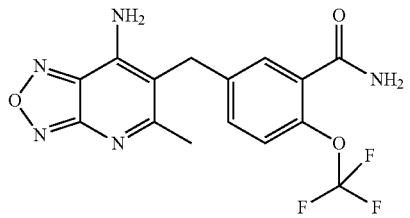 [SMILES: Cc1nc2nonc2c(N)c1Cc1ccc(OC(F)(F)F)c(C(N)=O)c1]

5-({7-Amino-5-methyl-[1,2,5]oxadiazolo[3,4-b]pyridin-6-yl}methyl)-2-(trifluoromethoxy)benzamide Analogously to compound 14.1 the following compound is obtained by starting from intermediate 15b 5-({7-Amino-5-methyl-[1,2,5]oxadiazolo[3,4-b]pyridin-6-yl}methyl)-2-(trifluoromethoxy)benzoic acid and ammonia (32%).

Yield: 70 mg (91% of theory)
Mass spectrometry (ESI$^+$): m/z=368 [M+H]$^+$
HPLC (Method 3): Retention time=0.782 min.
Intermediate 15c

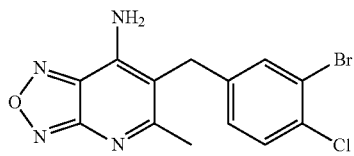 [SMILES: Cc1nc2nonc2c(N)c1Cc1ccc(Cl)c(Br)c1]

6-[(3-Bromo-4-chlorophenyl)methyl]-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.64a (3-Bromo-4-chloro-phenyl)magnesium chloride. The mixture is cooled to −55° C. rather than −40° C., quenched with methanol and put on silica gel.

The mixture is purified by silica gel chromatography (eluent: cyclohexane/ethyl acetate 0%->70%).

Yield: 2.587 g (66% of theory)
Mass spectrometry (ESI$^+$): m/z=353 [M+H]$^+$
HPLC (Method 1): Retention time=1.004 min.
Intermediate 15d

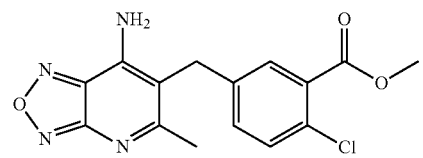 [SMILES: COC(=O)c1cc(Cc2c(C)nc3nonc3c2N)ccc1Cl]

Methyl 5-({7-amino-5-methyl-[1,2,5]oxadiazolo[3,4-b]pyridin-6-yl}methyl)-2-chlorobenzoate Analogously to intermediate 15a the following compound is obtained by starting from intermediate 15c 6-[(3-Bromo-4-chlorophenyl)methyl]-5-methyl-[1,2,5]oxadiazolo-[3,4-b]pyridin-7-amine. The mixture is only concentrated and not purified by reverse phase chromatography-HPLC Yield: 160 mg (94% of theory)
Mass spectrometry (ESI$^+$): m/z=333 [M+H]$^+$
HPLC (Method 3): Retention time=0.908 min.
Intermediate 15e

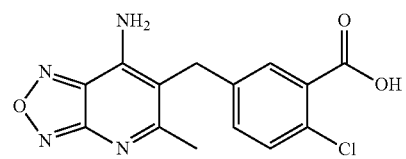 [SMILES: Cc1nc2nonc2c(N)c1Cc1ccc(Cl)c(C(=O)O)c1]

5-({7-Amino-5-methyl-[1,2,5]oxadiazolo[3,4-b]pyridin-6-yl}methyl)-2-chlorobenzoic Acid Analogously to intermediate 3a the following compound is obtained by starting from intermediate 15d Methyl 5-({7-amino-5-methyl-[1,2,5]oxadiazolo[3,4-b]pyridin-6-yl}methyl)-2-chlorobenzoate and lithium hydroxide (2 M aqueous solution). The mixture is stirred over night at room temperature and for 4 h at 40° C. instead of 2 h. The mixture is concentrated and purified by reverse phase chromatography-HPLC (modifier: NH$_4$OH).

Yield: 100 mg (65% of theory)
Mass spectrometry (ESI$^+$): m/z=319 [M+H]$^+$
HPLC (Method 1): Retention time=0.515 min.
Compound 15.3

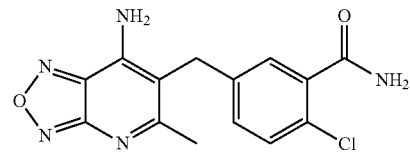 [SMILES: Cc1nc2nonc2c(N)c1Cc1ccc(Cl)c(C(N)=O)c1]

5-({7-Amino-5-methyl-[1,2,5]oxadiazolo[3,4-b]pyridin-6-yl}methyl)-2-chlorobenzamide Analogously to compound 14.1 the following compound is obtained by starting from intermediate 15e 5-({7-Amino- 5-methyl-[1,2,5]oxadiazolo[3,4-b]pyridin-6-yl}methyl)-2-chlorobenzoic acid and ammonia (7 mol/L in methanol).
Yield: 24 mg (24% of theory)
Mass spectrometry (ESI$^+$): m/z=318 [M+H]$^+$
HPLC (Method 1): Retention time=0.703 min.
Compound 15.4

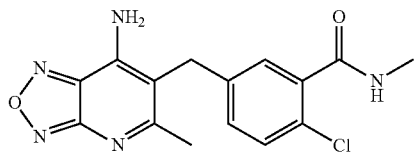 [SMILES: CNC(=O)c1cc(Cc2c(C)nc3nonc3c2N)ccc1Cl]

5-({7-Amino-5-methyl-[1,2,5]oxadiazolo[3,4-b]pyridin-6-yl}methyl)-2-chloro-N-methylbenzamide Analogously to compound 14.1 the following compound is obtained by starting from intermediate 15e 5-({7-Amino-5-methyl-[1,2,5]oxadiazolo[3,4-b]pyridin-6-yl}methyl)-2-chlorobenzoic acid and Methyl amine (2 M solution in tetrahydrofuran).
Yield: 13 mg (27% of theory)
Mass spectrometry (ESI$^+$): m/z=332 [M+H]$^+$
HPLC (Method 1): Retention time=0.750 min.
Compound 15.5

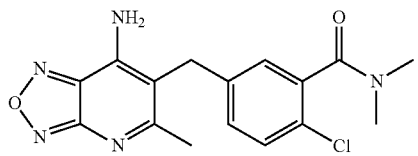 [SMILES: Cc1nc2nonc2c(N)c1Cc1ccc(Cl)c(C(=O)N(C)C)c1]

5-({7-Amino-5-methyl-[1,2,5]oxadiazolo[3,4-b]pyridin-6-yl}methyl)-2-chloro-N,N-dimethylbenzamide Analogously to compound 14.1 the following compound is obtained by starting from intermediate 15e 5-({7-Amino-5-methyl-[1,2,5]oxadiazolo[3,4-b]pyridin-6-yl}methyl)-2-chlorobenzoic acid and Dimethylamine (2 M solution in tetrahydrofuran).
Yield: 10 mg (20% of theory)
Mass spectrometry (ESI$^+$): m/z=346 [M+H]$^+$
HPLC (Method 1): Retention time=0.823 min.
Intermediate 15f

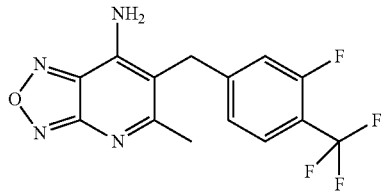 [SMILES: Cc1nc2nonc2c(N)c1Cc1ccc(C(F)(F)F)c(F)c1]

6-{[3-Bromo-4-(trifluoromethyl)phenyl]methyl}-5-methyl-[1,2,5]oxadiazolo[3,4-b]pyridin-7-amine Analogously to compound 4.50 the following compound is obtained by starting from intermediate 3c 6-Chloromethyl-5-methyl-[1,2,5]oxadiazolo[3,4-b]pyridin-7-amine and intermediate 4.65a 3-Bromo-4-(trifluoromethyl)phenyl]-magnesium chloride. The mixture is cooled to −55° C. rather than −40° C., quenched with methanol and the solvent is evaporated. The residue is taken up in dichloromethane and washed with a saturated aqueous solution of ammonium chloride. The organic layer is dried and concentrated. The residue is solved in acetonitrile and water and purified by reverse phase chromatography-HPLC (modifier: ammonium hydroxide).
Yield: 0.108 g (17% of theory)
Mass spectrometry (ESI$^+$): m/z=387 [M+H]$^+$
HPLC (Method 3): Retention time=1.052 min.
Intermediate 15g

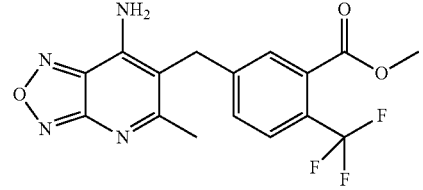 [SMILES: COC(=O)c1cc(Cc2c(C)nc3nonc3c2N)ccc1C(F)(F)F]

Methyl 5-({7-amino-5-methyl-[1,2,5]oxadiazolo[3,4-b]pyridin-6-yl}methyl)-2-(trifluoromethyl)benzoate Analogously to intermediate 15a the following compound is obtained by starting from intermediate 15f 6-{[3-Bromo-4-(trifluoromethyl)phenyl]methyl}-5-methyl-[1,2,5]oxadiazolo[3,4-b]pyridin-7-amine.
Yield: 24 mg (23% of theory)
HPLC (Method 3): Retention time=0.986 min.
Intermediate 15h

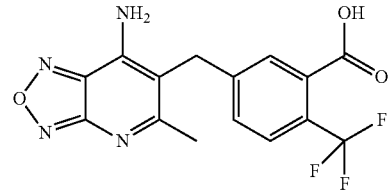 [SMILES: Cc1nc2nonc2c(N)c1Cc1ccc(C(F)(F)F)c(C(=O)O)c1]

5-({7-Amino-5-methyl-[1,2,5]oxadiazolo[3,4-b]pyridin-6-yl}methyl)-2-(trifluoromethyl)benzoic Acid Analogously to intermediate 3a the following compound is obtained by starting from Intermediate 15g Methyl 5-({7-amino-5-methyl-[1,2,5]oxadiazolo[3,4-b]pyridin-6-yl}methyl)-2-(trifluoromethyl)benzoate and lithium hydroxide (2 M aqueous solution).
The pH-value is adjusted to 1 instead of 6.
Yield: 17 mg (73% of theory)
HPLC (Method 3): Retention time=0.885 min.
Compound 15.6

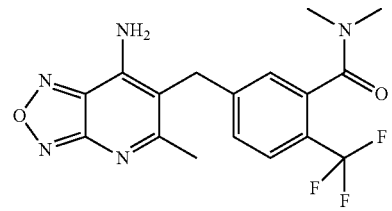 [SMILES: Cc1nc2nonc2c(N)c1Cc1ccc(C(F)(F)F)c(C(=O)N(C)C)c1]

5-({7-Amino-5-methyl-[1,2,5]oxadiazolo[3,4-b]pyridin-6-yl}methyl)-N,N-dimethyl-2-(trifluoromethyl)benzamide Analogously to compound 14.1 the following compound is obtained by starting from Intermediate 15h 5-({7-Amino- 5-methyl-[1,2,5]oxadiazolo[3,4-b]pyridin-6-yl}methyl)-2-(trifluoromethyl)benzoic acid and Dimethylamine (2 M solution in tetrahydrofuran).

Yield: 3 mg (18% of theory)
Mass spectrometry (ESI$^+$): m/z=380 [M+H]$^+$
HPLC (Method 1): Retention time=0.863 min.

Procedure 16

Compound 16.1

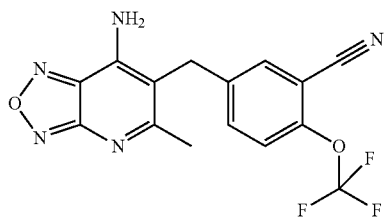 [SMILES: Cc1nc2nonc2c(N)c1Cc1ccc(OC(F)(F)F)c(C#N)c1]

5-({7-Amino-5-methyl-[1,2,5]oxadiazolo[3,4-b]pyridin-6-yl}methyl)-2-(trifluoromethoxy)benzonitrile Compound 2.14 6-{[3-Bromo-4-(trifluoromethoxy)phenyl]methyl}-5-methyl-[1,2,5]oxadiazolo[3,4-b]pyridin-7-amine (30.0 mg; 0.07 mmol) and zinc cyanide (21.8 mg; 0.19 mmol) are dissolved in 1 mL N,N-dimethylformamide and flushed with argon for 10 minutes. Tetrakis(triphenylphosphine)palladium(0) (51.6 mg; 0.04 mmol) is added and the mixture is flushed with argon for 5 minutes. After stirring for 30 minutes at 110° C., 45 minutes at 160° C. and 45 minutes at 200° C. in a microwave the mixture is purified by reverse phase chromatography-HPLC (modifier: trifluoroacetic acid).

Yield: 9.00 mg (35% of theory)
Mass spectrometry (ESI$^+$): m/z=350 [M+H]$^+$
HPLC (Method 3): Retention time=0.972 min.

Procedure 17

Compound 17.1

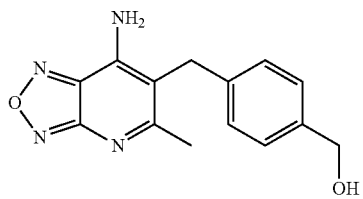 [SMILES: Cc1nc2nonc2c(N)c1Cc1ccc(CO)cc1]

[4-({7-Amino-5-methyl-[1,2,5]oxadiazolo[3,4-b]pyridin-6-yl}methyl)phenyl]methanol 1,1'-Carbonyldiimidazole (274 mg; 1.69 mmol) is added to intermediate 14a 4-({7-Amino-5-methyl-[1,2,5]oxadiazolo[3,4-b]pyridin-6-yl}methyl)benzoic acid (400 mg; 1.41 mmol) in 15 mL tetrahydrofuran. After stirring at room temperature for 18 hours sodium borohydride (63.9 mg; 1.69 mmol) is added. After further 18 hours of stirring the mixture is poured into water and extracted three times with dichloromethane. The combined organic layers are dried and evaporated. The residue is purified by reverse phase chromatography-HPLC (modifier: trifluoroacetic acid).

Yield: 105 mg (28% of theory)
Mass spectrometry (ESI$^+$): m/z=271 [M+H]$^+$
HPLC (Method 2): Retention time=0.608 min.

Intermediate 17a

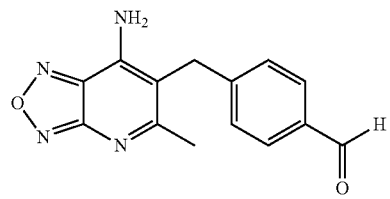 [SMILES: Cc1nc2nonc2c(N)c1Cc1ccc(C=O)cc1]

4-({7-Amino-5-methyl-[1,2,5]oxadiazolo[3,4-b]pyridin-6-yl}methyl)benzaldehyde

Compound 17.1 [4-({7-Amino-5-methyl-[1,2,5]oxadiazolo[3,4-b]pyridin-6-yl}methyl)phenyl]methanol (560 mg; 2.07 mmol) is dissolved in 20 mL dichloromethane and Dess-Martin-periodinane (1.23 g; 2.90 mmol) is added at room temperature. After stirring for 18 hours the mixture is purified by silica gel chromatography (eluent: petrol ether/ethyl acetate 0%->40%).

Yield: 80.0 mg (14% of theory)
Mass spectrometry (ESI$^+$): m/z=269 [M+H]$^+$
HPLC (Method 3): Retention time=0.785 min.

Compound 17.2

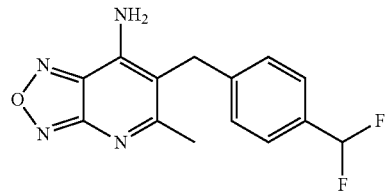 [SMILES: Cc1nc2nonc2c(N)c1Cc1ccc(C(F)F)cc1]

6-{[4-(difluoromethyl)phenyl]methyl}-5-methyl-[1,2,5]oxadiazolo[3,4-b]pyridin-7-amine Intermediate 17a 4-({7-Amino-5-methyl-[1,2,5]oxadiazolo[3,4-b]pyridin-6-yl}methyl)benzaldehyde (40.0 mg; 0.15 mmol) is dissolved in 1 mL dichloromethane and cooled to −60° C. Diethylaminosulfur trifluoride (23.6 µL, 0.18 mmol) is added and the mixture allowed to warm up to room temperature and is stirred for 18 hours. The mixture is poured into ice water and basified with NaHCO$_3$. The aqueous layer is extracted three times with ethyl acetate. The combined organic layers are dried, evaporated and purified by reverse phase chromatography-HPLC (modifier: trifluoroacetic acid).

Yield: 20.0 mg (46% of theory)
Mass spectrometry (ESI$^+$): m/z=291 [M+H]$^+$
HPLC (Method 3): Retention time=0.934 min.

Procedure 18

Compound 18.1

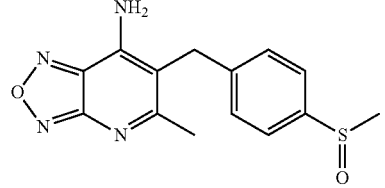 [SMILES: Cc1nc2nonc2c(N)c1Cc1ccc(S(C)=O)cc1]

6-[(4-Methanesulfinylphenyl)methyl]-5-methyl-[1,2,5]oxadiazolo[3,4-b]pyridin-7-amine Compound 4.19 5-Methyl-6-{[4-(methylsulfanyl)phenyl]methyl}-[1,2,5]oxadiazolo[3,4-b]pyridin-7-amine (50.00 mg; 0.175 mmol) and 3-chloroperoxybenzoic acid (33.15 mg; 0.192 mmol) in 1 mL chloroform are stirred at room temperature over night. The mixture is extracted with dichloromethane and saturated aqueous solution of sodium carbonate and the organic phase is dried and concentrated. The mixture is diluted with water and acetonitrile and purified by reverse phase chromatography-HPLC (modifier: ammonium hydroxide).

Yield: 5 mg (10% of theory)
Mass spectrometry (ESI+): m/z=303 [M+H]+
HPLC (Method 1): Retention time=0.696 min.

Procedure 19

Compound 19.1

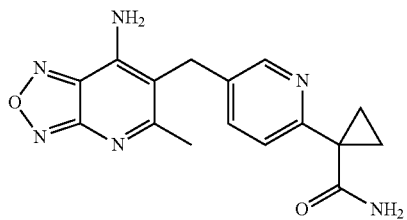 [SMILES: Cc1nc2nonc2c(N)c1Cc1ccc(C2(C(N)=O)CC2)nc1]

1-[5-({7-Amino-5-methyl-[1,2,5]oxadiazolo[3,4-b]pyridin-6-yl}methyl)pyridin-2-yl]cyclopropane-1-carboxamide Compound 4.8 1-[5-({7-Amino-5-methyl-[1,2,5]oxadiazolo[3,4-b]pyridin-6-yl}methyl)pyridin-2-yl]cyclopropane-1-carbonitrile (210.0 mg; 0.548 mmol) and sodium hydroxide 4 M (600 µL; 2.400 mmol) in 1 mL ethanol are stirred at 100° C. for 2.5 h. Cooled to room temperature, add hydrochloric acid 4 M (400 µl; 1.600 mmol) and purified by reverse phase chromatography-HPLC (modifier: ammonium hydroxide).

Yield: 63 mg (35% of theory)
Mass spectrometry (ESI+): m/z=325 [M+H]+
HPLC (Method 3): Retention time=0.605 min.

Compound 19.2

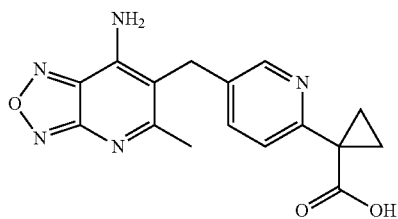 [SMILES: Cc1nc2nonc2c(N)c1Cc1ccc(C2(C(=O)O)CC2)nc1]

1-[5-({7-Amino-5-methyl-[1,2,5]oxadiazolo[3,4-b]pyridin-6-yl}methyl)pyridin-2-yl]cyclopropane-1-carboxylic Acid Analogously to compound 19.1 the following compound is obtained by starting from compound 4.8 1-[5-({7-Amino-5-methyl-[1,2,5]oxadiazolo[3,4-b]pyridin-6-yl}methyl)pyridin-2-yl]cyclopropane-1-carbonitrile.

Yield: 13 mg (30% of theory)
Mass spectrometry (ESI+): m/z=326 [M+H]+
HPLC (Method 1): Retention time=0.517 min.

Compound 19.3

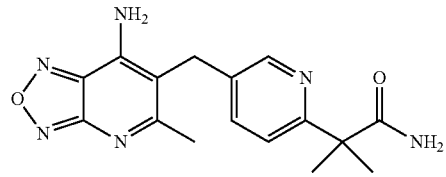 [SMILES: Cc1nc2nonc2c(N)c1Cc1ccc(C(C)(C)C(N)=O)nc1]

2-[5-({7-Amino-5-methyl-[1,2,5]oxadiazolo[3,4-b]pyridin-6-yl}methyl)pyridin-2-yl]-2-methylpropanamide Analogously to compound 19.1 the following compound is obtained by starting from compound 4.24 2-[5-({7-Amino-5-methyl-[1,2,5]oxadiazolo[3,4-b]pyridin-6-yl}methyl)pyridin-2-yl]-2-methylpropanenitrile.

Yield: 24 mg (22% of theory)
Mass spectrometry (ESI+): m/z=327 [M+H]+
HPLC (Method 1): Retention time=0.706 min.

Compound 19.4

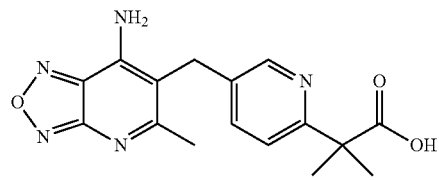 [SMILES: Cc1nc2nonc2c(N)c1Cc1ccc(C(C)(C)C(=O)O)nc1]

2-[5-({7-Amino-5-methyl-[1,2,5]oxadiazolo[3,4-b]pyridin-6-yl}methyl)pyridin-2-yl]-2-methylpropanoic Acid Analogously to compound 19.1 the following compound is obtained by starting from compound 4.24 2-[5-({7-Amino-5-methyl-[1,2,5]oxadiazolo[3,4-b]pyridin-6-yl}methyl)-pyridin-2-yl]-2-methylpropanenitrile.

Yield: 5 mg (5% of theory)
Mass spectrometry (ESI+): m/z=328 [M+H]+
HPLC (Method 1): Retention time=0.540 min.

Compound 19.5

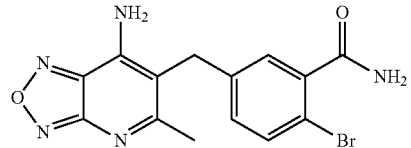 [SMILES: Cc1nc2nonc2c(N)c1Cc1ccc(Br)c(C(N)=O)c1]

5-({7-Amino-5-methyl-[1,2,5]oxadiazolo[3,4-b]pyridin-6-yl}methyl)-2-bromobenzamide Compound 4.61 5-({7-Amino-5-methyl-[1,2,5]oxadiazolo[3,4-b]pyridin-6-yl}methyl)-2-bromobenzonitrile (50 mg; 0.15 mmol) is dissolved in 1 mL methanol and 2 mL acetonitrile. Sodium hydroxide (4 M in water; 0.182 mL; 0.73 mmol) is added and stirred at 60° C. over night. The reaction is purified by reverse phase chromatography (modifier: ammonium hydroxide).

Yield: 22 mg (42% of theory)
Mass spectrometry (ESI+): m/z=362 [M+H]+
HPLC (Method 1): Retention time=0.717 min.

Compound 19.6

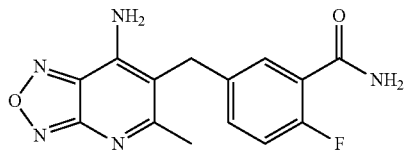

5-({7-Amino-5-methyl-[1,2,5]oxadiazolo[3,4-b]pyridin-6-yl}methyl)-2-fluorobenzamide Analogously to compound 19.5 the following compound is obtained by starting from compound 2.9 5-({7-Amino-5-methyl-[1,2,5]oxadiazolo[3,4-b]pyridin-6-yl}methyl)-2-fluorobenzonitrile.
Yield: 20 mg (24% of theory)
Mass spectrometry (ESI⁺): m/z=302 [M+H]⁺
HPLC (Method 1): Retention time=0.697 min.

Compound 19.7

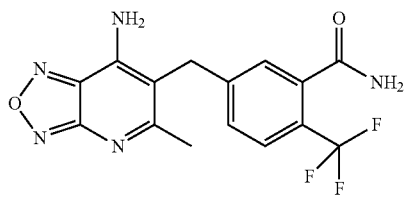 [SMILES: Cc1nc2nonc2c(N)c1Cc1ccc(C(F)(F)F)c(C(N)=O)c1]

5-({7-Amino-5-methyl-[1,2,5]oxadiazolo[3,4-b]pyridin-6-yl}methyl)-2-(trifluoromethyl) benzamide Compound 4.57 5-({7-Amino-5-methyl-[1,2,5]oxadiazolo[3,4-b]pyridin-6-yl}methyl)-2-(trifluoromethyl) benzonitrile (25 mg; 0.08 mmol) is dissolved in 500 µL sulphuric acid and stirred at room temperature over night and at 40° C. for 6 hours. The reaction is quenched with cooled Na₂CO₃ (saturated aqueous solution) and extracted three times with dichloromethane, dried and concentrated under reduced pressure. The residue is purified by reverse phase chromatography (modifier: trifluoroacetic acid).
Yield: 9 mg (34% of theory)
Mass spectrometry (ESI⁺): m/z=352 [M+H]⁺
HPLC (Method 1): Retention time=0.774 min.

Procedure 20

Intermediate 20a

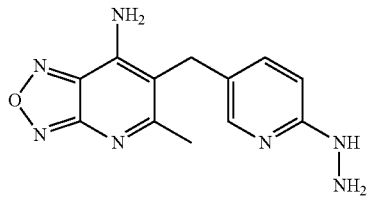 [SMILES: Cc1nc2nonc2c(N)c1Cc1ccc(NN)nc1]

6-[(6-Hydrazinylpyridin-3-yl)methyl]-5-methyl-[1,2,5]oxadiazolo[3,4-b]pyridin-7-amine Analogously to intermediate 4.12a the following compound is obtained by starting from compound 4.4 6-[(6-Fluoropyridin-3-yl)methyl]-5-methyl-[1,2,5]oxadiazolo[3,4-b]pyridin-7-amine and without ethanol, stirred vigorously over night.
Yield: 0.368 g (88% of theory)
Mass spectrometry (ESI⁺): m/z=272 [M+H]⁺
HPLC (Method 1): Retention time=0.644 min.

Compound 20.1

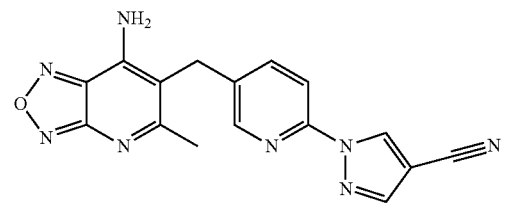 [SMILES: Cc1nc2nonc2c(N)c1Cc1ccc(-n2cc(C#N)cn2)nc1]

1-[5-({7-Amino-5-methyl-[1,2,5]oxadiazolo[3,4-b]pyridin-6-yl}methyl)pyridin-2-yl]-1H-pyrazole-4-carbonitrile Trifluoro-Acetic Acid Salt To a solution of intermediate 20a 6-[(6-Hydrazinylpyridin-3-yl)methyl]-5-methyl-[1,2,5]oxadiazolo[3,4-b]pyridin-7-amine (15.0 mg; 0.06 mmol) in ethanol (1.0 mL) was added 3-Dimethylamino-2-formyl-acrylonitrile (6.9 mg; 0.06 mmol) and concentrated HCl (18 µL; 0.08 mmol). The mixture was stirred at 100° C. for 10 minutes, then purified directly by reverse phase chromatography-HPLC (modifier: trifluoroacetic acid) Yield: 19 mg (77% of theory)
Mass spectrometry (ESI⁺): m/z=333 [M+H]⁺
HPLC (Method 3): Retention time=0.875 min.

Compound 20.2

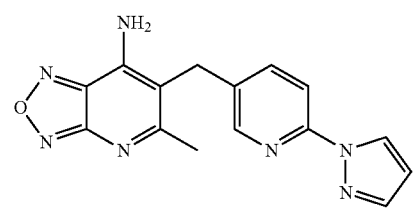 [SMILES: Cc1nc2nonc2c(N)c1Cc1ccc(-n2cccn2)nc1]

5-Methyl-6-{[6-(1H-pyrazol-1-yl)pyridin-3-yl]methyl}-[1,2,5]oxadiazolo[3,4-b]pyridin-7-amine Trifluoro-Acetic Acid Salt Obtained by starting from intermediate 20a 6-[(6-Hydrazinylpyridin-3-yl)methyl]-5-methyl-[1,2,5]oxadiazolo[3,4-b]pyridin-7-amine and 1,1,3,3-Tetramethoxypropane, using hydrochloric acid instead of acetic acid. The mixture is purified by reverse phase chromatography-HPLC (modifier: trifluoroacetic acid)
Yield: 74 mg (95% of theory)
Mass spectrometry (ESI⁺): m/z=308 [M+H]⁺
HPLC (Method 3): Retention time=0.829 min.

Procedure 21
Compound 21.1

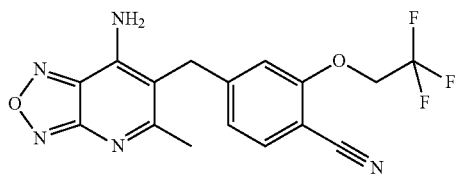 [SMILES: Cc1nc2nonc2c(N)c1Cc1ccc(C#N)c(OCC(F)(F)F)c1]

4-({7-Amino-5-methyl-[1,2,5]oxadiazolo[3,4-b]pyridin-6-yl}methyl)-2-(2,2,2-trifluoroethoxy)benzonitrile Compound 4.31 4-({7-Amino-5-methyl-[1,2,5]oxadiazolo[3,4-b]pyridin-6-yl}methyl)-2-fluorobenzonitrile (25.00 mg; 0.088 mmol), 2,2,2-Trifluoro-ethanol (0.500 mL; 6.945 mmol) and cesium carbonate (71.89 mg; 0.221 mmol) are dissolved in 1 mL of tetrahydrofuran. The mixture is stirred at 100° C. for 30 minutes. The mixture is purified by reverse phase chromatography-HPLC (modifier: ammonium hydroxide).
Yield: 20 mg (62% of theory)
Mass spectrometry (ESI⁺): m/z=364 [M+H]⁺
HPLC (Method 1): Retention time=0.959 min.
Compound 21.2

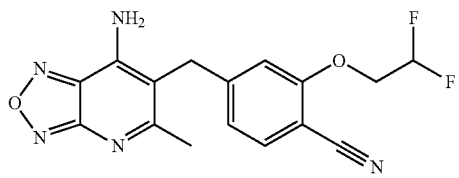 [SMILES: Cc1nc2nonc2c(N)c1Cc1ccc(C#N)c(OCC(F)F)c1]

4-({7-Amino-5-methyl-[1,2,5]oxadiazolo[3,4-b]pyridin-6-yl}methyl)-2-(2,2-difluoroethoxy)benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and 2,2-difluoro-ethanol.
Yield: 18 mg (59% of theory)
Mass spectrometry (ESI⁺): m/z=346 [M+H]⁺
HPLC (Method 1): Retention time=0.918 min.
Compound 21.3

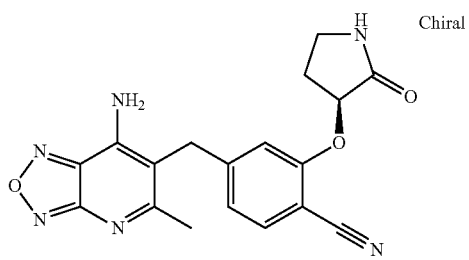 [SMILES: Cc1nc2nonc2c(N)c1Cc1ccc(C#N)c(O[C@H]2CCNC2=O)c1]

4-({7-Amino-5-methyl-[1,2,5]oxadiazolo[3,4-b]pyridin-6-yl}methyl)-2-{[(3S)-2-oxopyrrolidin-3-yl]oxy}benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and (S)-3-hydroxy-pyrrolidin-2-one.
Yield: 17 mg (53% of theory)
Mass spectrometry (ESI⁺): m/z=365 [M+H]⁺
HPLC (Method 1): Retention time=0.761 min.
Compound 21.4

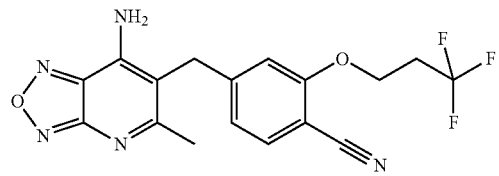 [SMILES: Cc1nc2nonc2c(N)c1Cc1ccc(C#N)c(OCCC(F)(F)F)c1]

4-({7-Amino-5-methyl-[1,2,5]oxadiazolo[3,4-b]pyridin-6-yl}methyl)-2-(3,3,3-trifluoropropoxy)benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and 3,3,3-Trifluoro-1-propanol.
Yield: 11 mg (33% of theory)
Mass spectrometry (ESI⁺): m/z=378 [M+H]⁺
HPLC (Method 1): Retention time=0.920 min.
Compound 21.5

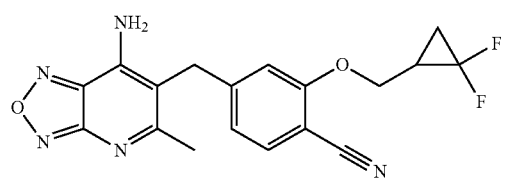 [SMILES: Cc1nc2nonc2c(N)c1Cc1ccc(C#N)c(OCC2CC2(F)F)c1]

4-({7-Amino-5-methyl-[1,2,5]oxadiazolo[3,4-b]pyridin-6-yl}methyl)-2-[(2,2-difluorocyclopropyl)methoxy]benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and (2,2-difluorocyclopropyl)methanol.
Yield: 18 mg (56% of theory)
Mass spectrometry (ESI⁺): m/z=372 [M+H]⁺
HPLC (Method 1): Retention time=0.918 min.
Compound 21.6

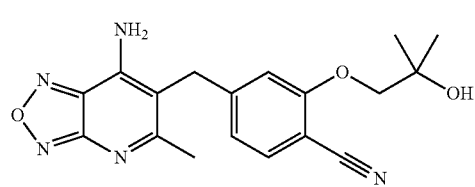 [SMILES: Cc1nc2nonc2c(N)c1Cc1ccc(C#N)c(OCC(C)(C)O)c1]

4-({7-Amino-5-methyl-[1,2,5]oxadiazolo[3,4-b]pyridin-6-yl}methyl)-2-(2-hydroxy-2-methylpropoxy)benzonitrile Analogously to compound 21.1 the following compound is obtained by starting from Compound 4.31 4-({7-Amino- 5-methyl-[1,2,5]oxadiazolo[3,4-b]pyridin-6-yl}methyl)-2-fluorobenzonitrile and 2-Methyl-propane-1,2-diol.

Yield: 11 mg (35% of theory)

Mass spectrometry (ESI⁺): m/z=354 [M+H]⁺

HPLC (Method 1): Retention time=0.829 min.

Compound 21.7

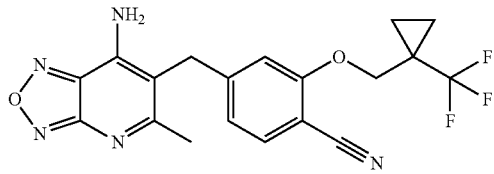 [SMILES: Cc1nc2nonc2c(N)c1Cc1ccc(C#N)c(OCC2(C(F)(F)F)CC2)c1]

4-({7-Amino-5-methyl-[1,2,5]oxadiazolo[3,4-b]pyridin-6-yl}methyl)-2-{[1-(trifluoromethyl)cyclopropyl]methoxy}benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and [1-(Trifluoromethyl)cyclopropyl]methanol.

Yield: 15 mg (43% of theory)

Mass spectrometry (ESI⁺): m/z=404 [M+H]⁺

HPLC (Method 1): Retention time=0.977 min.

Compound 21.8

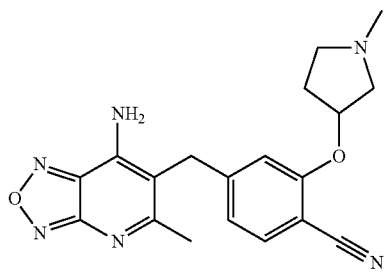 [SMILES: Cc1nc2nonc2c(N)c1Cc1ccc(C#N)c(OC2CCN(C)C2)c1]

4-(7-Amino-5-methyl-[1,2,5]oxadiazolo[3,4-b]pyridin-6-ylmethyl)-2-(1-methyl-pyrrolidin-3-yloxy)-benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and 1-Methyl-pyrrolidin-3-ol. Dimethyl sulfoxide was used instead of tetrahydrofuran and potassium butylate was used instead of cesium carbonate.

Yield: 12 mg (37% of theory)

Mass spectrometry (ESI⁺): m/z=365 [M+H]⁺

HPLC (Method 1): Retention time=0.828 min.

Compound 21.9

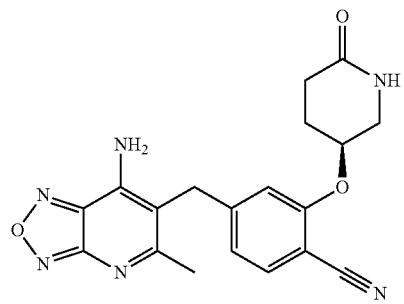 [SMILES: Cc1nc2nonc2c(N)c1Cc1ccc(C#N)c(O[C@H]2CCC(=O)NC2)c1]

4-({7-Amino-5-methyl-[1,2,5]oxadiazolo[3,4-b]pyridin-6-yl}methyl)-2-{[(3S)-6-oxopiperidin-3-yl]oxy}benzonitrile Analogously to compound 21.1 the following compound is obtained by starting from Compound 4.31 4-({7-Amino-5-methyl-[1,2,5]oxadiazolo[3,4-b]pyridin-6-yl}methyl)-2-fluorobenzonitrile and (S)-5-Hydroxy-piperidin-2-one.

Yield: 6 mg (18% of theory)

Mass spectrometry (ESI⁺): m/z=379 [M+H]⁺

HPLC (Method 1): Retention time=0.759 min.

Compound 21.10

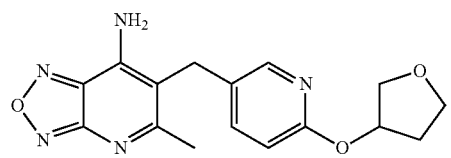 [SMILES: Cc1nc2nonc2c(N)c1Cc1ccc(OC2CCOC2)nc1]

5-Methyl-6-{[6-(oxolan-3-yloxy)pyridin-3-yl]methyl}-[1,2,5]oxadiazolo[3,4-b]pyridin-7-amine Analogously to compound 21.1 the following compound is obtained by starting from compound 4.4 6-[(6-Fluoropyridin-3-yl)methyl]-5-methyl-[1,2,5]oxadiazolo[3,4-b]pyridin-7-amine and 3-Hydroxytetrahydrofuran.

Yield: 4 mg (10% of theory)

Mass spectrometry (ESI⁺): m/z=328 [M+H]⁺

HPLC (Method 5): Retention time=0.61 min.

Compound 21.11

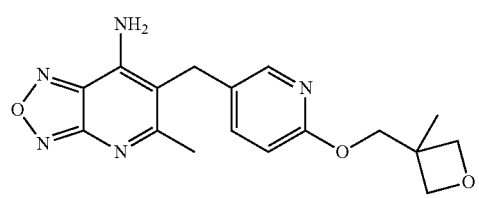 [SMILES: Cc1nc2nonc2c(N)c1Cc1ccc(OCC2(C)COC2)nc1]

5-Methyl-6-({6-[(3-methyloxetan-3-yl)methoxy]pyridin-3-yl}methyl)-[1,2,5]oxadiazolo[3,4-b]pyridin-7-amine Analogously to compound 21.1 the following compound is obtained by starting from compound 4.4 6-[(6-Fluoropyridin-3-yl)methyl]-5-methyl-[1,2,5]oxadiazolo[3,4-b]pyridin-7-amine, 3-Methyl-3-oxetanemethanol and sodium hydrate instead of cesium carbonate.

Yield: 38 mg (58% of theory)

Mass spectrometry (ESI$^+$): m/z=342 [M+H]$^+$

HPLC (Method 14): Retention time=0.63 min.

Compound 21.12

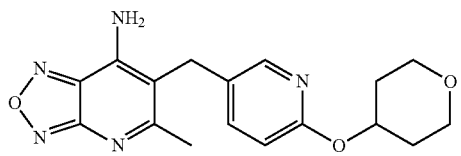 [SMILES: Cc1nc2nonc2c(N)c1Cc1ccc(OC2CCOCC2)nc1]

5-Methyl-6-[6-(tetrahydro-pyran-4-yloxy)-pyridin-3-ylmethyl]-[1,2,5]oxadiazolo[3,4-b]pyridin-7-ylamine Analogously to compound 21.1 the following compound is obtained by starting from compound 4.4 6-[(6-Fluoropyridin-3-yl)methyl]-5-methyl-[1,2,5]oxadiazolo[3,4-b]pyridin-7-amine, Tetrahydro-4H-pyran-4-ol and sodium hydrate instead of cesium carbonate. Stirred at room temperature over night and then for 4.5 h at 90° C. Cooled, diluted with methanol and filtered. The mixture is purified by reverse phase chromatography-HPLC (modifier: trifluoroacetic acid).

Yield: 17 mg (27% of theory)

Mass spectrometry (ESI$^+$): m/z=342 [M+H]$^+$

HPLC (Method 13): Retention time=0.39 min.

Compound 21.13

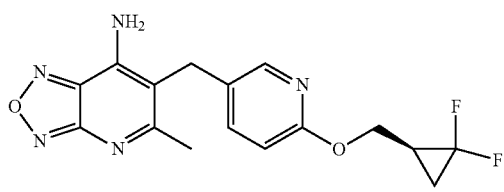 [SMILES: Cc1nc2nonc2c(N)c1Cc1ccc(OC[C@@H]2CC2(F)F)nc1]

6-[(6-{[(1R)-2,2-Difluorocyclopropyl]methoxy}pyridin-3-yl)methyl]-5-methyl-[1,2,5]oxadiazolo[3,4-b]pyridin-7-amine Analogously to compound 21.1 the following compound is obtained by starting compound 4.4 6-[(6-Fluoropyridin-3-yl)methyl]-5-methyl-[1,2,5]oxadiazolo[3,4-b]pyridin-7-amine, [(1 S)-2,2-Difluorocyclopropyl]methanol and sodium hydride instead of cesium carbonate. Stirred at 90° C. for 5 h, cooled and diluted with methanol. The mixture is purified by reverse phase chromatography-HPLC (modifier: ammonium hydroxide).

Yield: 21 mg (31% of theory)

Mass spectrometry (ESI$^+$): m/z=348 [M+H]$^+$

HPLC (Method 10): Retention time=0.78 min.

Procedure 22

Intermediate 22a

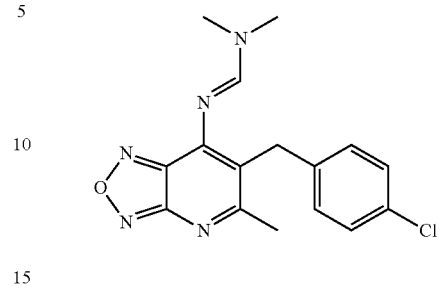

(E)-N'-{6-[(4-Chlorophenyl)methyl]-5-methyl-[1,2,5]oxadiazolo[3,4-b]pyridin-7-yl}-N,N-dimethyl-methanimidamide Intermediate 3g (E)-N'-(6-Iodo-5-methyl-[1,2,5]oxadiazolo[3,4-b]pyridin-7-yl)-N,N-dimethylmethanimidamide (50 mg; 0.151 mmol), 2-(4-Chloro-benzyl)-4,4,5,5-tetramethyl-[1,3,2]dioxaborolane (0.076 mg; 0.302 mmol), cesium carbonate (147 mg; 0.453 mmol) are dissolved in 2 mL tetrahydrofurane/water (9/1). Argon is bubbled into the mixture and [1,1'-bis(di-tert-butylphosphino)-ferrocene]palladium (II) dichloride (147 mg; 0.453 mmol) is added and the mixture is stirred at 80° C. for 18 h. It is purified by silica gel chromatography (eluent: cyclohexane/ethyl acetate 0%->80%).

Yield: 18 mg (37% of theory)

Mass spectrometry (ESI$^+$): m/z=330 [M+H]$^+$

HPLC (Method 1): Retention time=1.101 min.

Compound 22.1

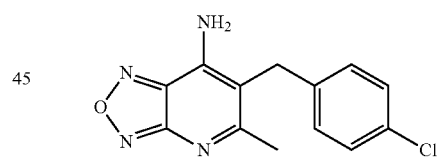

6-[(4-Chlorophenyl)methyl]-5-methyl-[1,2,5]oxadiazolo[3,4-b]pyridin-7-amine

Intermediate 22a (E)-N'-{6-[(4-Chlorophenyl)methyl]-5-methyl-[1,2,5]oxadiazolo[3,4-b]pyridin-7-yl}-N,N-dimethylmethanimidamide (18.00 mg; 0.05 mmol) is dissolved in 10 mL methanol, 1 mL conc. hydrochloric acid is added and the mixture is stirred for 18 h at 50° C. The solvent is evaporated and the residue is purified by reverse phase chromatography (modifier: ammonium hydroxide).

Yield: 13 mg (86% of theory)

Mass spectrometry (ESI$^+$): m/z=275 [M+H]$^+$

HPLC (Method 1): Retention time=0.937 min.

Intermediate 22b

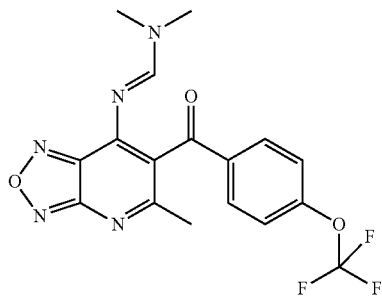 [SMILES: Cc1nc2nonc2c(/N=C/N(C)C)c1C(=O)c1ccc(OC(F)(F)F)cc1]

(E)-N,N-Dimethyl-N'-{5-methyl-6-[4-(trifluoromethoxy)benzoyl]-[1,2,5]oxadiazolo[3,4-b]pyridin-7-yl}methanimidamide The reaction is carried out under an argon atmosphere. To a mixture of intermediate 3g (E)-N'-(6-Iodo-5-methyl-[1,2,5]oxadiazolo[3,4-b]pyridin-7-yl)-N,N-dimethylmethanimidamide (100 mg; 0.30 mmol), [4-(Trifluoromethoxy)phenyl]boronic acid (124.38 mg; 0.60 mmol), potassium carbonate (127.77 mg; 0.91 mmol), Molybdenum hexacarbonyl (122.03 mg; 0.45 mmol) in 4.5 mL anisole is added PEPPSI-IPr™ catalyst [1,3-Bis(2,6-Diisopropylphenyl)imidazol-2-ylidene](3-chloropyridyl)palladium(II) dichloride (21 mg; 0.03 mmol) and stirred for 45 minutes at 140° C. in the microwave. Anisole is removed and the residue is filtered through Alox and washed with ethyl acetate. The organic layer is concentrated under reduced pressure and purified by reverse phase chromatography (modifier: ammonium hydroxide).

Yield: 6.0 mg (5% of theory)
Mass spectrometry (ESI⁺): m/z=394 [M+H]⁺
HPLC (Method 1): Retention time=1.083 min Compound 22.2

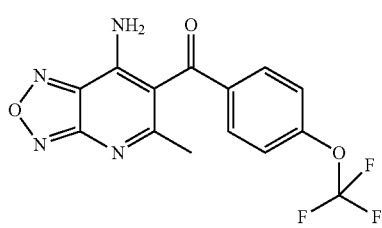 [SMILES: Cc1nc2nonc2c(N)c1C(=O)c1ccc(OC(F)(F)F)cc1]

5-Methyl-6-[4-(trifluoromethoxy)benzoyl]-[1,2,5]oxadiazolo[3,4-b]pyridin-7-amine Intermediate 22b (E)-N,N-Dimethyl-N'-{5-methyl-6-[4-(trifluoromethoxy)benzoyl]-[1,2,5]oxadiazolo[3,4-b]pyridin-7-yl}methanimidamide (10 mg; 0.03 mmol) is dissolved in 5 mL methanol and 0.5 mL conc. HCL is added. It is stirred for 2 hours at 60° C. The reaction is quenched with NaHCO₃ (saturated aqueous solution) and extracted three times with ethyl acetate. The organic layer is dried and concentrated under reduced pressure. The residue is purified by reverse phase chromatography (modifier: ammonium hydroxide).

Yield: 5.2 mg (60% of theory)
Mass spectrometry (ESI⁺): m/z=339 [M+H]⁺
HPLC (Method 1): Retention time=0.963 min Procedure 23
Intermediate 23.1a

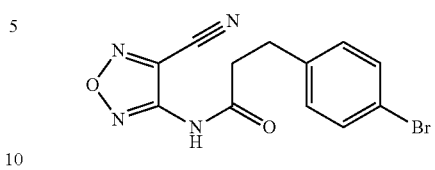

3-(4-Bromophenyl)-N-(4-cyano-1,2,5-oxadiazol-3-yl)propanamide

4-Amino-1,2,5-oxadiazole-3-carbonitrile (200 mg; 1.82 mmol) is taken up in 5 mL tetrahydrofuran and Triethylamine (505 μL; 3.63 mmol). 3-(4-Bromophenyl)propanoic acid (0.416; 1.8 mmol) is added and stirred at room temperature for a few minutes. 1-Propanephosphonic acid cyclic anhydride (PPA 50% in ethyl acetate) (1.89 mL; 3.18 mmol) is added. After stirring at room temperature over night it is diluted with ethyl acetate and washed with NaHCO₃ (saturated aqueous solution), water and brine. The organic layer is dried and concentrated under reduced pressure. The residue is dissolved in dioxan and lyophilized.

Yield: 174 mg (30% of theory)
Mass spectrometry (ESI⁻): m/z=320 [M–H]⁻
HPLC (Method 3): Retention time=1.059 min.

Intermediate 23.1b

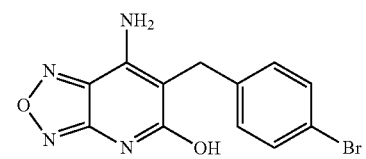 [SMILES: Nc1c(Cc2ccc(Br)cc2)c(O)nc2nonc12]

7-Amino-6-[(4-bromophenyl)methyl]-[1,2,5]oxadiazolo[3,4-b]pyridin-5-ol

A mixture of intermediate 23.1a [3-(4-Bromophenyl)-N-(4-cyano-1,2,5-oxadiazol-3-yl)propanamide] (120 mg; 0.37 mmol) and 1,8-Diazabicyclo[5.4.0]undec-7-ene (DBU) (171 mg; 1.12 mmol) in 3 mL dimethyl sulfoxide is stirred at 140° C. over night. The mixture is purified by reverse phase chromatography (modifier: ammonium hydroxide).

Yield: 50 mg (42% of theory)
Mass spectrometry (ESI⁻): m/z=320 [M–H]⁻
HPLC (Method 3): Retention time=0.916 min.

Compound 23.1

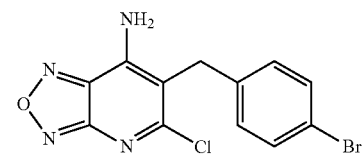 [SMILES: Nc1c(Cc2ccc(Br)cc2)c(Cl)nc2nonc12]

6-[(4-Bromophenyl)methyl]-5-chloro-[1,2,5]oxadiazolo[3,4-b]pyridin-7-amine

Intermediate 23.1b [7-Amino-6-[(4-bromophenyl)methyl]-[1,2,5]oxadiazolo[3,4-b]pyridin-5-ol] (50 mg; 0.16 mmol) and 2 mL phosphorus oxychloride are stirred at 100° C. for 1 hour. The residue is purified by reverse phase chromatography (modifier: trifluoroacetic acid).
Yield: 0.21 g (40% of theory)
Mass spectrometry (ESI⁺): m/z=339 [M+H]⁺
HPLC (Method 3): Retention time=1.089 min.
Compound 23.2

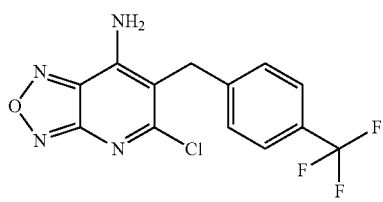 [SMILES: Nc1c(Cc2ccc(C(F)(F)F)cc2)c(Cl)nc2nonc12]

5-Chloro-6-{[4-(trifluoromethyl)phenyl]methyl}-[1,2,5]oxadiazolo[3,4-b]pyridin-7-amine Analogously to compound 23.1 the following compound is obtained by starting 4-Amino-1,2,5-oxadiazole-3-carbonitrile and 3-[4-(Trifluoromethyl) phenyl]propanoic acid.
Yield: 24 mg (76% of theory)
Mass spectrometry (ESI⁺): m/z=329 [M+H]⁺
HPLC (Method 3): Retention time=1.100 min.
Compound 23.3

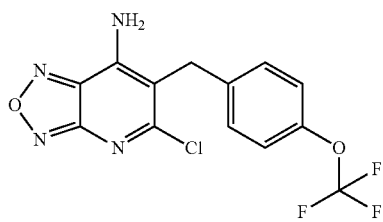 [SMILES: Nc1c(Cc2ccc(OC(F)(F)F)cc2)c(Cl)nc2nonc12]

5-Chloro-6-{[4-(trifluoromethoxy)phenyl]methyl}-[1,2,5]oxadiazolo[3,4-b]pyridin-7-amine Analogously to compound 23.1 the following compound is obtained by starting 4-Amino-1,2,5-oxadiazole-3-carbonitrile and 3-[4-(Trifluoromethoxy)phenyl]propanoic acid.
Yield: 26 mg (74% of theory)
Mass spectrometry (ESI⁺): m/z=345 [M+H]⁺
HPLC (Method 3): Retention time=1.117 min.
Compound 23.4

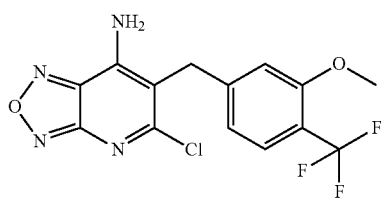 [SMILES: COc1cc(Cc2c(Cl)nc3nonc3c2N)ccc1C(F)(F)F]

5-Chloro-6-{[3-methoxy-4-(trifluoromethyl)phenyl]methyl}-[1,2,5]oxadiazolo[3,4-b]pyridin-7-amine Analogously to compound 23.1 the following compound is obtained by starting 4-Amino-1,2,5-oxadiazole-3-carbonitrile and 3-[3-Methoxy-4-(trifluoromethyl)phenyl]propanoic.

Yield: 4.7 mg (4% of theory)
Mass spectrometry (ESI⁺): m/z=359 [M+H]⁺
HPLC (Method 3): Retention time=1.048 min.
Compound 23.5

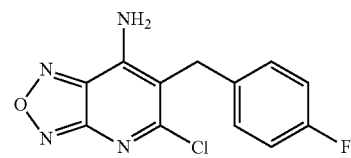 [SMILES: Nc1c(Cc2ccc(F)cc2)c(Cl)nc2nonc12]

5-Chloro-6-[(4-fluorophenyl)methyl]-[1,2,5]oxadiazolo[3,4-b]pyridin-7-amine

Analogously to compound 23.1 the following compound is obtained by starting 4-Amino-1,2,5-oxadiazole-3-carbonitrile and 3-(4-Fluorophenyl)propanoic acid.
Yield: 19.8 mg (35% of theory)
Mass spectrometry (ESI⁺): m/z=279 [M+H]⁺
HPLC (Method 3): Retention time=1.006 min.
Compound 23.6

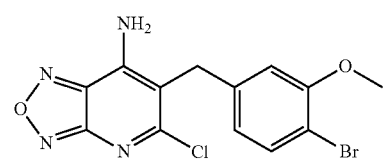 [SMILES: COc1cc(Cc2c(Cl)nc3nonc3c2N)ccc1Br]

6-[(4-Bromo-3-methoxyphenyl)methyl]-5-chloro-[1,2,5]oxadiazolo[3,4-b]pyridin-7-amine Analogously to compound 23.1 the following compound is obtained by starting 4-Amino-1,2,5-oxadiazole-3-carbonitrile and 3-(4-Bromo-3-methoxyphenyl)propanoic acid.
Yield: 12.6 mg (80% of theory)
Mass spectrometry (ESI⁺): m/z=369 [M+H]⁺
HPLC (Method 3): Retention time=1.063 min.
Compound 23.7

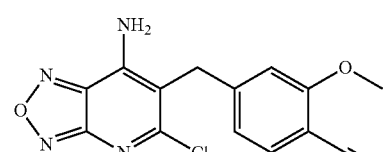

4-({7-Amino-5-chloro-[1,2,5]oxadiazolo[3,4-b]pyridin-6-yl}methyl)-2-methoxybenzonitrile Analogously to compound 23.1 the following compound is obtained by starting 4-Amino-1,2,5-oxadiazole-3-carbonitrile and 3-(4-Cyano-3-methoxyphenyl)propanoic acid.
Yield: 3.5 mg (19% of theory)
Mass spectrometry (ESI⁺): m/z=316 [M+H]⁺
HPLC (Method 2): Retention time=0.851 min.

Procedure 24
Intermediate 24a

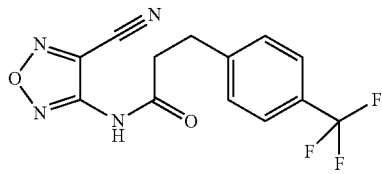 [SMILES: N#Cc1nonc1NC(=O)CCc1ccc(C(F)(F)F)cc1]

N-(4-Cyano-1,2,5-oxadiazol-3-yl)-3-[4-(trifluoromethyl)phenyl]propanamide

1-Propanephosphonic acid cyclic anhydride (PPA 50% in ethyl acetate) (23.66 mL; 39.75 mmol) and 3-[4-(Trifluoromethyl)phenyl] propanoic acid (4.955 g; 22.71 mmol) are stirred 15 minutes at room temperature. 4-Amino-1,2,5-oxadiazole-3-carbonitrile (2.5 g; 22.11 mmol) is added. The ethyl acetate is removed under reduced pressure and the residue is stirred 2 hours at 90° C. The reaction is quenched with ice water, the precipitate is filtered and dried.
Yield: 6.97 g (99% of theory)
Mass spectrometry (ESI−): m/z=309 [M−H]−
HPLC (Method 3): Retention time=1.071 min.
Intermediate 24b

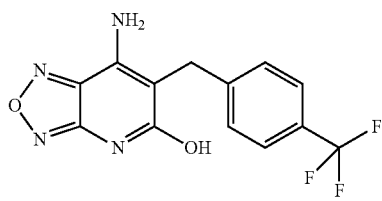 [SMILES: Nc1c(Cc2ccc(C(F)(F)F)cc2)c(O)nc2nonc12]

7-Amino-6-{[4-(trifluoromethyl)phenyl]methyl}-[1,2,5]oxadiazolo[3,4-b]pyridin-5-ol A mixture of intermediate 24a N-(4-Cyano-1,2,5-oxadiazol-3-yl)-3-[4-(trifluoromethyl)-phenyl]propanamide (6.97 g; 22.47 mmol) and 1,8-Diazabicyclo[5.4.0]undec-7-ene (DBU) (8.40 mL; 56.17 mmol) in 200 mL dimethyl sulfoxide is stirred at 140° C. for 18 hours. The reaction is quenched with ice water and acidified with HCl (1 M aqueous solution). The precipitate is filtered and dried. The mixture is purified by silica gel chromatography (eluent: cyclohexene/ethyl acetate 0->50%).
Yield: 3.4 g (49% of theory)
Mass spectrometry (ESI+): m/z=311 [M+H]+
HPLC (Method 3): Retention time=0.954 min.
Compound 24.1

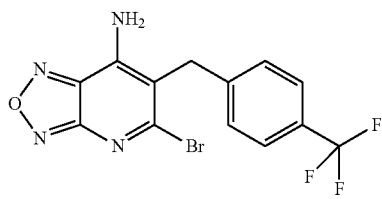 [SMILES: Nc1c(Cc2ccc(C(F)(F)F)cc2)c(Br)nc2nonc12]

5-Bromo-6-{[4-(trifluoromethyl)phenyl]methyl}-[1,2,5]oxadiazolo[3,4-b]pyridin-7-amine Intermediate 24b 7-Amino-6-{[4-(trifluoromethyl)phenyl]methyl}-[1,2,5]oxadiazolo-[3,4-b]pyridin-5-ol (1.5 g; 4.84 mmol) and 5 mL phosphorus oxybromide are stirred at 90° C. for 45 minutes. The reaction is quenched with water, extracted three times with ethyl acetate, dried and concentrated under reduced pressure. The mixture is purified by silica gel chromatography (eluent: cyclohexene/ethyl acetate 0->50%).
Yield: 1.40 g (77% of theory)
Mass spectrometry (ESI+): m/z=373 [M+H]+
HPLC (Method 3): Retention time=1.106 min.
Intermediate 24c

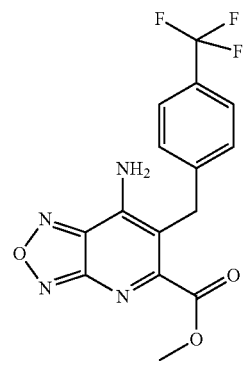 [SMILES: COC(=O)c1nc2nonc2c(N)c1Cc1ccc(C(F)(F)F)cc1]

Methyl 7-amino-6-{[4-(trifluoromethyl)phenyl]methyl}-[1,2,5]oxadiazolo[3,4-b]pyridine-5-carboxylate Compound 24.1 5-Bromo-6-{[4-(trifluoromethyl)phenyl]methyl}-[1,2,5]oxadiazolo[3,4-b]pyridin-7-amine (400 mg; 1.07 mmol), sodium acetate (203 mg; 2.48 mmol), 1,1'-Bis(diphenylphosphino) ferrocenedichloropalladium(II) (20.3 mg; 0.03 mmol) are dissolved in 15 mL methanol. The reaction is stirred under a CO atmosphere at 5 bar for 2 days at room temperature. The mixture is purified by silica gel chromatography (eluent: cyclohexene/ethyl acetate 0->40%).
Yield: 200 mg (53% of theory)
Mass spectrometry (ESI+): m/z=353 [M+H]+
HPLC (Method 3): Retention time=1.023 min.
Compound 24.2

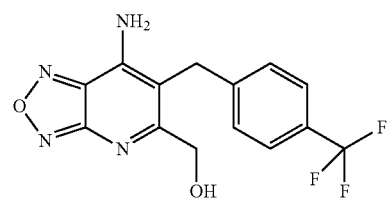 [SMILES: Nc1c(Cc2ccc(C(F)(F)F)cc2)c(CO)nc2nonc12]

(7-Amino-6-{[4-(trifluoromethyl)phenyl]methyl}-[1,2,5]oxadiazolo[3,4-b]pyridin-5-yl)methanol Intermediate 24c Methyl 7-amino-6-{[4-(trifluoromethyl)phenyl]methyl}-[1,2,5]oxadiazolo[3,4-b]pyridine-5-carboxylate (250 mg; 0.71 mmol) is dissolved in 2 mL toluol and 4 mL tetrahydrofuran. At 0° C. sodium 2,5,7,10-tetraoxa-6-alumina-undecan-6-uide ((Red-Al) 65% ig in toluol; 0.43 mL; 1.42 mmol) is added and stirred for 2 hours at 0° C. Sodium potassium tartrate-solution is dropped into the reaction and the aqueous layer is extracted three times with ethyl acetate, dried and concentrated under reduced pressure. The residue is purified by reverse phase chromatography (modifier: trifluoroacetic acid) and by reverse phase chromatography (modifier: ammonium hydroxide).

Yield: 31 mg (13% of theory)
Mass spectrometry (ESI+): m/z=325 [M+H]+
HPLC (Method 1): Retention time=0.945 min.

Compound 24.3

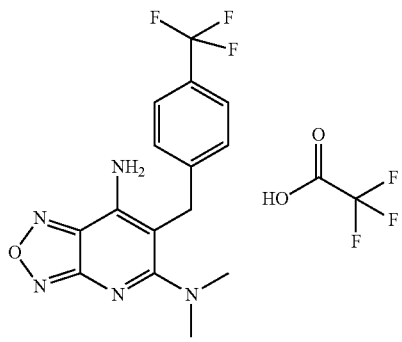 [SMILES: CN(C)c1nc2nonc2c(N)c1Cc1ccc(C(F)(F)F)cc1 ; O=C(O)C(F)(F)F]

N5,N5-Dimethyl-6-{[4-(trifluoromethyl)phenyl]methyl}-[1,2,5]oxadiazolo[3,4-b]pyridine-5,7-diamine Trifluoroacetic Acid Salt Compound 24.1 5-Bromo-6-{[4-(trifluoromethyl)phenyl]methyl}-[1,2,5]oxadiazolo[3,4-b]pyridin-7-amine] (100 mg; 0.27 mmol), zinc cyanide (31.5 mg; 0.27 mmol) and 1,1'-Bis(diphenylphosphino) ferrocene (6.56 mg; 0.01 mmol) are dissolved in 1 mL N,N-Dimethylacetamide, stirred for 1.5 hours at 150° C. and for 1.5 hours at 180° C. The mixture is purified by silica gel chromatography (eluent: cyclohexene/ethyl acetate 0->500%) and by reverse phase chromatography (modifier: trifluoroacetic acid).

Yield: 17 mg (14% of theory)
Mass spectrometry (ESI+): m/z=338 [M+H]+
HPLC (Method 3): Retention time=1.071 min.

Compound 24.4

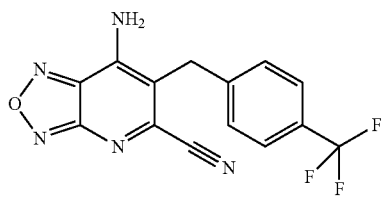 [SMILES: N#Cc1nc2nonc2c(N)c1Cc1ccc(C(F)(F)F)cc1]

7-Amino-6-{[4-(trifluoromethyl)phenyl]methyl}-[1,2,5]oxadiazolo[3,4-b]pyridine-5-carbonitrile Compound 24.1 5-Bromo-6-{[4-(trifluoromethyl)phenyl]methyl}-[1,2,5]oxadiazolo[3,4-b]pyridin-7-amine (50 mg; 0.13 mmol) and potassium cyanide (10.5 mg; 0.16 mmol) are dissolved in 0.5 mL N-methylpyrrolidine and stirred for 30 minutes at 130° C. The reaction is purified by reverse phase chromatography (modifier: trifluoroacetic acid).

Yield: 12.7 mg (30% of theory)
Mass spectrometry (ESI+): m/z=320 [M+H]+
HPLC (Method 3): Retention time=1.062 min.

Compound 24.5

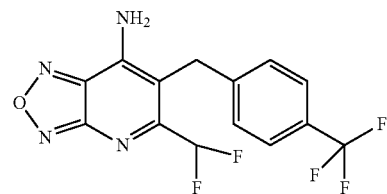 [SMILES: Nc1c(Cc2ccc(C(F)(F)F)cc2)c(C(F)F)nc2nonc12]

5-(Difluoromethyl)-6-{[4-(trifluoromethyl)phenyl]methyl}-[1,2,5]oxadiazolo[3,4-b]pyridin-7-amine Compound 24.1 5-Bromo-6-{[4-(trifluoromethyl)phenyl]methyl}-[1,2,5]oxadiazolo[3,4-b]pyridin-7-amine (100 mg; 0.27 mmol) and ethyl 2-bromo-2,2-difluoroacetate (130 mg; 0.64 mmol) is dissolved in 1 mL dimethyl sulfoxide and bronze powder (67.9 mg; 1.07 mmol) is added. The reaction is stirred for 5 hours at 50° C. It is filtered and the filtrate is purified by reverse phase chromatography (modifier: trifluoroacetic acid). The product is dissolved in 4 mL methanol and sodium hydroxide (1 M aqueous solution) (528 µl; 0.53 mmol) is added. The reaction is stirred for 5 hours at room temperature. The solution is acidified with trifluoroacetic acid and purified by reverse phase chromatography (modifier: trifluoroacetic acid).

Yield: 37 mg (41% of theory)
Mass spectrometry (ESI+): m/z=345 [M+H]+
HPLC (Method 3): Retention time=1.090 min.

Procedure 25

Compound 25.1

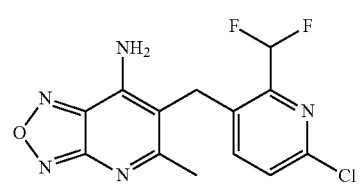 [SMILES: Cc1nc2nonc2c(N)c1Cc1ccc(Cl)nc1C(F)F]

6-{[6-Chloro-2-(difluoromethyl)pyridin-3-yl]methyl}-5-methyl-[1,2,5]oxadiazolo[3,4-b]pyridin-7-amine Compound 4.18 6-[(6-Chloropyridin-3-yl)methyl]-5-methyl-[1,2,5]oxadiazolo[3,4-b]pyridin-7-amine (350 mg; 1.27 mmol) is dissolved in 9 mL dichloromethane and 3 mL water. (difluoromethanesulfonyloxy)zincio difluoromethanesulfonate (1.123 g; 3.43 mmol), trifluoroacetic acid (102 µL; 1.32 mmol) and 2-methylpropane-2-peroxol (517 mg; 6.35 mmol) are added and stirred for 18 hours at room temperature. The solvent is evaporated and the residue is purified by silica gel chromatography (eluent: cyclohexene/ethyl acetate 0->40%

Yield: 53 g (13% of theory)
Mass spectrometry (ESI+): m/z=326 [M+H]+
HPLC (Method 1): Retention time=0.914 min.

Compound 25.2

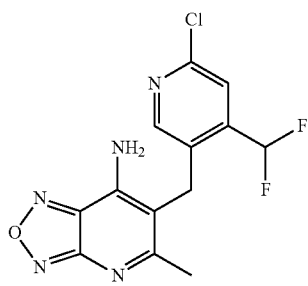 [SMILES: Cc1nc2nonc2c(N)c1Cc1cnc(Cl)cc1C(F)F]

6-{[6-Chloro-4-(difluoromethyl)pyridin-3-yl]methyl}-5-methyl-[1,2,5]oxadiazolo[3,4-b]pyridin-7-amine Analogously to compound 25.1 the following compound is obtained by starting with compound 4.18 6-[(6-Chloro-pyridin-3-yl)methyl]-5-methyl-[1,2,5]oxadiazolo[3,4-b]pyridin-7-amine and (difluoromethanesulfonyloxy)zincio difluoromethanesulfonate.

Yield: 30 mg (7% of theory)
Mass spectrometry (ESI$^+$): m/z=326 [M+H]$^+$
HPLC (Method 1): Retention time=0.892 min.

Compound 25.3

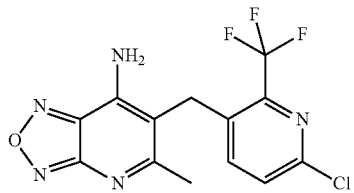 [SMILES: Cc1nc2nonc2c(N)c1Cc1ccc(Cl)nc1C(F)(F)F]

6-{[6-Chloro-2-(trifluoromethyl)pyridin-3-yl]methyl}-5-methyl-[1,2,5]oxadiazolo[3,4-b]pyridin-7-amine Analogously to compound 25.1 the following compound is obtained by starting with compound 4.18 6-[(6-Chloro-pyridin-3-yl)methyl]-5-methyl-[1,2,5]oxadiazolo[3,4-b]pyridin-7-amine and (trifluoromethanesulfinyloxy)zincio trifluoromethanesulfinate.

Yield: 39.5 mg (9% of theory)
Mass spectrometry (ESI$^+$): m/z=344 [M+H]$^+$
HPLC (Method 1): Retention time=0.913 min.

Compound 25.4

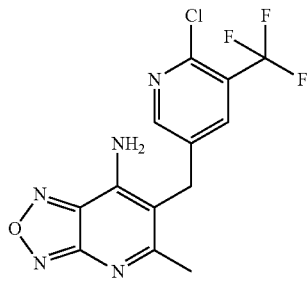 [SMILES: Cc1nc2nonc2c(N)c1Cc1cnc(Cl)c(C(F)(F)F)c1]

6-{[6-chloro-5-(trifluoromethyl)pyridin-3-yl]methyl}-5-methyl-[1,2,5]oxadiazolo[3,4-b]pyridin-7-amine Analogously to compound 25.1 the following compound is obtained by starting with compound 4.18 6-[(6-Chloro-pyridin-3-yl)methyl]-5-methyl-[1,2,5]oxadiazolo[3,4-b]pyridin-7-amine and (trifluoromethanesulfinyloxy)zincio trifluoromethanesulfinate.

Yield: 16.0 mg (4% of theory)
Mass spectrometry (ESI$^+$): m/z=344 [M+H]$^+$
HPLC (Method 1): Retention time=0.942 min.

The invention claimed is:
1. A compound of formula

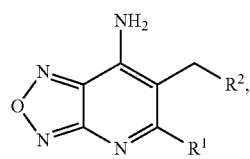

(I)

wherein
R$^1$ is selected from the group consisting of Cl, Br, CN, CH$_3$, and —N(CH$_3$)$_2$,
wherein the CH$_3$ group is optionally substituted with 1-3 F or with one OH;
R$^2$ is selected from the group consisting of:
a) a phenyl, pyridin-3-yl or pyridin-4-yl group optionally substituted by 1-3 substituents independently of each other selected from the group consisting of F, Cl, Br, I, CN, C$_{1-6}$-alkyl, C$_{3-7}$-cycloalkyl, OH, —O—(C$_{1-6}$-alkyl), —O—(C$_{1-3}$-alkyl)-(C$_{3-7}$-cycloalkyl), —O—(C$_{1-3}$-alkyl)-heterocyclyl, —O—(C$_{3-7}$-cycloalkyl), —O-heterocyclyl, —S—(C$_{1-3}$-alkyl), —SO—(C$_{1-3}$-alkyl), —SO$_2$—(C$_{1-3}$-alkyl), —C(=O)—NR$^{N1}$R$^{N2}$, —C(=O)OH, —C(=O)—O—(C$_{1-4}$-alkyl), and —N=S(=O)(C$_{1-3}$-alkyl)$_2$ and heteroaryl,
wherein R$^{N1}$ is selected from the group consisting of: H, C$_{1-6}$-alkyl, —(C$_{1-3}$-alkyl)-(C$_{3-7}$-cycloalkyl), —(C$_{1-3}$-alkyl)-heterocyclyl, —(C$_{1-3}$-alkyl)-heteroaryl, C$_{3-7}$-cycloalkyl, heterocyclyl and heteroaryl;
and R$^{N2}$ is H or C$_{1-4}$-alkyl, and
wherein each alkyl group is optionally substituted with 1-3 F or with one OH, CN, COOH or —C(=O)—NH$_2$;
wherein each cycloalkyl group is optionally substituted with one or two F and/or with one CN, COOH, —C(=O)—NH$_2$ or —CH$_3$, which is optionally substituted with 1-3 F or with one OH;
wherein each heterocyclyl group is selected from the group consisting of a mono- or spirocyclic 4-7-membered cycloalkyl group, in which 1, 2 or 3 CH$_2$-groups are independently of each other replaced by O, S, NH or C=O, and
wherein each heterocyclyl group is optionally substituted with 1 or 2 substituents independently of each other selected from the group consisting of F, CN, OH and C$_{1-3}$-alkyl,
wherein each heteroaryl group is selected from the group consisting of a 5-membered aromatic cycle containing 1, 2 or 3 heteroatoms independently selected from the group consisting of N, O and S or from a 6-membered aromatic cycle containing 1 or 2 N, and
wherein each heteroaryl group is optionally substituted with 1 or 2 substituents independently of each other selected from the group consisting of a group consisting of F, CN and C$_{1-3}$-alkyl, which is optionally substituted with one or more F;

b) a bicyclic heteroaryl selected from the group consisting of:

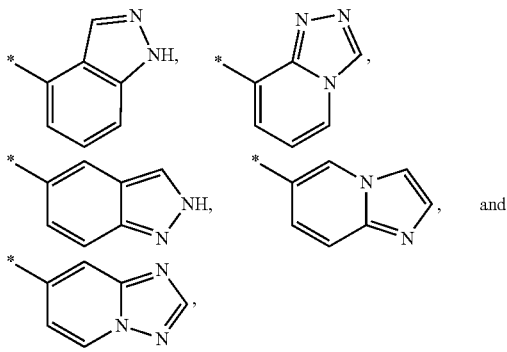

which are each optionally substituted by one substituent selected from the group consisting of Cl, $C_{1-3}$-alkyl, cyclopropyl, —O—($C_{1-3}$-alkyl-), —C(=O)—O—($C_{1-4}$-alkyl), and heteroaryl,
wherein each alkyl group is optionally substituted with 1-3 F;
wherein each heteroaryl group is selected from the group consisting of a 5-membered aromatic cycle containing 1 or 2 heteroatoms independently selected from the group consisting of N, O and S; and
wherein each heteroaryl group is optionally substituted with 1 or 2 $CH_3$ groups or with one CN group;
wherein each of the above-mentioned alkyl groups may be substituted with one or more F;
or a salt thereof.

2. The compound of formula (I) according to claim 1, wherein the group $R^2$ is independently of each other selected from the group consisting of:
a1) a phenyl group optionally substituted by 1-3 substituents $R^3$ independently of each other selected from the group consisting of F, Cl, Br, I, CN, $C_{1-6}$-alkyl, OH, —O—($C_{1-6}$-alkyl-), —O—($C_{1-3}$-alkyl)-($C_{3-7}$-cycloalkyl), —O-heterocyclyl, —S—($C_{1-3}$-alkyl), —SO—($C_{1-3}$-alkyl), —SO$_2$—($C_{1-3}$-alkyl), —C(=O)—$NR^{N1}R^{N2}$, —C(=O)OH, —C(=O)—O—($C_{1-4}$-alkyl), and —N=S(=O)($C_{1-3}$-alkyl)$_2$;
wherein $R^{N1}$ is selected from the group consisting of: H, $C_{1-6}$-alkyl, —($C_{1-3}$-alkyl)-($C_{3-7}$-cycloalkyl), —($C_{1-3}$-alkyl)-heterocyclyl, —($C_{1-3}$-alkyl)-heteroaryl, $C_{3-7}$-cycloalkyl, heterocyclyl and heteroaryl;
and $R^{N2}$ is H or $C_{1-4}$-alkyl, and
wherein each alkyl group is optionally substituted with 1-3 F or with one OH or CN;
wherein each cycloalkyl group is optionally substituted with one or two F or with one —$CH_3$, which is optionally substituted with 1-3 F or with one OH;
wherein each heterocyclyl group is selected from the group consisting of a mono- or spirocyclic 4-7-membered cycloalkyl group, in which 1, 2 or 3 $CH_2$-groups are independently of each other replaced by O, S, NH or C=O, and
wherein each heterocyclyl group is optionally substituted with 1 or 2 substituents independently of each other selected from the group consisting of F, OH and $C_{1-3}$-alkyl,
wherein each heteroaryl group is selected from the group consisting of a 5-membered aromatic cycle containing 1, 2 or 3 heteroatoms independently selected from the group consisting of N, O and S or from a 6-membered aromatic cycle containing 1 or 2 N, and
wherein each heteroaryl group is optionally substituted with 1 or 2 substituents independently of each other selected from the group consisting of F, CN and $C_{1-3}$-alkyl, which is optionally substituted with one or more F;
a2) a pyridin-3-yl or pyridin-4-yl group optionally substituted by 1-3 substituents $R^3$ independently of each other selected from the group $R^3$-G3 consisting of F, Cl, Br, I, CN, $C_{1-6}$-alkyl, $C_{3-7}$-cycloalkyl, OH, —O—($C_{1-6}$-alkyl), —O—($C_{1-3}$-alkyl)-($C_{3-7}$-cycloalkyl), —O—($C_{1-3}$-alkyl)-heterocyclyl, —O—($C_{3-7}$-cycloalkyl), —O-heterocyclyl and heteroaryl,
wherein each alkyl group is optionally substituted with 1-3 F or with one OH, CN, COOH or —C(=O)—$NH_2$;
wherein each cycloalkyl group is optionally substituted with one or two F and/or with one CN, COOH, —C(=O)—$NH_2$ or —$CH_3$, which is optionally substituted with 1-3 F or with one OH;
wherein each heterocyclyl group is selected from the group consisting of a mono- or spirocyclic 4-7-membered cycloalkyl group, in which 1, 2 or 3 $CH_2$-groups are independently of each other replaced by O, S, NH or C=O, and
wherein each heterocyclyl group is optionally substituted with 1 or 2 substituents independently of each other selected from the group consisting of CN and $C_{1-3}$-alkyl,
wherein each heteroaryl group is selected from the group consisting of a 5-membered aromatic cycle containing 1 or 2 heteroatoms independently selected from the group consisting of N, O and S, and
wherein each heteroaryl group is optionally substituted with 1 or 2 substituents independently of each other selected from the group consisting of CN and $C_{1-3}$-alkyl, which is optionally substituted with one or more F; or
b) a bicyclic heteroaryl selected from the group consisting of:

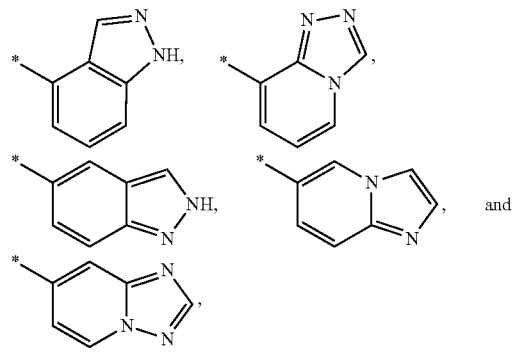

which are each optionally substituted by one substituent selected from the group consisting of Cl, $C_{1-3}$-alkyl, cyclopropyl, —O—($C_{1-3}$-alkyl-), —C(=O)—O—($C_{1-4}$-alkyl), and heteroaryl,
wherein each alkyl group is optionally substituted with 1-3 F;

wherein each heteroaryl group is selected from the group consisting of a 5-membered aromatic cycle containing 1 or 2 heteroatoms independently selected from the group consisting of N, O and S; and wherein each heteroaryl group is optionally substituted with 1 or 2 CH$_3$ groups or with one CN group.

3. The compound of formula (I) according to claim 2, wherein the group R$^2$ is independently of each other selected from the group consisting of:

a1) a phenyl group optionally substituted by 1-3 substituents R$^3$ independently of each other selected from the group consisting of F, Cl, Br, I, CN, CH$_3$, OH, —O—(C$_{1-4}$-alkyl), —O—(CH$_2$)-cyclopropyl, —O-heterocyclyl, —S—CH$_3$, —SO—CH$_3$, —SO$_2$—CH$_3$, —C(=O)—NR$^{N1}$R$^{N2}$, —C(=O)OH, —C(=O)—O—CH$_3$, and —N=S(=O)(CH$_3$)$_2$;

wherein R$^{N1}$ is selected from the group consisting of: H, C$_{1-5}$-alkyl, —CH$_2$-cyclopropyl, —CH$_2$-heterocyclyl, —CH$_2$-heteroaryl, cyclopropyl, heterocyclyl and heteroaryl;

and R$^{N2}$ is H or CH$_3$, and wherein each alkyl group within the substituents of R$^2$, within R$^{N1}$ and within R$^{N2}$ is optionally substituted with 1-3 F or with one OH or CN;

wherein each cyclopropyl group within the substituents of R$^2$ and within R$^{N1}$ is optionally substituted with one or two F or with one —CH$_3$, which is optionally substituted with 1-3 F or with one OH;

wherein each heterocyclyl group is selected from the group consisting of pyrrolidinyl, piperidinyl, oxetanyl, tetrahydrofuranyl, tetrahydropyranyl, and morpholinyl, wherein one CH$_2$-group is optionally replaced by C=O, and/or wherein each heterocyclyl group is optionally substituted with one CH$_3$ group, wherein each heteroaryl group is selected from the group consisting of pyrazolyl, triazolyl, pyridazinyl and pyrazinyl, wherein each heteroaryl group is optionally substituted with 1 or 2 substituents independently selected from the group consisting of CF$_3$ and CH$_3$; or a2)

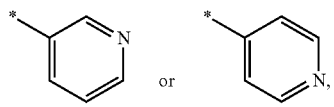 [SMILES: *c1cccnc1 ; *c1ccncc1]

which may be substituted with 1 or 2 substituents R$^3$ independently of each other selected from the group consisting of: F, Cl, Br, I, CN, C$_{1-6}$-alkyl, C$_{3-6}$-cycloalkyl, —O—CH$_3$, —O—CH$_2$-cyclopropyl, —O—CH$_2$-heterocyclyl, —O-cyclobutyl, —O—heterocyclyl and heteroaryl, wherein each alkyl group is optionally substituted with 1-3 F or with one CN, COOH or —C(=O)—NH$_2$;

wherein each cycloalkyl group is optionally substituted with one or two F and/or with one CN, COOH or —C(=O)—NH$_2$;

wherein each heterocyclyl group is selected from the group consisting of oxetanyl, tetrahydrofuranyl, and tetrahydropyranyl, which may each be substituted with one CN or CH$_3$, wherein each heteroaryl group is selected from the group consisting of furanyl, pyrazolyl, imidazolyl, thienyl, oxazolyl, and isoxazolyl, wherein each heteroaryl group is optionally substituted with 1 or 2 substituents independently of each other selected from the group consisting of CN, CF$_3$ and CH$_3$.

4. The compound of formula (I) according to claim 3, wherein R$^2$ is independently selected from the group consisting of:

an aryl group selected from the group consisting of:

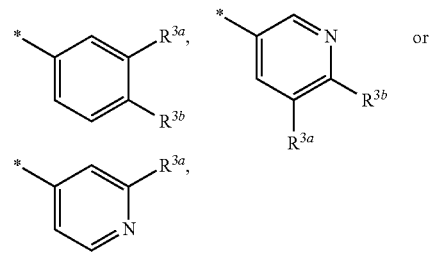

wherein

R$^{3a}$ and R$^{3b}$ are independently of each other selected from the group consisting of:

H, F, Cl, Br, I, —CN, —CH$_3$, —C(CH$_3$)$_3$, —CF$_3$, —CHF$_2$, —CH$_2$F, —CH$_2$—CN, —CH$_2$OH, —OH, —O—CH$_3$, —O—CF$_3$, —O—CHF$_2$, —O—CH$_2$F,

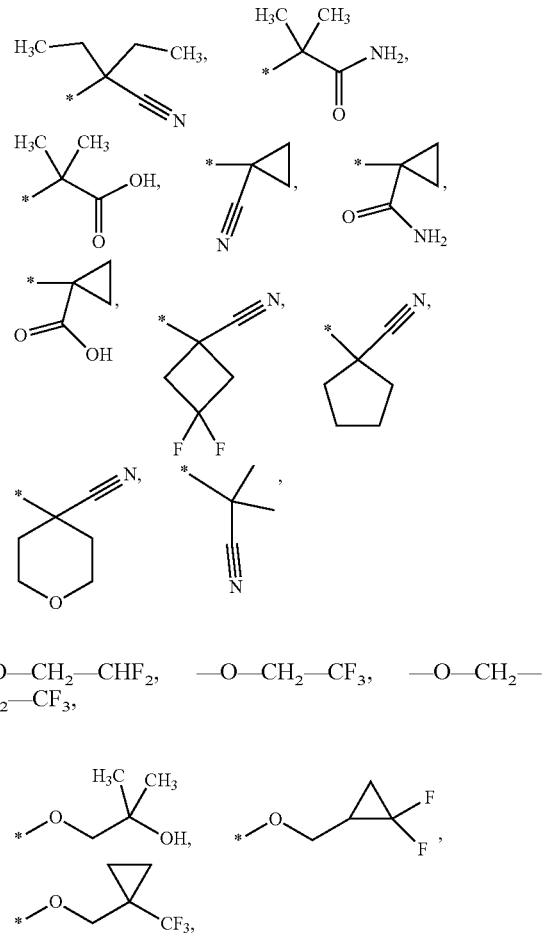

—O—CH$_2$—CHF$_2$, —O—CH$_2$—CF$_3$, —O—CH$_2$—CH$_2$—CF$_3$,

-continued
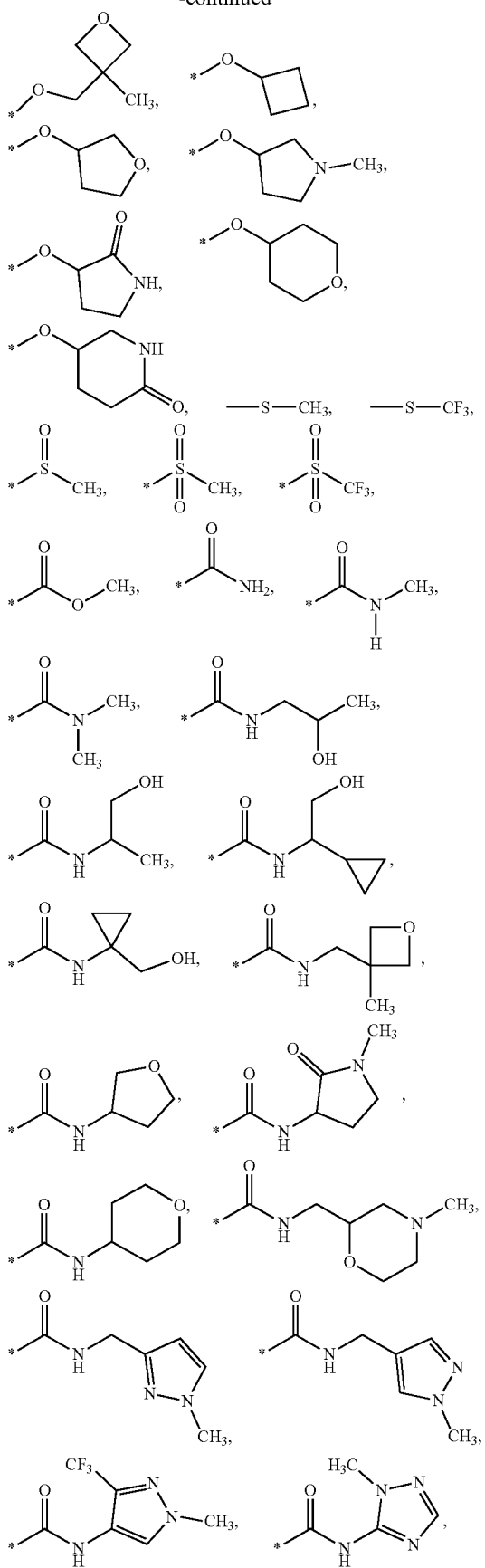
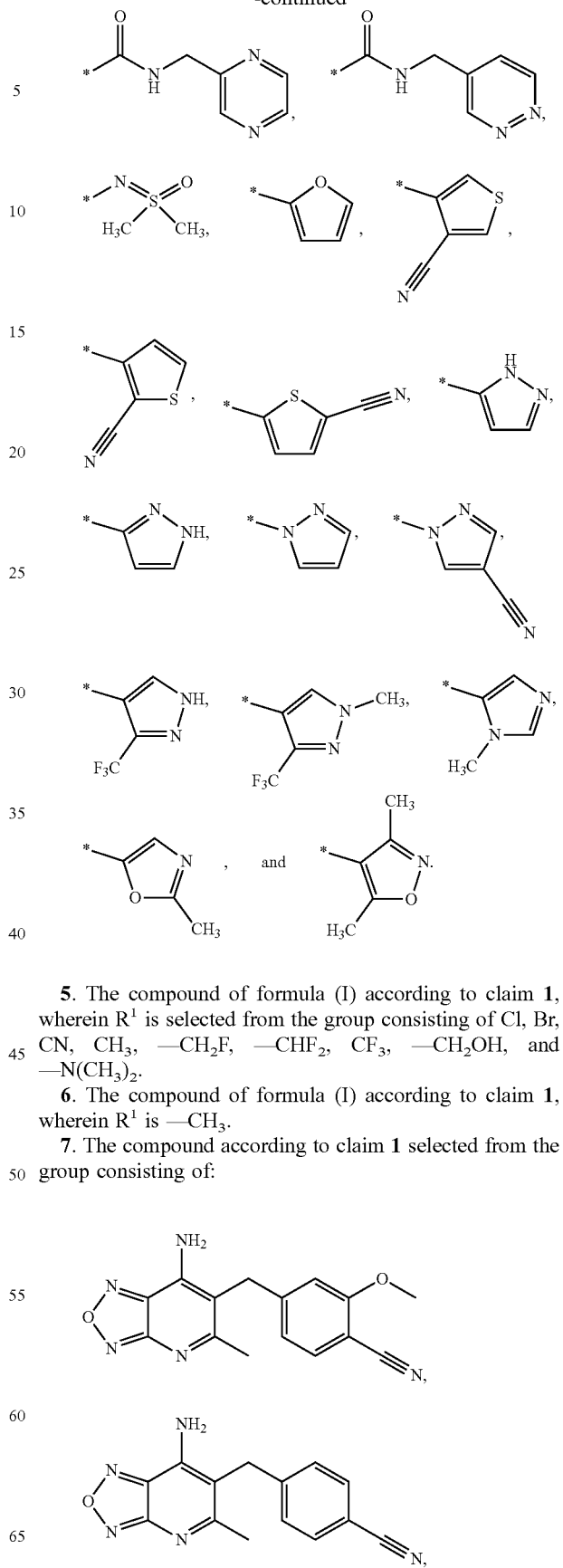
5. The compound of formula (I) according to claim 1, wherein $R^1$ is selected from the group consisting of Cl, Br, CN, CH$_3$, —CH$_2$F, —CHF$_2$, CF$_3$, —CH$_2$OH, and —N(CH$_3$)$_2$.
6. The compound of formula (I) according to claim 1, wherein $R^1$ is —CH$_3$.
7. The compound according to claim 1 selected from the group consisting of:
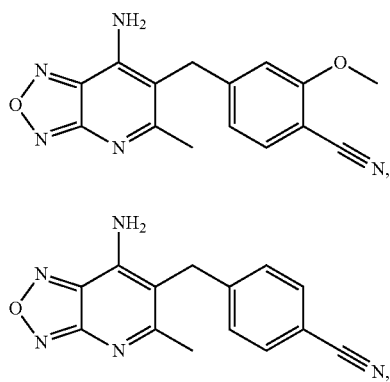

-continued

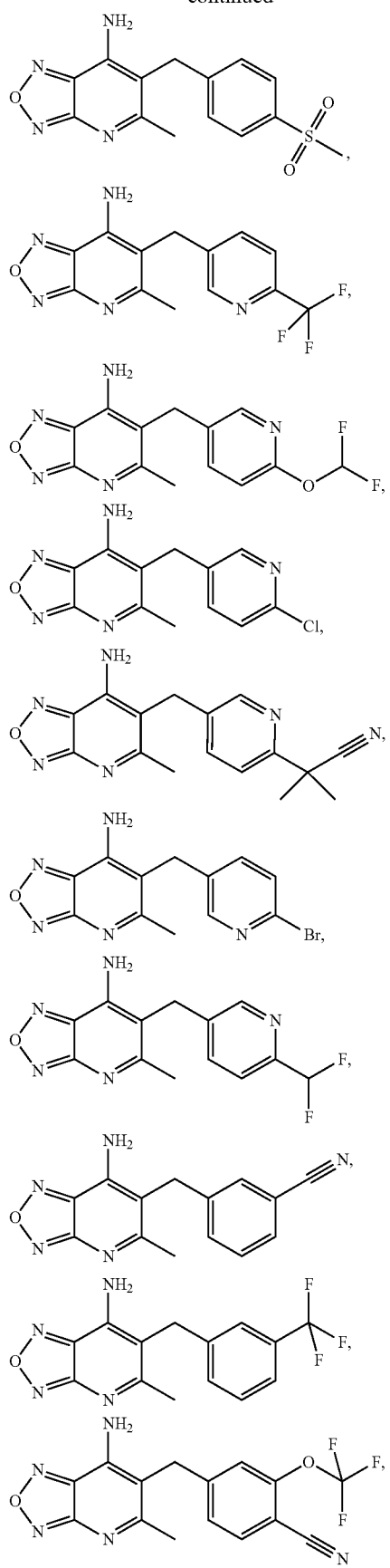

-continued

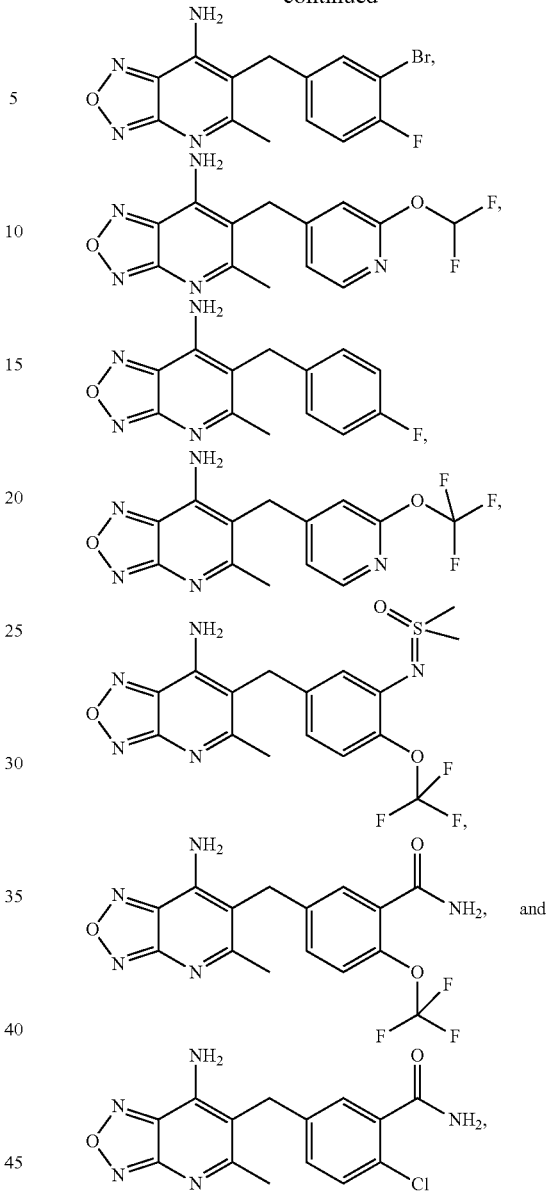

or a salt thereof.

8. A pharmaceutically acceptable salt of a compound according to claim 1.

9. A method for treating obesity, type 2 diabetes mellitus, and/or insulin resistance in patients suffering from Prader-Willi-Syndrome, the method comprising administering a pharmaceutically effective amount of a compound according to claim 1, or a pharmaceutically acceptable salt thereof, to a patient in need thereof.

10. A pharmaceutical composition comprising a compound according to claim 1, or a pharmaceutically acceptable salt thereof, optionally together with one or more inert carriers and/or diluents.

11. A method for treating a disease or condition which is mediated by inhibiting the activity of the ghrelin O-acyl transferase (GOAT), the method comprising administering a pharmaceutically effective amount of a compound according to claim 1, or a pharmaceutically acceptable salt thereof, to a patient in need thereof.

12. A pharmaceutical composition comprising one or more compounds according to claim 1, or a pharmaceutically acceptable salt thereof, and one or more additional therapeutic agents, optionally together with one or more inert carriers and/or diluents.

13. The compound according to claim 7 wherein said compound is:

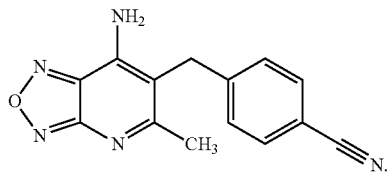 [SMILES: Cc1nc2nonc2c(N)c1Cc1ccc(C#N)cc1]

14. The compound according to claim 7, wherein said compound is:

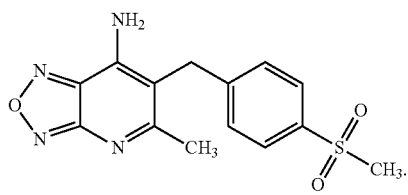 [SMILES: Cc1nc2nonc2c(N)c1Cc1ccc(S(C)(=O)=O)cc1]

15. The compound according to claim 7, wherein said compound is:

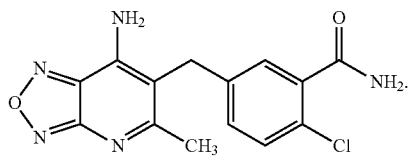 [SMILES: Cc1nc2nonc2c(N)c1Cc1ccc(Cl)c(C(N)=O)c1]

16. The compound according to claim 7, wherein said compound is:

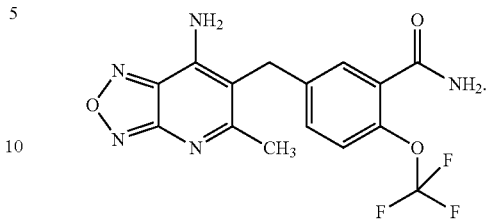

17. The compound according to claim 7, wherein said compound is:

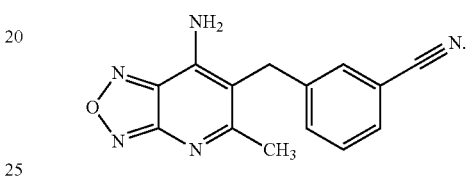

18. The compound according to claim 7, wherein said compound is:

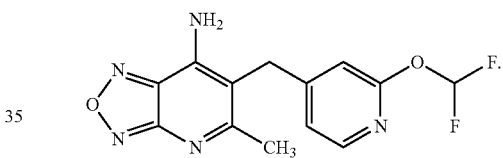

* * * * *